US007115406B2

(12) United States Patent
Gerard et al.

(10) Patent No.: US 7,115,406 B2
(45) Date of Patent: Oct. 3, 2006

(54) RECOMBINANT METHOD FOR MAKING RSV REVERSE TRANSCRIPTASES AND MUTANTS THEREOF

(75) Inventors: Gary F Gerard, Frederick, MD (US); Michael D Smith, Rockville, MD (US); Deb K Chatterjee, North Potomac, MD (US)

(73) Assignee: Invitrogen Corporation, Carlsbad, CA (US)

( * ) Notice: Subject to any disclaimer, the term of this patent is extended or adjusted under 35 U.S.C. 154(b) by 394 days.

(21) Appl. No.: 10/292,604

(22) Filed: Nov. 13, 2002

(65) Prior Publication Data

US 2003/0186270 A1 Oct. 2, 2003

Related U.S. Application Data

(62) Division of application No. 09/064,057, filed on Apr. 22, 1998, now Pat. No. 6,989,259.

(60) Provisional application No. 60/049,874, filed on Jun. 17, 1997, provisional application No. 60/044,589, filed on Apr. 22, 1997.

(51) Int. Cl.
*C12N 9/12* (2006.01)

(52) U.S. Cl. .................................... 435/194

(58) Field of Classification Search ............... 435/194, 435/325, 252.33, 254.1, 320.1; 536/23.1, 536/23.2

See application file for complete search history.

(56) References Cited

U.S. PATENT DOCUMENTS

| 4,663,290 A | 5/1987 | Weis et al. ............ 435/252.33 |
| 4,748,233 A | 5/1988 | Sloma ........................ 530/351 |
| 4,889,818 A | 12/1989 | Gelfand et al. ............. 435/194 |
| 4,965,188 A | 10/1990 | Mullis et al. ................... 435/6 |
| 5,219,989 A | 6/1993 | Sonenberg et al. ......... 530/350 |
| 5,244,797 A | 9/1993 | Kotewicz et al. ........... 435/194 |
| 5,310,652 A | 5/1994 | Gelfand et al. ................ 435/6 |
| 5,322,770 A | 6/1994 | Gelfand ......................... 435/6 |
| 5,374,553 A | 12/1994 | Gelfand et al. .......... 435/252.3 |
| 5,405,776 A | 4/1995 | Kotewicz et al. ...... 435/252.33 |
| 5,407,800 A | 4/1995 | Gelfand et al. ................ 435/6 |
| 5,436,149 A | 7/1995 | Barnes ....................... 435/194 |
| 5,512,462 A | 4/1996 | Cheng ....................... 435/91.2 |
| 5,556,771 A | 9/1996 | Shen et al. ................. 435/91.2 |
| 5,556,772 A | 9/1996 | Sorge et al. ............... 435/91.2 |
| 5,561,058 A | 10/1996 | Gelfand et al. ............ 435/91.2 |
| 5,618,702 A | 4/1997 | Scanlon ..................... 435/91.2 |
| 5,618,703 A | 4/1997 | Gelfand et al. ............ 435/91.2 |
| 5,618,711 A | 4/1997 | Gelfand et al. ............. 435/194 |
| 5,624,833 A | 4/1997 | Gelfand et al. ............. 435/194 |
| 5,641,864 A | 6/1997 | Gelfand ...................... 530/350 |
| 5,668,005 A | 9/1997 | Kotewicz et al. ........... 435/194 |
| 5,693,517 A | 12/1997 | Gelfand et al. ............. 435/193 |
| 6,013,488 A | 1/2000 | Hayashizaki ............. 435/91.51 |
| 6,060,240 A | 5/2000 | Kamb et al. ..................... 435/6 |
| 6,063,608 A | 5/2000 | Kotewicz et al. ........... 435/194 |
| 6,495,350 B1 | 12/2002 | Lee et al. .................. 435/91.2 |
| 6,518,019 B1 | 2/2003 | Gerard et al. ................... 435/6 |
| 6,589,768 B1 | 7/2003 | Kotewicz et al. ........... 435/194 |
| 6,610,522 B1 | 8/2003 | Kotewicz et al. ........... 435/194 |
| 6,630,333 B1 | 10/2003 | Hughes, Jr. |
| 2002/0028447 A1 | 3/2002 | Li et al. |
| 2002/0060618 A1 | 5/2002 | Nakao et al. |
| 2002/0090618 A1 | 7/2002 | Smith |
| 2003/0032086 A1 | 2/2003 | Gerard et al. |
| 2003/0198944 A1 | 10/2003 | Gerard et al. |

FOREIGN PATENT DOCUMENTS

| EP | 0 791 650 A1 | 8/1997 |
| JP | 7-39378 | 2/1995 |
| RU | 1490961 A1 | 7/1994 |
| WO | WO 92/06188 | 4/1992 |
| WO | WO 92/06200 | 4/1992 |
| WO | WO 96/10640 | 4/1996 |
| WO | WO 97/24455 | 7/1997 |
| WO | WO 98/44161 A1 | 10/1998 |
| WO | WO 98/51789 | 11/1998 |

OTHER PUBLICATIONS

Chernov et al. Recombinant RNA-dependent DNA polymerase . Biochemistry-Moscow (1990) 55 (4), 429-435.*
Barnes, W.M., "PCR amplification of up to 35-kb DNA with high fidelity and high yield from λ bacteriophage templates," *Proc. Natl. Sci. USA 91*:2216-2220, National Academy of Sciences (1994).
Jones, M.D. and Foulkes, N.S., "Reverse transcription of mRNA by *Thermus aquaticus* DNA polymerase," *Nucl. Acids Res. 17*:8387-8388, IRL Press at Oxford University Press (1989).
Copy of Supplementary Partial European Search Report for European Application No. 98 92 0859, European Patent Office, Netherlands, mailed Oct. 25, 2004.
Ford, C.F., et al., "Fusion Tails for the Recovery and Purification of Recombinant Proteins," *Prot. Expr. Purif. 2*:95-107, Academic Press (1991).

(Continued)

*Primary Examiner*—Nashaat T. Nashed
(74) *Attorney, Agent, or Firm*—Sterne, Kessler, Goldstein & Fox PLLC

(57) ABSTRACT

A method of producing a Rous Sarcoma Virus reverse transcriptase (RSV RT) by expressing one orniore nucleic acid sequences encoding one or more subunits of RSV RT in a eukaryotic host cell and culturing the host cell under conditions sufficient to produce the recombinant RSV RT. The resulting RSV RT has a specific activity of between about 30,000 and 150,000 units per milligram and is suitable for methods including RT-polyinerase chain reaction (RT-PCR).

62 Claims, 53 Drawing Sheets

OTHER PUBLICATIONS

Pending Non-Provisional U.S. Appl. No. 09/245,025, Gerard et al., filed Feb. 5, 1999 (Not Published).

Aatinski, J.T., et al., "A Coupled One-Step Reverse Transcription PCR Procedure For Generation of Full-Length Open Reading Frames," *BioTechniques* 16:282, 284, 286 and 288, Eaton Publishing Co. (1994).

Abbotts, J., et al., "Mechanism of HIV-1 Reverse Transcriptase. Termination of Processive Synthesis on a Natural DNA Template is Influenced by the Sequence of the Template-Primer Stem," *J. Biol. Chem.* 268:10312-10323, The American Society for Biochemistry and Molecular Biology (1993).

Alexander, F., et al., "Proteolytic Processing of Avian Sarcoma and Leukosis Viruses *pol-endo* Recombinant Proteins Reveals Another *pol* Gene Domain," *J. Virol.* 61:534-542 (Feb. 1987).

Anderson, D., et al., "Rapid Generation of Recombinant Baculovirus and Expression of Foreign Genes Using the Bac-To-Bac™ Baculovirus Expression System," *FOCUS* 17:53-58 (1995).

Barnes, W.M., "The fidelity of Taq polymerase catalyzing PCR is improved by an N-terminal deletion," *Gene* 112:29-35, Elsevier Science B.V. (1992).

Barr, P.J., et al., "Expression of Active Human Immunodeficiency Virus Reverse Transcriptase in *Saccharomyces cerevisiae*," *BioTechnology* 5:486-489, Nature Publishing Co. (1987).

Berger, S.L., et al., "Reverse Transcriptase and Its Associated Ribonuclease H: Interplay of Two Enzyme Activities Controls the Yield of Single-Stranded Complementary Deoxyribonucleic Acid," *Biochemistry* 22:2365-2372, American Chemical Society (1983).

Chattopadhyay, D., et al., "Purification and Characterization of Heterodimeric Human Immunodeficiency Virus Type 1 (HIV-1) Reverse Transcriptase Produced by *in Vitro* Processing of p66 with Recombinant HIV-1 Protease," *J. Biol. Chem.* 267:14227-14232, The American Society for Biochemistry and Molecular Biology (1992).

Chernov, A.P., et al., "Recombinant reverse transcriptase of Rous sarcoma virus: characterization of DNA polymerase and RNAase H activities," *Biomed. Sci.* 2:49-53, Academy of Sciences of the USSR, Turpin Transactions Limited, Pion Limited (1991).

Dudding, L.R., et al., "Analysis of the RNA- and DNA-Dependent DNA Polymerase Activities of Point Mutants of HIV-1 Reverse Transcriptase Lacking Ribonuclease H Activity," *Biochemistry* 30:10498-10506, American Chemical Society (1991).

Freeman, W.M., et al., "Use of Elevated Reverse Transcription Reaction Temperature in RT-PCR," *BioTechniques* 20:782-783, Eaton Publishing Co. (May 1996).

Flaman, J.-M., et al., "A Rapid PCR Fidelity Assay," *Nucl. Acids Res.* 22:3259-3260, Oxford University Press (1994).

Gerard, G.F., et al., "Poly(2'-0-methylcytidylate) Oligodeoxyguanylate as a Template for the Ribonucleic Acid Directed Deoxyribonucleic Acid Polymerase in Ribonucleic Acid Tumor Virus Particles and a Specific Probe for the Ribonucleic Acid Directed Enzyme in Transformed Murine Cells," *Biochemistry* 13:1632-1641, American Chemical Society (1974).

Gerard, G.F., et al., "cDNA Synthesis by Cloned Moloney Murine Leukemia Virus Reverse Transcriptase Lacking RNase H Activity," *FOCUS* 11:66-69, Life Technologies, Inc. (1989).

Gerard, G.F., et al., "cDNA Synthesis by Moloney Murine Leukemia Virus RNase H-Minus Reverse Transcriptase Possessing Full DNA Polymerase Activity," *FOCUS* 14:91-93, Life Technologies, Inc. (1992).

Gerard, G.F., "Reverse Transcriptase: A Historical Perspective," *FOCUS* 20:65-67, Life Technologies, Inc. (1998).

Grandgenett, D.P., et al., "A Single Subunit from Avian Myeloblastosis Virus with Both RNA-Directed DNA Polymerase and Ribonuclease H Activity," *Proc. Natl. Acad. Sci. USA* 70:230-234 (Jan. 1973).

Grandgenett, D.P., et al., "Large-Scale Purification of Ribonucleic Acid Tumor Viruses by Use of Continuous-Flow Density Gradient Centrifugation," *Appl. Microbiol.* 26:452-454, American Society for Microbiology (1973).

Gubler, U., and Hoffman, B.J., "A simple and very efficient method for generating cDNA libraries," *Gene* 25:263-269, Elsevier Science (1983).

Hizi, A., and Joklik, W.K., et al., "RNA-dependent DNA Polymerase of Avian Sarcoma Virus B77," *J. Biol. Chem.* 252:2281-2289, The American Society of Biological Chemists (1977).

Hizi, A., et al., "Mutational Analysis of the Ribonuclease H Activity of Human Immunodeficiency Virus 1 Reverse Transcriptase," *Virol.* 175:575-580, Academic Press (1990).

Hostomsky, Z., et al., "Reverse Transcriptase of Human Immunodeficiency Virus Type 1:Functionality of Subunits of the Heterodimer in DNA Synthesis," *J. Virol.* 66:3179:3182, American Society for Microbiology (1992).

Houts, G.E., et al., "Reverse Transsscriptase from Avian Myeloblastosis Virus," *J. Virol.* 29:517-522, American Society for Microbiology (1979).

Huber, H.E., et al., "Human Immunodeficiency Virus 1 Reverse Transcriptase. Template Binding, Processivity, Strand Displacement Synthesis, and Template Switching," *J. Biol. Chem.* 264:4669-4678, The American Society for Biochemistry and Molecular Biology (1989).

Johnson, M.S., et al., "Computer analysis of retroviral *pol* genes: Assignment of enzymatic functions to specific sequences and homologies with nonviral enzymes," *Proc. Natl. Acad. Sci. USA* 83:7648-7652, National Academy of Sciences (1986).

Kanaya, S., et al., "Identification of the Amino Acid Residues Involved in an Active Site of *Escherichia coli* Rivonuclease H by Site-directed Mutagenesis," *J. Biol. Chem.* 265:4615-4621, The American Society for Biochemistry and Molecular Biology (1990).

Kawa, S., et al., "Expression and Puriication of the HIV-1 Reverse Transcriptase Using the Baculovirus Expression Vector System," *Prot. Exp. Purif.* 4:298-303, Academic Press (1993).

Knapp, B., et al., "*In vitro* translation of *Plasmodium falciparum* aldolase is not initiated at an unusual site," *EMBO J.* 10:3095-3097, Oxford University Press (1991).

Kokko, H.I., et al., "Single-Step Immunocapture RT-PCR in the Detection of Raspberry Bushy Dwarf Virus," *BioTechniques* 20:842-846, Eaton Publishing Co. (May 1996).

Kotewicz, M.L., et al., "Isolation of cloned Maloney murine leukemia virus reverse transcriptase lacking ribonuclease H activity," *Nucl. Acids Res.* 16:265-277, IRL Press (1988).

Krug, M.S., et al., "First-Strand cDNA Synthesis Primed with Obligo(dT)," *Meth. Enzymol.* 152:316-325, Academic Press (1987).

Lawyer, F.C., et al., "High-level Expression, Purification, and Enzymatic Characterization of Full-length *Thermus aquaticus* DNA Polymerase and a Truncated Form Deficient in 5' to 3' Exonuclease Activity," *PCR Meth. Appl.*2:275-287, Cold Spring Harbor Laboratory Press (1993).

Lee, E.H., et al., "A Highly Sensitive Method for One-Step Amplification of RNA by Polymeraase Chain Reaction," *FOCUS* 19:39-42, Life Technologies, Inc. (Spring 1997).

Le Grice, S.F.J., and Grüninger-Leitch, F., "Rapid purification of homodimer and heterodimer HIV-1 reverse transcriptase by metal chelate affinity chromatography," *Eur. J. Biochem.* 187:307-314, Springer International (1990).

Le Grice, S.F.J, "Human Immunodeficiency Virus Reverse Transcriptase," in *Reverse Transcriptase*, Shalka, A.M., and Goff, S.P., Eds., Cold Spring Harbor, New York: Cold Spring Harbor Laboratory Press, pp. 163-191 (1993).

Lowe, D.M., et al., "HIV-1 Reverse Transcriptase: Crystallization and Analysis of Domain Structure by Limited Proteolysis," *Biochemistry* 27:8884-8889, American Chemical Society (1988).

Mallet, F., et al., "Continuous RT-PCR Using AMV-RT and *Taq* DNA Polymerase: Characterization and Comparison to Uncoupled Procedures," *BioTechniques* 18:678-687, Eaton Publishing Co. (1995).

Messer, L.I., et al., "Functional Analysis of Reverse Transcription by a Frameshift *pol* Mutant of Murine Leukemia Virus," *Virology* 146:146-152, Academic Press (1985).

Mizrahi, V., et al., "Recombinant HIV-1 Reverse Transcriptase: Purification, Primary Structure, and Polymerase/Ribonuclease H activities," *Arch. Biochem. Biophys.* 273:347-358, Academic Press (1989).

Mizrahi, V., et al., "Site-directed mutagenesis of the conserved Asp-443 and Asp-498 carboxy-terminal residues of HIV-1 reverse transcriptase," *Nucl. Acids Res. 18*:5359-5363, Oxford University Press (1990).

Müller, B., et al., "Co-expression of the Subunits of the Heterodimer of HIV-1 Reverse Transcriptase in *Escherichia coli,*" *J. Biol. Chem. 267*:13975-13978, The American Society for Biochemistry and Molecular Biology (1989).

Myers, T.W., and Gelfand, D.H., "Reverse Transcription and DNA Amplification by a *Thermus thermophilus* DNA Polymerase," *Biochemistry 30*:7661-7666, American Chemical Society (1991).

Prasad, V.R., et al., "Genetic Analysis of Retroviral Reverse Transcriptase Structure and Function," in *Reverse Transcriptase,* Shalka, A.M., and Goff, S.P., Eds., Cold Spring Harbor, New York: Cold Spring Harbor Laboratory Press, pp. 135-162 (1993).

Repaske, R., et al., "Inhibition of RNase H Activity and Viral Replication by Single Mutations in the 3' Region of Moloney Murine Leukemia Virus Reverse Transcriptase," *J. Virol. 63*:1460-1464, American Society for Microbiology (1993).

Saiki, R.K., et al., "Primer-Directed Enzymatic Amplification of DNA with a Thermostable DNA Polymerase," *Science 239*:487-491, American Association for the Advancement of Science (1988).

Sambrook, J., et a., "Protocol for the Synthesis of the First Strand of cDNA," in *Molecular Cloning: A Laboratory Manual* 2nd Edition, Cold Spring Harbor, New York: Cold Spring Harbor Laboratory Press, pp. 8.60-8.63 (1989).

Schwartz, D.E., et al., "Nucleotide Sequence of Rous Sarcoma Virus," *Cell 32*:853-869, The MIT Press (1983).

Sellner, L.N., et al., "Reverse transcriptase inhibits Taq polymerase activity," *Nucl. Acids Res. 20*:1487-1490, Oxford University Press (1992).

Sitaraman, K., et al., "RT-PCR of Difficult Templates Using the Superscript One-Step™ RT-PCR System," *FOCUS 19*:43-44, Life Technologies, Inc. (Spring 1997).

Skalka, A.M., et al., "Endonuclease Activity Associated with Reverse Transcriptase of Avian Sarcoma-Leukosis Viruses," in *Reverse Transcriptase,* Skalka, A.M., and Goff, S.P., Eds., Cold Spring Harbor, New York: Cold Spring Harbor Laboratory Press, pp. 193-204 (1993).

Soltis, D.A., and Skalka, A.M., "The α and β chains of avian retrovirus reverse transcriptase independently expressed in *Escherichia coli*: Characterization of enzymatic activities," *Proc. Natl. Acad. Sci. USA 85*:3372-3376, National Academy of Sciences (1988).

Stahlhut, M., et al., "Purification and Chacterization of HIV-1 Reverse Transcriptase Having a 1:1 Ratio of p66 and p51 Subunits," *Prot. Exp. Purif. 5*:614-621, Academic Press (1994).

Strauss, E.M., et al., "Efficient Production of Mammalian RNA Tumor Viruses in Serum-Free Culture Medium Allows Rapid RNA Subunit Purification," *J. Virol. Meth. 1*:213-221, Elsevier/North Holland Biomedical Press (1980).

Telesnitsky, A., and Goff, S.P., "RNase H domain mutations affect the interaction between Moloney murine leukemia virus reverse transcriptase and its primer-templated," *Proc. Natl. Acad. Sci. USA 90*:1276-1280, National Academy of Sciences (1993).

Wang, R.F., et al., "A Simplified, Single Tube, Single Buffer System for RNA-PCR," *BioTechniques 12*:702, 704, Eaton Publishing Co. (1992).

Weaver, D.T., and DePamphilis, M.L., "Specific Sequences in Native DNA that Arrest Synthesis by DNA Polymerase α," *J. Biol. Chem. 257*:2075-2086, The American Society of Biological Chemists (1982).

Boehringer Mannheim Biochemicals, "Reverse Transcriptase AMV,"; "Reverse Transcriptase M-MuLV," and "Reverse Transcriptase, HIV-1," Products Catalogue, pp. 92-93, Boehringer Mannheim (1995).

Life Technologies, Inc., "GIBCO BRL Baculovirus Expression Products," Product Technical Literature, nine (9) pages, Life Technologies, Inc. (1996).

Toyobo, Tokyo, Japan, "M-MLV Reverse Transcriptase (Rnase H-) ReverTra Ace," Product Literature, 1 page, Toyobo (1998).

Chernov, A.P., et al., "Recombinant RNA-Dependent DNA-Polymers RSV: Isolation and General Properties," *Biokhimiia (USSR) 55*:586-594, Nauka (1990).

Dialog File 155 (Medline), Accession No. 90335319, English-language abstract for Chernov et al., one (1) page (Doc. No. AT20).

Gerard, G.F., et al., "Reverse Transcriptase. The Use of Cloned Moloney Murine Leukemia Virus Reverse Transcriptase to Synthesize DNA from RNA," *Molec. Biotechnol. 8*:61-77, Humana Press (Aug. 1997).

Nathan, M., et al., "Optimizing Long RT-PCR," *FOCUS 17*:78-80, Life Technologies, Inc. (1995).

Schwabe, W., et al., "ThermoScript™ RT, a New Avian Reverse Transcriptase for High-Temperature cDNA Synthesis to Improve RT-PCR," *FOCUS 20*:30-33, Life Technologies, Inc. (Mar. 1998).

Werner, S., and Wörl, B.M., "Soluble Rous Sarcoma Virus Reverse Transcriptases α, α6, and 6, Purified from Insect Cells Are Processive DNA Polymerase That Lack an RNase H 3'-5' Directed Processing Activity," *J. Biol. Chem. 274*:26329-26336, The American Society for Biochemistry and Molecular Biology (Sep. 1999).

Life Technologies, Inc., "GIBCO/BRL®, Instructional Manual, SUPERSCRIPT™ First-Strand Synthesis System for RT-PCR (Cat. No. 11904-018)" pp. i-31, Life Technologies, Inc. (Jan. 1999).

Life Technologies, Inc., "SUPERSCRIPT™ Preamplification System for First-Strand cDNA synthesis (Cat. No. 18089-011)" pp. i-32, Life Technologies, Inc. (Jan. 1999).

Champoux, J.J., "Roles of Ribonuclease H in Reverse Transcription," in: *Reverse Transcriptase,* A.M. Skalka and S.P. Goff, eds., Cold Spring Harbor, NY: Cold Spring Harbor Laboratory Press, pp. 103-117 (1993).

Chattopadhyay, D., et al., "Resolution of Microheterogeneity Associated with Recombinant HIV-1 Heterodimeric Reverse Transcriptase," *Prot. Exp. Purif. 3*:151-159, Academic Press (1992).

Gerard, G.F., "Synthesis of High Specific Activity cDNA," *FOCUS 10*:12-13, Life Technologies, Inc. (1988).

Myers, J.C., and Spiegelman, S., "Sodium pyrophosphate inhibition of RNA•DNA hybrid degradation by reverse transcriptase," *Proc. Natl. Acad. Sci. USA 75*:5329-5333, National Academy of Sciences (1978).

Verma, I.M., "Studies on Reverse Transcriptase of RNA Tumor Viruses. III. Properties of Purified Moloney Murine Leukemia Virus DNA Polymerase and Associated RNase H," *J. Virol. 15*:843-854, American Society for Microbiology (1975).

Wang, L.-H., and Duesberg, P.H., "DNA of Polymerase Murine Sarcoma-Leukemia Virus: Lack of Detectable RNase H and Low Activity With Viral RNA and Natural DNA Templates," *J. Virol. 12*:1512-1521, American Society for Microbiology (1973).

Yu, H., and Goodman, M.F., "Comparison of HIV-1 and Avian Myeloblastosis Virus Reverse Transcriptase Fidelity on RNA and DNA Templates," *J. Biol. Chem. 267*:10888-10896, The American Society for Biochemistry and Molecular Biology (1992).

Dialog File 351 (Derwent World Patents Index), unverified English-language abstract for JPO Publication No. 7-39378 A (Doc. No. AN2), WPI Accession No. 10216605.

National Institutes of Health, National Library of Medicine/NCBI, NCBI Sequence listing for JPO Publication No. 7-39378 A (Doc. No. AN2), obtained from Internet at <<http://www.ncbi.nlm.nih.gov/entrez/viewer.cgi>>, Accession No. E08693.

"Memorandum Opinion" and attached "Order" dated May 4, 2001, from Invitrogen Corporation vs. Clontech Laboratories, Inc., in the United States District Court for the District of Maryland Southern Division, Civil Action No. AW 96-4080 and AW 00-1879.

Freeman-Wittig, M.-J. et al., "Differential Effects of Captan on DNA Polymerase and Ribonuclease H Activities of Avian Myeloblastosis Virus Reverse Transcriptase," *Biochemistry 25*:3050-3055, American Chemical Society (1986).

Moelling, K., "Further Characterization of the Friend Murine Leukemia Virus Reverse Transcriptase-RNase H Complex," *J. Virol. 18*:418-425, American Society for Microbiology (1976).

Tosh, C., et al., "One-Tube and One-Buffer System of RT-PCR Amplification of 1D Gene of Foot-and-Mouth Disease Virus Field Isolates," *Acta Virol. 41*:153-155, Slovak Academic Press, Ltd. (Jun. 1997).

Dialog File 351, Accession No. 1995-129461/199517, Derwent WPI English language abstract for SU 1490961, (1994).

Ando, T., et al., "A One-Tube Method of Reverse Transcription-PCR To Efficiently Amplify a 3-Kilobase Region from the RNA Polymerase Gene to the Poly(A) Tail of Small Round-Structured Viruses (Norwalk-Like Viruses)," *J. Clin. Microbiol.* 35:570-577, American Society for Microbiology (Mar. 1997).

Balzarini, J., et al., "9- [(2RS) -3-Fluoro-2-phosphonylmethoxpropyl] derivatives of purines: A class of highly selective antiretroviral agents *in vitro and in vivo,*" *Proc. Natl. Acad. Sci. USA* 88:4961-4965, National Academy of Sciences (1991).

Dimcheff, D.E., et al., "Evolution and Characterization of Tetraonine Endogenous Retrovirus: a New Virus Related to Avian Sarcoma and Leukosis Viruses," *J. Virol.* 75:2002-2009, American Society for Microbiology (Feb. 2001).

Fields, B.N., et al., eds., "The Avian Leukosis-Sarcoma Virus (ALSV) Group," in: *Fundamental Virology*, Lippincott—Raven Publishers, Philadelphia, PA, pp. 765 (1995).

Georgiadis, M.M., et al., "Mechanistic implications from the structure of a catalytic fragment of Moloney murine leukemia virus reverse transcriptase," *Structure* 3:879-892, Current Biology (1995).

Neyts, J. and De Clercq, E., "Mechanism of action of acyclic nucleoside phosphonates against herpes virus replications," *Biochem. Pharm.* 47:39-41, Pergamon Press (1994).

Viktorova, L.S., et al., "Acyclic Analogs of 2',3'-Dideoxy-2',3'-Didehydronucleoside 5'-Triphosphates, Termination Substrates in DNA Synthesis by a Range of DNA Polymerases," *Molekul. Biol. (Mosk)* 27:143-152, Izdatelstvo Nauka (1993).

Viktorova, L.S., et al., "Acyclic Analogs of 2',3'-Dideoxy-2',3'-Didehydronucleoside 5'-Triphosphates, Termination Substrates in DNA Synthesis by a Range of DNA Polymerases," *Mol. Biol.* 27:85-90, Plenum Publishing Company (1993) (English translation of Viktorova, L.S., et al., *Molekul. Biol.* 27:143-152 (1993) (Document AR51).

Volkmann, S., et al., "Enzymatic Analysis of Two HIV-1 Reverse Transcriptase Mutants with Mutations in Carboxyl-terminal Amino Acid Residues Conserved among Retroviral Ribonucleases H," *J. Biol. Chem.* 268:2674-2683, The American Society for Biochemistry and Molecular Biology, Inc. (1993).

The Universal Virus Database of the International Committee in Taxonomy of Viruses, "ICTVdB. Index of Viruses," available online at http://www.ictvdb.iacr.ac.uk/Ictv/fs_retro.htm (Dec. 2001).

Joliot, V., et al., "Pathogenic Potential of Myeloblastosis-Associated Virus: Implication of *ENV* Proteins for Osteopetrosis Induction," *Virol.* 195:812-819, Academic Press, Inc. (1993).

Ratner, L., "Complete nucleotide sequence of the AIDS virus, HTLV-III," *Nature* 313:277-284, Macmillan Publishers (1985).

Shinnick, T.M., et al., "Nucleotide sequence of Moloney murine leukaemia virus," *Nature* 293:543-548, Macmillan Publishers (1981).

Copy of Co-Pending U.S. Appl. No. 09/076,115, Gruber et al., filed May 12, 1998 (Not Published).

Gao, G. et al. "Conferring RNA polymerase Activity to a DNA polymerase: A single residue in reverse transcriptase controls substrate selection," *Proc. Natl. Acad. Sci (USA)* 94:407-411, National Academy of Sciences (Jan. 1997).

Kohlstaedt, L.A. et al., "Crystal Structure at 3.5 Å Resolution of HIV-1 Reverse Transcriptase Complexed with an Inhibitor," *Science* 256:1783-1790, American Association for the Advancement of Science (1992).

Stewart, L., and Vogt, V.M., "Reverse Transcriptase and Protease Activities of Avian Leukosis Virus Gag-Pol Fusion Proteins Expressed in Insect Cells," *J. Virol.* 67:7582-7596, American Society for Microbiology (1993).

Allain, B. et al., "*CIS* Elements and Trans-acting Factors required for Minus Strand DNA Transfer during Reverse Transcription of the Genomic RNA of Murine Leukemia Virus," *J. Mol. Biol.* 277:225-235, Academic Press Limited (Mar. 1998).

Arion, D. et al., "The K65R Mutation Confers Increased DNA Polymerase Processivity to HIV-1 Reverse Transcriptase," *J. Biol. Chem.* 271:19860-19864, The American Society for Biochemistry and Molecular Biology, Inc. (Aug. 1996).

Arnold, E. et al., "Structure of HIV-1 reverse transcriptase/DNA complex at 7 Å resolution showing active site locations," *Nature* 357:85-89, Macmillan Publishers Ltd. (1992).

Bahar, I., "Collective Motions in HIV-1 Reverse Transcriptase: Examination of Flexibility and Enzyme Function," *J. Mol. Biol.* 285:1023-1037, Academic Press (Jan. 1999).

Basu, S. et al., "Sulphydryl groups in the template-primer-binding domain of murine leukaemia virus reverse transcriptase," *Biochem. J.* 296:577-583, The Biochemical Society (1993).

Beard, W.A. et al., "Structure/Function Studies of Human Immunodeficiency Virus Type 1 Reverse Transcriptase," *J. Biol. Chem.* 269:28091-28097, American Society for Biochemistry and Molecular Biology (1994).

Ben-Artzi, H. et al., "Characterization of the double stranded RNA dependent RNAse activity associated with recombinant reverse transcriptases," *Nucl. Acids Res.* 20:5115-5118, Oxford University Press (1992).

Blain, S.W. and Goff, S.P., "Effects on DNA Synthesis and Translocation Caused by Mutations in the RNase H Domain of Moloney Murine Leukemia Virus Reverse Transcriptase," *J. Virol.* 69:4440-4452, American Society for Microbiology (1995).

Blain, S.W. and Goff, S.P., "Differential Effects of Moloney Murine Leukemia Virus Reverse Transcriptase Mutations on RNase H Activity in $Mg^{2-}$ and $Mn^{2+}$," *J. Biol. Chem.* 271:1448-1454, The American Society for Biochemistry and Molecular Biology, Inc. (Jan. 1996).

Carl, P.L. et al., "Isolation and Mapping of a Mutation in *Escherichia coli* with Altered Levels of Ribonuclease H," *J. Bacteriol.* 144:28-35, American Society for Microbiology (1980).

Chowdhury, K. et al, "Elucidation of the Role of Arg 110 of Murine Leukemia Virus Reverse Transcriptase in the Catalytic Mechanism: Biochemical Characterization of Its Mutant Enyzmes," *Biochemistry* 35:16610-16620, American Chemical Society (Dec. 1996).

DeStefano, J.J. et al., "Requirements for Strand Transfer between Internal Regions of Heteropolymer Templates by Human Immunodeficiency Virus Reverse Transcriptase," *J. Virol.* 66:6370-6378, American Society for Microbiology (1992).

Diaz, L. and DeStefano, J.J., "Strand transfer is enhanced by mismatched nucleotides at the 3' primer terminus: a possible link between HIV reverse transcriptase fidelity and recombination," *Nucl. Acids Res.* 24:3086-3092, Oxford University Press (Aug. 1996).

Drosopoulos, W.C. and Prasad, V.R., "Increased Polymerase Fidelity of E89G, a Nucleoside Analog-Resistant Variant of Human Immunodeficiency Virus Type 1 Reverse Transcriptase," *J. Virol.* 70:4834-4838, American Society for Microbiology (Jul. 1996).

Feng, J.Y. and Anderson, K.S., "Mechanistic Studies Examining the Efficiency and Fidelity of DNA Synthesis by the 3TC-Resistant Mutant (184V) of HIV-1 Reverse Transcriptase," *Biochemistry* 38:9440-9448, American Chemical Society (Jul. 1999; published on the web Jun. 30, 1999).

Gao, G. et al., "Conferring RNA polymerase Activity to a DNA polymerase: A single residue in reverse transcriptase controls substrate selection," *Proc. Natl. Acad. Sci (USA)* 94:407-411, National Academy of Sciences (Jan. 1997).

Gao, G. and Goff, S.P., "Replication Defect of Moloney Murine Leukemia Virus with a Mutant Reverse Transcriptase That Can Incorporate Ribonucleotides and Deoxyribonucleotides," *J. Virol.* 72:5905-5911, American Society for Microbiology (Jul. 1998).

Gao, H.-Q. et al., "Similarities and Differences in the RNase H Activities of Human Immunodeficiency Virus Type 1 Reverse Transcriptase and Moloney Murine Leukemia Virus Reverse Transcriptase," *J. Mol. Biol.* 294:1097-1113 (Dec. 1999).

Georgiadis, M.M. et al., "Mechanistic implications from the structure of a catalytic fragment of Moloney murine leukemia virus reverse transcriptase," *Structure* 3:879-892, Current Biology Ltd. (1995).

Gerard, G.F., "Multiple RNase H Activities in Mammalian Type C Retravirus Lysates," *J. Virol.* 26:16-28, American Society Microbiology (1978).

Gerard, G.F. and D'Alessio, J.M., "Reverse Transcriptase (EC 2.7.7.49) : The Use of Cloned Moloney Murine Leukemia Virus Reverse Transcriptase to Synthesize DNA from RNA," in *Methods in Molecular Biology, vol. 16: Enzymes of Molecular Biology*, Burrell, M.M., ed., Humana Press Inc., Totowa, N.J., pp. 73-93 (1993).

Goedken, E.R. and Marqusee, S., "Folding the Ribonuclease H Domain of Moloney Murine Leukemia Virus Reverse Transcriptase Requires Metal Binding or a Short N-Terminal Extension," *Proteins: Structure, Function, and Genetics* 33:135-143, Wiley-Liss, Inc. (Oct. 1998).

Goff, S. et al., "Isolation and Properties of Moloney Murine Leukemia Virus Mutants: Use of a Rapid Assay for Release of Virion Reverse Transcriptase," *J. Virol.* 38:239-248, American Society for Microbiology (1981).

Goff, S.P., "Retroviral Reverse Transcriptase: Synthesis, Structure, and Function," *J. Acquired Immune Deficiency Syndromes* 3:817-831, Raven Press, Ltd. (1990).

Goobar-Larsson, L. et al., "Disruption of a Salt Bridge between Asp 488 and Lys 465 in HIV-1 Reverse Transcriptase Alters Its Proteolytic Processing and Polymerase Activity," *Virology* 196:731-738, Academic Press, Inc. (1993).

Gopalakrishnan, V. et al., "Human immunodeficiency virus type 1 reverse transcriptase: Spatial and temporal relationship between the polymerase and RNase H activities," *Proc. Natl. Acad. Sci. (USA)* 89:10763-10767, National Academy of Sciences (1992).

Guo, J. et al., "Defects in Primer-Template Binding, Processive DNA Synthesis, and RNase H Activity Associated with Chimeric Reverse Transcriptases Having the Murine Leukemia Virus Polymerase Domain Joined to *Escherichia coli* RNase H," *Biochemistry* 34:5018-5029, American Chemical Society (1995).

Jacobo-Molina, A. et al., "Crystal structure of human immunodeficiency virus type 1 reverse transcriptase complexed with double-stranded DNA at 3.0 Å resolution shows bent DNA," *Proc. Natl. Acad. Sci. (USA)* 90:6320-6324, National Academy of Sciences (1993).

Jaeger, J. et al. "The structure of HIV-1 reverse transcriptase complexed with an RNA pseudoknot inhibitor," *EMBO J.* 17:4535-4542, Oxford University Press (Aug. 1998).

Keck, J.L., et al., "Activation/Attenuation Model for RNase H. A One-Metal Mechanism with Second-Metal Inhibition," *J. Biol. Chem.* 273:34128-34133, The American Society for Biochemistry and Molecular Biology, Inc. (Dec. 1998).

Kelleher, C.D. and Champoux, J.J., "Characterization of RNA Strand Displacement Synthesis by Moloney Murine Leukemia Virus Reverse Transcriptase," *J. Biol. Chem.* 273:9976-9986, The American Society for Biochemistry and Molecular Biology, Inc. (Apr. 1998).

Lavignon, M. et al., "Inhibition of Moloney Murine Leukemia Virus Reverse Transcriptase by α-Anomeric Oligonucleotides," *Biochem. Biophys. Res. Commun.* 161:1184-1190, Academic Press, Inc. (1989).

Levin, H.L., "An Unusual Mechanism of Self-Primed Reverse Transcription Requires the RNase H Domain of Reverse Transcriptase To Cleave an RNA Duplex," *Mol. Cell. Biol.* 16:5645-5654, American Society for Microbiology (Oct. 1996).

Levine, H.L., "It's Prime Time for Reverse Transcriptase," *Cell* 88:5-8, Cell Press (Jan. 1997).

Loya, S. and Hizi, A., "The Interaction of Illimaquinone, a Selective Inhibitor of the RNase H Activity, with the Reverse Transcriptases of Human Immunodeficiency and Murine Leukemia Retrovirusis," *J. Biol. Chem.* 268:9323-9328, The American Society for Biochemistry and Molecular Biology, Inc. (1993).

Misra, H.S. et al., "An Ensymatically Active Chimeric HIV-1 Reverse Transcriptase (RT) with the RNase-H Domain of Murine Leukemia Virus RT Exists as a Monomer," *J. Biol. Chem.* 16:9785-9789, The American Society for Biochemistry and Molecular Biology, Inc. (Apr. 1998).

Patel, P.H. et al., "Insights into DNA Polymerization Mechanism from Structure and Function Analysis of HIV-1 Reverse Transcriptase," *Biochemistry* 34:5351-5363, American Chemical Society (1995).

Peliska, J.A. and Benkovic, E.J., "Mechanism of DNA Strand Transfer Reactions Catalyzed by HIV-1 Reverse Transcriptase," *Science* 258:1112-1118, American Association for the Advancement of Science (1992).

Post, K. et al., "A Large Deletion in the Connection Subdomain of Murine Leukemia Virus Reverse Transcriptase or Replacement of the RNase H Domain with *Escherichia coli* RNase H Results in Altered Polymerase and RNase H Activities," *Biochemistry* 32:5508-5517, American Chemical Society (1993).

Shirasawa, Y. et al., "Transdominant Inhibition of Moloney Murine Leukemia Virus Proliferation by Defective Mutants of Reverse Transcriptase," *J. Biochem.* 119:1070-1075, The Japanese Biochemical Society (Jun. 1996).

Smith, C.M. et al, "Sequence Requirements for Removal of tRNA by an Isolated Human Immunodeficiency Virus Type 1 RNase H Domain," *J. Virol.* 72:6805-6812, American Society for Microbiology (Aug. 1998).

Spedding, G. et al., "Inhibition of reverse transcriptases by flavonoids," *Antiviral Res.* 12:99-110, Elsevier Science Publishers B.V. (Biomedical Division) (1989).

Sun, D. et al., "Cloning, expression, and purification of a catalytic fragment of Moloney murine leukemia virus reverse transcriptase: Crystallization of nucleic acid complexes," *Protein Sci.* 7:1575-1582, Cambridge University Press (Jul. 1998).

Tanese, N et al., "Abortive Reverase Transcription by Mutants of Moloney Murine Leukemia Virus Deficient in the Reverse Transcriptase-Associated RNase H Function," *J. Virol.* 65:4367-4397, American Society for Microbiology (1991).

Trentin, B. et al., "Human T-cell Leukemia Virus Type 1 Reverse Transcriptase (RT) Originates from the *pro* and *pol* Open Reading Frames and Requires the Presence of RT-RNase H (RH) and RT-RH-Integrase Proteins for its Activity," *J. Virol.* 72:6504-6510, American Society for Microbiology (Aug. 1998).

Veal, G.J. et al., "Sequence-specific RNase H cleavage of *gag* mRNA from HIV-1 infected cells by an antisense oligonucleotide *in vitro*," *Nucl. Acids Res.* 26:5670-5675, Oxford University Press (Dec. 1998).

Yadav, P.N.S. et al., "A Computer-assisted Analysis of Conserved Residues in the Three-dimensional Structures of the Polymerase Domains of *Escherichia coli* DNA Polymerase I and HIV-1 Reverse Transcriptase," *J. Biol. Chem.* 269:716-720, The American Society for Biochemistry and Molecular Biology, Inc. (1994).

Whiting, S.H. and Champoux, J.J., "Properties of Strand Displacement Synthesis by Moloney Murine Leukemia Virus Reverse Transcriptase: Mechanistic Implications," *J. Mol. Biol.* 278:559-577, Academic Press Limited (May 1998).

Wilson, J.E. et al., "Human Immunodeficiency Virus Type-1 Reverse Transcriptase. Contribution of Met-184 to Binding of Nucleoside 5'-Triphosphate," *J. Biol. Chem.* 271:13656-13662, The American Society for Biochemistry and Molecular Biology, Inc. (Jun. 1996).

Wöhrl, B.M. et al., "Footprint Analysis of Replicating Murine Leukemia Virus Reverse Transcriptase," *Science* 267:96-99, The American Association for the Advancement of Science (1995).

Aatsinki, J.T., "Coupled One-Step Reverse Transcription and Polymerase Chain Reaction Procedure for Cloning Large cDNA Fragments," in: *PCR Cloning Protocols. From Molecular Cloning to Genetic Engineering*, White, B.A., ed., Humana Press, Totowa, NJ, pp. 55-60 (Feb. 1997).

Argos, P., "A sequence motif in many polymerase," *Nucl. Acids Res.* 16:9909-9916, IRL Press at Oxford University Press (1988).

Ausubel, F.M., et al., eds., "Enzymatic Amplification of RNA by the Polymerase Chain Reaction," in: *Current Protocols in Molecular Biology*, John Wiley & Sons, Inc., Somerset, NJ, pp. 15.4.1-15.4.4 (1992).

Casas, I., et al., "Two Different PCR Assays to Detect Enteroviral RNA in CSF Samples From Patients With Acute Aseptic Meningitis," *J. Med. Virol.* 47:378-385, Wiley-Liss, Inc. (1995).

Delarue, M., et al., "An attempt to unify the structure of polymerases," *Prot. Eng.* 3:461-467, IRL Press at Oxford University Press (1990).

Gerard, G.F., et al., "The role of template-primer in protection of reverse transcriptase from thermal inactivation," *Nucl. Acids Res.* *30*:3118-3129, Oxford University Press (Jul. 2002).

Goblet, C., et al., "One-step amplification of transcripts in total RNA using the polymerase chain reaction," *Nucl. Acids Res.* *17*:2144, IRL Press at Oxford University Press (1989).

Payan, C., et al., "Detection of hepatitis C virus RNA by a reliable, optimized single-step reverse transcription polymerase chain reaction," *Res. Virol. 14*:363-370, Elsevier (1995).

Poch, O., et al., "Identification of four conserved motifs among the RNA-dependent polymerase encoding elements," *EMBO J. 8*:3867-3874, IRL Press at Oxford University Press (1989).

Kohlstaedt, L.A., et al., "Crystal Structure at 3.5 Å Resolution of HIV-1 Reverse Transcriptase Complexed with an Inhibitor," *Science 256*:1783-1790, American Association for the Advancement of Science (1992).

NCBI Entrez, GenBank Report, Accession No. AAA46298, from Kan, N.C., et al. (first available in 1993).

NCBI Entrez, GenBank Report, Accession No. AAC15906, from Rushlow, K.E., et al. (first available in 1993).

NCBI Entrez, GenBank Report, Accession No. GNMV1M, from Shinnick, T.M., et al. (first available in 1993).

NCBI Entrez, GenBank Report, Accession No. J02342, from Haseltine, W.A., et al. (first available in 1993).

NCBI Entrez, GenBank Report, Accession No. L10923, from Joliot, V., et al. (first available in 1993).

NCBI Entrez, GenBank Report, Accession No. L10924, from Joliot, V., et al. (first available in 1993).

NCBI Entrez, GenBank Report, Accession No. AAA66622, from Martinelli, S.C. and Goff, S.P. (1995).

NCBI Entrez, GenBank Report, Accession No. AAC0988, from Bouck, J., et al. (Apr. 1998).

NCBI Entrez, GenBank Report, Accession No. 1MML, from Georgiadis, M.M., et al. (Sep. 1998).

NCBI Entrez, GenBank Report, Accession No. L10922, from Joliot, V., et al. (Nov. 2002).

* cited by examiner

SEQUENCE LISTING

```
<160> NUMBER OF SEQ ID NOS: 24

<210> SEQ ID NO 1
<211> LENGTH: 39
<212> TYPE: DNA
<213> ORGANISM: Artificial Sequence
<220> FEATURE:
<223> OTHER INFORMATION: Oligonucleotide

<400> SEQUENCE: 1
auggagaucu cucatatgac tgttgcgcta catctggct                              39

<210> SEQ ID NO 2
<211> LENGTH: 37
<212> TYPE: DNA
<213> ORGANISM: Artificial Sequence
<220> FEATURE:
<223> OTHER INFORMATION: Oligonucleotide

<400> SEQUENCE: 2
aacgcguacu agugttaaca gcgcgcaaat catgcag                                37

<210> SEQ ID NO 3
<211> LENGTH: 36
<212> TYPE: DNA
<213> ORGANISM: Artificial Sequence
<220> FEATURE:
<223> OTHER INFORMATION: Oligonucleotide

<400> SEQUENCE: 3
cuacuacuac uaggtaccct ctcgaaaagt taaacc                                 36

<210> SEQ ID NO 4
<211> LENGTH: 45
<212> TYPE: DNA
<213> ORGANISM: Artificial Sequence
<220> FEATURE:
<223> OTHER INFORMATION: Oligonucleotide

<400> SEQUENCE: 4
caucaucauc auctcgagtt atgcaaaaag agggctcgcc tcatc                       45
```

<210> SEQ ID NO 5
<211> LENGTH: 36
<212> TYPE: DNA
<213> ORGANISM: Artificial Sequence
<220> FEATURE:
<223> OTHER INFORMATION: Oligonucleotide

<400> SEQUENCE: 5
ggacccactg tctttaccgc ggcctcctca agcacc                          36

<210> SEQ ID NO 6
<211> LENGTH: 39
<212> TYPE: DNA
<213> ORGANISM: Artificial Sequence
<220> FEATURE:
<223> OTHER INFORMATION: Oligonucleotide

<400> SEQUENCE: 6
caucaucauc aucccgggtt aatacgcttg gaaggtggc                       39

<210> SEQ ID NO 7
<211> LENGTH: 35
<212> TYPE: DNA
<213> ORGANISM: Artificial Sequence
<220> FEATURE:
<223> OTHER INFORMATION: Oligonucleotide

<400> SEQUENCE: 7
cuacuacuac uatcatgact gttgcgctac atctg                           35

<210> SEQ ID NO 8
<211> LENGTH: 33
<212> TYPE: DNA
<213> ORGANISM: Artificial Sequence
<220> FEATURE:
<223> OTHER INFORMATION: Oligonucleotide

<400> SEQUENCE: 8
cuacuacuac uaggtaccct ctcgaaaagt taa                             33

<210> SEQ ID NO 9
<211> LENGTH: 52
<212> TYPE: DNA
<213> ORGANISM: Artificial Sequence
<220> FEATURE:
<223> OTHER INFORMATION: Oligonucleotide

<400> SEQUENCE: 9
caucaucauc augaggaatt cagtgatggt gatggtgatg tgcaaaaaga gg        52

<210> SEQ ID NO 10
<211> LENGTH: 41
<212> TYPE: DNA
<213> ORGANISM: Artificial Sequence
<220> FEATURE:
<223> OTHER INFORMATION: Oligonucleotide

<400> SEQUENCE: 10
actggaattc atgccaatcc atcaccatca ccatcacccg t                    41

<210> SEQ ID NO 11
<211> LENGTH: 41
<212> TYPE: DNA
<213> ORGANISM: Artificial Sequence
<220> FEATURE:
<223> OTHER INFORMATION: Oligonucleotide

```
-continued

<400> SEQUENCE: 11
acgtgtcgac catatggatg actaggtgaa acgggtgatg g                        41

<210> SEQ ID NO 12
<211> LENGTH: 71
<212> TYPE: DNA
<213> ORGANISM: Artificial Sequence
<220> FEATURE:
<223> OTHER INFORMATION: Annealed primer product

<400> SEQUENCE: 12
actggaattc atgccaatcc atcaccatca ccatcacccg tttcacctag tcatccatat    60
ggtcgacacg t                                                        71

<210> SEQ ID NO 13
<211> LENGTH: 48
<212> TYPE: DNA
<213> ORGANISM: Artificial Sequence
<220> FEATURE:
<223> OTHER INFORMATION: Oligonucleotide

<400> SEQUENCE: 13
gactagttct agatcgcgag cggccgccca ttaactctcg ttggcagc                 48

<210> SEQ ID NO 14
<211> LENGTH: 16
<212> TYPE: DNA
<213> ORGANISM: Artificial Sequence
<220> FEATURE:
<223> OTHER INFORMATION: Oligonucleotide

<400> SEQUENCE: 14
tcgacccacg cgtccg                                                   16

<210> SEQ ID NO 15
<211> LENGTH: 12
<212> TYPE: DNA
<213> ORGANISM: Artificial Sequence
<220> FEATURE:
<223> OTHER INFORMATION: Oligonucleotide

<400> SEQUENCE: 15
cggacgcgtg gg                                                       12

<210> SEQ ID NO 16
<211> LENGTH: 42
<212> TYPE: DNA
<213> ORGANISM: Artificial Sequence
<220> FEATURE:
<223> OTHER INFORMATION: Oligonucleotide

<400> SEQUENCE: 16
auggagaucu cugaattcat gactgttgcg ctacatctgg ct                       42

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide

<400> SEQUENCE: 17
attattcata tgactgttgc gctacatctg gc                                 32
```

```
<210> SEQ ID NO 18
<211> LENGTH: 25
<212> TYPE: DNA
<213> ORGANISM: Artificial Sequence
<220> FEATURE:
<223> OTHER INFORMATION: Oligonucleotide

<400> SEQUENCE: 18
tacgatctct ctccaggcca ttttc                                           25

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide

<400> SEQUENCE: 19
actcgagcag cccgggaacc tttg                                            24

<210> SEQ ID NO 20
<211> LENGTH: 48
<212> TYPE: DNA
<213> ORGANISM: Artificial Sequence
<220> FEATURE:
<223> OTHER INFORMATION: Oligonucleotide

<400> SEQUENCE: 20
attacccggg aggatatcat atgttagcga tgacaatgga acataaag                  48

<210> SEQ ID NO 21
<211> LENGTH: 36
<212> TYPE: DNA
<213> ORGANISM: Artificial Sequence
<220> FEATURE:
<223> OTHER INFORMATION: Oligonucleotide

<400> SEQUENCE: 21
atatgtcgac tcacagtggc cctccctata aatttg                               36

<210> SEQ ID NO 22
<211> LENGTH: 35
<212> TYPE: DNA
<213> ORGANISM: Artificial Sequence
<220> FEATURE:
<223> OTHER INFORMATION: Oligonucleotide

<400> SEQUENCE: 22
tattaggatc ccatgactgt tgcgctacat ctggc                                35

<210> SEQ ID NO 23
<211> LENGTH: 29
<212> TYPE: DNA
<213> ORGANISM: Artificial Sequence
<220> FEATURE:
<223> OTHER INFORMATION: Oligonucleotide

<400> SEQUENCE: 23
gcaatccttg agctctaaga ccatcaggg                                       29

<210> SEQ ID NO 24
<211> LENGTH: 36
<212> TYPE: DNA
<213> ORGANISM: Artificial Sequence
<220> FEATURE:
<223> OTHER INFORMATION: Oligonucleotide
```

```
<400> SEQUENCE: 24
ggacccactg tctttaccgc ggcctcctca agcacc                              36
```

US 7,115,406 B2

RECOMBINANT METHOD FOR MAKING RSV REVERSE TRANSCRIPTASES AND MUTANTS THEREOF

CROSS REFERENCE TO RELATED APPLICATIONS

The present application claims the benefit of U.S. Provisional Application Nos. 60/044,589, filed Apr. 22, 1997, and 60/049,874, filed Jun. 17, 1997, the disclosures of which are entirely incorporated by reference herein.

FIELD OF THE INVENTION

The present invention is in the fields of molecular and cellular biology. The invention is generally related to reverse transcriptase enzymes and methods for the reverse transcription of nucleic acid molecules, especially messenger RNA molecules. Specifically, the invention relates to compositions comprising mixtures of reverse transcriptase enzymes, and to methods of producing, amplifying or sequencing nucleic acid molecules (particularly cDNA molecules) using these reverse transcriptase enzymes or compositions. The invention also relates to nucleic acid molecules produced by these methods and to the use of such nucleic acid molecules to produce desired polypeptides. The invention also concerns kits comprising such compositions.

BACKGROUND OF THE INVENTION cDNA and cDNA Libraries

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene encodes. In order to produce a protein, a complementary copy of one strand of the DNA double helix (the "coding" strand) is produced by polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist myriad mRNA species, each encoding a separate and specific protein. This fact provides a powerful tool to investigators interested in studying genetic expression in a tissue or cell—mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or agarose, to which oligomers of thymidine (T) have been complexed. Since the 3' termini on most eukaryotic mRNA molecules contain a string of adenosine (A) bases, and since A binds to T, the mRNA molecules can be rapidly purified from other molecules and substances in the tissue or cell extract. From these purified mRNA molecules, cDNA copies may be made using the enzyme reverse transcriptase (RT), which results in the production of single-stranded cDNA molecules. The single-stranded cDNAs may then be converted into a complete double-stranded DNA copy (i.e., a double-stranded cDNA) of the original mRNA (and thus of the original double-stranded DNA sequence, encoding this mRNA, contained in the genome of the organism) by the action of a DNA polymerase. The protein-specific double-stranded cDNAs can then be inserted into a plasmid or viral vector, which is then introduced into a host bacterial, yeast, animal or plant cell. The host cells are then grown in culture media, resulting in a population of host cells containing (or in many cases, expressing) the gene of interest.

This entire process, from isolation of mRNA to insertion of the cDNA into a plasmid or vector to growth of host cell populations containing the isolated gene, is termed "cDNA cloning." If cDNAs are prepared from a number of different mRNAs, the resulting set of cDNAs is called a "cDNA library," an appropriate term since the set of cDNAs represents a "population" of genes comprising the functional genetic information present in the source cell, tissue or organism. Genotypic analysis of these cDNA libraries can yield much information on the structure and function of the organisms from which they were derived.

Retroviral Reverse Transcriptase Enzymes

Three prototypical forms of retroviral RT have been studied thoroughly. Moloney Murine Leukemia Virus (M-MLV) RT contains a single subunit of 78 kDa with RNA-dependent DNA polymerase and RNase H activity. This enzyme has been cloned and expressed in a fully active form in *E. coli* (reviewed in Prasad, V. R., *Reverse Transcriptase*, Cold Spring Harbor, N.Y.: Cold Spring Harbor Laboratory Press, p. 135 (1993)). Human Immunodeficiency Virus (HIV) RT is a heterodimer of p66 and p51 subunits in which the smaller subunit is derived from the larger by proteolytic cleavage. The p66 subunit has both a RNA-dependent DNA polymerase and an RNase H domain, while the p51 subunit has only a DNA polymerase domain. Active HIV p66/p51 RT has been cloned and expressed successfully in a number of expression hosts, including *E. coli* (reviewed in Le Grice, S. F. J., *Reverse Transcriptase*, Cold Spring Harbor, N.Y.: Cold Spring Harbor Laboratory press, p. 163 (1993)). Within the HIV p66/p51 heterodimer, the 51-kD subunit is catalytically inactive, and the 66-kD subunit has both DNA polymerase and RNase H activity (Le Grice, S. F. J., et al., *EMBO Journal* 10:3905 (1991); Hostomsky, Z., et al., *J. Virol.* 66:3179 (1992)). Avian Sarcoma-Leukosis Virus (ASLV) RT, which includes but is not limited to Rous Sarcoma Virus (RSV) RT, Avian Myeloblastosis Virus (AMT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2 Helper Virus UR2AV RT, Avian Sarcoma Virus Y73 Helper Virus YAV RT, Rous Associated Virus (RAV) RT, and Myeloblastosis Associated Virus (MAV) RT, is also a heterodimer of two subunits, α (approximately 62 kDa) and β (approximately 94 kDa), in which α is derived from β by proteolytic cleavage (reviewed in Prasad, V. R., *Reverse Transcriptase,* Cold Spring Harbor, N.Y.: Cold Spring Harbor Laboratory Press (1993), p. 135). ASLV RT can exist in two additional catalytically active structural forms, ββ and α (Hizi, A. and Joklik, W. K., *J. Biol. Chem.* 252: 2281 (1977)). Sedimentation analysis suggests αβ and ββ are dimers and that the α form exists in an equilibrium between monomeric and dimeric forms (Grandgenett, D. P., et al.,

*Proc. Nat. Acad. Sci. USA* 70: 230 (1973); Hizi, A. and Joklik, W. K., *J. Biol. Chem.* 252: 2281 (1977); and Soltis, D. A. and Skalka, A. M., *Proc. Nat. Acad. Sci. USA* 85: 3372 (1988)). The ASLV αβ and ββ RTs are the only known examples of retroviral RT that include three different activities in the same protein complex: DNA polymerase, RNase H, and DNA endonuclease (integrase) activities (reviewed in Skalka, A. M., *Reverse Transcriptase*, Cold Spring Harbor, N.Y.: Cold Spring Harbor Laboratory Press (1993), p. 193). The α form lacks the integrase domain and activity.

Various forms of the individual subunits of ASLV RT have been cloned and expressed. These include a 98-kDa precursor polypeptide that is normally processed proteolytically to β and a 4-kDa polypeptide removed from the β carboxy end (Alexander, F., et_al., *J. Virol.* 61: 534 (1987) and Anderson, D. et al., *Focus* 17:53 (1995)), and the mature β subunit (Weis, J. H. and Salstrom, J. S., U.S. Pat. No. 4,663,290 (1987); and Soltis, D. A. and Skalka, A. M., *Proc. Nat. Acad. Sci. USA* 85:3372 (1988)). Heterodimeric RSV αβ RT has also been purified from *E. coli* cells expressing a cloned RSV β gene (Chernov, A. P., et al., *Biomed. Sci.* 2:49 (1991)). However, there have been no reports heretofore of the simultaneous expression of cloned ASLV RT α and β genes resulting in the formation of heterodimeric αβ RT.

Reverse Transcription Efficiency

As noted above, the conversion of mRNA into cDNA by RT-mediated reverse transcription is an essential step in the study of proteins expressed from cloned genes. However, the use of unmodified RT to catalyze reverse transcription is inefficient for at least two reasons. First, RT sometimes destroys an RNA template before reverse transcription is initiated, primarily due to the activity of intrinsic RNase H activity present in RT. Second, RT often fails to complete reverse transcription after the process has been initiated (Berger, S. L., et al., *Biochemistry* 22:2365–2372 (1983); Krug, M. S., and Berger, S. L., *Meth. Enzymol.* 152:316 (1987)). Removal of the RNase H activity of RT can eliminate the first problem and improve the efficiency of reverse transcription (Gerard, G. F., et al., *FOCUS* 11(4):60 (1989); Gerard, G. F., et al., *FOCUS* 14(3):91 (1992)). However RTs, including those forms lacking RNase H activity ("RNase H⁻" forms), still tend to terminate DNA synthesis prematurely at certain secondary structural (Gerard, G. F., et al., *FOCUS* 11(4):60 (1989); Myers, T. W., and Gelfand, D. H., *Biochemistry* 30:7661(1991)) and sequence (Messer, L. I., et al., *Virol.* 146:146 (1985)); Abbotts, J., et al., *J. Biol. Chem.* 268:10312–10323 (1993)) barriers in nucleic acid templates.

Even in the most efficient reverse transcription systems available today, which use RNase H⁻ M-MLV RT, yields of total cDNA product generally do not exceed 50% of input mRNA and the fraction of the product that is full-length does not exceed 50%. The secondary structural and sequence barriers in the mRNA template, which as described above can give rise to these limitations, occur frequently at homopolymer stretches (Messer, L. I., et al., *Virol.* 146:146 (1985); Huber, H. E., et al., *J. Biol. Chem.* 264:4669–4678 (1989); Myers, T. W., and Gelfand, D. H., *Biochemistry* 30:7661 (1991)), are more often sequence rather than secondary structural barriers (Abbotts, J., et al., *J. Biol. Chem.* 268:10312–10323 (1993)), and are often distinct for different RTs (Abbotts, J., et al., *J. Biol. Chem.* 268:10312–10323 (1993)). If these barriers could be overcome, yield of total and full-length cDNA product in reverse transcription reactions could be increased.

SUMMARY OF THE INVENTION

The present invention provides reverse transcriptase enzymes, compositions comprising such enzymes and methods useful in overcoming the above-described cDNA length limitations. In general, the invention provides compositions for use in reverse transcription of a nucleic acid molecule comprising two or more different polypeptides having reverse transcriptase activity. Such compositions may further comprise one or more nucleotides, a suitable buffer, and/or one or more DNA polymerases. The compositions of the invention may also comprise one or more oligonucleotide primers. Each reverse transcriptase used in the compositions of the invention may have a different transcription pause site on a given mRNA molecule. The reverse transcriptases in these compositions preferably are reduced or substantially reduced in RNase H activity, and most preferably are enzymes selected from the group consisting of Moloney Murine Leukemia Virus (M-MLV) H⁻ reverse transcriptase, Rous Sarcoma Virus (RSV) H⁻ reverse transcriptase, Avian Myeloblastosis Virus (AMV) H⁻ reverse transcriptase, Rous Associated Virus (RAV) H⁻ reverse transcriptase, Myeloblastosis Associated Virus (MAV) H⁻ reverse transcriptase and Human Immunodeficiency Virus (HIV) H⁻ reverse transcriptase or other ASLV H⁻ reverse transcriptases. In preferred compositions, the reverse transcriptases are present at working concentrations.

The invention is also directed to methods for making one or more nucleic acid molecules, comprising mixing one or more nucleic acid templates (preferably one or more RNA templates and most preferably one or more messenger RNA templates) with two or more polypeptides having reverse transcriptase activity and incubating the mixture under conditions sufficient to make a first nucleic acid molecule or molecules complementary to all or a portion of the one or more nucleic acid templates. In a preferred embodiment, the first nucleic acid molecule is a single-stranded cDNA. Nucleic acid templates suitable for reverse transcription according to this aspect of the invention include any nucleic acid molecule or population of nucleic acid molecules (preferably RNA and most preferably mRNA), particularly those derived from a cell or tissue. In a preferred aspect, a population of mRNA molecules (a number of different mRNA molecules, typically obtained from cells or tissue) are used to make a cDNA library, in accordance with the invention. Preferred cellular sources of nucleic acid templates include bacterial cells, fungal cells, plant cells and animal cells.

The invention also concerns methods for making one or more double-stranded nucleic acid molecules. Such methods comprise (a) mixing one or more nucleic acid templates (preferably RNA or mRNA, and more preferably a population of mRNA templates) with two or more polypeptides having reverse transcriptase activity; (b) incubating the mixture under conditions sufficient to make a first nucleic acid molecule or molecules complementary to all or a portion of the one or more templates; and (c) incubating the first nucleic acid molecule under conditions sufficient to make a second nucleic acid molecule or molecules complementary to all or a portion of the first nucleic acid molecule or molecules, thereby forming one or more double-stranded nucleic acid molecules comprising the first and second nucleic acid molecules. Such methods may include the use of one or more DNA polymerases as part of the process of making the one or more double-stranded nucleic acid molecules. The invention also concerns compositions useful for making such double-stranded nucleic acid molecules. Such compositions comprise two or more reverse transcriptases and optionally one or more DNA polymerases, a suitable buffer and one or more nucleotides.

The invention also relates to methods for amplifying a nucleic acid molecule. Such amplification methods comprise mixing the double-stranded nucleic acid molecule or molecules produced as described above with one or more DNA polymerases and incubating the mixture under conditions sufficient to amplify the double-stranded nucleic acid molecule. In a first preferred embodiment, the invention concerns a method for amplifying a nucleic acid molecule, the method comprising (a) mixing one or more nucleic acid templates (preferably one or more RNA or mRNA templates and more preferably a population of mRNA templates) with two or more different polypeptides having reverse transcriptase activity and with one or more DNA polymerases and (b) incubating the mixture under conditions sufficient to amplify nucleic acid molecules complementary to all or a portion of the one or more templates. Preferably, the reverse transcriptases are reduced or substantially reduced in RNase H activity and the DNA polymerases comprise a first DNA polymerase having 3' exonuclease activity and a second DNA polymerase having substantially reduced 3' exonuclease activity. The invention also concerns compositions comprising two or more reverse transcriptases and one or more DNA polymerases for use in amplification reactions. Such compositions may further comprise one or more nucleotides and a buffer suitable for amplification. The compositions of the invention may also comprise one or more oligonucleotide primers.

In accordance with the invention, at least two, at least three, at least four, at least five, at least six, or more, reverse transcriptases may be used. Preferably, two to six, two to five, two to four, two to three, and most preferably two, reverse transcriptases are used in the compositions and methods of the invention. Such multiple reverse transcriptases may be added simultaneously or sequentially in any order to the compositions or in the methods of the invention. Alternatively, multiple different reactions with different enzymes may be performed separately and the reaction products may be mixed. Thus, the invention relates to the synthesis of the nucleic acid molecules by the methods of the invention in which multiple reverse transcriptases are used simultaneously or sequentially or separately. In particular, the invention relates to a method of making one or more nucleic acid molecules comprising incubating one or more nucleic acid templates (preferably one or more RNA templates or mRNA templates, and more preferably a population of mRNA templates) with a first reverse transcriptase under conditions sufficient to make one or more nucleic acid molecules complementary to all or a portion of the one or more templates. In accordance with the invention, the one or more nucleic acid molecules (including mRNA templates and/or synthesized nucleic acid molecules) may be incubated with a second reverse transcriptase under conditions sufficient to make additional nucleic acid molecules complementary to all or a portion of the templates or to increase the length of the previously made nucleic acid molecules. In accordance with the invention, this procedure may be repeated any number of times with the same or different reverse transcriptases of the invention. For example, the first and second reverse transcriptases may be the same or different. Furthermore, the first and third reverse transcriptases (in aspects of the invention where the procedure is repeated three times using a first, second, and third reverse transcriptase) may be the same while the second reverse transcriptase may be different from the first and the third reverse transcriptase. Thus, any combination of the same and/or different reverse transcriptases may be used in this aspect of the invention. Preferably, when multiple reverse transcriptases are used, at least two reverse transcriptases are different.

In a related aspect of the invention, the reverse transcriptase used in the reaction may retain all or a portion of its activity during subsequent reaction steps. Alternatively, the reverse transcriptase used in the reaction may be inactivated by any method prior to incubation with additional reverse transcriptases. Such an inactivation may include but is not limited to heat inactivation, organic extraction (e.g., with phenol and/or chloroform), ethanol precipitation and the like.

The synthesized nucleic acid molecules made by simultaneous or sequential or separate addition of reverse transcriptases may then be used to make double stranded nucleic acid molecules. Such synthesized nucleic acid molecules serve as a template which when incubated under appropriate conditions (e.g., preferably in the presence of one or more DNA polymerases) make nucleic acid molecules complementary to all or a portion of the synthesized nucleic acid molecules, thereby forming a number of double stranded nucleic acid molecules. The double stranded molecules may then be amplified in accordance with the invention.

The invention is also directed to nucleic acid molecules (particularly single- or double-stranded cDNA molecules) or amplified nucleic acid molecules produced according to the above-described methods and to vectors (particularly expression vectors) comprising these nucleic acid molecules or amplified nucleic acid molecules.

The invention is also directed to recombinant host cells comprising the above-described nucleic acid molecules, amplified nucleic acid molecules or vectors. Preferred such host cells include bacterial cells, yeast cells, plant cells and animal cells (including insect cells and mammalian cells).

The invention is further directed to methods of producing a polypeptide comprising culturing the above-described recombinant host cells and isolating the polypeptide, and to a polypeptide produced by such methods.

The invention also concerns methods for sequencing one or more nucleic acid molecules using the compositions or enzymes of the invention. Such methods comprise (a) mixing one or more nucleic acid molecules (e.g., one or more RNA or DNA molecules) to be sequenced with one or more primers, one or more polypeptides having reverse transcriptase activity, one or more nucleotides and one or more terminating agents, such as one or more dideoxynucleoside triphosphates; (b) incubating the mixture under conditions sufficient to synthesize a population of nucleic acid molecules complementary to all or a portion of the one or more nucleic acid molecules to be sequenced; and (c) separating the population of nucleic acid molecules to determine the nucleotide sequence of all or a portion of the one or more nucleic acid molecules to be sequenced. In these sequencing methods of the invention, the one or more polypeptides having reverse transcriptase activity may be added simultaneously, sequentially, or separately to the reaction mixtures as described above.

The invention is also directed to kits for use in the methods of the invention. Such kits can be used for making, sequencing or amplifying nucleic acid molecules (single- or double-stranded). The kits of the invention comprise a carrier, such as a box or carton, having in close confinement therein one or more containers, such as vials, tubes, bottles and the like. In the kits of the invention, a first container contains one or more of the reverse transcriptase enzymes (preferably one or more such enzymes that are reduced or substantially reduced in RNase H activity) or one or more of the compositions of the invention. In another aspect, the kit may contain one or more containers comprising two or more, three or more, four or more, five or more, six or more, and the like, reverse transcriptases, preferably one or more containers comprising two to six, two to five, two to four, two to three, or more preferably two, reverse transcriptases. The kits of the invention may also comprise, in the same or different containers, one or more DNA polymerase (preferably thermostable DNA polymerases), a suitable buffer for nucleic acid synthesis and one or more nucleotides. Alternatively, the components of the composition may be divided into separate containers (e.g., one container for each enzyme). In preferred kits of the invention, the reverse transcriptases are reduced or substantially reduced in RNase H activity, and are most preferably selected from the group consisting of M-MLV H$^-$ reverse transcriptase, RSV H$^-$ reverse transcriptase, AMV H$^-$ reverse transcriptase, RAV H$^-$ reverse transcriptase, MAV H$^-$ reverse transcriptase and HIV H$^-$ reverse transcriptase. In additional preferred kits of the invention, the enzymes (reverse transcriptases and/or DNA polymerases) in the containers are present at working concentrations.

The invention also relates to methods of producing RSV reverse transcriptase (and/or subunits thereof). In particular, the invention relates to methods for producing RSV reverse transcriptase (and/or subunits thereof) containing RNase H activity, to methods for producing RSV reverse transcriptase (and/or subunits thereof) that is reduced or substantially reduced in RNase H activity, and to RSV reverse transcriptases (and/or subunits thereof) produced by such methods.

The invention further relates to methods for using such reverse transcriptases and to kits comprising such reverse transcriptases. In particular, the RSV reverse transcriptases (and/or subunits thereof) of the invention may be used in methods of sequencing, amplification and production (via, e.g., reverse transcription) of nucleic acid molecules.

The invention also relates to methods of producing AMV reverse transcriptase (and/or subunits thereof). In particular, the invention relates to methods for producing AMV reverse transcriptase (and/or subunits thereof) containing RNase H activity, to methods for producing AMV reverse transcriptase (and/or subunits thereof) that is reduced or substantially reduced in RNase H activity, and to AMV reverse transcriptases (and/or subunits thereof) produced by such methods.

The invention further relates to methods for using such reverse transcriptases and to kits comprising such reverse transcriptases. In particular, the AMV reverse transcriptases (and/or subunits thereof) of the invention may be used in methods of sequencing, amplification and production (via, e.g., reverse transcription) of nucleic acid molecules.

The invention also generally relates to methods of producing ASLV reverse transcriptases (and/or subunits thereof). In particular, the invention relates to methods for producing ASLV reverse transcriptases (and/or subunits thereof) containing RNase H activity, to methods for producing such ASLV reverse transcriptases that are reduced or substantially reduced in RNase H activity, and to ASLV reverse transcriptases produced by such methods.

The invention further relates to methods for using such reverse transcriptases and to kits comprising such reverse transcriptases. In particular, the ASLV reverse transcriptases (and/or subunits thereof) of the invention may be used in methods of sequencing, amplification and production (e.g., via reverse transcription) of nucleic acid molecules.

The invention further relates to methods for elevated- or high-temperature reverse transcription of a nucleic acid molecule comprising (a) mixing one or more nucleic acid templates (preferably one or more RNA molecules (e.g., one or more mRNA molecules or polyA+ RNA molecules, and more preferably a population of mRNA molecules) or one or more DNA molecules) with one or more polypeptides having reverse transcriptase activity; and (b) incubating the mixture at a temperature of 50° C. or greater and under conditions sufficient to make a first nucleic acid molecule or molecules (such as a full length cDNA molecule) complementary to all or a portion of the one or more nucleic acid templates. In a preferred aspect, a population of mRNA molecules is used to make a cDNA library at elevated or high temperatures. In another aspect, elevated- or high-temperature nucleic acid synthesis is conducted with multiple reverse transcriptases (i.e., two or more, three or more, four or more, five or more, six or more, and the like, more preferably two to six, two to five, two to four, two to three, and still more preferably two, reverse transcriptases), which may be added to the reaction mixture simultaneously or sequentially or separately as described above. In preferred such methods, the mixture is incubated at a temperature of about 51° C. or greater, about 52° C. or greater, about 53° C. or greater, about 54° C. or greater, about 55° C. or greater, about 56° C. or greater, about 57° C. or greater, about 58° C. or greater, about 59° C. or greater, about 60° C. or greater, about 61° C. or greater, about 62° C. or greater, about 63° C. or greater, about 64° C. or greater, about 65° C. or greater, about 66° C. or greater, about 67° C. or greater, about 68° C. or greater, about 69° C. or greater, about 70° C. or greater, about 71° C. or greater, about 72° C. or greater, about 73° C. or greater, about 74° C. or greater, about 75° C. or greater, about 76° C. or greater, about 77° C. or greater, or about 78° C. or greater; or at a temperature range of from about 50° C. to about 75° C., about 51° C. to about 75° C., about 52° C. to about 75° C., about 53° C. to about 75° C., about 54° C. to about 75° C., about 55° C. to about 75° C., about 50° C. to about 70° C., about 51° C. to about 70° C., about 52° C. to about 70° C., about 53° C. to about 70° C., about 54° C. to about 70° C., about 55° C. to about 70° C., about 55° C. to about 65° C., about 56° C. to about 65° C., about 56° C. to about 64° C. or about 56° C. to about 62° C. The invention is also directed to such methods which further comprise incubating the first nucleic acid molecule or molecules under conditions sufficient to make a second nucleic acid molecule or molecules complementary to all or portion of the first nucleic acid molecule or molecules. According to the invention, the first and second nucleic acid molecules produced by these methods may be DNA molecules, and may form a double stranded DNA molecule or molecules which may be a full length cDNA molecule or molecules, such as a cDNA library. The one or more polypeptides having reverse transcriptase activity that are used in these methods preferably are reduced or substantially reduced in RNase H activity, and are preferably selected from ASLV reverse transcriptases (and/or subunits thereof) such as one or more subunits of AMV reverse transcriptase and/or one or more subunits of RSV reverse transcriptase and/or one or more subunits of MAV reverse transcriptase, and/or one or more subunits of RAV reverse transcriptase, particularly wherein the subunits are reduced or substantially reduced in RNase H activity.

The invention also relates to kits for elevated- or high-temperature nucleic acid synthesis, which may comprise one or more components selected from the group consisting of one or more reverse transcriptases (preferably one or more ASLV reverse transcriptases such as AMV or RSV reverse transcriptases (or one or more subunits thereof), and more preferably one or more AMV or RSV reverse transcriptases (or one or more subunits thereof) which are reduced or substantially reduced in RNase H activity), one or more nucleotides, one or more primers and one or more suitable buffers.

The invention is also directed to nucleic acid molecules produced by the above-described methods which may be full-length cDNA molecules, to vectors (particularly expression vectors) comprising these nucleic acid molecules and to host cells comprising these vectors and nucleic acid molecules.

Other preferred embodiments of the present invention will be apparent to one of ordinary skill in light of the following drawings and description of the invention, and of the claims.

BRIEF DESCRIPTION OF THE DRAWINGS

FIG. 1: pJD100, pAMP18, pAMP18N, pAMP 1, pAM1C, pAMP1 8NM and pAMP18B.
FIG. 2: M13, M13RT, pAMP18BH- and M13RTH-.
FIG. 3: pAMP1A.
FIG. 4: pDBH-Kpn, pDABH-, pDBH-KpnHis.
FIG. 5: pFastBac DUAL, pFastBac DUAL Nde, pDBH- and pDA.
FIG. 6: pDABH-His.

FIG. 7: pJD100.
FIG. 8: pAMP18N.
FIG. 9: pAMP1C.
FIG. 10: pAMP18NM.
FIG. 11: PAMP18B.
FIG. 12: M13RT.
FIG. 13: M13RTH-.
FIG. 14: pAMP18BH-.
FIG. 15: pDBH-.
FIG. 16: pAMP1A.
FIG. 17: pDBH-Kpn.
FIG. 18: pDBH-KpnHis.
FIG. 19: pDA.
FIG. 20: pDABH-.
FIG. 21: pDABH-His.

FIGS. 22–25 describe, in schematic form (with details omitted for clarity), the construction of the expression vector (pDAMVAH-BH-)which places the AMV RT α and β genes under control of insect viral promoters:

FIG. 22: Cloning of AMV RT gene from RNA; pSPORT8.
FIG. 24: Construction of clones for the AMV RT α subunit by PCR; pAMVA and pAMVAH-.

FIG. 26: pAMVN.
FIG. 27: pAMVC.
FIG. 28: pAMVNM.
FIG. 29: pAMVNMH-.
FIG. 30: pAMVBH-.
FIG. 31: pAMVA.
FIG. 32: pAMVAH-.
FIG. 33: pFastBacDual (pD).
FIG. 34: pDAMVA.
FIG. 35: pDAMVAH-.
FIG. 36: pDAMVABH-.
FIG. 37: pJAMVBH-.
FIG. 38: pDAMVAH-BH-.

DETAILED DESCRIPTION OF THE INVENTION

Overview

Figure 1:
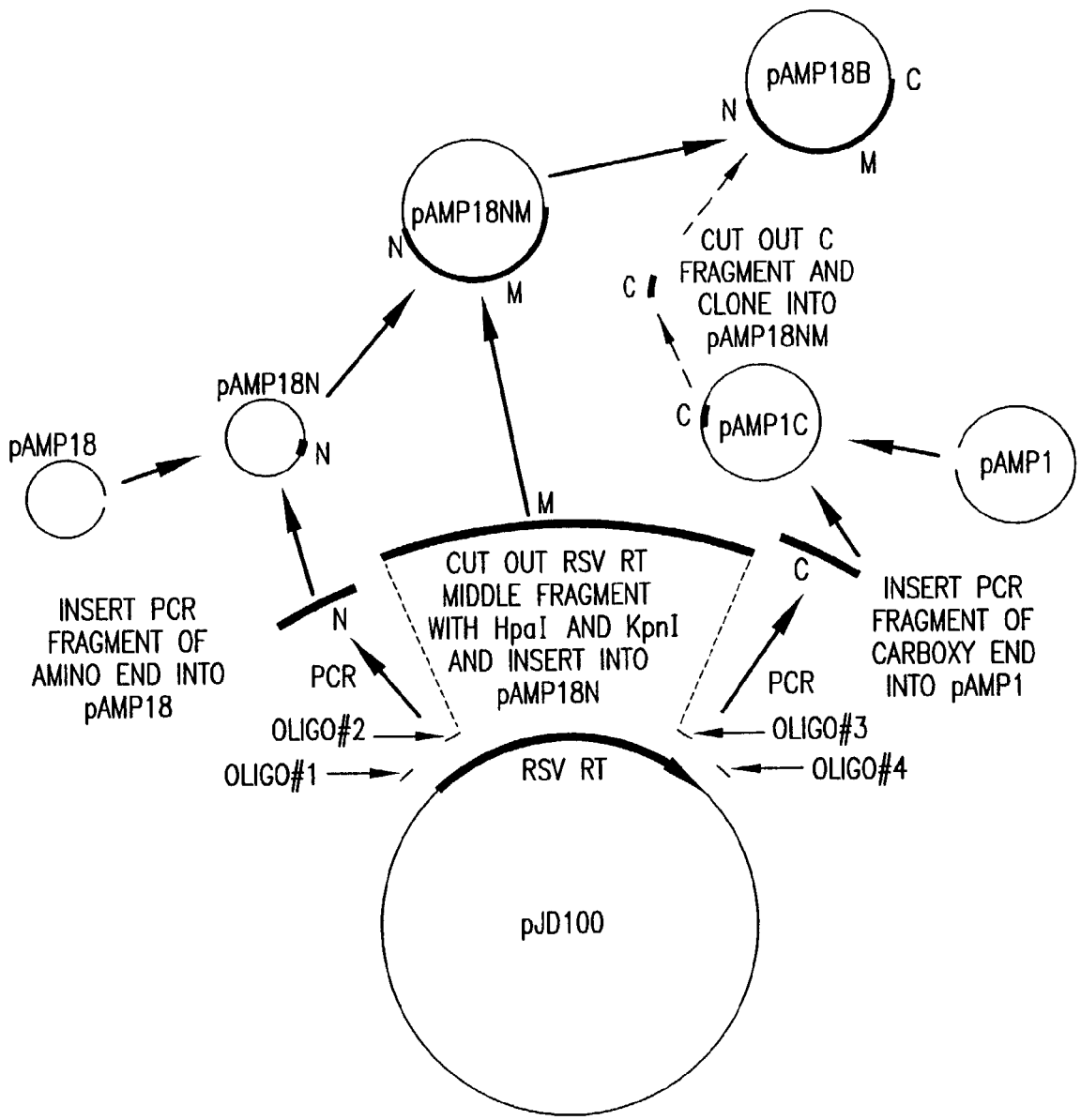
FIGS. 1–6 describe, in schematic form (with details omitted for clarity), the construction of the expression vector (pDABH⁻His) which places the RSV RT α and β genes under control of insect viral promoters.

The present invention provides compositions and methods useful in overcoming the length limitations often observed during reverse transcription of nucleic acid molecules. Thus, the invention facilitates the production of full-length cDNA molecules not heretofore possible.

In general, the invention provides compositions for use in reverse transcription of a nucleic acid molecule comprising two or more, three or more, four or more, five or more, six or more, and the like, different polypeptides having reverse transcriptase activity. The compositions of the invention preferably comprise two to six, two to five, two to four, two to three, and more preferably comprise two, polypeptides having reverse transcriptase activity. The enzymes in these compositions are preferably present in working concentrations and are reduced or substantially reduced in RNase H activity, although mixtures of enzymes, some having RNase H activity and some reduced or substantially reduced in RNase H activity, may be used in the compositions of the invention. Alternatively, the reverse transcriptases used in the compositions of the invention may have RNase H activity. Preferred reverse transcriptases include M-MLV H⁻ reverse transcriptase, RSV H⁻ reverse transcriptase, AMV H⁻ reverse transcriptase, RAV H⁻ reverse transcriptase, MAV H⁻ reverse transcriptase and HIV H⁻ reverse transcriptase or other ASLV H⁻ reverse transcriptases.

The invention is also directed to methods for reverse transcription of one or more nucleic acid molecules comprising mixing one or more nucleic acid templates, which is preferably RNA or messenger RNA (mRNA) and more preferably a population of mRNA molecules, with two or more polypeptides having reverse transcriptase activity (or with the compositions of the invention) and incubating the mixture under conditions sufficient to make a nucleic acid molecule or molecules complementary to all or a portion of the one or more templates. Such nucleic acid synthesis may be accomplished by sequential or simultaneous or separate addition of multiple reverse transcriptases. Preferably, two or more, three or more, four or more, five or more, six or more, and the like, reverse transcriptases are used, or a range of two to six, two to five, two to four, two to three and more preferably two, reverse transcriptases are used. To make the nucleic acid molecule or molecules complementary to the one or more templates, a primer (e.g., an oligo(dT) primer) and one or more nucleotides are used for nucleic acid synthesis in the 3' to 5' direction. Nucleic acid molecules suitable for reverse transcription according to this aspect of the invention include any nucleic acid molecule, particularly those derived from a prokaryotic or eukaryotic cell. Such cells may include normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant or an animal (e.g., human, cow, pig, mouse, sheep, horse, monkey, canine, feline, rat, rabbit, bird, fish, insect, etc.). Such nucleic acid molecules may also be isolated from viruses.

The invention further provides methods for amplifying or sequencing a nucleic acid molecule comprising contacting the nucleic acid molecule with two or more polypeptides having reverse transcriptase activity (or with the compositions of the invention). Such reactions may be accomplished by sequential or simultaneous or separate addition of the two or more polypeptides having reverse transcriptase activity to the reaction mixtures. Preferred such methods comprise one or more polymerase chain reactions (PCRs).

The invention also provides cDNA molecules or amplified nucleic acid molecules produced according to the above-described methods, vectors (particularly expression vectors) comprising these cDNA molecules or amplified nucleic acid molecules, and recombinant host cells comprising such cDNA molecules, amplified nucleic acid molecules or vectors. The invention also provides methods of producing a polypeptide comprising culturing these recombinant host cells and isolating the polypeptide, and provides a polypeptide produced by such methods.

The invention also provides kits for use in accordance with the invention. Such kits comprise a carrier means, such as a box or carton, having in close confinement therein one or more container means, such as vials, tubes, bottles and the like, wherein the kit comprises, in the same or different containers, two or more polypeptides having reverse transcriptase activity. The kits of the invention may also comprise, in the same or different containers, one or more DNA polymerases, a suitable buffer and/or one or more nucleotides (such as deoxynucleoside triphosphates (dNTPs)).

The invention also concerns a substantially pure RSV reverse transcriptase (RSV RT), which may or may not be reduced or substantially reduced in RNase H activity. Such RSV RTs may comprise one or more subunits (or derivatives, variants, fragments or mutants thereof) selected from one or more α subunits, one or more β subunits, and one or more βp4 subunits, any or all of which may or may not be reduced or substantially reduced in RNase H activity. In one preferred aspect of the invention, the RSV RT may comprise an α subunit reduced or substantially reduced in RNase H activity and a β subunit having RNase H activity (i.e., RSV αH⁻ βH⁺ RT). In a preferred aspect of this embodiment, the gene encoding the α subunit has been modified or mutated to reduce RNase H activity while the gene encoding the β subunit has not been mutated or modified in this manner. Such mutations or modifications are preferably made within the RNase H domain of the α subunit. Unexpectedly, the phenotype of this construct showed substantially reduced (i.e., approximately 5% of wildtype) RNase H activity. In another preferred aspect, the RSV RT may comprise an α subunit reduced or substantially reduced in RNase H activity and a β subunit also reduced or substantially reduced in RNase H activity (i.e., RSV αH⁻/βH⁻ RT). In another preferred aspect, the RSV RT may comprise two β subunits, either or both of which may or may not be reduced or substantially reduced in RNAse H activity (i.e., RSV βH⁻/βH⁻ RT; RSV βH⁻/βH⁺ RT; or RSV βH⁺/βH⁺ RT). In another preferred aspect, the RSV RT may comprise a single α subunit, which may or may not be reduced or substantially reduced in RNAse H activity (i.e., RSV αH⁻ RT or RSV αH⁺RT). In another preferred aspect, the RSV RT may comprise one or more βp4 subunits, any or all of which may or may not be reduced or substantially reduced in RNAse H activity (e.g., RSV βp4H⁻/βp4H⁻ RT; RSV βp4H⁻/βp4H⁺ RT; RSV βp4H⁺/βp4H⁺RT; RSV αH⁻/βp4H⁺ RT; RSV αH⁺/βp4H⁺ RT; RSV αH⁻/βp4H⁻ RT; RSV αH⁺/βp4H⁻ RT; RSV βH⁻/βp4H⁺ RT; RSV βH⁻/βp4H⁻ RT; RSV βPH⁺/βp4H⁻ RT; RSV βH⁺/βp4H⁺RT; etc.). As will be recognized, derivatives, variants, fragments or mutants of any or all of the above subunits may also be used in accordance with the invention.

In a related aspect of the invention, where the RSV RTs comprise two or more subunits (or derivatives, variants, fragments or mutants thereof) and preferably comprise two subunits (e.g., a dimer), at least one but preferably not all of these subunits may be modified or mutated to reduce, substantially reduce or eliminate the polymerase activity of at least one subunit (e.g., pol–). In a preferred aspect, for an RSV RT which comprises an α and β subunit, the β subunit has been modified or mutated (preferably by recombinant techniques) to reduce, substantially reduce or eliminate the polymerase activity while the polymerase activity of the α subunit has not been mutated or modified in this manner. Preferably, the α subunit of such RSV RT has also been modified or mutated to reduce or substantially reduce RNase H activity while the β subunit has not been mutated or modified in this manner. Such a construct may be designated αH–/βH+pol–. Any number of combinations of subunits can be prepared in which mutations or modifications are made in one subunit of a two subunit enzyme, and these constructs may be combined with other modifications or mutations, such as those which reduce or substantially reduce RNase H activity. Illustrated examples include but are not limited to RSV αH–/βH+pol–; RSV αH+/βH+pol–; RSV αH–pol–/βH+; RSV αH–pol–/βH–; RSV αH+pol–/βH+; RSV βH–/βH–pol–; RSV βH–/βH+pol–; RSV βH+/βH+pol–; RSV βp4H–/βp4H–pol–; RSV βp4H–/βp4H+pol–; RSV βp4H+/βp4H+pol–; RSV αH–/βp4H–pol–; RSV αH+/βp4H+pol–; RSV αH+/βp4H–pol–; RSV βH–/βp4H+pol–; RSV βH–/βp4H+pol–; RSV βH+/βp4H–pol–; etc. In a preferred aspect, the polymerase domain of the subunit is modified or mutated (one or more point mutations, deletion mutations and/or insertion mutations) by recombinant techniques. In another aspect, the nucleotide binding site of the polymerase domain is modified or mutated. In a preferred aspect, one or more acidic amino acids within the nucleotide binding site are substituted with different amino acids. Particularly preferred amino acids within the nucleotide binding site for mutation or modification include, but are not limited to, Asp$^{107}$, Leu$^{108}$, Lys$^{109}$, and Asp$^{110}$, or the corresponding amino acid sequence.

The invention also relates to methods of producing the RSV RTs of the invention, which methods comprise obtaining a host cell comprising a nucleic acid sequence encoding one or more α subunits (or derivatives, variants, fragments or mutants thereof) and/or a nucleic acid sequence encoding one or more β subunits (or derivatives, variants, fragments or mutants thereof) and/or a nucleic acid sequence encoding one or more βp4 subunits (or derivatives, variants, fragments or mutants thereof), and culturing the host cell under conditions sufficient to produce the RSV RTs of the invention. The nucleic acid sequences encoding such α subunit(s) and/or such β subunit(s) and/or such βp4 subunit(s) may be contained in the same vector or in different vectors. In accordance with the invention, such α subunit(s) and/or β subunit(s) and/or βp4 subunit(s) may be produced separately and mixed before or after isolation of each subunit to form the RSV RTs of the invention. Alternatively, such α and/or β subunits and/or βp4 subunits may be expressed simultaneously (i.e., co-expressed) in the same host cell, thereby producing an RSV RT comprising an α and a β subunit, an α subunit alone, β subunit alone, a βp4 subunit alone, a β subunit and a βp4 subunit, two β subunits, or two βp4 subunits, or derivatives, variants, fragments or mutants thereof. In a preferred aspect, the α subunit (or derivatives, variants, fragments or mutants thereof) is simultaneously expressed in a host cell with the β subunit (or derivatives, variants, fragments or mutants thereof). In a related aspect of the invention, the β or βp4 subunits (or derivatives, fragments or mutants thereof) may be expressed in a host or host cell which accomplishes in vivo processing of some or all of such β or βp4 subunits to form the corresponding α subunit. The presence of both the β and the α subunits allows in vivo formation of an RSV RT which comprises an α and β subunit. Such in vivo processing is preferably accomplished by expressing the β and/or βp4 subunits (or derivatives, variants, fragments or mutants thereof) in a host cell, which may be prokaryotic or eukaryotic, having appropriate processing enzymes or proteins which cleave such β or βp4 subunits to form a corresponding α subunit. Such processing enzymes or proteins may be introduced and expressed in the host system by recombinant means or may exist naturally in the host system. Preferred hosts for in vivo processing include eukaryotic cells or organelles such as yeast, fungi, plants, animals, insects, fish, and the like. Recombinant systems (vectors, expression vectors, promoters, etc.) which allow cloning of the β or βp4 subunits (or derivatives, fragments or mutants thereof) for in vivo processing are well known to one of ordinary skill in the art. As noted above, any or all of the α and/or β and/or βp4 subunits of the RSV RT (or derivatives, variants, fragments or mutants thereof) produced by these recombinant techniques may be reduced or substantially reduced in RNase H activity.

These RSV RTs or subunits thereof may then be isolated from the host cell, and may be substantially purified by any method of protein purification that will be familiar to those of ordinary skill in the art (e.g., chromatography, electrophoresis, dialysis, high-salt precipitation, or combinations thereof). The invention also relates to kits comprising one or more of the RSV RTs of the invention.

The invention also concerns a substantially pure Avian Myeloblastosis Virus reverse transcriptase (AMV RT), which may or may not be reduced or substantially reduced in RNase H activity. Such AMV RTs may comprise one or more subunits selected from one or more α subunits, one or more β subunits, and one or more βp4 subunits (or derivatives, variants, fragments or mutants thereof), any or all of which may or may not be reduced or substantially reduced in RNase H activity. In one preferred aspect of the invention, the AMV RT may comprise an α subunit reduced or substantially reduced in RNase H activity and a β subunit having RNase H activity (i.e., AMV αH$^-$ βH$^+$ RT). In a particularly preferred aspect of this embodiment, the gene encoding the α subunit has been modified or mutated to reduce RNase activity (preferably within the RNase H domain) while the gene encoding the β subunit has not been modified or mutated to affect RNase H activity. Unexpectedly, this construct demonstrates a phenotype in which the RNase H activity of the AMV RT comprising the α subunit and the β subunit is substantially reduced in RNase H activity (i.e., approximately 5% of wildtype). In another preferred aspect, the AMV RT may comprise an α subunit reduced or substantially reduced in RNase H activity and a β subunit also reduced or substantially reduced in RNase H activity (i.e., AMV αH$^-$/H$^-$ RT). In another preferred aspect, the AMV RT may comprise two β subunits, either or both of which may or may not be reduced or substantially reduced in RNAse H activity (i.e., AMV βH$^-$/βH$^-$ RT; AMV βH$^-$/βH$^+$RT; or AMV βH$^+$/βH$^+$ RT). In another preferred aspect, the AMV RT may comprise a single α subunit, which may or may not be reduced or substantially reduced in RNAse H activity (i.e., AMV αH$^-$ RT or AMV αH$^+$RT). In another preferred aspect, the AMV RT may comprise one or more βp4 subunits, any or all of which may or may not be reduced or substantially reduced in RNAse H activity (e.g., AMV βp4H$^-$/βp4H$^-$ RT; AMV βp4H$^-$/βp4H$^+$ RT; AMV βp4H$^+$/βp4H$^+$ RT; AMV αH$^-$/βp4H$^+$ RT; AMV αH$^+$/βp4H$^+$ RT; AMV αH$^-$/βp4H$^-$ RT; AMV αH$^+$/βp4H$^-$ RT; AMV βH$^-$/βp4H$^-$ RT; AMV βH$^+$/βp4H$^-$ RT; etc.).

In a related aspect of the invention, where the AMV RTs comprise two or more subunits (or derivatives, variants, fragments or mutants thereof) and preferably comprise two subunits (e.g., a dimer), at least one but preferably not all of these subunits may be modified or mutated to reduce, substantially reduce or eliminate the polymerase activity of at least one subunit (e.g., pol−). In a preferred aspect, for an AMV RT which comprises an α and β subunit, the β subunit has been modified or mutated (preferably by recombinant techniques) to reduce, substantially reduce or eliminate the polymerase activity while the polymerase activity of the α subunit has not been mutated or modified in this manner. Preferably, the α subunit of such AMV RT has also been modified or mutated to reduce or substantially reduce RNase H activity while the β subunit has not been mutated or modified in this manner. Such a construct may be designated αH−/βH+pol−. Any number of combinations of subunits can be prepared in which mutations or modifications are made in one subunit of a two subunit enzyme, and these constructs may be combined with other modifications or mutations, such as those which reduce or substantially reduce RNase H activity. Illustrated examples include but are not limited to AMV αH−/βH−pol−; AMV αH+/βH+pol−; AMV αH−pol−/βH+; AMV αH−pol−/βH−; AMV αH+pol−/βH+; AMV βH−/βH−pol−; AMV βH−/βH+pol−; AMV βH+/βH+pol−; AMV βp4H−/βp4H−pol−; AMV βp4H−/βp4H+pol−;

AMV βp4H+/βp4H+pol−; AMV αH−/βp4H−pol−; AMV αH+/βp4H+pol−; AMV αH+/βp4H−pol−; AMV βH−/βp4H+pol−; AMV βH−/βp4H+pol−; AMV βH+/βp4H−pol−; etc. In a preferred aspect, the polymerase domain of the subunit is modified or mutated (one or more point mutations, deletion mutations and/or insertion mutations) by recombinant techniques. In another aspect, the nucleotide binding site of the polymerase domain is modified or mutated. In a preferred aspect, one or more acidic amino acids within the nucleotide binding site are substituted with different amino acids. Particularly preferred amino acids within the nucleotide binding site for mutation or modification include, but are not limited to, $Asp^{107}$, $Leu^{108}$, $Lys^{109}$, and $Asp^{110}$, or the corresponding amino acid sequence.

The invention also relates to methods of producing the AMV RTs of the invention, which methods comprise obtaining a host cell comprising a nucleic acid sequence encoding one or more α subunits (or derivatives, variants, fragments or mutants thereof) and/or a nucleic acid sequence encoding one or more β subunits (or derivatives, variants, fragments or mutants thereof) and/or a nucleic acid sequence encoding one or more βp4 subunits (or derivatives, variants, fragments or mutants thereof), and culturing the host cell under conditions sufficient to produce the AMV RTs. The nucleic acid sequences encoding such α subunit(s) and/or such β subunit(s) and/or such βp4 subunit(s) may be contained in the same vector or in different vectors. In accordance with the invention, such α subunit(s) and/or β subunit(s) and/or βp4 subunit(s) may be produced separately and mixed before or after isolation of each subunit to form the AMV RTs of the invention. Alternatively, such α and/or β and/or βp4 subunits may be expressed simultaneously (i.e., co-expressed) in the same host cell, thereby producing an AMV RT comprising an α and a β subunit, an α subunit alone, a β subunit alone, a βp4 subunit alone, a β subunit and a βp4 subunit, two β subunits, or two βp4 subunits, or derivatives, variants, fragments or mutants thereof In a preferred aspect, the α subunit is simultaneously expressed in a host cell with the β subunit. In a related aspect of the invention, the β or βp4 subunits (or derivatives, variants, fragments or mutants thereof) may be expressed in a host or host cell which accomplishes in vivo processing as described above for production of RSV RTs. Thus, by expressing a β subunit and/or a βp4 subunit (or derivatives, fragments or mutants thereof) in a host system which has appropriate processing enzymes or proteins, the corresponding α subunit may be produced allowing formation of an AMV RT which comprises an α and a β subunit, an α and a βp4 subunit, etc. As noted above, any or all of the α and/or β and/or βp4 subunits (or derivatives, variants, fragments or mutants thereof) of the AMV RT may be reduced or substantially reduced in RNase H activity. These AMV RTs or subunits thereof may then be isolated from the host cell and may be substantially purified by those methods described above for purification of RSV RTs. The invention also relates to kits comprising one or more of the AMV RTs of the invention.

The invention also relates to other substantially pure ASLV reverse transcriptases, which may or may not be reduced or substantially reduced in RNase H activity. Such ASLV RTs may comprise one or more subunits (or derivatives, variants, fragments or mutants thereof) selected from one or more a subunits, one or more β subunits, and one or more βp4 subunits, as described for RSV RT and AMV RT above. The invention also relates to methods of producing such ASLV RTs of the invention as described above for RSV RT and AMV RT.

The invention also concerns the RSV reverse transcriptases and AMV reverse transcriptases or other ASLY reverse transoriptases and subunits thereof (and derivatives, variants, fragments and mutants thereof) of the Invention which have functionaL activity, as measured by the ability of the proteins to produce first strand cDNA from a mRNA template. Such functional activity may be measured in accordance with the invention based on the total fall-length reverse transcribed product made during the synthesis reaction. The amount of product is preferably measured based on the mass (e.g., nano grains) of products produced, although other means of measuring the amount of product will be recognized by one of ordinary skill in the art. Additionally, functional activity may be measured in terms of the percentage of frill-length products produced during a cDNA synthesis reaction. For example, the percent frill-length functional activity may be determined by dividing the amount of full-length product by the amount of total product produced during a cDNA synthesis reaction and multiplying the result by 100 to obtain the percentage. The RSV and AMV reverse transcriptases and their subunits (and derivatives, variants, fragments and mutants thereof) of the invention produce greater than about 4%, preferably greater than about 5%, more preferably greater than about 7.5%, still more preferably greater than about 10%, still more preferably greater than about 20%, and most preferably greater than about 25%, full-length cDNA in a nucleic acid synthesis reaction. Preferred ranges of such percentages include about 5% to about 100%, about 7.5% to about 75%, about 7.5% to about 50%, about 10% to about 50%, about 15% to about 40%, about 20% to about 40%, and about 20% to about 50%. Functional activity may also be measured in accordance with the invention by determining the percentage of total cDNA product compared to the amount of input mRNA in the synthesis reaction. Thus, the total amount of cDNA product is divided by the amount of input mRNA, the result of which is multiplied by 100 to determine the percentage functional activity associated with amount of product produced compared to amount of the template used, Preferably, the reverse transcriptases of the invention produce, greater than about 15%, more preferably greater than about 20%, still more preferably greater than about 25%, still more preferably greater than about 30%, and most preferably greater than about 40%, of cDNA compared to input mRNA in the cDNA synthesis reaction. Preferred ranges of such percentages include about 5% to about 100%, about 10% to about 80%, about 15% to about 80%, about 15% to about 75%, about 20% to about 75%, about 20% to about 70%, about 25% to about 75%, about 25% to about 70%, about 25% to about 60%, and about 25% to about 50%. The AMV and RSV reverse transcriptases and their subunits (and derivatives, variants, fragments and mutants thereof) of the invention preferably have specific activities greater than about 5 units/mg, more preferably greater than about 50 units/mg, still more preferably greater than about 100 units/mg, 250 units/mg, 500 units/mg, 1000 units/mg, 5000 units/mg or 10,000 units/mg, and most preferably greater than about 15,000 units/mg, greater than about 16,000 units/mg, greater than about 17,000 units/mg, greater than about 18,000 units/mg, greater than about 19,000 units/mg and greater than about 20,000 units/mg. Preferred ranges of specific activities for the AMV and RSV RTs and their subunits (or derivatives, variants, fragments or mutants thereof) of the invention include a specific activity from about 5 units/mg to about 140,000 units/mg, a specific activity from about 5 units/mg to about 125,000 units/mg, a specific activity of from about 50 units/mg to about 100,000 units/mg, a specific activity from about 100 units/mg to about 100,000 units/mg, a specific activity from about 250 units/mg to about 100,000 units/mg, a specific activity from about 500 units/mg to about 100,000 units/mg, a specific activity from about 1000 units/mg to about 100,000 units/mg, a specific activity from about 5000 units/mg to about 100,000 units/mg, a specific activity from about 10,000 units/mg to about 100,000 units/mg, a specific activity from about 25,000 units/mg to about 75,000 units/mg. Other preferred ranges of specific activities include a specific activity of from about 20,000 units/mg to about 140,000 units/mg, a specific activity from about 20,000 units/mg to about 130,000 units/mg, a specific activity from about 20,000 units/mg to about 120,000 units/mg, a specific activity from about 20,000 units/mg to about 110,000 units/mg, a specific activity from about 20,000 units/mg to about 100,000 units/mg, a specific activity from about 20,000 units/mg to about 90,000 units/mg, a specific activity from about 25,000 units/mg to about 140,000 units/mg, a specific activity from about 25,000 units/mg to about 130,000 units/mg, a specific activity from about 25,000 units/mg to about 120,000 units/mg, a specific activity from about 25,000 units/mg to about 110,000 units/mg, a specific activity from about 25,000 units/mg to about 100,000 units/mg, and a specific activity from about 25,000 units/mg to about 90,000 units/mg. Preferably, the lower end of the specific activity range may vary from 30,000, 35,000, 40,000, 45,000, 50,000, 55,000, 60,000, 65,000, 70,000, 75,000, and 80,000 units/mg, while the upper end of the range may vary from 150,000, 140,000, 130,000, 120,000, 110,000, 100,000, and 90,000 units/mg. In accordance with the invention, specific activity is a measurement of the enzymatic activity (in units) of the protein or enzyme relative to the total amount of protein or enzyme used in a reaction. The measurement of a specific activity may be determined by standard techniques well-known to one of ordinary skill in the art. Preferred assays for determining the specific activity of an enzyme or protein are described in detail in the Examples below.

The RSV RTs and AMV RTs or other ASLV RTs and their subunits (or derivatives, variants, fragments or mutants thereof) of the invention may be used to make nucleic acid molecules from one or more templates. Such methods comprise mixing one or more nucleic acid templates (e.g., mRNA, and more preferably a population of mRNA molecules) with one or more of the RSV RTs and/or one or more AMV RTs and/or other ASLV RTs of the invention and incubating the mixture under conditions sufficient to make one or more nucleic acid molecules complementary to all or a portion of the one or more nucleic acid templates.

The invention also relates to methods for the amplification of one or more nucleic acid molecules comprising mixing one or more nucleic acid templates with one or more of the RSV RTs and/or one or more of the AMV RTs and/or other ASLV RTs of the invention and optionally with one or more DNA polymerases, and incubating the mixture under conditions sufficient to amplify one or more nucleic acid molecules complementary to all or a portion of the one or more nucleic acid templates.

The invention also concerns methods for the sequencing of one or more nucleic acid molecules comprising (a) mixing one or more nucleic acid molecules to be sequenced with one or more primer nucleic acid molecules, one or more RSV RTs and/or one or more AMV RTs and/or other ASLV RTs of the invention, one or more nucleotides and one or more terminating agents; (b) incubating the mixture under conditions sufficient to synthesize a population of nucleic acid molecules complementary to all or a portion of the one or more nucleic acid molecules to be sequenced; and (c) separating the population of nucleic acid molecules to determine the nucleotide sequence of all or a portion of the one or more nucleic acid molecules to be sequenced.

The invention also concerns methods for elevated- or high-temperature reverse transcription of a nucleic acid molecule comprising (a) mixing a nucleic acid template (preferably an RNA (e.g., a mRNA molecule or a polyA+ RNA molecule) or a DNA molecule) with one or more polypeptides having reverse transcriptase activity; and (b) incubating the mixture at a temperature of 50° C. or greater and under conditions sufficient to make a first nucleic acid molecule (such as a full length cDNA molecule) complementary to all or a portion of the nucleic acid template. In preferred such methods, the mixture is incubated at a temperature of about 51° C. or greater, about 52° C. or greater, about 53° C. or greater, about 54° C. or greater, about 55° C. or greater, about 56° C. or greater, about 57° C. or greater, about 58° C. or greater, about 59° C. or greater, about 60° C. or greater, about 61° C. or greater, about 62° C. or greater; or at a temperature range of from about 50° C. to about 70° C., about 51° C. to about 70° C., about 52° C. to about 70° C., about 53° C. to about 70° C., about 54° C. to about 70° C., about 55° C. to about 70° C., about 55° C. to about 65° C., about 56° C. to about 65° C., about 56° C. to about 64° C., or about 56° C. to about 62° C. The invention is also directed to such methods which further comprise incubating the first nucleic acid molecule under conditions sufficient to make a second nucleic acid molecule complementary to all or portion of the first nucleic acid molecule. According to the invention, the first and second nucleic acid molecules produced by these methods may be DNA molecules, and may form a double stranded DNA molecule which may be a full length cDNA molecule. The one or more polypeptides having reverse transcriptase activity that are used in these methods preferably are reduced or substantially reduced in RNase H activity, and may be selected from the group consisting of one or more subunits of AMV reverse transcriptase and one or more subunits of RSV reverse transcriptase and one or more subunits of other ASLV reverse transcriptases (or derivatives, variants, fragments or mutants thereof). As noted above, such AMV RTs or RSV RTs or other ASLV RTs may comprise one or more α subunits, one or more β subunits, and/or one or more βp4 subunits, any or all of which subunits may be reduced or substantially reduced in RNase H activity. Particularly preferred polymerases having RT activity for use in these methods are those RSV RTs and AMV RTs or other ASLV RTs and their subunits (or derivatives, variants, fragments or mutants thereof) described above.

The invention also concerns nucleic acid molecules produced by such methods (which may be full-length cDNA molecules), vectors (particularly expression vectors) comprising these nucleic acid molecules and host cells comprising these vectors and nucleic acid molecules.

Sources of Enzymes

Enzymes for use in the compositions, methods and kits of the invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., *Science* 239:487–491 (1988); U.S. Pat. Nos. 4,889,818 and 4,965,188), Tne DNA polymerase (WO 96/10640), Tma DNA polymerase (U.S. Pat. No. 5,374,553)

and mutants, fragments, variants or derivatives thereof (see, e.g., commonly owned, co-pending U.S. patent application Ser. Nos. 08/706,702 and 08/706,706, both filed Sep. 9, 1996, which are incorporated by reference herein in their entireties). As will be understood by one of ordinary skill in the art, modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases of the invention. Fragments of reverse transcriptases may be obtained by deletion mutation by recombinant techniques that are routine and well-known in the art, or by enzymatic digestion of the reverse transcriptase(s) of interest using any of a number of well-known proteolytic enzymes.

Preferred enzymes for use in the invention include those that are reduced or substantially reduced in RNase H activity. Such enzymes that are reduced or substantially reduced in RNase H activity may be obtained by mutating the RNase H domain within the reverse transcriptase of interest, preferably by one or more point mutations, one or more deletion mutations, and/or one or more insertion mutations as described above. By an enzyme "substantially reduced in RNase H activity" is meant that the enzyme has less than about 30%, less than about 25%, 20%, more preferably less than about 15%, less than about 10%, less than about 7.5%, or less than about 5%, and most preferably less than about 5% or less than about 2%, of the RNase H activity of the corresponding wildtype or RNase H$^+$ enzyme such as wild-type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al., *Nucl. Acids Res.* 16:265 (1988), in Gerard, G. F., et al., *FOCUS* 14(5):91 (1992), and in U.S. Pat. No. 5,668,005, the disclosures of all of which are fully incorporated herein by reference.

Particularly preferred enzymes for use in the invention include, but are not limited to, M-MLV H$^-$ reverse transcriptase, RSV H$^-$ reverse transcriptase, AMV H$^-$ reverse transcriptase, RAV H$^-$ reverse transcriptase, MAV H$^-$ reverse transcriptase and HIV H$^-$ reverse transcriptase. It will be understood by one of ordinary skill, however, that any enzyme capable of producing a DNA molecule from a ribonucleic acid molecule (i.e., having reverse transcriptase activity) that is substantially reduced in RNase H activity may be equivalently used in the compositions, methods and kits of the invention.

Enzymes used in the invention may have distinct reverse transcription pause sites with respect to the template nucleic acid. Whether or not two enzymes have distinct reverse transcription pause sites may be determined by a variety of assays, including, for example, electrophoretic analysis of the chain lengths of DNA molecules produced by the two enzymes (Weaver, D. T., and DePamphilis, M. L., *J. Biol. Chem.* 257(4):2075–2086 (1982); Abbots, J., et al., *J. Biol. Chem.* 268(14): 10312–10323 (1993)), or by other assays that will be familiar to one of ordinary skill in the art. As described above, these distinct transcription pause sites may represent secondary structural and sequence barriers in the nucleic acid template which occur frequently at homopolymer stretches. Thus, for example, the second enzyme may reverse transcribe to a point (e.g., a hairpin) on the template nucleic acid that is proximal or distal (i.e., 3' or 5') to the point to which the first enzyme reverse transcribes the template nucleic acid. This combination of two or more enzymes having distinct reverse transcription pause sites facilitates production of full-length cDNA molecules since the secondary structural and sequence barriers may be overcome. Moreover, the elevated- or high-temperature reverse transcription of the invention may also assist in overcoming secondary structural and sequence barriers during nucleic acid synthesis. Thus, the elevated- or high-temperature synthesis may be used in combination with the two or more reverse transcriptases (preferably using an AMV RT, an RSV RT or other ASLV RT) to facilitate full-length cDNA synthesis.

A variety of DNA polymerases are useful in accordance with the present invention. Such polymerases include, but are not limited to, *Thermus thermophilus* (Tth) DNA polymerase, *Thermus aquaticus* (Taq) DNA polymerase, *Thermotoga neapolitana* (Tne) DNA polymerase, *Thermotoga maritima* (Tma) DNA polymerase, *Thermococcus litoralis* (Tli or VENT™) DNA polymerase, *Pyrococcus furiosis* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, *Mycobacterium* spp. DNA polymerase (Mtb, Mlep), and mutants, variants and derivatives thereof DNA polymerases used in accordance with the invention may be any enzyme that can synthesize a DNA molecule from a nucleic acid template, typically in the 5' to 3' direction. Such polymerases may be mesophilic or thermophilic, but are preferably thermophilic. Mesophilic polymerases include T5 DNA polymerase, T7 DNA polymerase, Klenow fragment DNA polymerase, DNA polymerase III, and the like. Preferred DNA polymerases are thermostable DNA polymerases such as Taq, Tne, Tma, Pfu, VEN™, DEEPVENT™, Tth and mutants, variants and derivatives thereof (U.S. Pat. No. 5,436,149; U.S. Pat. No. 5,512,462; WO 92/06188; WO 92/06200; WO 96/10640; Barnes, W. M., *Gene* 112:29–35 (1992); Lawyer, F. C., et al., *PCR Meth. Appl.* 2:275–287 (1993); Flaman, J.-M., et al., *Nucl. Acids Res.* 22(15):3259–3260 (1994)). For amplification of long nucleic acid molecules (e.g., nucleic acid molecules longer than about 3–5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Barnes, W. M., *Gene* 112:29–35 (1992); and commonly owned, co-pending U.S. patent application Ser. No. 08/801,720, filed Feb. 14, 1997, the disclosures of all of which are incorporated herein in their entireties. Examples of DNA polymerases substantially lacking in 3' exonuclease activity include, but are not limited to, Taq, Tne(exo$^-$), Tma, Pfu (exo$^-$), Pwo and Tth DNA polymerases, and mutants, variants and derivatives thereof Nonlimiting examples of DNA polymerases having 3' exonuclease activity include Pfu/DEEPVENT™ and Tli/VENT™ and mutants, variants and derivatives thereof Polypeptides having reverse transcriptase activity for use in the invention may be obtained commercially, for example from Life Technologies, Inc. (Rockville, Md.), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, the polypeptides having reverse transcriptase activity may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372–3376 (1988)).

DNA polymerases for use in the invention may be obtained commercially, for example from Life Technologies, Inc. (Rockville, Md.), Perkin-Elmer (Branchburg, N.J.), New England BioLabs (Beverly, Mass.) or Boehringer Mannheim Biochemicals (Indianapolis, Ind.).

Formulation of Enzyme Compositions

To form the compositions of the present invention, two or more reverse transcriptases are preferably admixed in a buffered salt solution. One or more DNA polymerases and/or one or more nucleotides may optionally be added to make the compositions of the invention. More preferably, the enzymes are provided at working concentrations in stable buffered salt solutions. The terms "stable" and "stability" as used herein generally mean the retention by a composition, such as an enzyme composition, of at least 70%, preferably at least 80%, and most preferably at least 90%, of the original enzymatic activity (in units) after the enzyme or composition containing the enzyme has been stored for about one week at a temperature of about 4° C., about two to six months at a temperature of about −20° C., and about six months or longer at a temperature of about −80° C. As used herein, the term "working concentration" means the concentration of an enzyme that is at or near the optimal concentration used in a solution to perform a particular function (such as reverse transcription of nucleic acids).

The water used in forming the compositions of the present invention is preferably distilled, deionized and sterile filtered (through a 0.1–0.2 micrometer filter), and is free of contamination by DNase and RNase enzymes. Such water is available commercially, for example from Sigma Chemical Company (Saint Louis, Mo.), or may be made as needed according to methods well known to those skilled in the art.

In addition to the enzyme components, the present compositions preferably comprise one or more buffers and cofactors necessary for synthesis of a nucleic acid molecule such as a cDNA molecule. Particularly preferred buffers for use in forming the present compositions are the acetate, sulfate, hydrochloride, phosphate or free acid forms of Tris-(hydroxymethyl)aminomethane (TRIS®), although alternative buffers of the same approximate ionic strength and pKa as TRIS® may be used with equivalent results. In addition to the buffer salts, cofactor salts such as those of potassium (preferably potassium chloride or potassium acetate) and magnesium (preferably magnesium chloride or magnesium acetate) are included in the compositions. Addition of one or more carbohydrates and/or sugars to the compositions and/or synthesis reaction mixtures may also be advantageous, to support enhanced stability of the compositions and/or reaction mixtures upon storage. Preferred such carbohydrates or sugars for inclusion in the compositions and/or synthesis reaction mixtures of the invention include, but are not limited to, sucrose, trehalose, and the like. Furthermore, such carbohydrates and/or sugars may be added to the storage buffers for the enzymes used in the production of the enzyme compositions and kits of the invention. Such carbohydrates and/or sugars are commercially available from a number of sources, including Sigma (St. Louis, Mo.).

It is often preferable to first dissolve the buffer salts, cofactor salts and carbohydrates or sugars at working concentrations in water and to adjust the pH of the solution prior to addition of the enzymes. In this way, the pH-sensitive enzymes will be less subject to acid- or alkaline-mediated inactivation during formulation of the present compositions.

To formulate the buffered salts solution, a buffer salt which is preferably a salt of Tris(hydroxymethyl)aminomethane (TRIS®), and most preferably the hydrochloride salt thereof, is combined with a sufficient quantity of water to yield a solution having a TRIS® concentration of 5–150 millimolar, preferably 10–60 millimolar, and most preferably about 20–60 millimolar. To this solution, a salt of magnesium (preferably either the chloride or acetate salt thereof) may be added to provide a working concentration thereof of 1–10 millimolar, preferably 1.5–8.0 millimolar, and most preferably about 3–7.5 millimolar. A salt of potassium (preferably a chloride or acetate salt of potassium) may also be added to the solution, at a working concentration of 10–100 millimolar and most preferably about 75 millimolar. A reducing agent such as dithiothreitol may be added to the solution, preferably at a final concentration of about 1–100 mM, more preferably a concentration of about 5–50 mM or about 7.5–20 mM, and most preferably at a concentration of about 10 mM. Preferred concentrations of carbohydrates and/or sugars for inclusion in the compositions of the invention range from about 5% (w/v) to about 30% (w/v), about 7.5% (w/v) to about 25% (w/v), about 10% (w/v) to about 25% (w/v), about 10% (w/v) to about 20% (w/v), and preferably about 10% (w/v) to about 15% (w/v). A small amount of a salt of ethylenediaminetetraacetate (EDTA), such as disodium EDTA, may also be added (preferably about 0.1 millimolar), although inclusion of EDTA does not appear to be essential to the function or stability of the compositions of the present invention. After addition of all buffers and salts, this buffered salt solution is mixed well until all salts are dissolved, and the pH is adjusted using methods known in the art to a pH value of 7.4 to 9.2, preferably 8.0 to 9.0, and most preferably about 8.4.

To these buffered salt solutions, the enzymes (reverse transcriptases and/or DNA polymerases) are added to produce the compositions of the present invention. M-MLV RTs are preferably added at a working concentration in the solution of about 1,000 to about 50,000 units per milliliter, about 2,000 to about 30,000 units per milliliter, about 2,500 to about 25,000 units per milliliter, about 3,000 to about 22,500 units per milliliter, about 4,000 to about 20,000 units per milliliter, and most preferably at a working concentration of about 5,000 to about 20,000 units per milliliter. AMV RTs, MAV RTs, RSV RTs and RAV RTs, including those of the invention described above, are preferably added at a working concentration in the solution of about 100 to about 5000 units per milliliter, about 125 to about 4000 units per milliliter, about 150 to about 3000 units per milliliter, about 200 to about 2500 units per milliliter, about 225 to about 2000 units per milliliter, and most preferably at a working concentration of about 250 to about 1000 units per milliliter. The enzymes in the thermophilic DNA polymerase group (Taq, Tne, Tma, Pfu, VEN™, DEEPVENT™, Tth and mutants, variants and derivatives thereof) are preferably added at a working concentration in the solution of about 100 to about 1000 units per milliliter, about 125 to about 750 units per milliliter, about 150 to about 700 units per milliliter, about 200 to about 650 units per milliliter, about 225 to about 550 units per milliliter, and most preferably at a working concentration of about 250 to about 500 units per milliliter. The enzymes may be added to the solution in any order, or may be added simultaneously.

The compositions of the invention may further comprise one or more nucleotides, which are preferably deoxynucleoside triphosphates (dNTPs) or dideoxynucleoside triphosphates (ddNTPs). The dNTP components of the present compositions serve as the "building blocks" for newly synthesized nucleic acids, being incorporated therein by the action of the polymerases, and the ddNTPs may be used in sequencing methods according to the invention. Examples of nucleotides suitable for use in the present compositions include, but are not limited to, dUTP, dATP, dTTP, dCTP, dGTP, dITP, 7-deaza-dGTP, α-thio-dATP, α-thio-dTTP, α-thio-dGTP, α-thio-dCTP, ddUTP, ddATP, ddTTP, ddCTP, ddGTP, ddITP, 7-deaza-ddGTP, α-thio-ddATP, α-thio-ddTTP, α-thio-ddGTP, α-thio-ddCTP or derivatives thereof, all of which are available commercially from sources including Life Technologies, Inc. (Rockville, Md.), New England BioLabs (Beverly, Mass.) and Sigma Chemical Company (Saint Louis, Mo.). The nucleotides may be unlabeled, or they may be detectably labeled by coupling them by methods known in the art with radioisotopes (e.g., $^3$H, $^{14}$C, $^{32}$P or $^{35}$S), vitamins (e.g., biotin), fluorescent moieties (e.g., fluorescein, rhodamine, Texas Red, or phycoerythrin), chemiluminescent labels (e.g., using the PHOTO-GENE™ or ACES™ chemiluninescence systems, available commercially from Life Technologies, Inc., Rockville, Md.), dioxigenin and the like. Labeled nucleotides may also be obtained commercially, for example from Life Technologies, Inc. (Rockville, Md.) or Sigma Chemical Company (Saint Louis, Mo.). In the present compositions, the nucleotides are added to give a working concentration of each nucleotide of about 10–4000 micromolar, about 50–2000 micromolar, about 100–1500 micromolar, or about 200–1200 micromolar, and most preferably a concentration of about 1000 micromolar.

To reduce component deterioration, storage of the reagent compositions is preferably at about 4° C. for up to one day, or most preferably at −20° C. for up to one year.

In another aspect, the compositions and reverse transcriptases of the invention may be prepared and stored in dry form in the presence of one or more carbohydrates, sugars, or synthetic polymers. Preferred carbohydrates, sugars or polymers for the preparation of dried compositions or reverse transcriptases include, but are not limited to, sucrose, trehalose, and polyvinylpyrrolidone (PVP) or combinations thereof See, e.g., U.S. Pat. Nos. 5,098,893, 4,891,319, and 5,556,771, the disclosures of which are entirely incorporated herein by reference. Such dried compositions and enzymes may be stored at various temperatures for extended times without significant deterioration of enzymes or components of the compositions of the invention. Preferably, the dried reverse transcriptases or compositions are stored at 4° C. or at −20° C.

Production of cDNA Molecules

Sources of Nucleic Acid Molecules

In accordance with the invention, cDNA molecules (single-stranded or double-stranded) may be prepared from a variety of nucleic acid template molecules. Preferred nucleic acid molecules for use in the present invention include single-stranded or double-stranded DNA and RNA molecules, as well as double-stranded DNA:RNA hybrids. More preferred nucleic acid molecules include messenger RNA (mRNA), transfer RNA (tRNA) and ribosomal RNA (rRNA) molecules, although mRNA molecules are the preferred template according to the invention.

The nucleic acid molecules that are used to prepare cDNA molecules according to the methods of the present invention may be prepared synthetically according to standard organic chemical synthesis methods that will be familiar to one of ordinary skill. More preferably, the nucleic acid molecules may be obtained from natural sources, such as a variety of cells, tissues, organs or organisms. Cells that may be used as sources of nucleic acid molecules may be prokaryotic (bacterial cells, including but not limited to those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas* and *Streptomyces*) or eukaryotic (including fungi (especially yeasts), plants, protozoans and other parasites, and animals including insects (particularly *Drosophila* spp. cells), nematodes (particularly *Caenorhabditis elegans* cells), and mammals (particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi oryeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

Once the starting cells, tissues, organs or other samples are obtained, nucleic acid molecules (such as mRNA) may be isolated therefrom by methods that are well-known in the art (See, e.g., Maniatis, T., et al., *Cell* 15:687–701 (1978); Okayama, H., and Berg, P., *Mol. Cell. Biol.* 2:161–170 (1982); Gubler, U., and Hoffman, B. J., *Gene* 25:263–269 (1983)). The nucleic acid molecules thus isolated may then be used to prepare cDNA molecules and cDNA libraries in accordance with the present invention.

In the practice of the invention, cDNA molecules or cDNA libraries are produced by mixing one or more nucleic acid molecules obtained as described above, which is preferably one or more mRNA molecules such as a population of mRNA molecules, with two or more polypeptides having reverse transcriptase activity, or with one or more of the compositions of the invention or with one or more of the RSV RTs and/or AMV RTs and/or other ASLV RTs of the invention, under conditions favoring the reverse transcription of the nucleic acid molecule by the action of the enzymes or the compositions to form a cDNA molecule (single-stranded or double-stranded). Thus, the method of the invention comprises (a) mixing one or more nucleic acid templates (preferably one or more RNA or mRNA templates, such as a population of mRNA molecules) with one or more reverse transcriptases of the invention and (b) incubating the mixture under conditions sufficient to make one or more nucleic acid molecules complementary to all or a portion of the one or more templates. Such methods may include the use of one or more DNA polymerases. The invention may be used in conjunction with methods of cDNA synthesis such as those described in the Examples below, or others that are well-known in the art (see, e.g., Gubler, U., and Hoffman, B. J., *Gene* 25:263–269 (1983); Krug, M. S., and Berger, S. L., *Meth. Enzymol.* 152:316–325 (1987); Sambrook, J., et al., *Molecular Cloning: A Laboratory Manual,* 2nd ed., Cold Spring Harbor, N.Y.: Cold Spring Harbor Laboratory Press, pp. 8.60–8.63 (1989)), to produce cDNA molecules or libraries.

The invention is also particularly directed to methods for reverse transcription of a nucleic acid molecule at elevated temperatures. As described in more detail in Example 5, retroviral RTs are generally not used at temperatures above 37° C. to 42° C. to copy nucleic acid templates such as RNA molecules because of the limited thermal stability of these mesophilic enzymes. At these temperatures, however, mRNA secondary structure may interfere with reverse transcription (Gerard, G. F., et al., *FOCUS* 11:60 (1989); Myers, T. W., and Gelfand, D. H., *Biochem.* 30:7661 (1991)), and the specificity of primer binding may be reduced during gene-specific reverse transcription processes, such as RT-PCR, causing high background signal (Myers, T. W., and Gelfand, D. H., *Biochem.* 30:7661(1991); Freeman, W. N., et al., *Bio Techniques* 20:782 (1996)). To help overcome these problems, the present invention therefore provides methods of RNA reverse transcription at more elevated temperatures, i.e., above 50° C.

Therefore, the invention is related to methods for reverse transcription of a nucleic acid molecule comprising (a) mixing a nucleic acid template with one or more polypeptides having reverse transcriptase activity; and (b) incubating the mixture at a temperature of about 50° C. or greater and under conditions sufficient to make a first nucleic acid molecule complementary to all or a portion of the nucleic acid template. Nucleic acid templates which may be copied according to these methods include, but are not limited to, an RNA molecule (e.g., a mRNA molecule or a polyA+RNA molecule) and a DNA molecule (e.g., a single-stranded or double-stranded DNA molecule). According to the invention, the first nucleic acid molecule produced by these methods may be a full length cDNA molecule. While any incubation temperature of about 50° C. or greater may be used in the present methods, particularly preferred incubation temperatures include, but are not limited to, temperatures of about 51° C. or greater, about 52° C. or greater, about 53° C. or greater, about 54° C. or greater, about 55° C. or greater, about 56° C. or greater, about 57° C. or greater, about 58° C. or greater, about 59° C. or greater, about 60° C. or greater, about 61° C. or greater, about 62° C. or greater, about 63° C. or greater, about 64° C. or greater, about 65° C. or greater, about 66° C. or greater, about 67° C. or greater, about 68° C. or greater, about 69° C. or greater or about 70° C. or greater. In other such methods, the incubation temperature may be over a range of incubation temperatures, including but not limited to a temperature range of from about 50° C. to about 70° C., about 51° C. to about 70° C., about 52° C. to about 70° C., about 53° C. to about 70° C., about 54° C. to about 70° C., about 55° C. to about 70° C., about 55° C. to about 69° C., about 55° about 68° C., about 55° C. to about 67° C., about 55° C. to about 66° C., about 55° C. to about 65° C., about 56° C. to about 65° C., about 56° C. to about 64° C. or about 56° C. to about 62° C. The invention is also directed to such methods which further comprise incubating the first nucleic acid molecule under conditions sufficient to make a second nucleic acid molecule complementary to all or portion of the first nucleic acid molecule. According to the invention, the first and second nucleic acid molecules produced by these methods may be DNA molecules, and may form a double stranded DNA molecule which may be a full length cDNA molecule. As described for the methods above, the one or more polypeptides having reverse transcriptase activity that are used in these higher-temperature methods preferably are reduced or substantially reduced in RNase H activity, and may be selected from the group consisting of one or more AMV reverse transcriptases or subunits thereof (or derivatives, variants, fragments or mutants thereof), and one or more RSV reverse transcriptases or subunits thereof (or derivatives, variants, fragments or mutants thereof) or other ASLV RTs or subunits thereof (or derivatives, variants, fragments or mutants thereof). Particularly preferred AMV RTs and RSV RTs and other ASLV RTs include those provided by the present invention and described in detail above. More particularly preferred are those AMV RTs and RSV RTs having the genotype AMV αH−/βH+ RT or RSV αH−/H+ RT. Such constructs are preferably made by mutating or modifying the gene encoding the α subunit to reduce or substantially reduce RNase H activity while the gene encoding the β subunit is not so mutated or modified. The resulting polypeptides (produced by co-expression) will be reduced or substantially reduced in RNase H activity.

Other methods of cDNA synthesis which may advantageously use the present invention will be readily apparent to one of ordinary skill in the art.

Having obtained cDNA molecules or libraries according to the present methods, these cDNAs may be isolated for further analysis or manipulation. Detailed methodologies for purification of cDNAs are taught in the GENETRAPPER™ manual (Life Technologies, Inc.; Rockville, Md.), which is incorporated herein by reference in its entirety, although alternative standard techniques of cDNA isolation such as those described in the Examples below or others that are known in the art (see, e.g., Sambrook, J., et al., *Molecular Cloning: A Laboratory Manual,* 2nd ed., Cold Spring Harbor, N.Y.: Cold Spring Harbor Laboratory Press, pp. 8.60–8.63 (1989)) may also be used.

In other aspects of the invention, the invention may be used in methods for amplifying and sequencing nucleic acid molecules. Nucleic acid amplification methods according to this aspect of the invention may be one-step (e.g., one-step RT-PCR) or two-step (e.g., two-step RT-PCR) reactions. According to the invention, one-step RT-PCR type reactions may be accomplished in one tube thereby lowering the possibility of contamination. Such one-step reactions comprise (a) mixing a nucleic acid template (e.g., mRNA) with two or more polypeptides having reverse transcriptase activity and with one or more DNA polymerases and (b) incubating the mixture under conditions sufficient to amplify a nucleic acid molecule complementary to all or a portion of the template. Alternatively, amplification may be accomplished by mixing a template with two or more polypeptides having reverse transcriptase activity (and optionally having DNA polymerase activity). Incubating such a reaction mixture under appropriate conditions allows amplification of a nucleic acid molecule complementary to all or a portion of the template. Such amplification may be accomplished by the reverse transcriptase activity alone or in combination with the DNA polymerase activity. Two-step RT-PCR reactions may be accomplished in two separate steps. Such a method comprises (a) mixing a nucleic acid template (e.g., mRNA) with two or more reverse transcriptases, (b) incubating the mixture under conditions sufficient to make a nucleic acid molecule (e.g., a DNA molecule) complementary to all or a portion of the template, (c) mixing the nucleic acid molecule with one or more DNA polymerases and (d) incubating the mixture of step (c) under conditions sufficient to amplify the nucleic acid molecule. For amplification of long nucleic acid molecules (i.e., greater than about 3–5 Kb in length), a combination of DNA polymerases may be used, such as one DNA polymerase having 3' exonuclease activity and another DNA polymerase being substantially reduced in 3' exonuclease activity. An alternative two-step procedure comprises the use of two or more polypeptides having reverse transcriptase activity and DNA polymerase activity (e.g., Tth, Tma or Tne DNA polymerases and the like) rather than separate addition of a reverse transcriptase and a DNA polymerase.

Nucleic acid sequencing methods according to this aspect of the invention may comprise both cycle sequencing (sequencing in combination with amplification) and standard sequencing reactions. The sequencing method of the invention thus comprises (a) mixing a nucleic acid molecule to be sequenced with one or more primers, two or more reverse transcriptases, one or more nucleotides and one or more terminating agents, (b) incubating the mixture under conditions sufficient to synthesize a population of nucleic acid molecules complementary to all or a portion of the molecule to be sequenced, and (c) separating the population to determine the nucleotide sequence of all or a portion of the molecule to be sequenced. According to the invention, one or more DNA polymerases (preferably thermostable DNA polymerases) may be used in combination with or separate from the reverse transcriptases.

Amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822). Nucleic acid sequencing techniques which may employ the present compositions include dideoxy sequencing methods such as those disclosed in U.S. Pat. Nos. 4,962,022 and 5,498,523, as well as more complex PCR-based nucleic acid fingerprinting techniques such as Random Amplified Polymorphic DNA (RAPD) analysis (Williams, J. G. K., et al., *Nucl. Acids Res.* 18(22): 6531–6535, 1990), Arbitrarily Primed PCR (AP-PCR; Welsh, J., and McClelland, M., *Nucl Acids Res.* 18(24): 7213–7218, 1990), DNA Amplification Fingerprinting (DAF; Caetano-Anollés et al., *Bio/Technology* 9:553–557, 1991), microsatellite PCR or Directed Amplification of Minisatellite-region DNA (DAMD; Heath, D. D., et al., *Nucl. Acids Res.* 21(24): 5782–5785, 1993), and Amplification Fragment Length Polymorphism (AFLP) analysis (EP 0 534 858; Vos, P., et al., *Nucl. Acids Res.* 23(21):4407–4414, 1995; Lin, J. J., and Kuo, J., *FOCUS* 17(2):66–70, 1995). In a particularly preferred aspects, the invention may be used in methods of amplifying or sequencing a nucleic acid molecule comprising one or more polymerase chain reactions (PCRs), such as any of the PCR-based methods described above.

Kits

In another embodiment, the present invention may be assembled into kits for use in reverse transcription or amplification of a nucleic acid molecule, or into kits for use in sequencing of a nucleic acid molecule. Kits according to this aspect of the invention comprise a carrier means, such as a box, carton, tube or the like, having in close confinement therein one or more container means, such as vials, tubes, ampules, bottles and the like, wherein a first container means contains one or more polypeptides having reverse transcriptase activity. These polypeptides having reverse transcriptase activity may be in a single container as mixtures of two or more polypeptides, or in separate containers. The kits of the invention may also comprise (in the same or separate containers) one or more DNA polymerases, a suitable buffer, one or more nucleotides and/or one or more primers.

In a specific aspect of the invention, the reverse transcription and amplification kits may comprise one or more components (in mixtures or separately) including one or more, preferably two or more, polypeptides having reverse transcriptase activity of the invention, one or more nucleotides needed for synthesis of a nucleic acid molecule, and/or a primer (e.g., oligo(dT) for reverse transcription). Such reverse transcription and amplification kits may further comprise one or more DNA polymerases. Sequencing kits of the invention may comprise one or more, preferably two or more, polypeptides having reverse transcriptase activity of the invention, and optionally one or more DNA polymerases, one or more terminating agents (e.g., dideoxynucleoside triphosphate molecules) needed for sequencing of a nucleic acid molecule, one or more nucleotides and/or one or more primers. Preferred polypeptides having reverse transcriptase activity, DNA polymerases, nucleotides, primers and other components suitable for use in the reverse transcription, amplification and sequencing kits of the invention include those described above. The kits encompassed by this aspect of the present invention may further comprise additional reagents and compounds necessary for carrying out standard nucleic acid reverse transcription, amplification or sequencing protocols. Such polypeptides having reverse transcriptase activity of the invention, DNA polymerases, nucleotides, primers, and additional reagents, components or compounds may be contained in one or more containers, and may be contained in such containers in a mixture of two or more of the above-noted components or may be contained in the kits of the invention in separate containers.

Use of Nucleic Acid Molecules

The nucleic acid molecules or cDNA libraries prepared by the methods of the present invention may be further characterized, for example by cloning and sequencing (i.e., determining the nucleotide sequence of the nucleic acid molecule), by the sequencing methods of the invention or by others that are standard in the art (see, e.g., U.S. Pat. Nos. 4,962,022 and 5,498,523, which are directed to methods of DNA sequencing). Alternatively, these nucleic acid molecules may be used for the manufacture of various materials in industrial processes, such as hybridization probes by methods that are well-known in the art. Production of hybridization probes from cDNAs will, for example, provide the ability for those in the medical field to examine a patient's cells or tissues for the presence of a particular genetic marker such as a marker of cancer, of an infectious or genetic disease, or a marker of embryonic development. Furthermore, such hybridization probes can be used to isolate DNA fragments from genomic DNA or cDNA libraries prepared from a different cell, tissue or organism for further characterization.

The nucleic acid molecules of the present invention may also be used to prepare compositions for use in recombinant DNA methodologies. Accordingly, the present invention relates to recombinant vectors which comprise the cDNA or amplified nucleic acid molecules of the present invention, to host cells which are genetically engineered with the recombinant vectors, to methods for the production of a recombinant polypeptide using these vectors and host cells, and to recombinant polypeptides produced using these methods.

Recombinant vectors may be produced according to this aspect of the invention by inserting, using methods that are well-known in the art, one or more of the cDNA molecules or amplified nucleic acid molecules prepared according to the present methods into a vector. The vector used in this aspect of the invention may be, for example, a phage or a plasmid, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments in this regard, the vectors provide for specific expression (and are therefore termed "expression vectors"), which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids or bacteriophages, and vectors derived from combinations thereof, such as cosmids and phagemids, and will preferably include at least one selectable marker such as a tetracycline or ampicillin resistance gene for culturing in a bacterial host cell. Prior to insertion into such an expression vector, the cDNA or amplified nucleic acid molecules of the invention should be operatively linked to an appropriate promoter, such as the phage lambda PL promoter, the *E. coli* lac, trp and tac promoters. Other suitable promoters will be known to the skilled artisan.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; pGEX, pTrxfus, pTrc99a, pET-5, pET-9, pKK223-3, pKK233-3, pDR540, pRIT5 available from Pharmacia; and pSPORT1, pSPORT2 and pSV•SPORT1, available from Life Technologies, Inc. Other suitable vectors will be readily apparent to the skilled artisan.

The invention also provides methods of producing a recombinant host cell comprising the cDNA molecules, amplified nucleic acid molecules or recombinant vectors of the invention, as well as host cells produced by such methods. Representative host cells (prokaryotic or eukaryotic) that may be produced according to the invention include, but are not limited to, bacterial cells, yeast cells, plant cells and animal cells. Preferred bacterial host cells include *Escherichia coli* cells (most particularly *E. coli* strains DH10B and Stbl2, which are available commercially (Life Technologies, Inc; Rockville, Md.)), *Bacillus subtilis* cells, *Bacillus megaterium* cells, *Streptomyces* spp. cells, *Erwinia* spp. cells, *Klebsiella* spp. cells and *Salmonella typhimurium* cells. Preferred animal host cells include insect cells (most particularly *Spodoptera frugiperda* Sf9 and Sf21 cells and *Trichoplusa* High-Five cells) and mammalian cells (most particularly CHO, COS, VERO, BHK and human cells). Such host cells may be prepared by well-known transformation, electroporation or transfection techniques that will be familiar to one of ordinary skill in the art.

In addition, the invention provides methods for producing a recombinant polypeptide, and polypeptides produced by these methods. According to this aspect of the invention, a recombinant polypeptide may be produced by culturing any of the above recombinant host cells under conditions favoring production of a polypeptide therefrom, and isolation of the polypeptide. Methods for culturing recombinant host cells, and for production and isolation of polypeptides therefrom, are well-known to one of ordinary skill in the art.

It will be readily apparent to one of ordinary skill in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLE 1

Cloning and Expression of RSV RNase H⁻ RT

General Methods

RSV H⁻ RT is a cloned form of retrovirus RT, in which both the α and the β subunits are mutated by a single amino acid change to eliminate RNase H activity. An RSV RT exhibiting substantially reduced RNase H activity is also produced when only the α subunit is mutated to substantially reduce RNase H activity (with the β subunit not being mutated in the RNase H domain). Mutations and plasmid constructions were conducted using standard molecular biology methods (see, e.g., Sambrook, J., et al., *Molecular Cloning: A Laboratory Manual,* 2nd Ed., Cold Spring Harbor, N.Y.: Laboratory Press (1989)), modified as described below.

Plasmid preparation. Plasmid preparations from 1 ml E. coli cultures were made by the alkaline lysis procedure (Sambrook, J., et al., *Molecular Cloning: A Laboratory Manual*, 2nd ed., Cold Spring Harbor, N.Y.: Laboratory Press (1989)). From 10 ml cultures, the preparation was additionally treated with phenol-chloroform, precipitated with ethanol, and resuspended in 50 μl of Tris-EDTA (TE) buffer (20 mM Tris-HCl, 1 mM EDTA, pH 8.0). For bacmid preparations, care was taken to avoid shear of the DNA during handling (i.e., no vortexing; phenol-chloroform extractions were gently rolled rather than shaken; slow pipetting).

PCR. Polymerase chain reactions were carried out in a Perkin-Elmer 9600 thermocycler. Reaction mixtures (50 μl each) contained 0.5 units of Taq DNA polymerase, 1 μM of each oligonucleotide, 50 μM each of dCTP, dGTP, dTTP, and dATP, and about 100 ng of target DNA in a reaction buffer consisting of 50 mM KCl, 20 mM Tris-HCl (pH 8.3) and 5 mM $MgCl_2$. Unless otherwise noted, the cycling conditions for each PCR were 5 minutes at 94° C., followed by eight cycles of 15 seconds at 55° C./30 seconds at 72° C./15 seconds at 94° C., and then 1 minute at 72° C.

Gel electrophoresis and DNA fragment isolation and cloning. DNA was electrophoresed at about 10 V/cm in agarose gels in Tris-acetate-EDTA buffer (Sambrook, J., et al., *Molecular Cloning: A Laboratory Manual*, 2nd ed., Cold Spring Harbor, N.Y.: Laboratory Press (1989)) containing about 0.3 μg/ml ethidium bromide. Fragments were visualized with ultraviolet light and isolated from gel slices by the GlassMAX method (Simms, D., et al., *Focus* 13:99 (1991)). DNA ligation reactions were performed using T4 DNA ligase under standard conditions (King, P. W., and Blakesley, R. W., *Focus* 8:1 (1986)), and *E. coli* DH10B cells were transformed by a modification of the $CaCl_2$ method (Lorow, D., and Jessee, J., *Focus* 12:19 (1990)).

Insect cell culture and baculovirus production. Samples (1 ml) of Sf21 insect cells at $5\times10^5$ cells/ml were transfected with a mixture of 1 μg of bacmid DNA and 8 μl of Cellfectin in 0.2 ml SF900-II serum-free insect cell culture medium (Life Technologies, Inc.; Rockville, Md.; see Godwin, G., and Whitford, W., *Focus* 15:44 (1993)), according to published procedures (Anderson, D., et al., *Focus* 16:53 (1995)). For growth and propagation, Sf9 and Sf21 insect cells were passaged in SF900-II medium at 27° C. in a shaking incubator at 100 rpm (for 600 ml cultures) or 130 rpm (for all other cultures). Care was taken to avoid allowing the cultures to exceed $4\times10^6$ cells/ml during growth or to drop below $0.5\times10^6$ cells/ml during dilution. To expand viral populations, Sf21 cells at about $1\times10^6$ cells/ml were infected with enough viral stock (about 0.2% (v/v) virus/culture) to allow growth to about $2\times10^6$ cells/ml, but not more than $4\times10^6$ cells/ml. After 72 hours, the culture was centrifuged (2,000 rpm for 10 min) and the supernatant was decanted and stored in the dark at 4° C. For infection of cells for protein production, Sf21 insect cells at about $1.5\times10^6$ cells/ml were infected with enough virus to allow no growth or growth to less than $2.5\times10^6$ cells/ml. After 72 hours, the culture was harvested by centrifugation at 1,000 rpm for 5 minutes and cells were resuspended in 15 ml of PBS (0.2 g/liter KCl, 0.2 g/liter $KH_2PO_4$, 8 g/liter NaCl, 1.15 g/liter $Na_2HPO_4$, 2.16 g/liter $Na_2HPO_4.7H_2O$) per 500 ml culture.

Cloning and Expression of Genes Encoding the RSV RT α and β Subunits

Both the α and β subunits of RSV RT are produced by proteolytic processing of larger polypeptide precursors (Gerard, G. F., in: *Enzymes of Nucleic Acid Synthesis and Modification, Vol. I: DNA Enzymes*, Jacob, S. T., ed., Boca Raton, Fla.: CRC Press, pp. 1–38 (1983)). To obviate the requirement for proteolytic processing, the coding sequence for RSV RT was mutagenized and subcloned such that both the α and β subunits were encoded by genes with standard start and stop translational signals. Both genes were mutagenized in the RNase H region, although construction of any combination of subunits (e.g., α RNase H⁻/βRNase H⁺; α RNase H⁺/β RNase H⁺; α RNase H⁺/β RNase H⁻; α RNase H⁻/β RNase H⁻) may be accomplished in this same manner. It has been discovered that RSV RT α RNase H⁻/β RNase H⁺ is substantially reduced in RNase H activity (approximately 5% of wildtype). A sequence encoding an affinity tag was added to the carboxy end of the β subunit.

Figure 7:
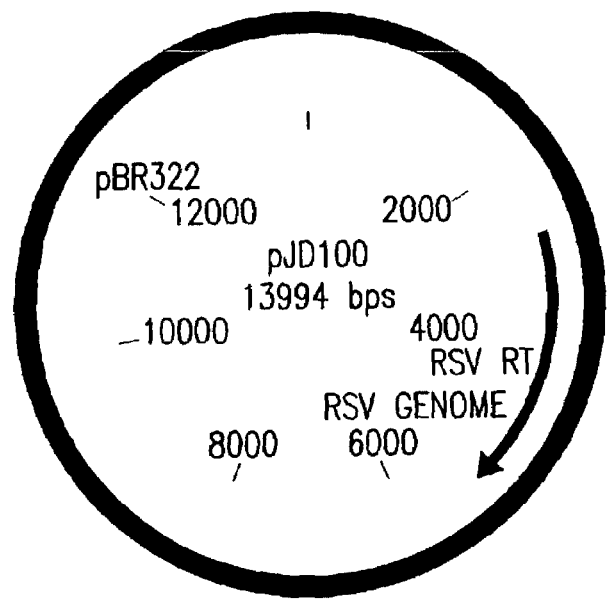
FIGS. 7–21 are more detailed maps of the plasmids described in FIGS. 1–6.

Mutagenesis and subcloning of the amino end, the carboxy end and the middle of the RSV RT, β subunit. The RSV RT gene was mutagenized to add an ATG codon and an NdeI site to the amino end of the sequence coding for the mature RT polypeptide. This mutagenesis was accomplished by PCR using a pJD100 target (FIGS. 1, 7) (Wilkerson, V. W., et al., *J. Virol.* 55:314–321 (1985)) and the following oligonucleotides:

```
AUG GAG AUC UCU CAT ATG ACT GTT GCG CTA CAT CTG GCT    (SEQ ID NO:1)

AAC GCG UAC UAG U GTT AAC AGC GCG CAA ATC ATG CAG.     (SEQ ID NO:2)
```

Figure 8:
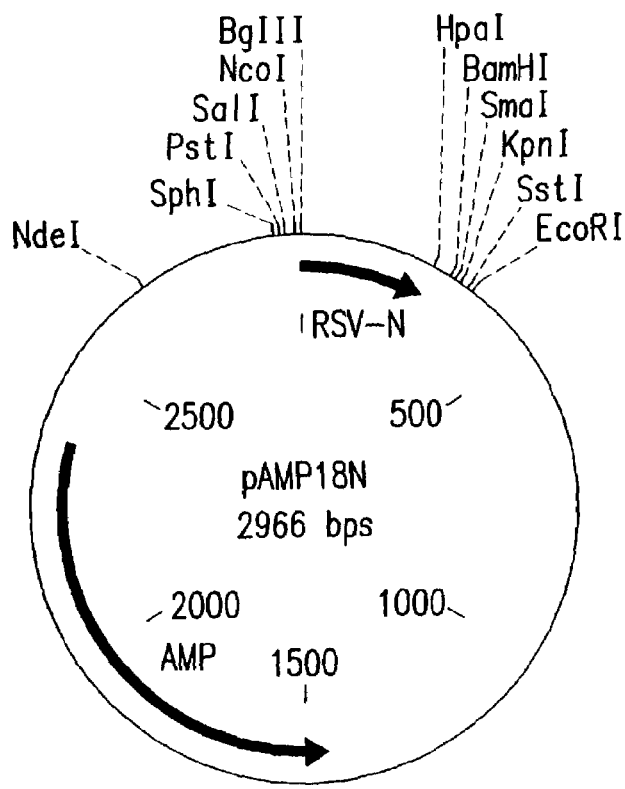

PCR was performed, and PCR products purified, as described above and the PCR products were cloned into pAMP18 by UDG cloning (Buchman, G. W., et al, *Focus* 15:36 (1993)) to form plasmid pAMP18N (FIGS. 1, 8).

Following mutagenesis and cloning of the amino end, the carboxy end of the gene for the β subunit of RSV was mutagenized and subcloned from PJD100 by PCR and UDG cloning into pAMPI (FIG. 1), using the following oligonucleotides:

```
CUA CUA CUA CUA GGT ACC CTC TCG AAA AGT TAA ACC         (SEQ ID NO:3)

CAU CAU CAU CAU CTC GAG TTA TGC AAA AAG AGG GCT CGC CTC. (SEQ ID NO:4)
ATC
```

Figure 9:
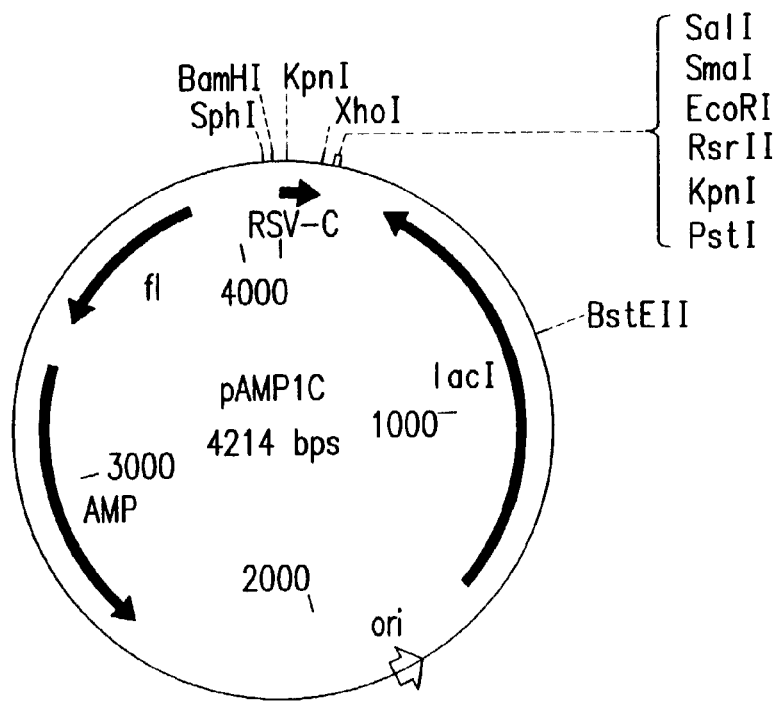

These oligonucleotides were designed to introduce a translational stop codon in the β gene at the site in which the "p4" region was cleaved from the βp4 polypeptide, and to add an XhoI site after the end of the gene. The PCR products were purified by gel electrophoresis and cloned into pAMP1 by UDG cloning, forming pAMP1C (FIGS. 1, 9). Note that this carboxy end is without a His tag, which was added later to form the final construct.

Figure 10:
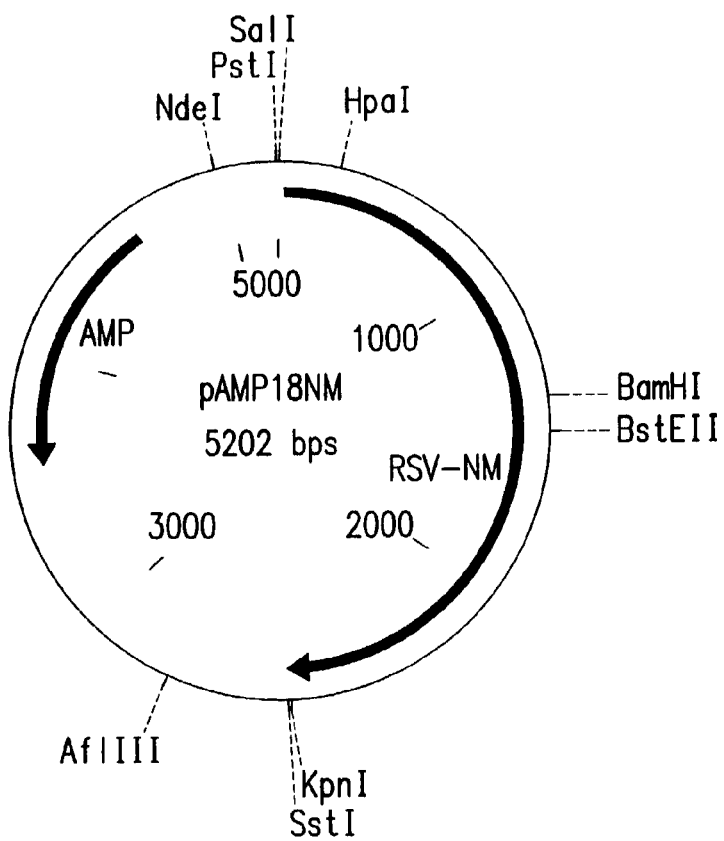
Figure 11:
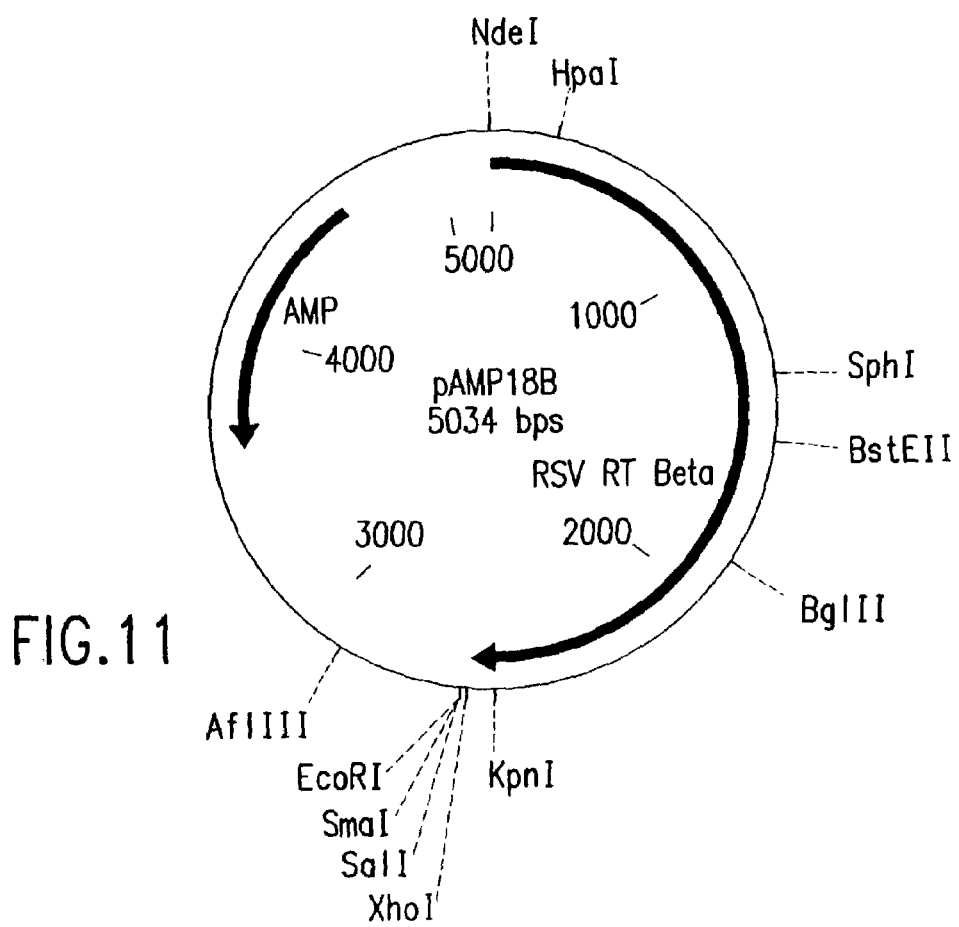

To add the middle region of the RSV RT β subunit, the 2.3 kb HpaI-KpnI fragment from pJD100 (FIG. 1) that encodes the middle of the β subunit of RSV RT was cloned into the HpaI-KpnI sites of pAMP18N, forming pAMP18NM (FIGS. 1, 10). To add the carboxy end of the RSV RT β subunit, the 113 bp KpnI-EcoRI fragment encoding the carboxy end of the β subunit gene was cloned from pAMP1C into the KpnI-EcoRI sites of pAM18NM, forming pAMP18B (FIGS. 2, 11).

Figure 12:
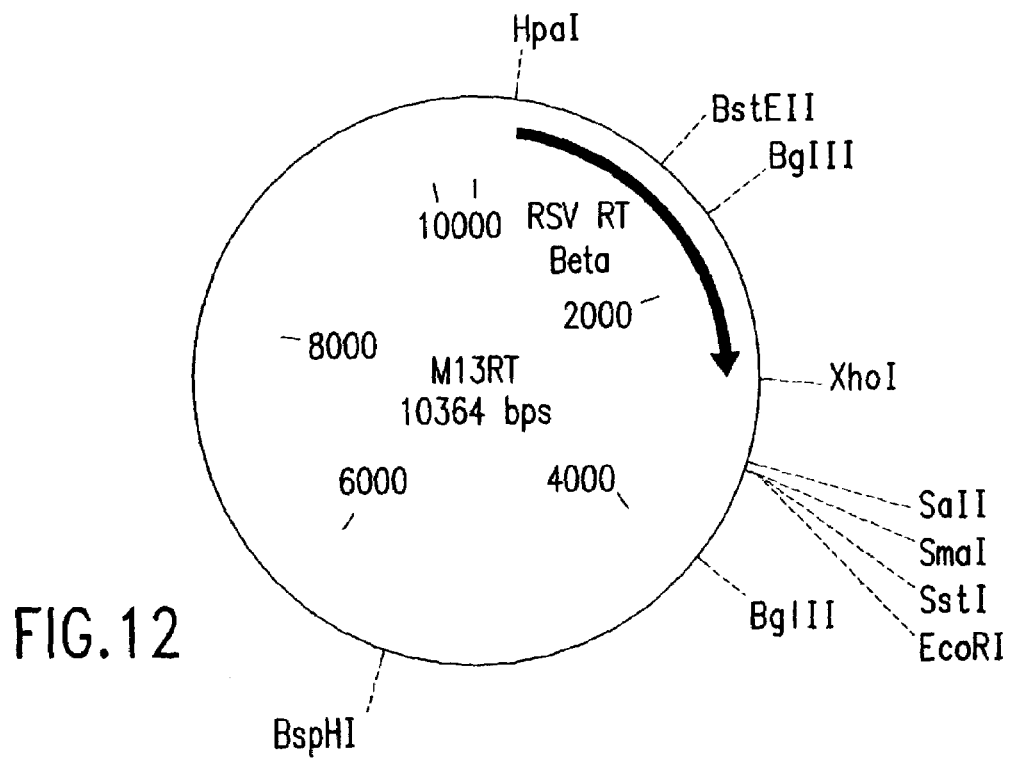

Following construction of the RSV RT β subunit, which contains RNase H activity, this gene was mutagenized by site-directed mutagenesis to produce a construct encoding a RSV RT β subunit that is substantially reduced in RNase H activity (i.e., "RNase H⁻"). A 3 Kb PstI fragment from pJD100 (FIG. 2) containing the entire RT gene was cloned into M13mp19, forming M13RT (FIGS. 2, 12). Single-stranded DNA containing uracil was isolated from *E. coli* strain CJ236 (Bio-Rad; Hercules, Calif.; and Cathy Joyce, Yale University, New Haven, Conn.) after infection with M13RT phage containing the PstI fragment. To mutate the RNase H region and to introduce an SstII site, the following oligonucleotide was used:

```
                                           (SEQ ID NO:5)
GGA CCC ACT GTC TTT ACC GCG GCC TCC TCA AGC ACC
```

Figure 2:
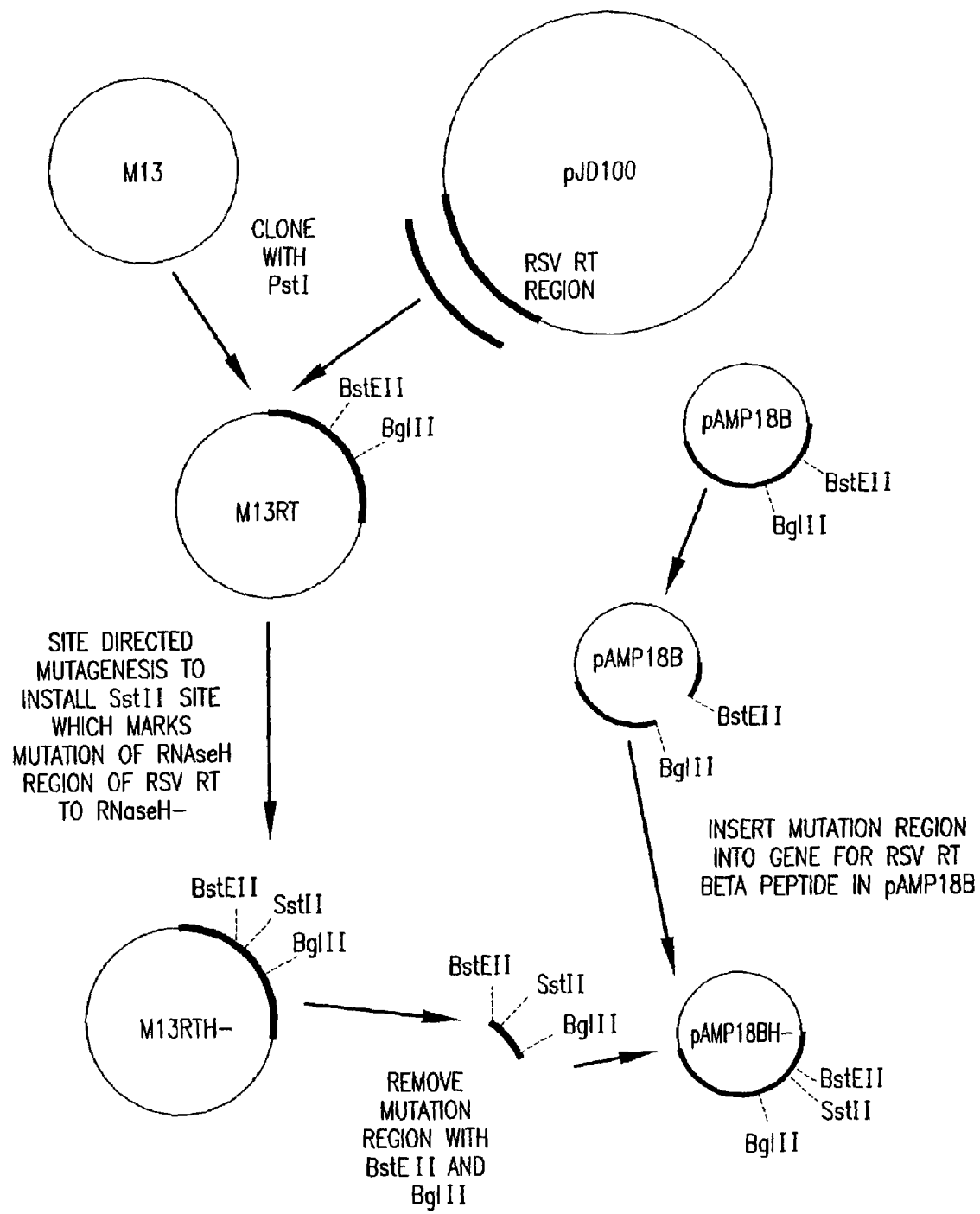
Figure 13:
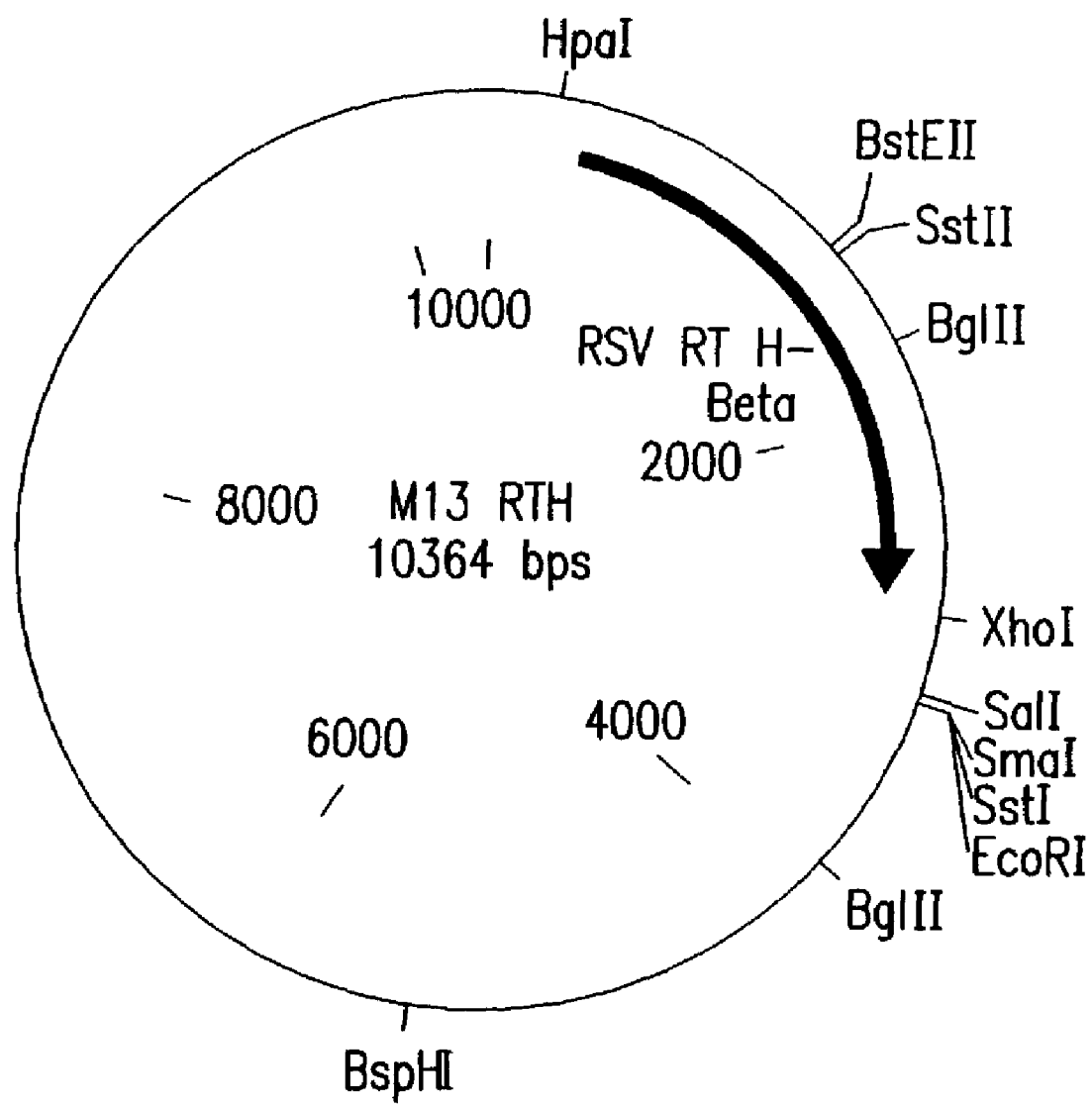
Figure 14:
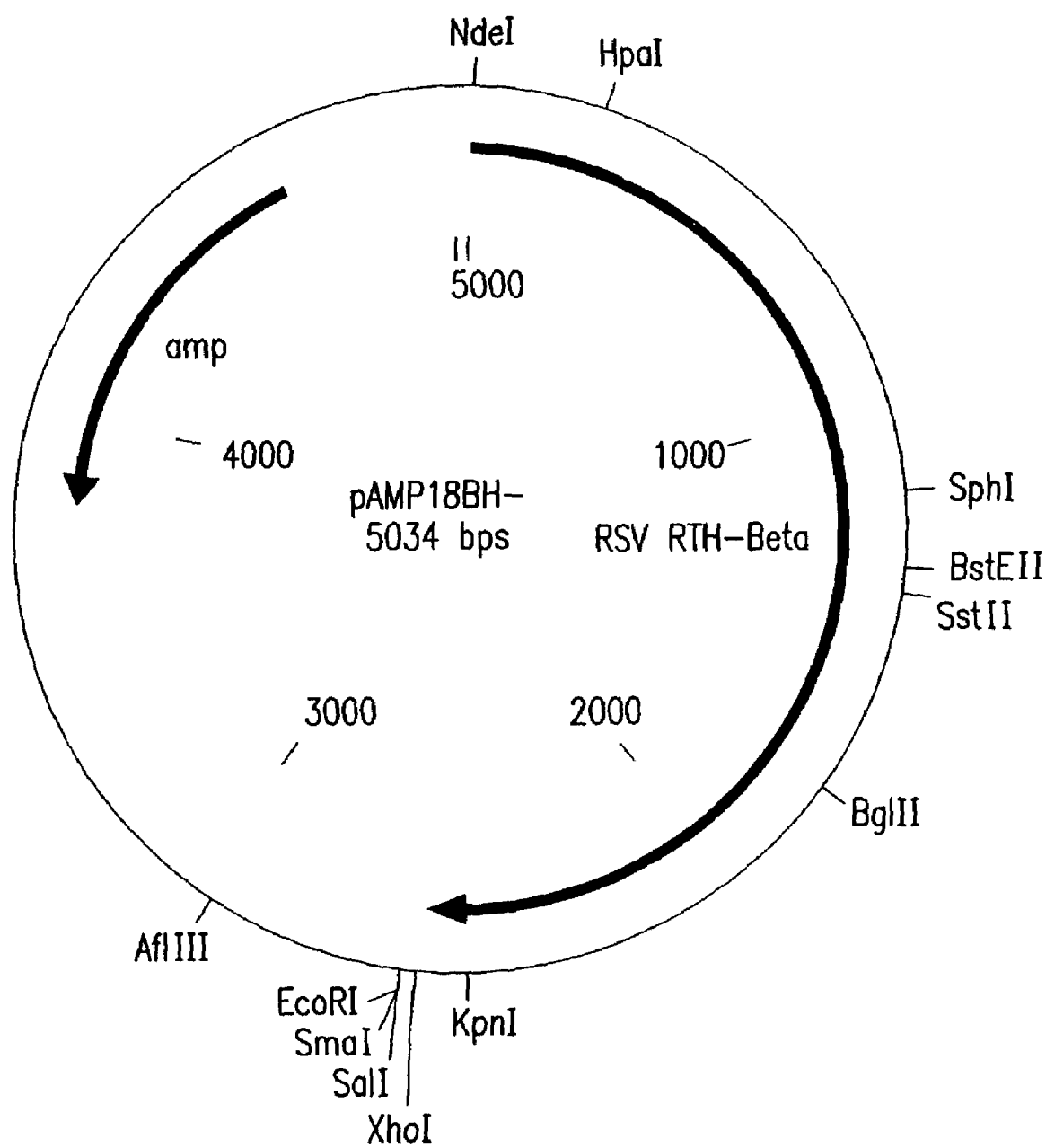

This oligonucleotide induced the substitution of an alanine residue in place of the aspartate residue at position 450 of the RT, forming M13RTH⁻ (FIGS. 2, 13). In an alternative approach to generate a RNase H⁻ RSV RT, Glu484 may be mutated to glutamine and/or Asp505 may be mutated to asparagine. To convert the β subunit back to RNase H+, an oligonucleotide primer having the wildtype sequence may be used. Alternatively, deletions or insertions can be made in the RNase H region to substantially reduce RNase H activity. DNA sequencing was used to confirm the Asp450→Ala450 mutation, and the 426 bp BglII-BstEII fragment from M13RTH⁻ was cloned into the BglII-BstEII sites of pAMP18B, replacing the RNase H region and forming pAMP18BH- (FIGS. 2, 14).

Figure 3:
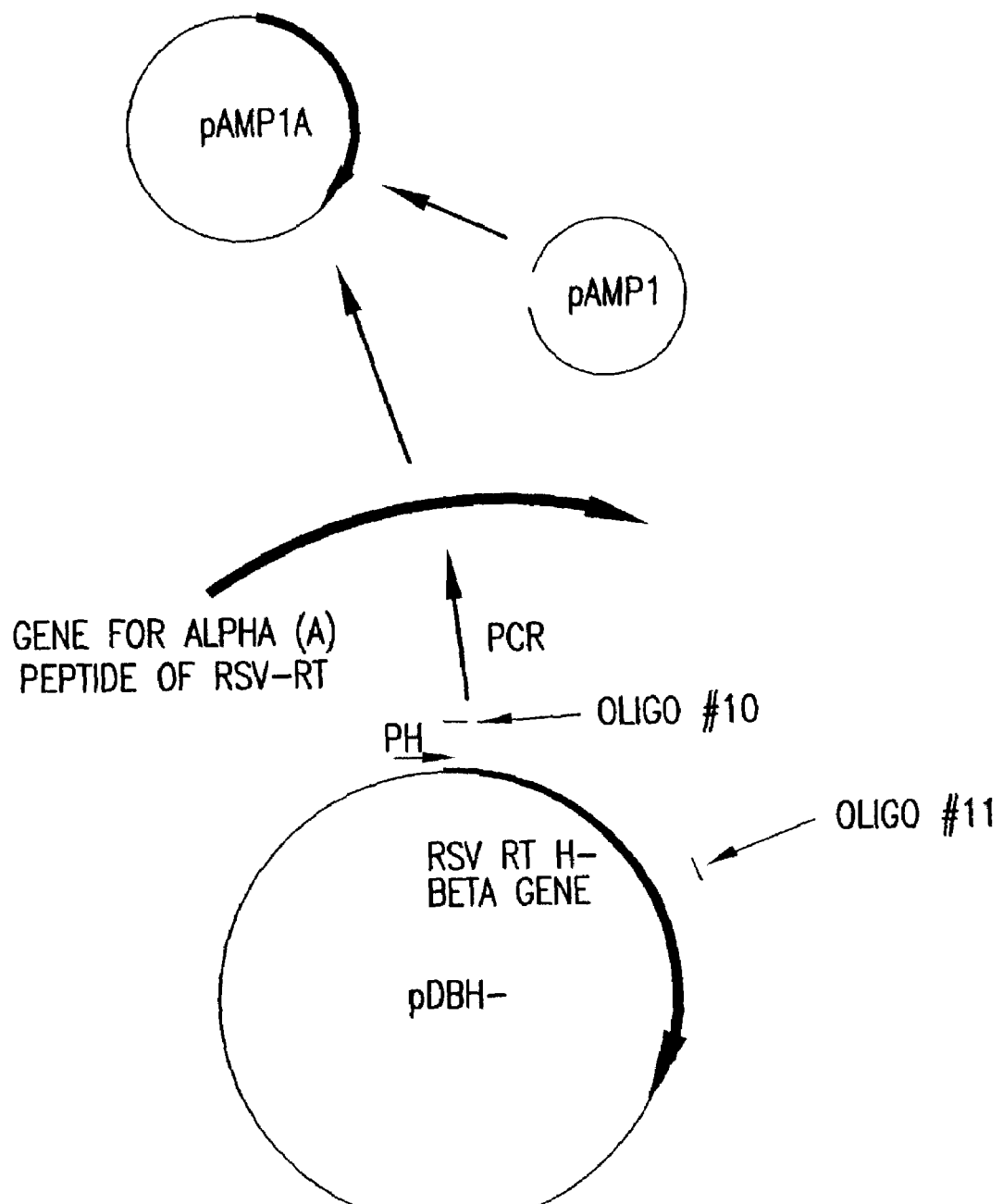

Mutagenesis and subcloning of the gene encoding the RSV RT α subunit. To create a gene which codes for the α subunit of RSV RT, two oligonucleotides were used to mutagenize the amino end of the RNase H⁻ mutant RSV RT gene from pDBH- (FIGS. 3, 15) and to introduce a translational stop codon where avian retroviral protease p15 normally cleaves the precursor polyprotein to make the α subunit:

```
CAU CAU CAU CAU CCC GGG TTA ATA CGC TTG GAA GGT GGC    (SEQ ID NO:6)

CUA CUA CUA CUA TCA TGA CTG TTG CGC TAC ATC TG         (SEQ ID NO:7)
```

Figure 16:
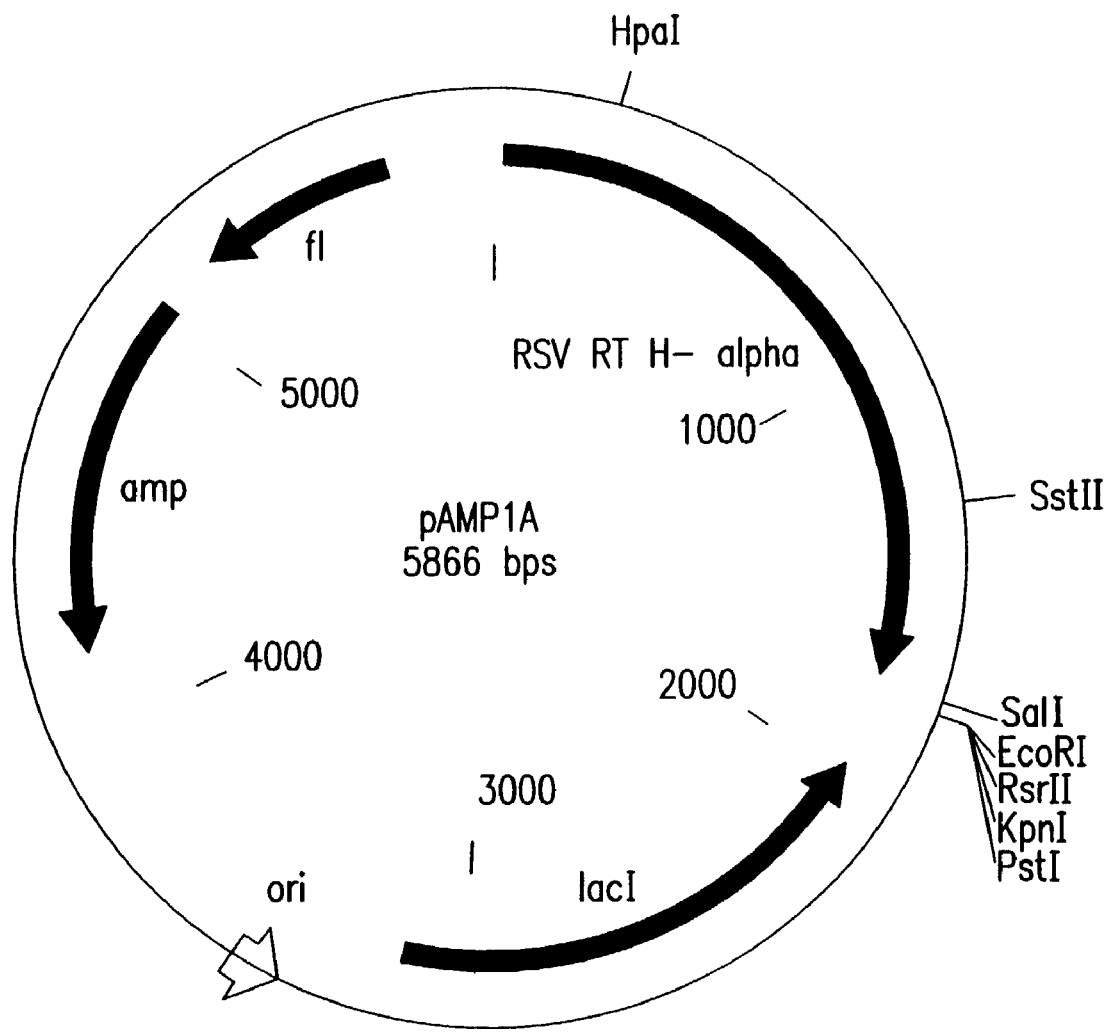

PCR cycling conditions were 5 minutes at 94° C., followed by 8 cycles of 15 seconds at 55° C./2 minutes at 72° C./15 seconds at 94° C., and then 2 minutes at 72° C. The PCR products were cloned into pAMP1 by UDG cloning as described above, forming pAMP1A (FIGS. 3, 16).

Addition of a His₆ tag to the carboxy end of the RSV β subunit. A His₆ tag was added to the carboxy end of the RSV RT β subunit by site-directed mutagenesis, and the mutant sequence was subcloned from pJD100 by PCR and UDG cloning as described above, using the following oligonucleotides:

```
CUA CUA CUA CUA GGT ACC CTC TCG AAA AGT TAA           (SEQ ID NO:8)

CAU CAU CAU CAU GAG GAA TTC AGT GAT GGT GAT GGT GAT GTG  (SEQ ID NO:9)

CAA AAAG AGG
```

These oligonucleotides were designed to introduce a translational stop codon in the gene, and to add a histidine tag to the end of the protein. The gene product was thus a polypeptide to which 6 histidines were added to the carboxy end. The PCR products were purified by gel electrophoresis and inserted into pAMP1 by UDG cloning, forming pAMPChis.

Figure 4:
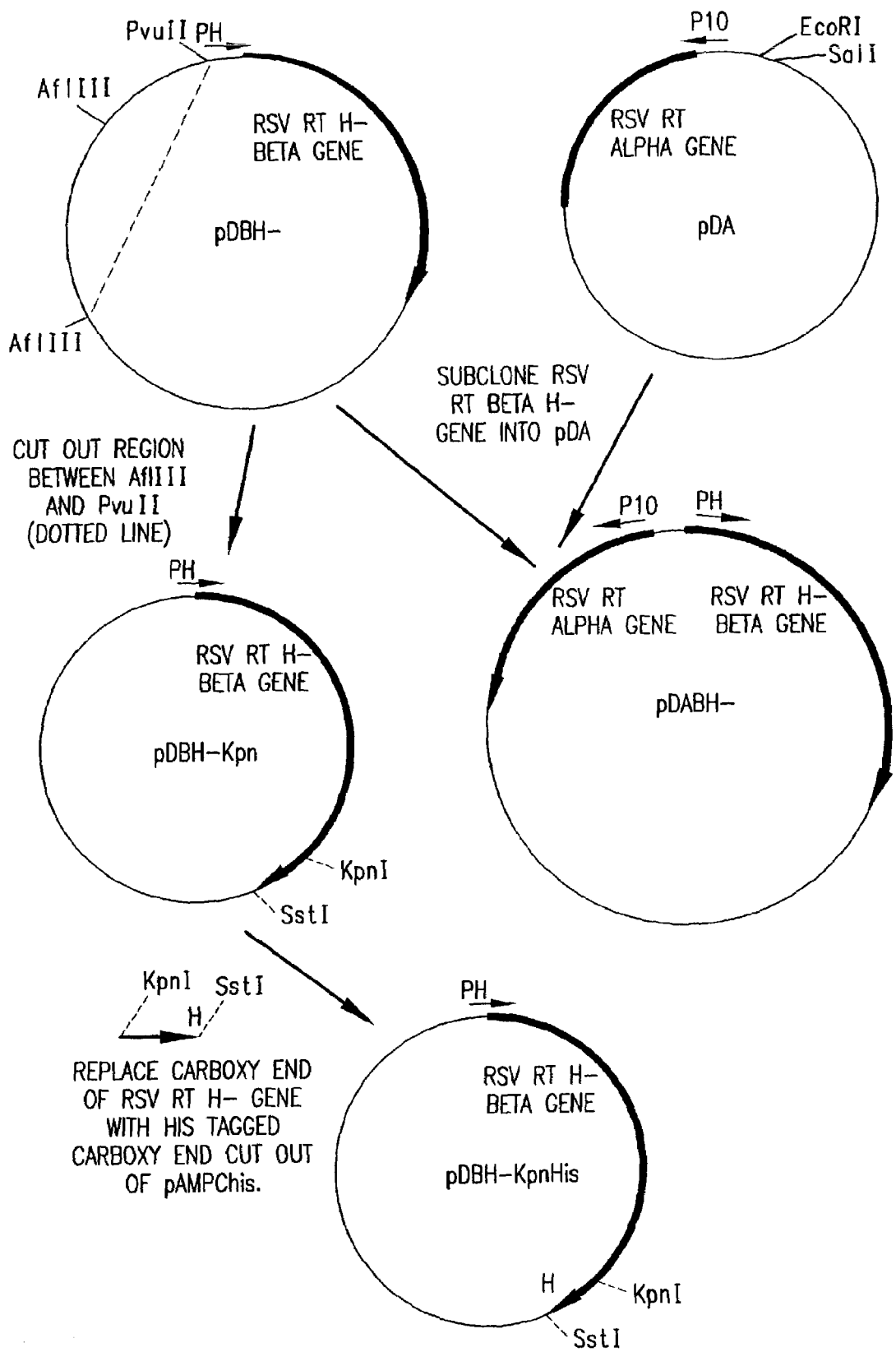
Figure 17:
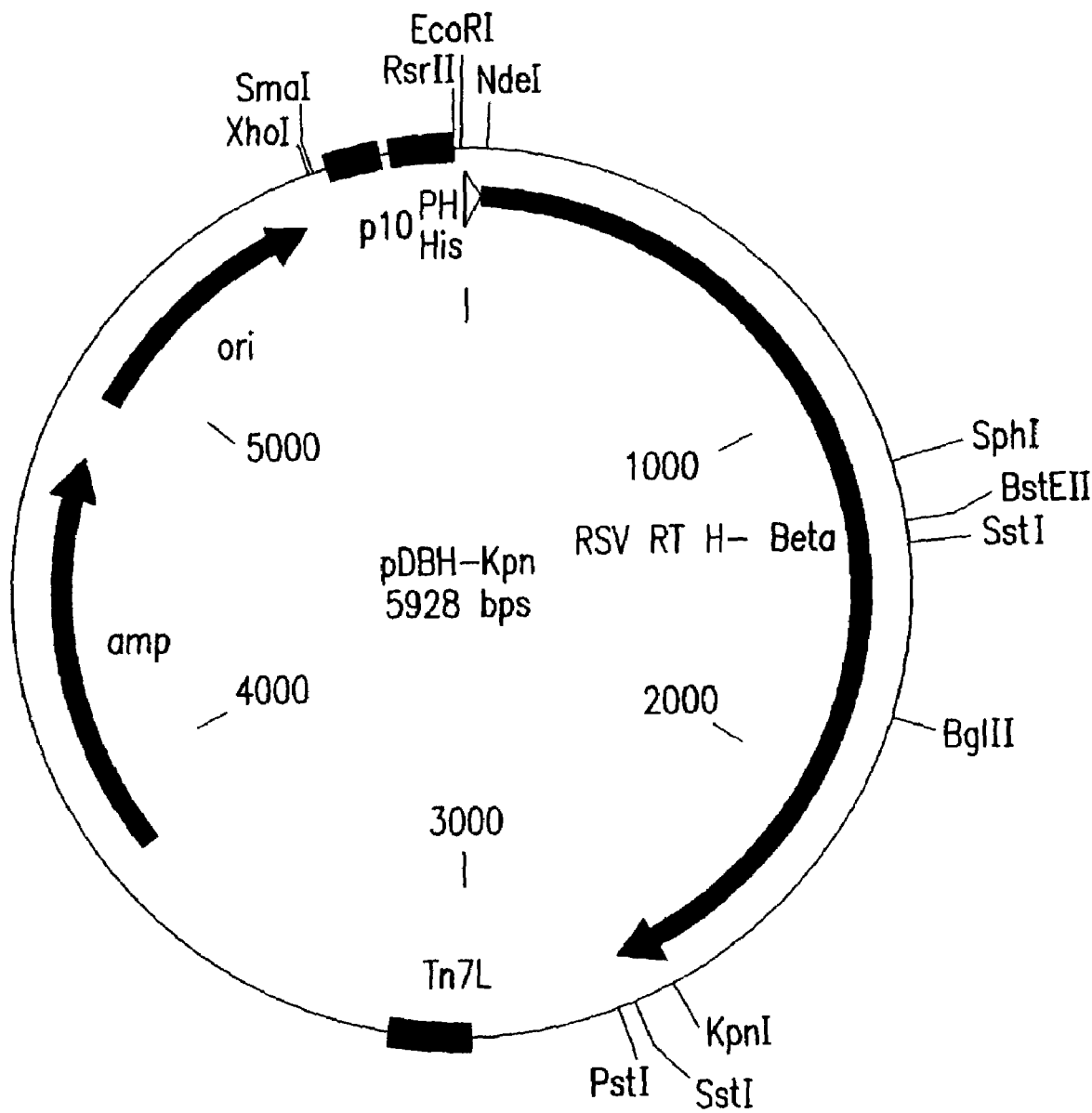
Figure 18:
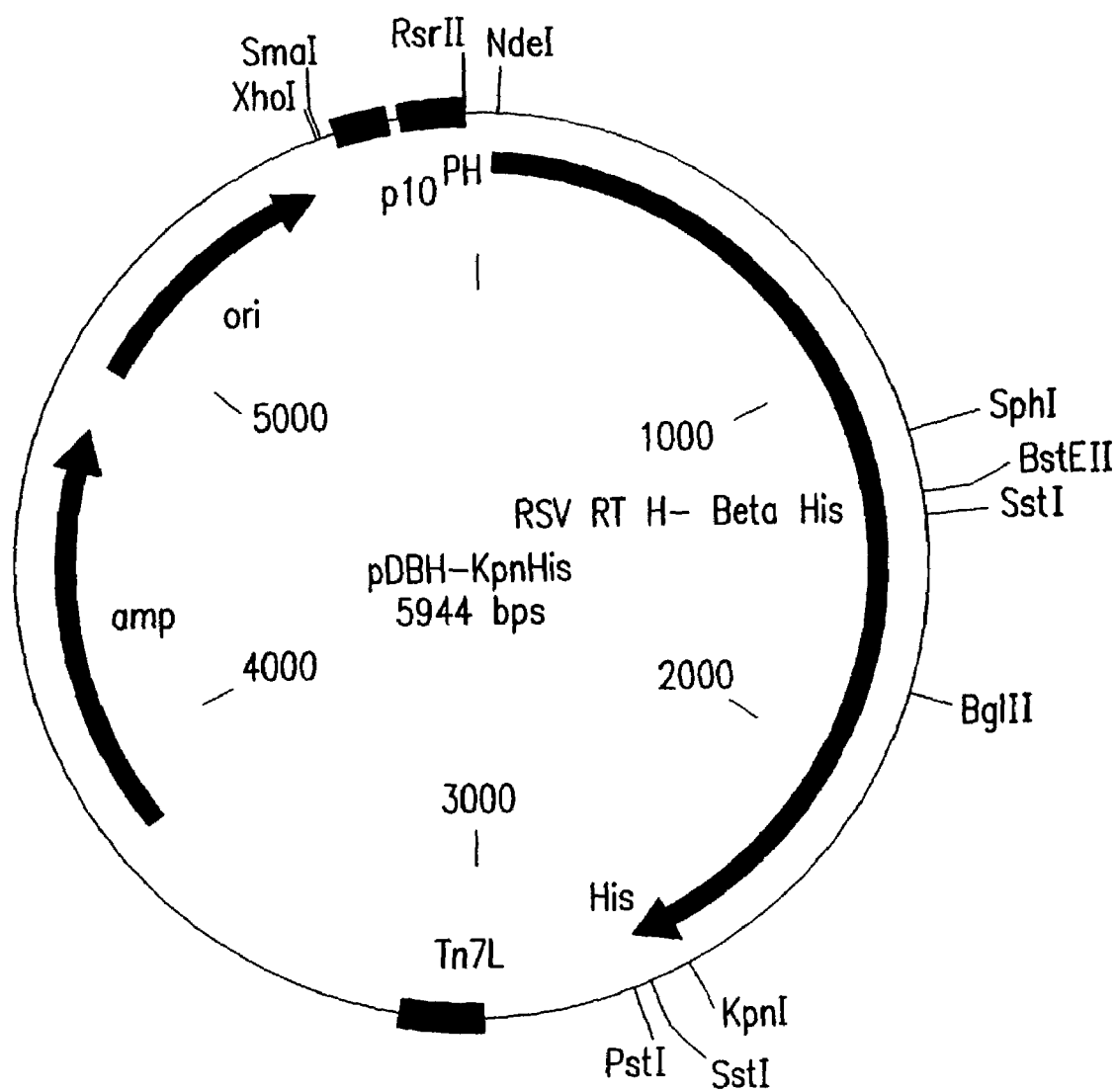

To remove the carboxy end of the RSV RT β gene and replace it with the carboxy end containing a His₆ tag, the number of KpnI sites in the baculovirus vector containing the RSV RT β gene had to be reduced. Plasmid pDBH- (FIG. 4) was cleaved with AflIII, and the site was "blunted" with the Klenow fragment of *E. coli* DNA polymerase I, the polymerase was inactivated by heat treatment, and the vector was further cleaved with PvuII (FIG. 4). The deleted vector (5.9 kb) was then purified by gel electrophoresis, ligated to itself and used to transform *E. coli* strain DH10B, forming pDBH-Kpn (FIGS. 4, 17). The KpnI-SstI fragment with the carboxy end of β with the HiS₆ tag was cloned from pAMPChis into the KpnI-SstI sites of pDBH-Kpn, forming pDBH-KpnHis (FIGS. 4, 18).

Cloning of RSV α and β subunits into a baculovirus expression vector. During the course of this work, a construct was made in which the RSV RT β gene was to be expressed in a baculovirus vector with a HiS₆ tag at the amino end. However, a mutation introduced during the construction caused the reading frame of the tag to be different from that of the β gene. Since portions of this construct were used to construct the final baculovirus expression vector, its construction is described here.

Figure 5:
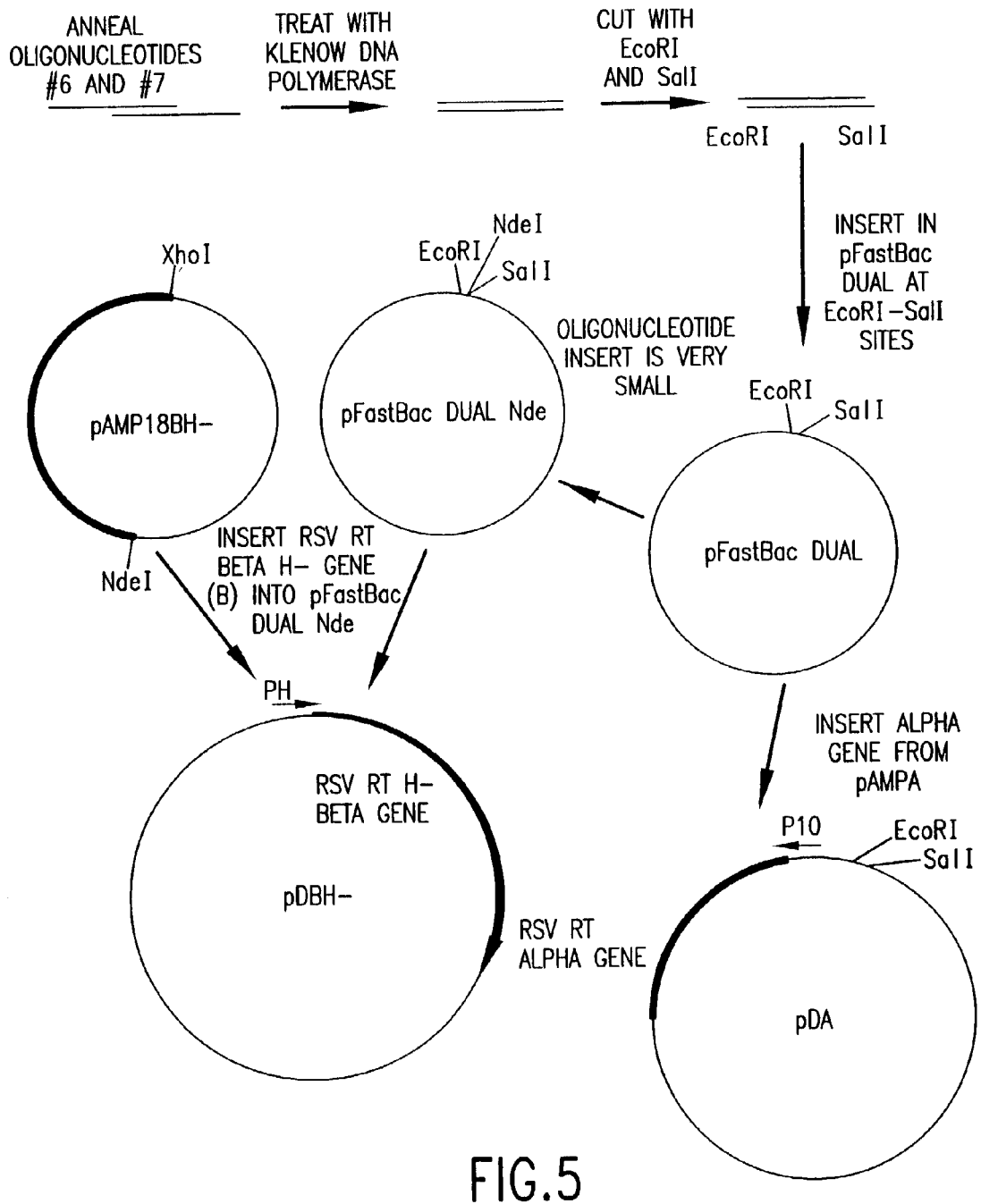

To introduce a HiS₆ tag and an NdeI site into the baculovirus vector, the following oligonucleotides were annealed and cloned into pFastBac Dual (Harris, R., and Polayes, D. A., *Focus* 19:6–8 (1997); FIG. 5):

```
ACTG GAA TTC ATG CCA ATC CAT CAC CAT CAC CAT CAC CCG T  (SEQ ID NO:10)

ACGT GTC GAC CAT ATG GAT GAC TAG GTG AAA CGG GTG ATG G  (SEQ ID NO:11)
```

Both oligonucleotides were formulated into TE buffer at a concentration of 100 μM, and 5 μl of each oligonucleotide formulation were mixed with 15 μl of water and 2 μl of 10× React2 buffer (500 mM NaCl, 500 mM Tris-HCl, 100 MM $MgCl_2$, pH 8.0) in a single tube. This tube was heated in a 65° C. water bath and cooled slowly over 60 minutes to 25° C. The resulting product was a double-stranded DNA molecule with an EcoRI site at the 5' end (underlined), and a SalI site at the 3' end (italicized):

```
5'-ACTG GAA TTC ATG CCA ATC CAT CAC CAT CAC CAT CAC   (SEQ ID NO:12)
CCG
TTT CAC CTA GTC ATC CAT ATG GTC GAC ACGT-3'
```

Figure 15:
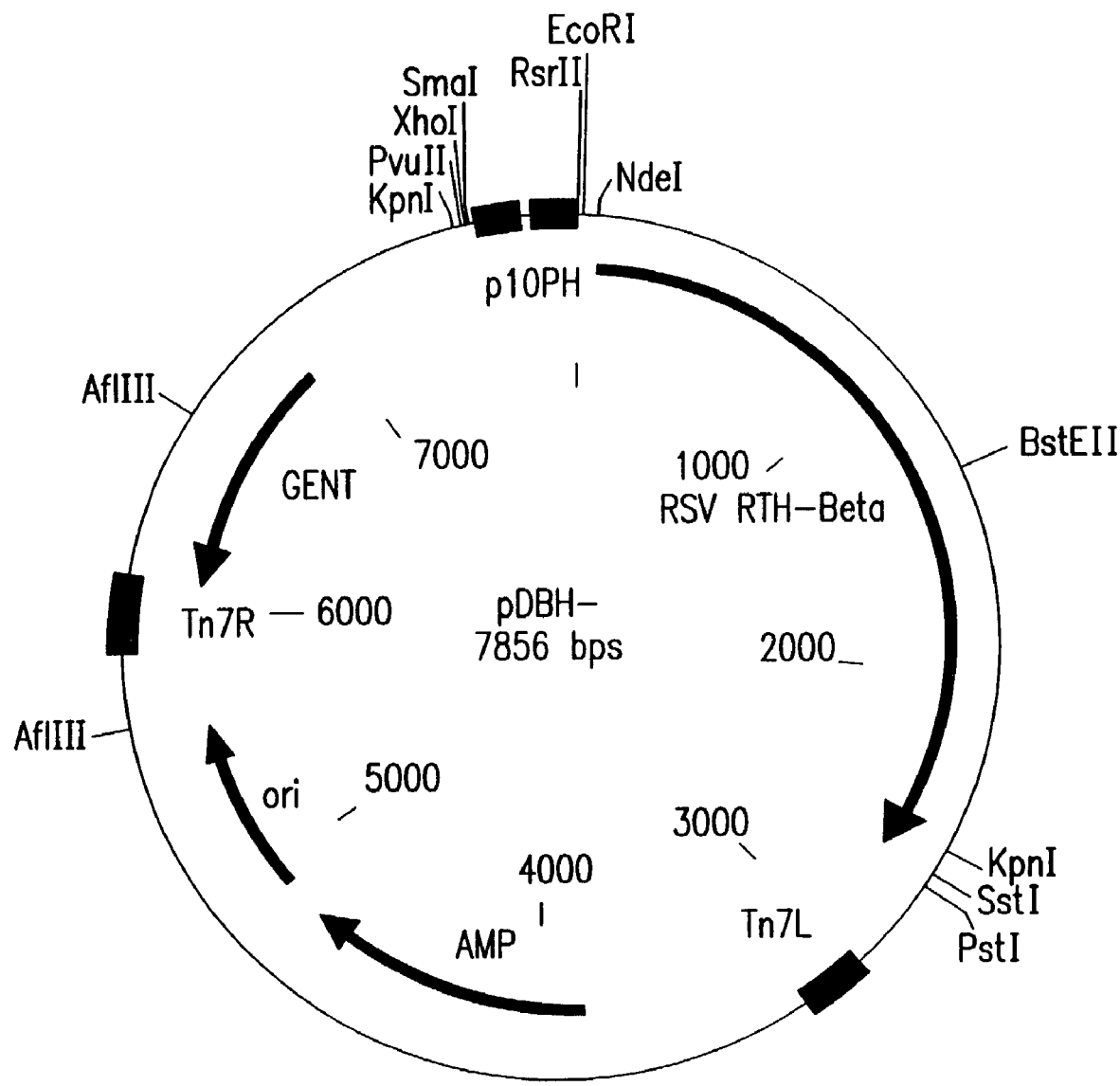

This product was cleaved with EcoRI and SalI and the desired fragment was cloned into the EcoRI-SalI sites of vector pFastBac Dual by standard techniques (Harris, R., and Polayes, D. A., Focus 19:6–8 (1997)), resulting in the formation of plasmid pFastBac Dual Nde (FIG. 5). The NdeI-AhoI B fragment of pAMP18BH⁻ was cloned into the NdeI-SalI sites of pFastBac Dual Nde to create pDBH⁻ (FIGS. 5, 15).

Figure 19:
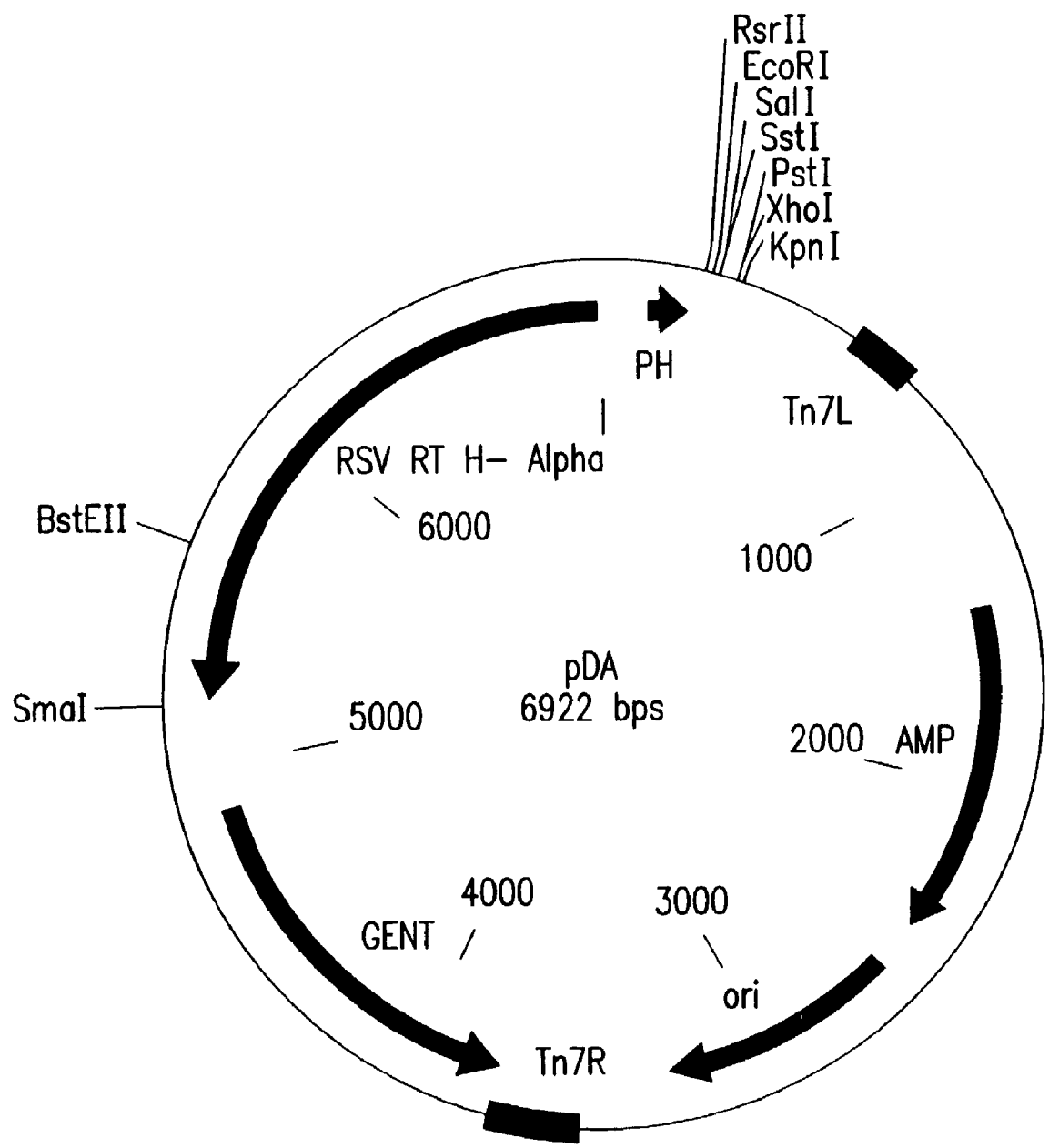
Figure 20:
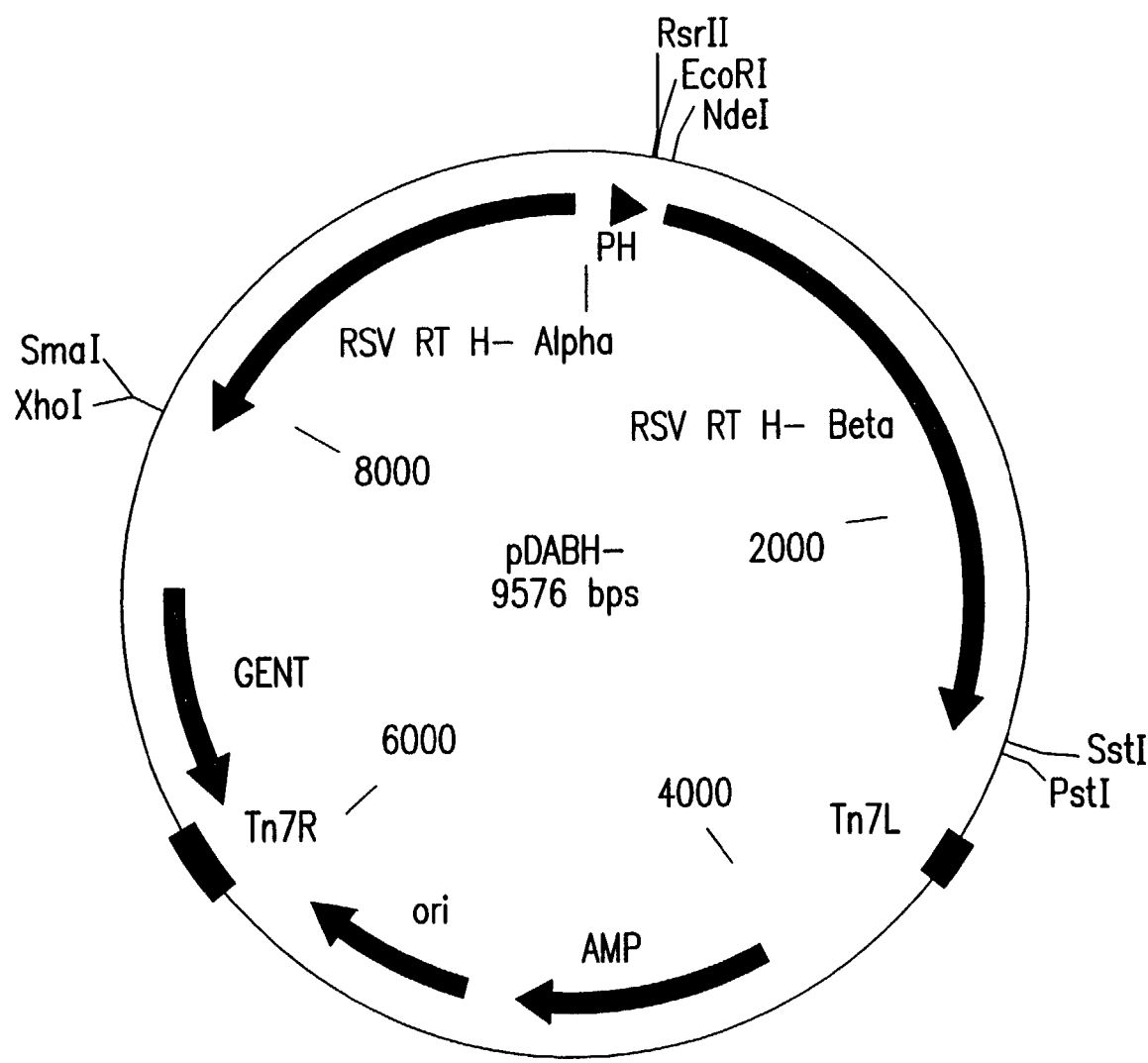

To clone the RSV RT α gene into a baculovirus vector, the α gene was excised from pAMP1A with SmaI and BspHI and subcloned into the NcoI-SmaI sites of pFastBac Dual, creating pDA (FIGS. 5, 19). This placed the RSV RT α gene downstream from the baculovirus P10 promoter. The RSV α peptide gene and P10 promoter were excised with RsrII and SmaI, and cloned into the RsrII-SmaI sites of pDBH-, forming pDABH- (FIGS. 4, 20).

Figure 6:
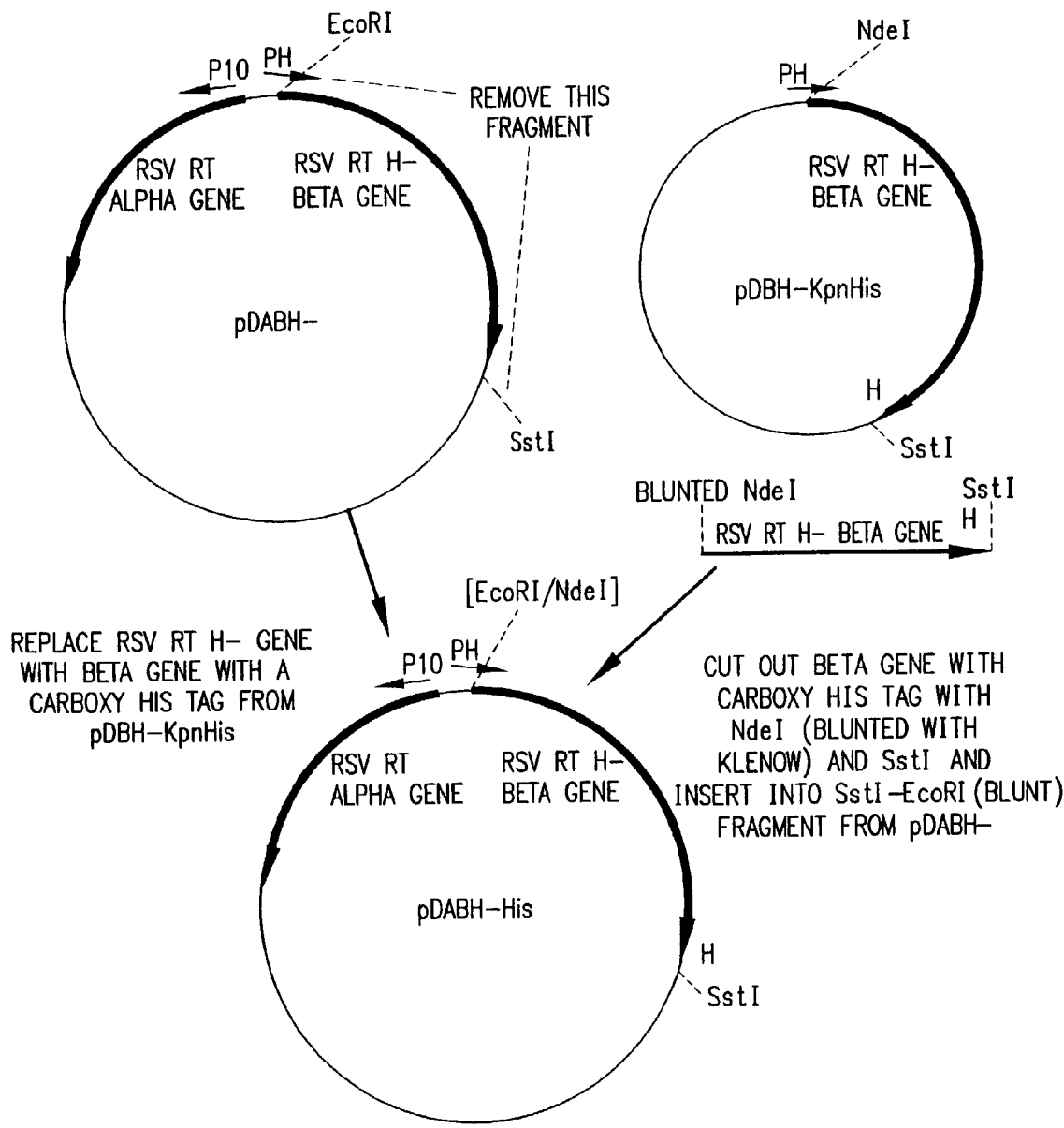
Figure 21:
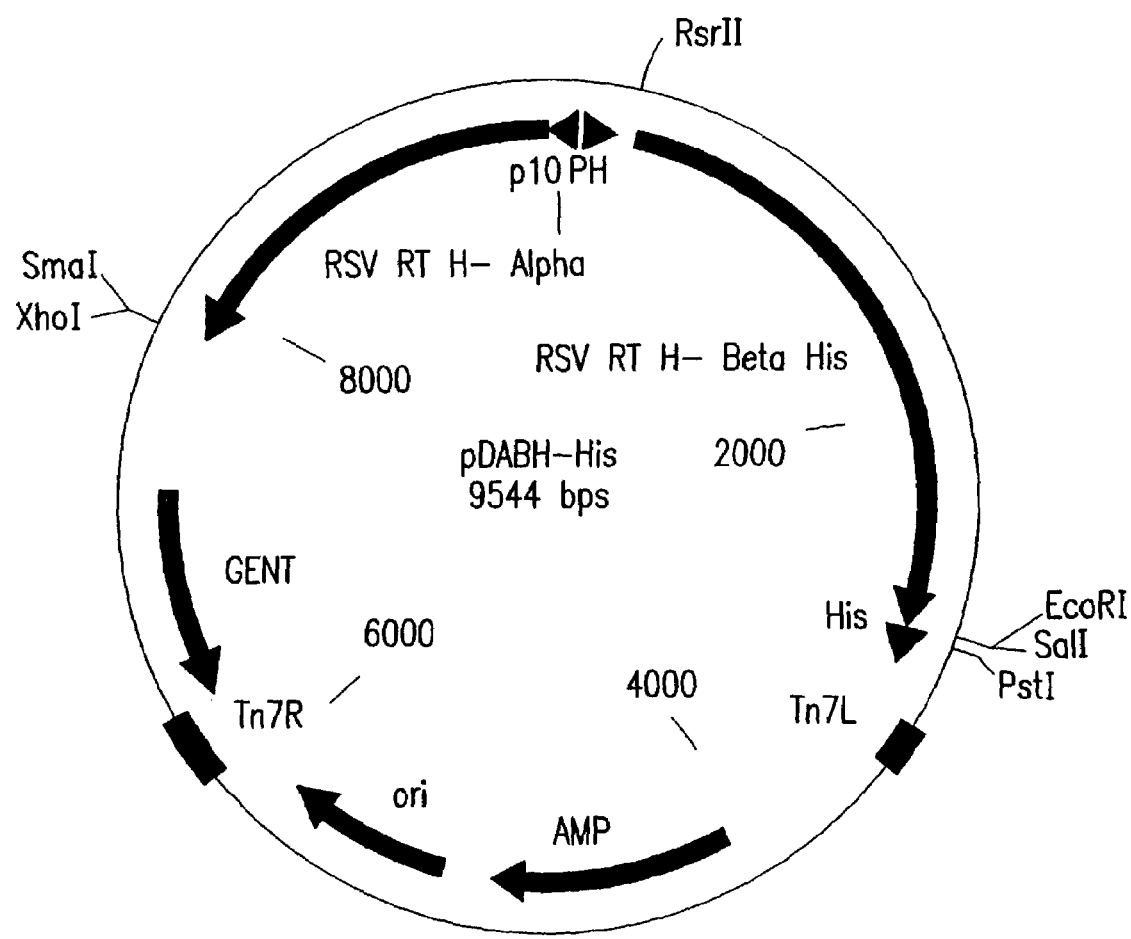

To replace the RSV RT β gene in pDABH- with the carboxy $His_6$-tagged β gene in pDBH-KpnHis, pDBH-KpnHis was cleaved with NdeI, the site blunt-ended with Klenow fragment, and the β gene with the carboxy $HiS_6$ tag was then released with SstI (FIG. 6). pDABH⁻ was cleaved with EcoRI, the site blunt-ended with Klenow fragment, and then the β gene was removed by digesting with SstI. The vector fragment, which was a blunt-end SstI fragment of pFastBac Dual with the α gene cloned in front of the p10 promoter, was ligated to the blunt-end SstI fragment with the carboxy His-tagged β gene from pDBH-KpnHis. E. coli DH10B cells were transformed with this construct, and a transformant containing pDABH-His (FIGS. 6, 21) was selected.

The recombinant host cell comprising plasmid pDABH-His, E. coli DH10B(pDABH-His), was deposited on Apr. 15, 1997, with the Collection, Agricultural Research Culture Collection (NRRL), 1815 North University Street, Peoria, Ill. 61604 USA, as Deposit No. NRRL B-21679.

Using the deposited plasmid, one of ordinary skill in the art may easily produce, using standard genetic engineering techniques (such as those for site-directed mutagenesis described above), plasmids encoding various forms of the α and/or β subunits of RSV RT (e.g., α RNase H⁺/β RNase H⁺; a RNase H⁻/β RNase H⁻; α RNase H⁺/β RNase H⁻; and α RNase H⁻/β RNase H⁺).

Transfection of insect cells for virus and RSV RT production. To prepare vectors for the transfection of insect cells, it was first necessary to insert the RSV RT gene constructs into a baculovirus genome. One method of accomplishing this insertion is by using the site-specific transposon Tn7 (Luckow, V. A., in: Recombinant DNA Technology and Applications, Prokop, A., et al, eds., New York: McGraw-Hill (1991)). In DH10Bac host cells, most of the baculovirus genome is represented on a low copy plasmid (a "bacmid") which also contains a Tn7 insertion site within a gene (Harris, R., and Polayes, D. A., Focus 19:6–8 (1997)). Transposition of Tn7 is facilitated by the Tn7 transposase, which is produced from a second plasmid in DH10Bac host cells, and pFastBac DUAL is constructed with the "right" and "left" regions of Tn7 flanking the promoter and cloning sites.

To insert the present constructs into a bacmid expression vector, pDABH-His was transformed into DH10Bac cells and transposition of sequences encoding the RSV RT β gene (whose synthesis is directed by the baculovirus polyhedrin promoter) and the RSV RT α gene (whose synthesis is directed by the baculovirus P10 promoter) was followed by screening for loss of β-galactosidase activity following transposition to the site on the bacmid which codes for the β-galactosidase α peptide (Harris, R., and Polayes, D. A., Focus 19:6–8 (1997)). Bacmid DNA was then prepared from 10 ml transformant cultures by a slight modification of a standard miniprep procedure (Sambrook, J., et al., Molecular Cloning: A Laboratory Manual, 2nd Ed., Cold Spring Harbor, N.Y.: Cold Spring Harbor Laboratory Press (1989)). About 1 μg of the bacmid DNA was then used to transfect Sf21 insect cells using the cationic lipid Cellfectin (Anderson, D., et al, Focus 16:53 (1995)).

For expansion of primary virus, the supernatant was removed from the transfected cells about 72 hours after transfection and 1 ml was used to infect 35 ml of Sf11 insect cells (about 1.2×10⁵ cells/ml). After 72 hours, the culture was centrifuged (2,000 rpm; 10 min) and the supernatant was decanted and used as a secondary viral stock. The secondary virus stock was expanded similarly by infecting 35 ml of S21 cells with 0.1 ml of the secondary stock.

Virus stocks were then used to infect Sf21 cells for the expression of RSV RT. In preliminary experiments, expression of RT activity from infected cells was found to be maximal about 72 hours after infection. For test expressions, 70 ml of Sf21 cells were infected with 5 ml of the virus stock, and the cells were harvested 72 hours after infection by centriflgation at 1,000 rpm for 5 minutes, resuspension in PBS (2.5% of the culture volume) and recentrifugation at 1,000 rpm for 5 minutes. Supernatants were removed and the cells were stored at −70° C. until use. For larger scale production, 600 ml of cells in 2.8 liter Fernbach flasks were infected with 2 ml of virus stock, and the cells were harvested 72 hours after infection.

EXAMPLE 2

Isolation of RSV RNase H⁻ RT

To provide purified recombinant RSV H⁻ RT, cloned RSV H⁻ RT was overexpressed in cultured insect cells as described in Example 1 and purified by affinity and ion-exchange chromatography. The RSV RT produced comprises the α and β subunits. Isolation of RSV RT provides a substantially pure RSV RT in which contaminating enzymes and other proteins have been substantially removed, although such contaminants need not be completely removed.

Buffers. The pH of all buffers was determined at 23° C., and buffers were stored at 4° C. until use. Crack Buffer contained 50 mM Tris-HCl (pH 7.9), 0.5 M KCl, 0.02% (v/v) Triton X-100 and 20% (v/v) glycerol. Just before use, the following protease inhibitors (Boehringer Mannheim; Indianapolis, Ind.) were added to Crack Buffer at the final concentrations indicated: leupeptin (2 µg/ml), Pefabloc (48 µg/ml), pepstatin A (2 µg/ml), benzamidine (800 µg/ml) and PMSF (50 µg/ml) Buffer A contained 20 mM Tris-HCl (pH 7.9), 0.25 M KCl, 0.02% (v/v) Triton X-100, and 10% (v/v) glycerol. Buffer B was Buffer A with 1 M imidazole added. Buffer S contained 50 mM Tris-HCl (pH 8.2), 0.02% (v/v) Triton X-100, 10% (v/v) glycerol, 0.1 mM EDTA and 1 mM dithiothreitol (DTT). Buffer T was Buffer S with 1 M KCl added. Buffer H contained 20 mM potassium phosphate (pH 7.1), 0.02% (v/v) Triton X-100, 20% (v/v) glycerol, 0.1 mM EDTA and 1 mM DTT. Buffer J was Buffer H with 1 M KCl added. Storage Buffer contained 200 mM potassium phosphate (pH 7.1), 0.05% (v/v) NP-40, 50% glycerol (v/v), 0.1 mM EDTA,1 mM DTT, and 10% (w/v) trehalose.

Extract preparation. Frozen insect cells (25 g) were thawed and a slurry prepared at 4° C. with 50 ml of Crack Buffer plus inhibitors. Cells were disrupted at 4° C. by sonication with a Fisher 550 Sonicator at 25% of maximum power. The disrupted crude extract was clarified by centrifugation at 27,000×g for 30 minutes at 4° C.

RSVR Tisolation. Following clarification, the extract was fractionated and RSV RT purified by column chromatography at 4° C. The clarified crude extract was loaded unto a 30 ml Chelating Sepharose Fast Flow column (Pharmacia; Piscataway, N.J.) charged with NiSO₄ as per manufacturer's instructions and equilibrated in 99.5% Buffer A+0.5% Buffer B. The column was washed with one column volume of 99% Buffer A+1% Buffer B and then with 10 column volumes of 98.5% Buffer A+1.5% Buffer B. RT was eluted with a 10-column volume linear gradient of 98.5% Buffer A+1.5% Buffer B to 75% Buffer A+25% Buffer B.

During purification, reverse transcriptase activity was assayed with poly(C)-oligo(dG), which is specific for reverse transcriptase (Gerard G. F., et al., *Biochemistry* 13:1632–1641 (1974)). RT unit activity was defined and assayed as described (Houts, G. E., et al., *J. Virol.* 29:517–522 (1979)). Using the poly(C)-oligo(dG) assay, the peak fractions of RT activity from the Chelating Sepharose Fast Flow column (10 to 17% Buffer B) were pooled, diluted with an equal volume of Buffer S, and loaded on a 5 ml AF-Heparin-650M column (TosoHaas; Montgomeryville, Pa.) equilibrated in Buffer S. After a wash with 12 column volumes of 90% Buffer S+10% Buffer T, the column was eluted with a 15-column volume linear gradient of Buffer S to 30% Buffer S+70% Buffer T. The peak fractions of RT activity (43 to 50% Buffer T) were pooled, diluted with 2.5 volumes of Buffer H, and loaded unto a Mono S HR 5/5 column (Pharmacia; Piscataway, N.J.) equilibrated in Buffer H. After a wash with 20 column volumes of 85% Buffer H+15% Buffer J, the column was eluted with a 20 column volume gradient of 85% Buffer H+15% Buffer J to 50% Buffer H+50% Buffer J. The RT peak fractions were pooled, dialyzed against Storage Buffer overnight, and stored at −20° C.

Following purification, RSV H⁻ RT was found to be >95% homogeneous as judged by SDS-PAGE. The purified enzyme was also found to be substantially lacking in RNase and DNase contamination, and substantially reduced in RNase H activity.

EXAMPLE 3

Preparation of Full-Length cDNA Molecules

Enzymes. SuperScript II RT (SS II RT), a cloned form of Moloney murine leukemia virus (M-MLV) RT lacking demonstrable RNase H activity (i.e., an "RNase H⁻ RT"), was from Life Technologies, Inc. (Rockville, Md.). M-MLV RT, a cloned murine RT with full RNase H activity (i.e., an "RNase H⁺ RT"), was also from Life Technologies, Inc. AMV RT, an RNase H⁺ uncloned form of avian myeloblastosis virus RT, was from Seikagaku America, Inc. RSV H⁻ RT was prepared as described in Examples 1 and 2. Recombinant Tth DNA polymerase, a cloned, thermophilic DNA polymerase from *Thermus thermophilus* with reverse transcriptase activity, was from Perkin Elmer.

Synthetic mRNA. A 7.5 kilobase (Kb) synthetic mRNA with a 120-nucleotide 3' poly(A) tail (Life Technologies, Inc.; Rockville, Md.) was used as template to test the efficiency of various enzymes alone or in combination.

cDNA Synthesis Reaction Mixtures. Reaction mixtures (20 µl each) contained the following components unless specified otherwise: 50 mM Tris-HCl (pH 8.4 at 24° C.), 75 mM KCl, 10 mM dithiothreitol, 1 mM each of [$^{32}$P]dCTP (300 cpm/pmole), dGTP, dTTP, and dATP, 25 µg/ml (p(dT)$_{25-30}$), 125 µg/ml of 7.5 Kb mRNA, and 35 units of cloned rat RNase inhibitor. Reaction mixtures with RTs alone or in combination contained the following:

| | |
|---|---|
| SS II RT alone: | 0.5 mM dNTPs, 3 mM MgCl₂, and 200 units of SS II RT |
| RSV H⁻ RT alone: | 7.5 mM MgCl₂ and 7 units of RSV H⁻ RT; |
| AMV RT alone: | 50 mM KCl, 10 mM MgCl₂, 4 mM sodium pyrophosphate and 14 units of AMV RT |
| SS II RT plus RSV H⁻ RT: | 5 mM MgCl₂, 200 units of SS II RT, and 7 units of RSV H⁻ RT; |
| Tth DNA Polymerase alone: | 0.5 mM dNTPs, 1 mM MnCl₂ and 5 units of Tth DNA Polymerase |
| M-MLV H⁺ RT alone: | 0.5 mM dNTPs, 3 mM MgCl₂, 50 µg/ml actinomycin D and 200 units of M-MLV H⁺ RT |
| Tth DNA Polymerase plus either SS II RT or RSV H⁻ RT: | same as Tth DNA Polymerase alone, plus either 200 units of SS II RT or 7 units of RSV H⁻ RT |
| M-MLV H⁺ RT plus SS II RT: | same as M-MLV H⁺ RT alone, plus 200 units of SS II RT; |
| M-MLV H⁺ plus either AMV RT or RSV H⁻ RT: | 5 mM MgCl₂, 50 µg/ml actinomycin D, 200 units of M-MLV H⁺ RT, and either 14 units of AMV RT or 7 units of RSV H⁻ RT |
| AMV RT plus either SS II RT or RSV H⁻ RT: | 5 mM MgCl₂, 50 µg/ml actinomycin D, 14 units of AMV RT, and either 200 units of SS II RT or 7 units of RSV H⁻ RT |

When RTs were used in combination, one enzyme was added first followed immediately by the addition of an aliquot of the second enzyme. In some cases in which a single enzyme was used, a second aliquot of the same enzyme was added as a control to assess the effect of doubling the amount of the single enzyme.

All cDNA synthesis reactions were carried out at 45° C. for 50 minutes, and the resultant cDNA product was detectably labeled by the RT-catalyzed incorporation of a $^{32}$P-labeled deoxyribonucleoside triphosphate precursor. The total yield of cDNA was determined by acid precipitation of a portion of the cDNA product and counting it in a scintillation counter. The $^{32}$P-labeled cDNA product in the remainder of the reaction mixture was fractionated by alkaline agarose gel electrophoresis (Carmichael, G. G., and McMaster, G. K., *Meth. Enzymol.* 65:380–385 (1980)). The gel was dried and the size distribution of the cDNA product was established by autoradiography. Using the autoradiographic film as a template, the dried gel was cut and analyzed by scintillation counting to establish the fraction of full length (7.5 Kb) product synthesized.

Tables 1 and 2 show the total amount of cDNA synthesized and full length cDNA synthesized, respectively, from the 7.5 Kb mRNA by enzymes alone or in combination. The following conclusions can be drawn:

1. When RTs were present alone, the highest yields of total and full length product were obtained with the RNase H⁻ forms of RT. With either RSV H⁻ RT or SS II RT, the total yield was almost double the highest yield obtained with an RNase H⁺ enzyme (1011 and 946 ng, respectively, versus 607 ng). The effect of removing RNase H from the reaction was even more dramatic when full length yields were examined. In this case, yields were at least tripled (234 and 208 ng for RSV H⁻ and SS II RT versus 79 and 26 for M-MLV H⁺RT and AMV RT, respectively). These results demonstrate the dramatic positive effect of eliminating RNase H from RT.

2. When RTs were combined, several effects were observed. Mixing RTs from different sources, whether RNase H⁻ or RNase H⁺, increased total and full length yields. This is consistent with the hypothesis that pausing at sites unique to one enzyme can be reduced by a second RT with a different set of pause sites. However, by far the greatest yields of total and full length cDNA product were obtained when two different RNase H⁻ RTs were combined (see shaded boxes in Tables 1 and 2). These results indicate that the two RNase H⁻ enzymes cooperate to synthesize full-length cDNA molecules: the first enzyme synthesizes truncated cDNA molecules, which are then extended to full-length via the activity of the second enzyme. Thus, the compositions and methods of the present invention facilitate the synthesis of full-length cDNA molecules.

TABLE 1

Total Yield of cDNA Synthesized by Various Enzymes from 7.5-Kb mRNA[1]

|  |  | Enzyme Added First | | | | |
|---|---|---|---|---|---|---|
|  |  | RSV H⁻ RT | SS II RT | M-MLV H⁺ RT | AMV RT | Tth DNA Polymerase |
| Enzyme Added Second | (None) | 1,011 | 946 | 607 | 316 | 297 |
|  | RSV H⁻RT | 952 | 1,286 | 802 | 479 | —[2] |
|  | SS II RT | 1,362 | 1,046 | 751 | 827 | — |
|  | M-MLV H⁺ RT | 848 | 621 | 599 | 867 | — |
|  | AMV RT | 533 | 922 | 802 | 353 | — |
|  | Tth DNA Polymerase | 218 | 996 | — | — | — |

[1]Mass (ng) of total cDNA product
[2]not tested

TABLE 2

Yield of Full Length cDNA Synthesized by Various Enzymes from 7.5 Kb mRNA[1]

|  |  | Enzyme Added First | | | | |
|---|---|---|---|---|---|---|
|  |  | RSV H⁻ RT | SS II RT | M-MLV H⁺ RT | AMV RT | Tth DNA Polymerase |
| Enzyme Added Second | (None) | 234 | 208 | 79 | 26 | <1 |
|  | RSV H⁻RT | 211 | 258 | 128 | 71 | —[2] |
|  | SS II RT | 290 | 229 | 105 | 141 | — |
|  | M-MLV H⁺ RT | 128 | 79 | 69 | 96 | — |
|  | AMV RT | 83 | 148 | 100 | 38 | — |
|  | Tth DNA Polymerase | 5 | 176 | — | — | — |

[1]Mass (ng) of full-length (7.5 kb) cDNA product
[2]not tested

In the mixing experiments summarized in Tables 1 and 2, two reverse transcriptases were added simultaneously to a reaction under conditions that may have been suboptimal for a single given RT. This was the case when an avian and a murine RT were used together, since the MgCl$_2$ concentration was set at 5 mM, between the optima of 3 mM and 7.5 mM for murine and avian RT, respectively. In addition, full advantage could not be taken in these experiments of the thermal stability of avian RNase H⁻ RT in reactions containing a less thermostable murine RT.

To use multiple enzymes and to address the fact that different enzymes may have different optimal conditions, sequential additions or separate use of the enzyme may be done in accordance with the methods of the invention. For example, cDNA could be synthesized from different aliquots of the same RNA in separate reaction tubes with different RTs under reaction conditions optimal for each RT. Subsequently, the cDNAs from each reaction could be mixed before performing further manipulations. Alternatively, RTs could be used singly and sequentially in one tube to perform cDNA synthesis. That is, SuperScript II could be used first to copy an RNA population under optimal reaction conditions, and then conditions could be adjusted to optimal for RSV H⁻ RT in the same tube, and further synthesis could be performed with the avian RT at elevated temperature.

EXAMPLE 4

Cloning and Expression of Avian Myeloblastosis Virus (AMV) RT and AMV RNase H⁻ (AMV H⁻) RT General Methods The AMV RT of the present invention is a cloned form of avian retrovirus RT. The AMV H⁻ RT is a variant of cloned AMV RT in which both the α and the β subunits are mutated by a single amino acid change to eliminate RNase H activity, although AMV RT substantially reduced in RNase H activity is also produced by mutating the α subunit alone (the β subunit not containing a mutation in the RNase H domain). Mutations and plasmid constructions were conducted using standard molecular biology methods (see, e.g., Sambrook, J., et al., *Molecular Cloning: A Laboratory Manual,* 2nd Ed., Cold Spring Harbor, N.Y.: Laboratory Press (1989)), modified as described below. Plasmid preparation, PCR, gel electrophoresis, DNA fragment isolation and cloning, insect cell culture and baculovirus production were all performed as described for RSV RT cloning and expression in Example 1.

Cloning and Expression of Genes Encoding the AMV RT α and β Subunits

Figure 22:
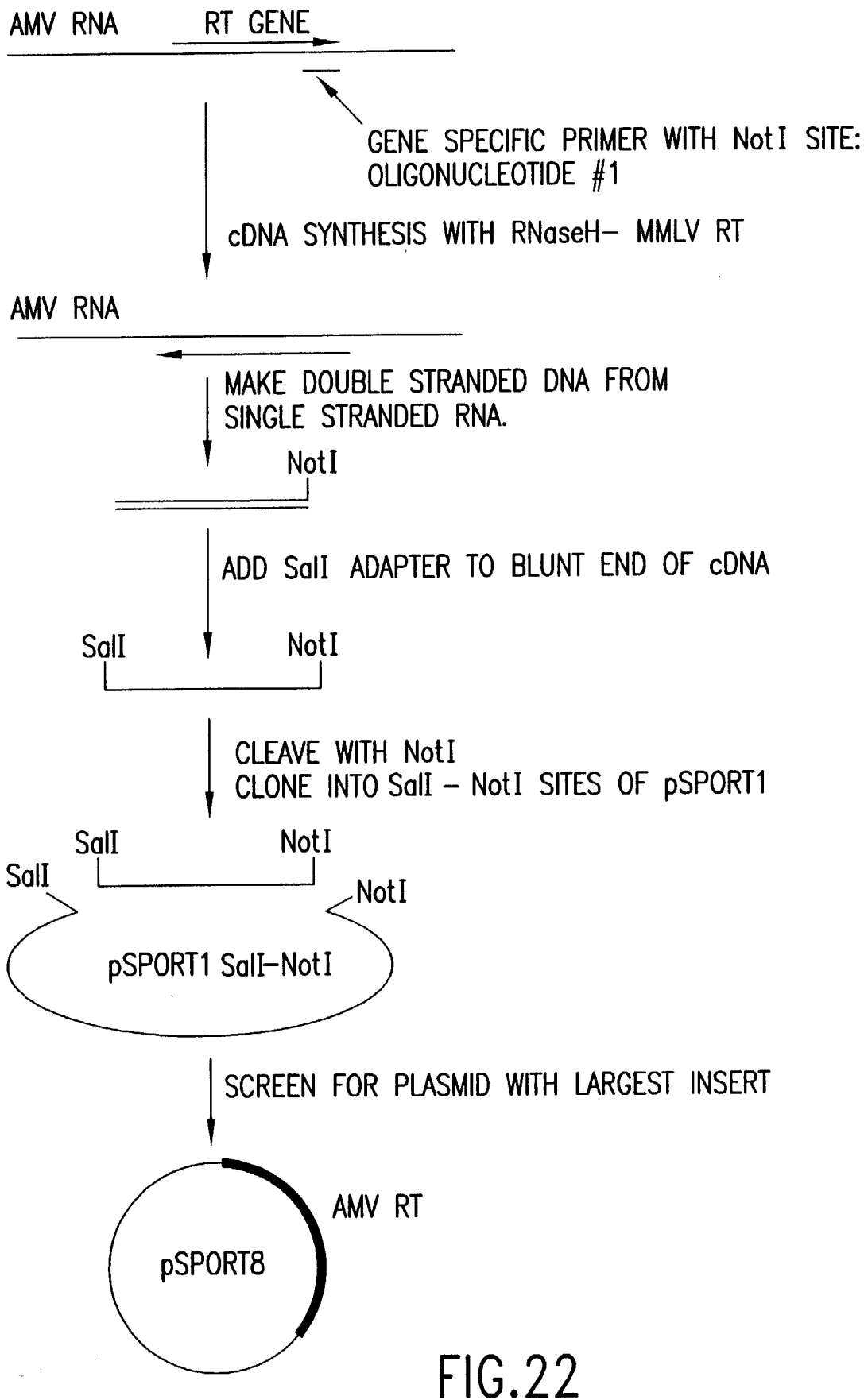

To clone AMV RT, AMv viral RNA was prepared (Strauss, E. M., et al., *J. Virol. Meth.* 1:213 (1980)) from purified (Grandgenett, D. P., et al., *Appl. Microbiol.* 26:452 (1973)) AMV obtained from Life Sciences (St. Petersburg, Fla.). AMV RT cDNA was prepared from AMV viral RNA with the SuperScript Plasmid System for cDNA Synthesis and Plasmid Cloning (Life Technologies, Inc.; Rockville, Md.) following the instructions in the kit manual. A primer specific for AMV RT was used that adds a NotI site to the cDNA. Following preparation, AMV RT cDNA was cloned into pSPORT1 that had been treated with SalI and NotI, resulting in a vector (pSPORT8) comprising the AMV RT gene (FIG. 22).

Both the α and β subunits of AMV RT are produced by proteolytic processing of larger polypeptide precursors (Gerard, G. F., in: *Enzymes of Nucleic Acid Synthesis and Modification, Vol. I: DNA Enzymes,* Jacob, S. T., ed., Boca Raton, Fla.: CRC Press, pp. 1–38 (1983)). To obviate the requirement for proteolytic processing, the coding sequence for AMV RT was mutagenized and subcloned such that both the α and β subunits were encoded by genes with standard start and stop translational signals. To make RNase H⁻ constructs, both α and β genes were mutagenized in the RNase H region, although construction of any combination of subunits (e.g., α RNase H⁻/β RNase H⁺; α RNase H⁺/β RNase H⁺; α RNase H⁻/β RNase H⁻; a RNase H⁻/β RNase H⁻) may be accomplished in this same manner. It has been discovered that AMV RT α RNase H⁻/β RNase H⁺ is substantially reduced in RNase H activity (approximately 5% of wildtype). A sequence encoding an affinity tag was added to the carboxy end of the β subunit.

Synthesis of cDNA from AMV RNA. The AMV RNA was copied into DNA using a 3' primer which is complementary to the 3' end of the AMV RT gene, and which adds a NotI site to the 3' end of the gene (FIG. 22). The 5' end of the resulting cDNA was made into a SalI end by the addition of a SalI adapter. This cDNA was then cloned into a SalI-NotI cleaved vector (pSPORT1). First strand cDNA was synthesized using Superscript II RT (Gerard, G. F., et al., *FOCUS* 11:66 (1989)) and a gene specific primer (Oligonucleotide #1) instead of the NotI primer-adapter:

```
Oligonucleotide #1:
5'GACTAGTTCTAGATCGCGAGCGGCCGCCCATTAACTCTCGTTGG    (SEQ ID NO:13)
CAGC 3'
```

The second strand synthesis was achieved using DNA polymerase I in combination with *E. coli* RNase H and DNA ligase at 16° C. and subsequently polishing the termini with T4 DNA polymerase. The cDNA was deproteinized and precipitated with ethanol, and SalI adapters consisting of Oligonucleotides #2 and #3 were ligated to the cDNA:

```
Oligonucleotide #2:
5'TCGACCCACGCGTCCG 3'          (SEQ ID NO: 14)

Oligonucleotide #3:
5'CGGACGCGTGGG 3'              (SEQ ID NO: 15)
```

The addition of the adapters was followed by digestion with NotI. Size fractionation of the cDNA was done on 1 ml prepacked columns provided with the cDNA cloning kit. The amount of cDNA in each fraction was calculated from the specific activity of incorporated $^{32}$P label, and the size of the cDNA was determined by autoradiography of an agarose gel. Those fractions that were greater than 3 Kb were selected for cloning.

Cloning AMV cDNA into a Vector. The cDNA was ligated into SalI-NotI cleaved pSPORT1 vector and then the ligated cDNA was used to transform *E. coli* MAX EFFICIENCY DH10B™ competent cells (Life Technologies, Inc., Rockville, Md.). After transformation, aliquots of cells were plated on LB plates containing ampicillin. Twelve colonies were picked and 1 ml cultures were grown for mini-preps. Gels were run to check for certain fragments after digesting with restriction enzymes SalI, MluI, PstI, ApaI, DraIII, SphI and Bg/II. One plasmid, pSPORT8, was selected since the insert was large enough to code for the AMV RT gene (3 Kb) and a PstI site was present which indicated that the 5' terminus of the AMV RT gene was present (FIG. 22).

Mutagenesis and subcloning of the amino end, the carboxy end and the middle of the AMV RT β subunit. The AMV RT gene was mutagenized to add an ATG codon and an EcoRI site to the amino end of the sequence coding for the mature RT polypeptide by PCR with pSPORT8 as the target and the following oligonucleotides:

Oligonucleotide #4:
5'AUG GAG AUC UCU GAA TTC ATG ACT GTT GCG CTA CAT CTG  (SEQ ID NO:16)
GCT 3'

Oligonucleotide #5:
5'AAC GCG UAC UAG U GTT AAC AGC GCG CAA ATC ATG CAG 3'  (SEQ ID NO:2)

Figure 23A:
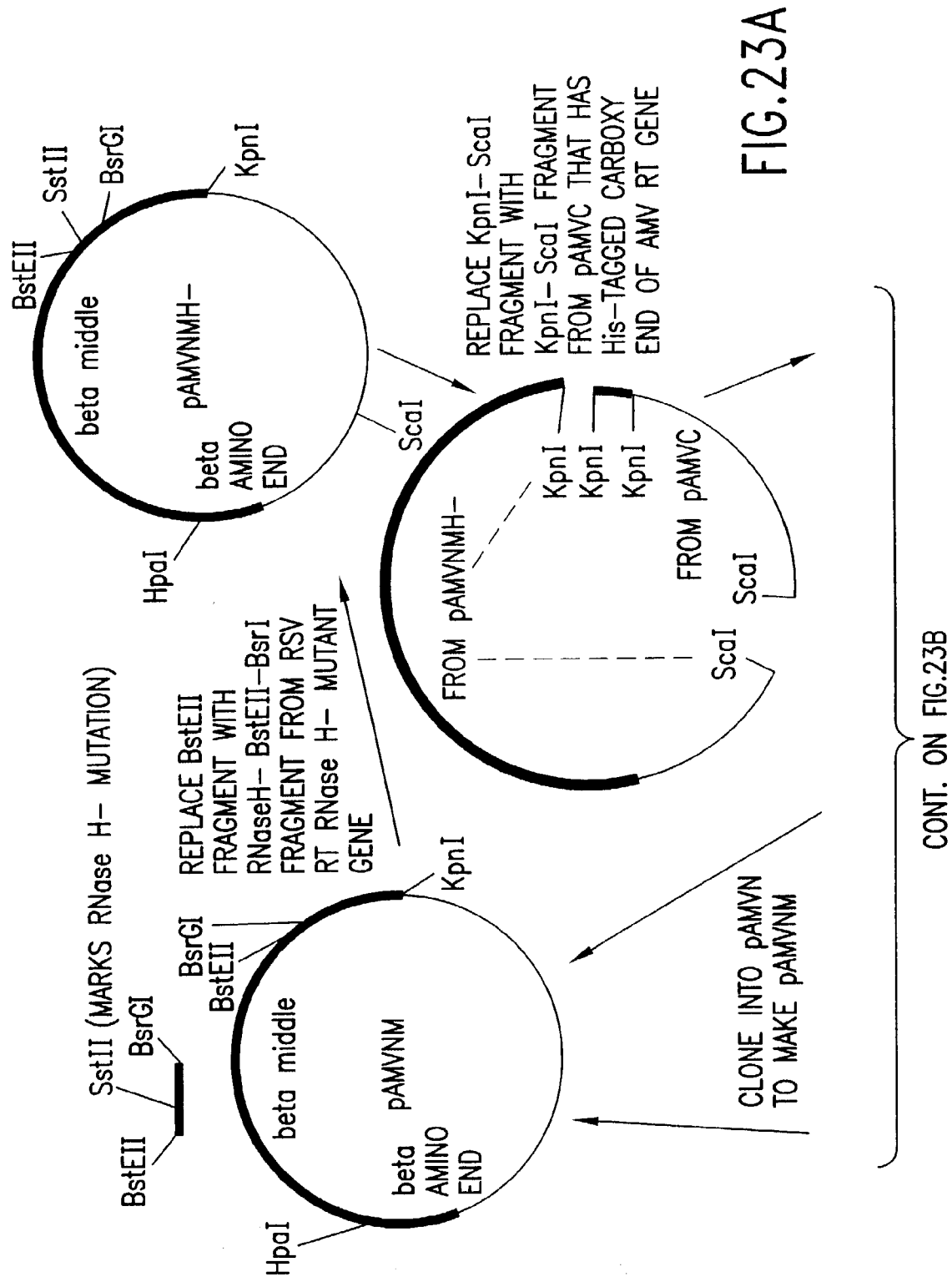
FIGS. 23A and 23B: Construction of a His-tagged AMV RT β gene; pAMVN, pAMVNM, pAMVNMH-, pAMVC and pAMVBH-.
Figure 23B:
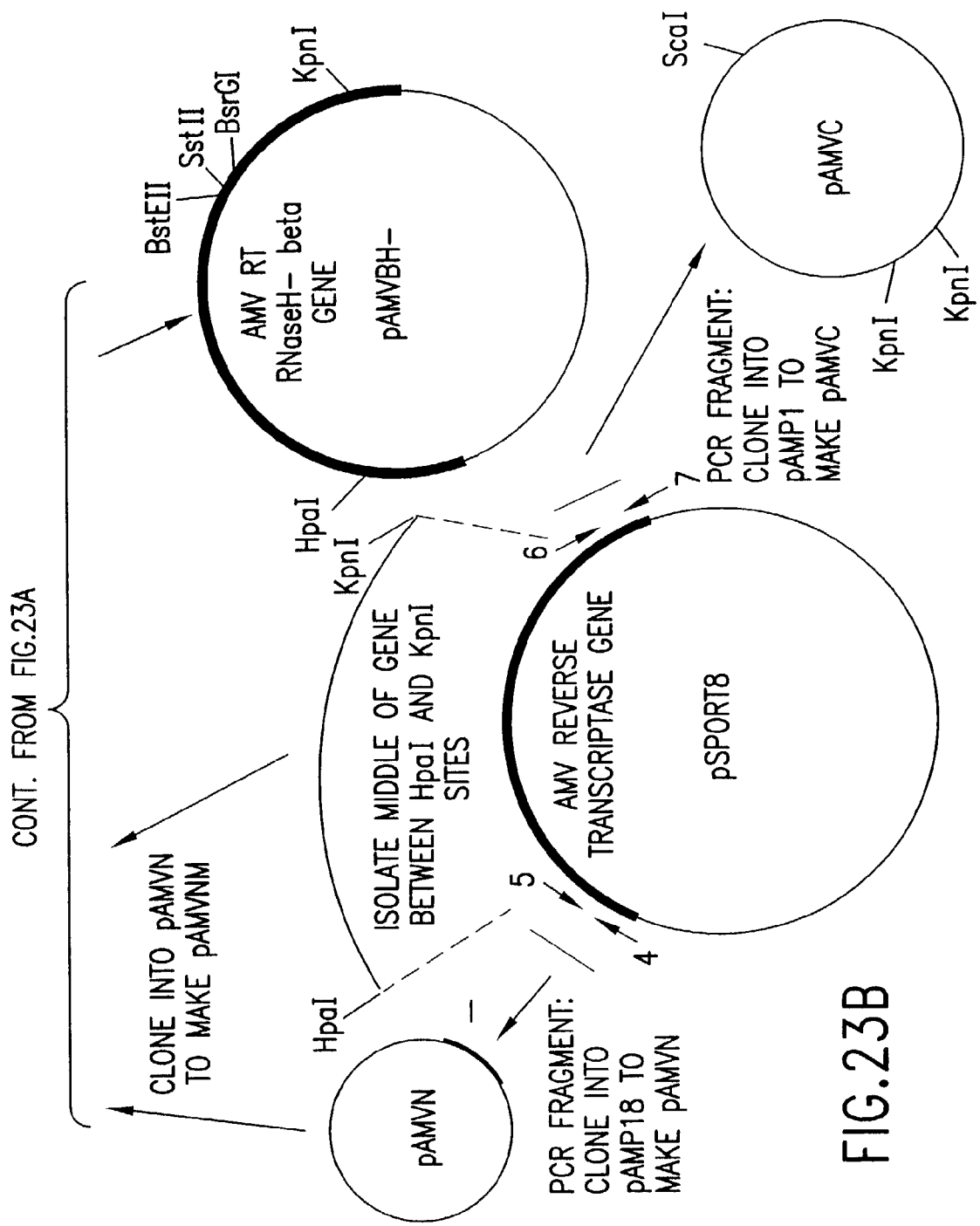
Figure 26:
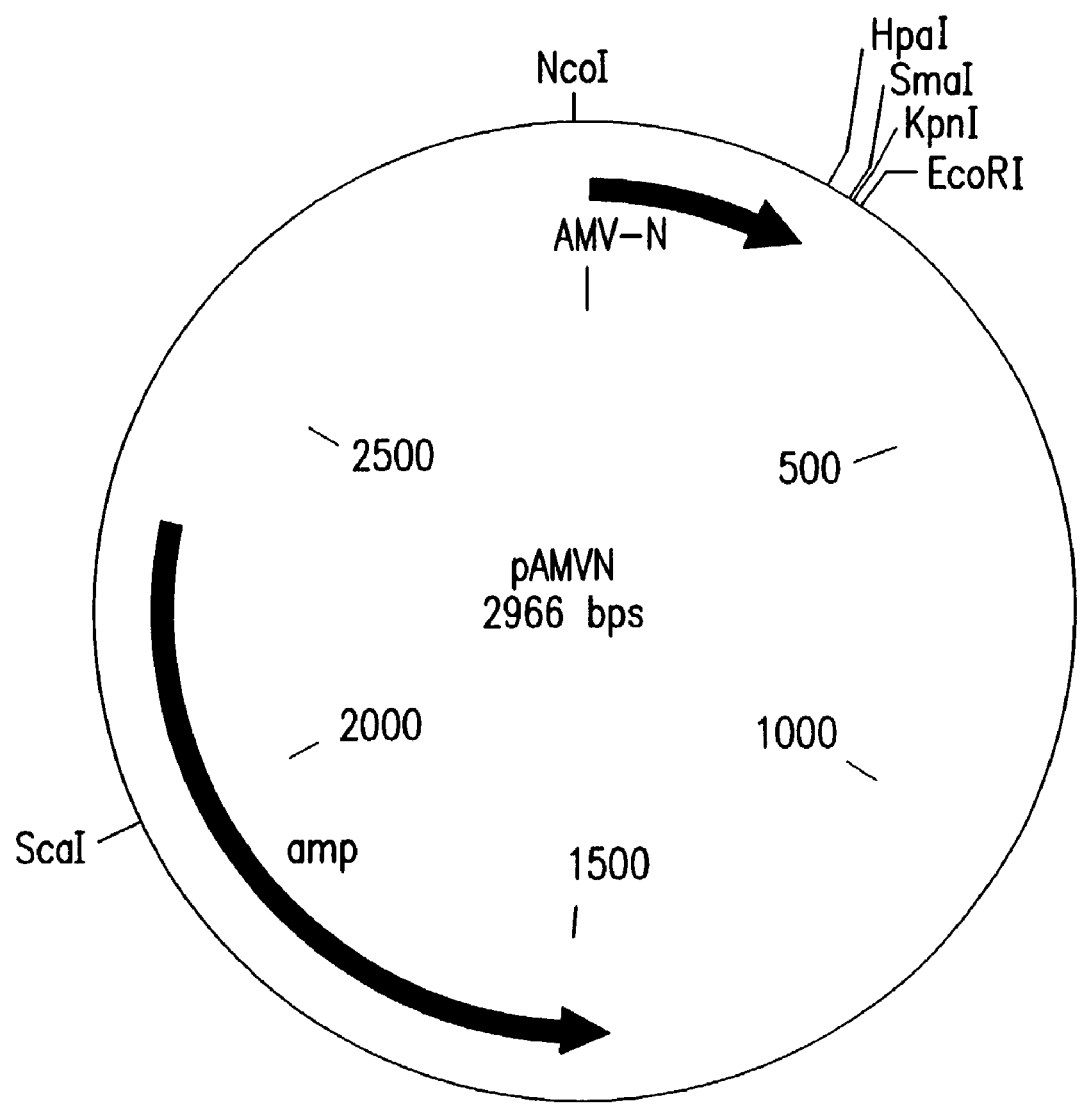
FIGS. 26–38 are more detailed maps of the plasmids described in FIGS. 22–25.

PCR was performed, and PCR products purified, as described above. The PCR reaction was treated with DpnI to destroy the target and the PCR product was cloned into pAMP18 by UDG cloning (Buchman, G. W., et al., *Focus* 15:36 (1993)), forming plasmid pAMVN (FIGS. 23, 26).

Following mutagenesis and cloning of the amino end, a $His_6$ affinity tag, a XhoI site and a translational stop codon were added to the carboxy end of the gene for the β subunit of AMV RT in pSPORT8 by PCR using the following oligonucleotides:

Oligonucleotide #6:
5' CUA CUA CUA CUA GGT ACC CTC TCG AAA AGT TAA ACC 3'  (SEQ ID NO:3)

Oligonucleotide #7:
5' CAU CAU CAU CAU GAG GAA TTC AGT GAT GGT GAT GGT GAT  (SEQ ID NO:9)
GTG CAA A AAG AGG 3'

Figure 27:
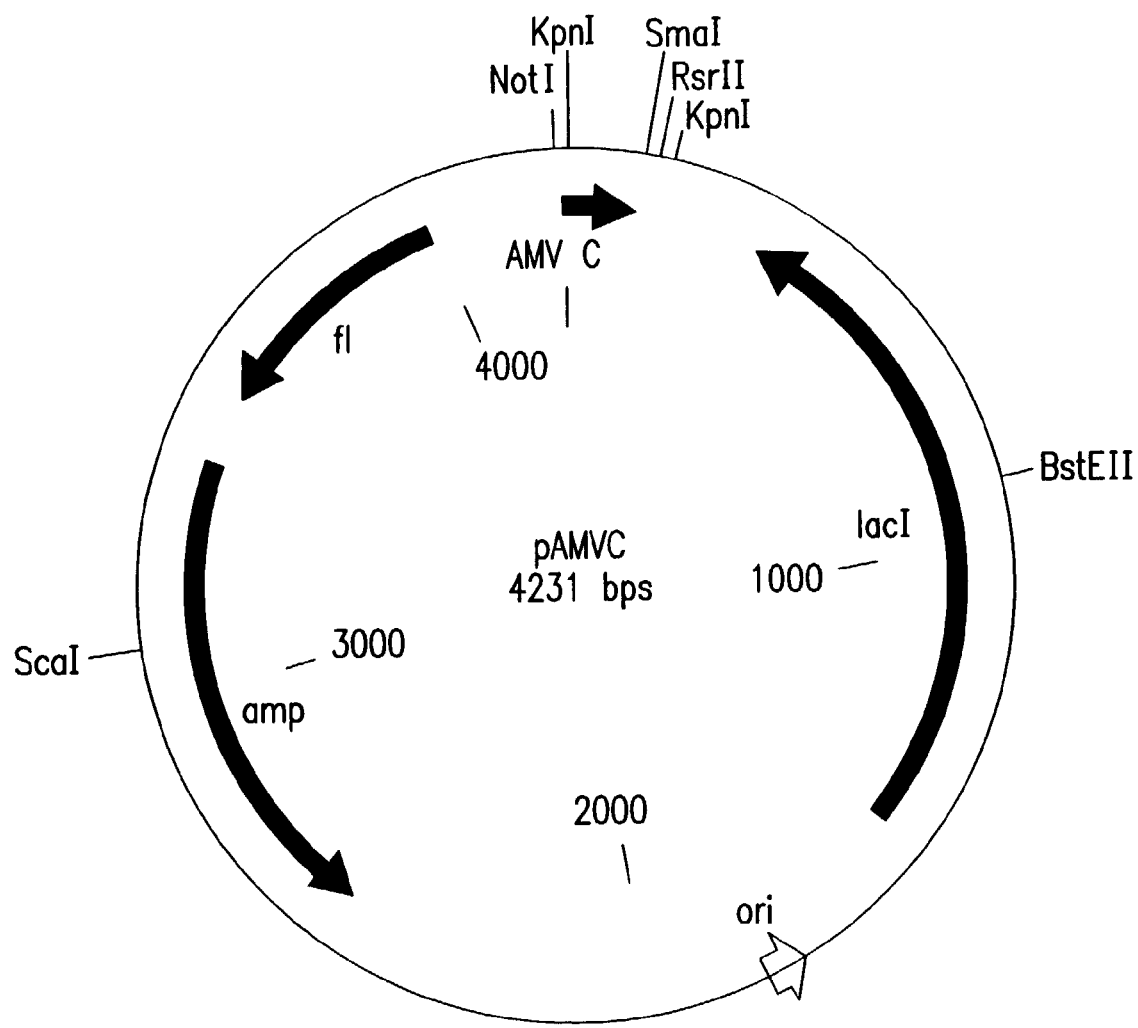

PCR was performed, and PCR products purified, as described above. The PCR reaction was treated with DpnI to destroy the target and the PCR product was cloned into pAMP18 by UDG cloning (Buchman, G. W., et al., *Focus* 15:36 (1993), forming plasmid pAMVC (FIGS. 23, 27).

Figure 28:
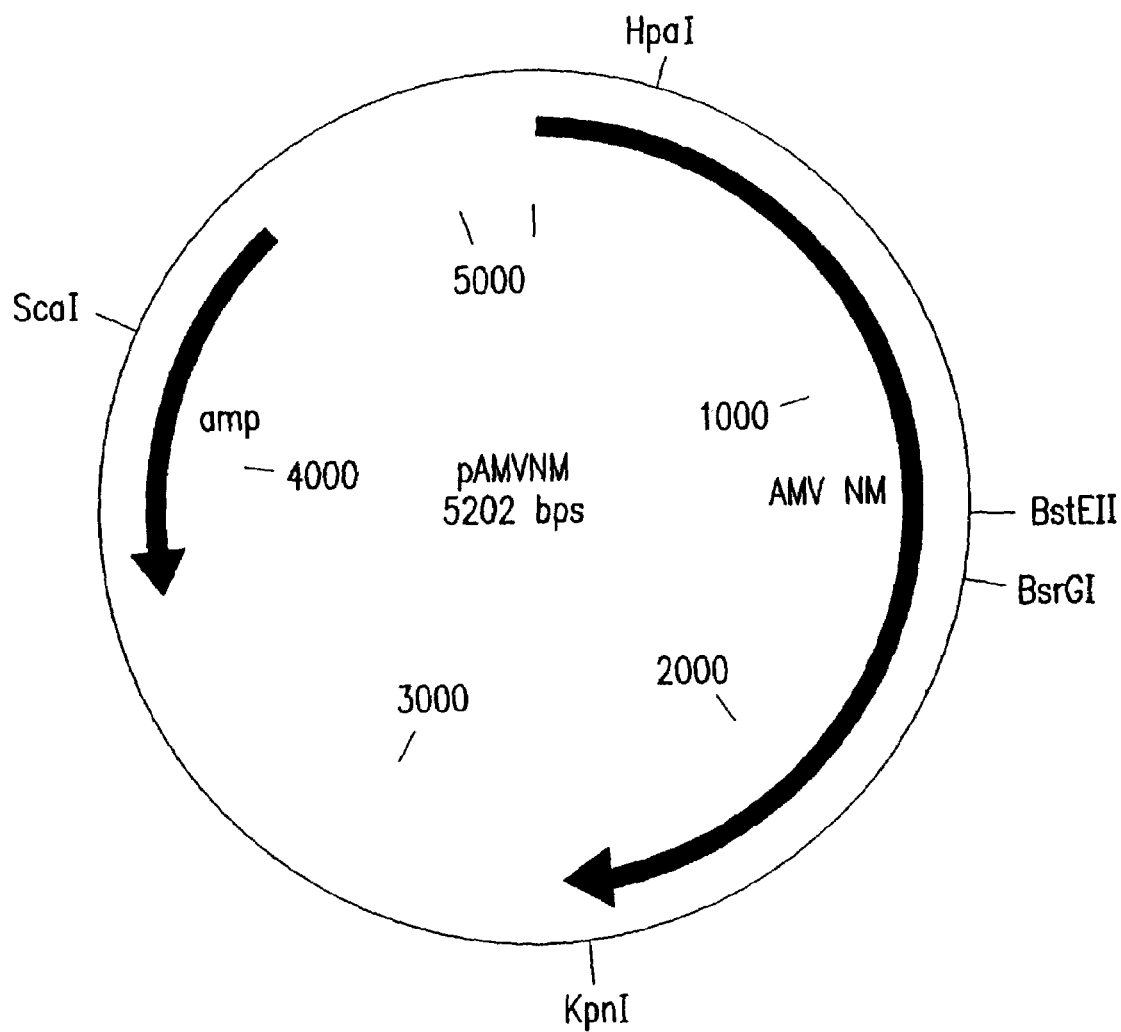
Figure 29:
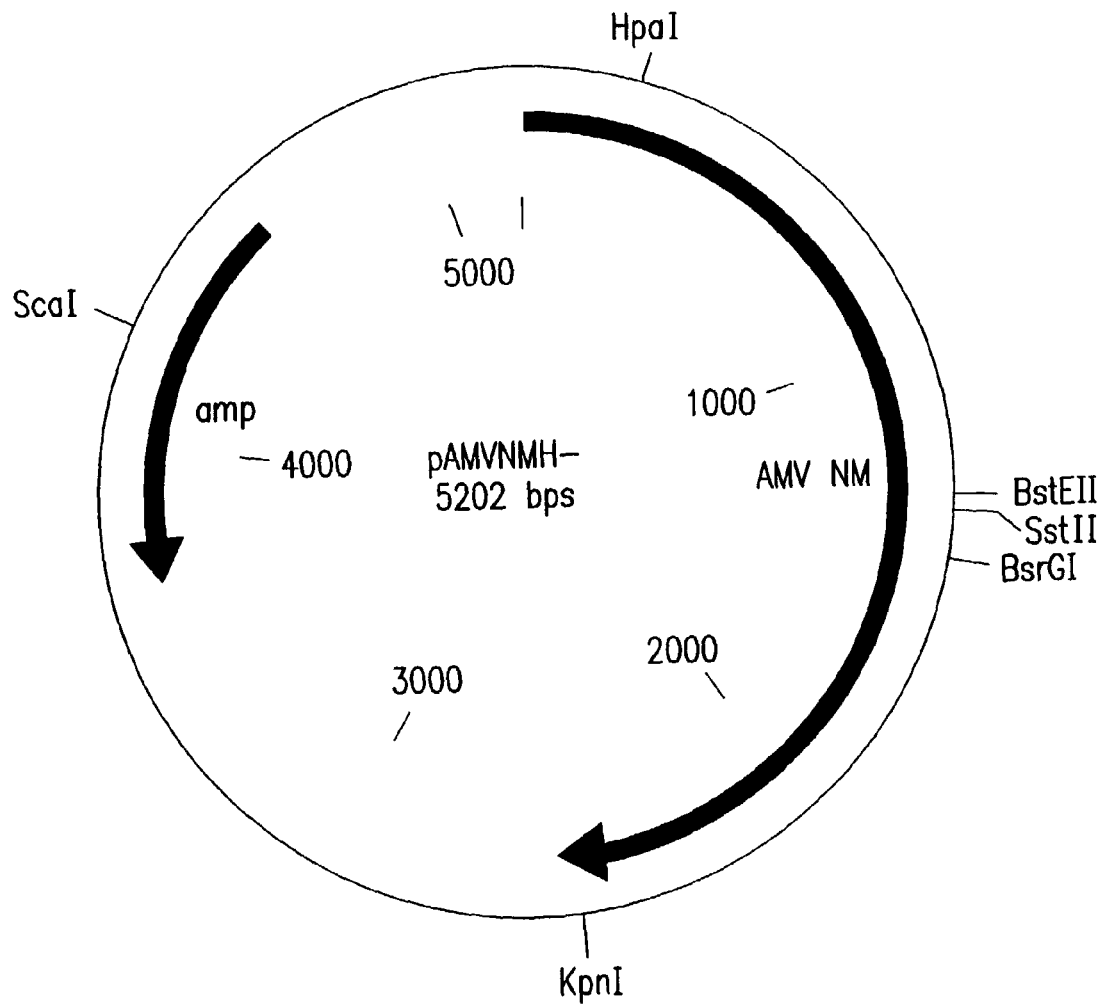
Figure 30:
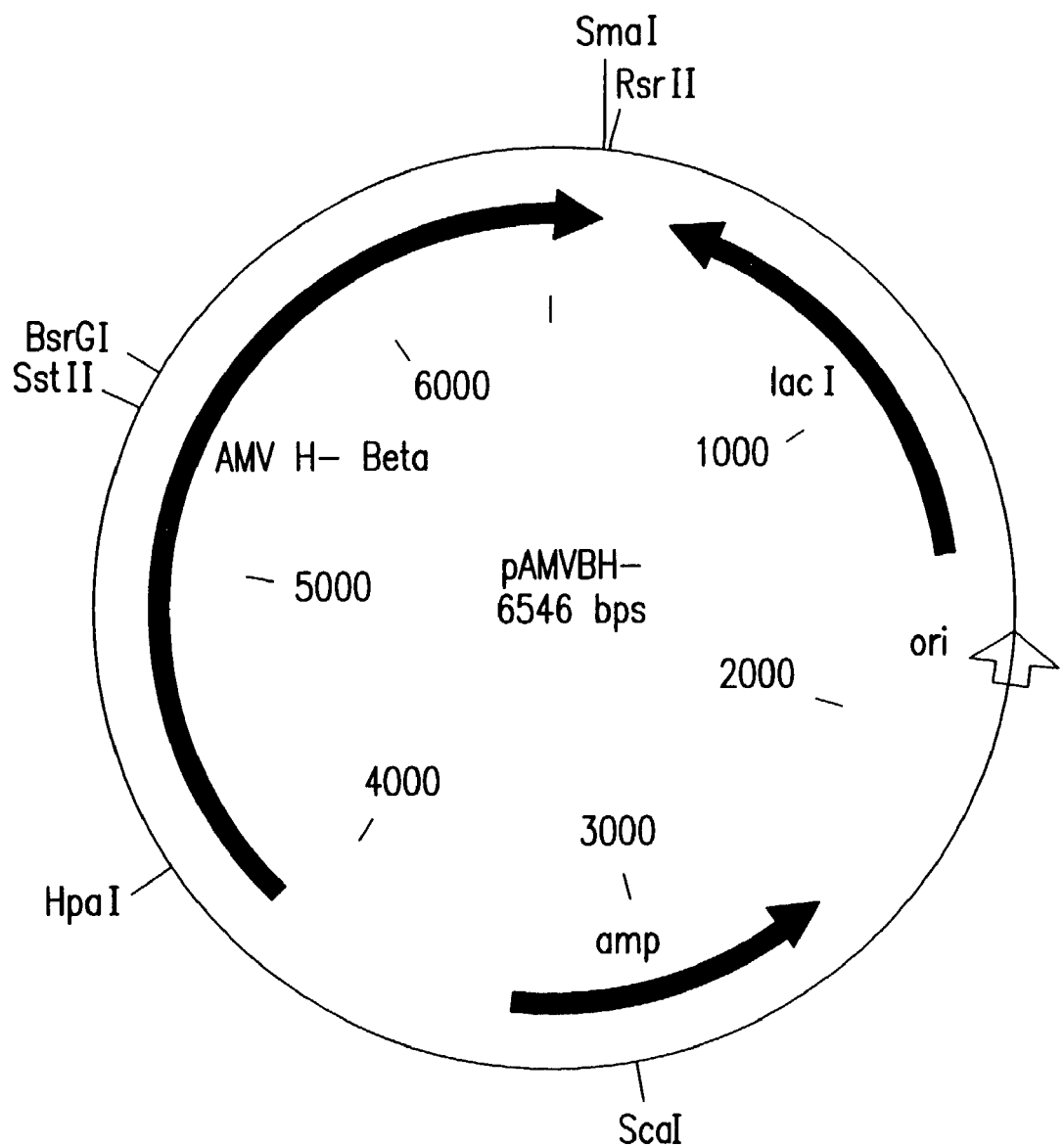

To add the middle region of the AMV RT β subunit, the 2.3 Kb HpaI-KpnI fragment from pSPORT8 that encodes the middle of the β subunit of AMV RT was cloned into the HpaI-KpnI sites of pAMVN, forming pAMVNM (FIGS. 23, 28). To add the carboxy end of the AMV RT β subunit, since pAMVC has two KpnI sites (FIG. 27), it was partially cleaved with KpnI, then completely cleaved with ScaI, and the 3 Kb fragment with the carboxy end of AMV RT was isolated and ligated to the 3.5 Kb ScaI-KpnI fragment of pAMVNMH- (FIG. 29), forming pAMVBH- (FIGS. 23, 30).

Mutagenesis of the beta subunit to RNase H−. The RSV RT and AMV RT genes are related (GenBank sequences J02342, J02021 and J02343 for RSV-C; L10922, L10923, L10924 for AMV). These genes code for an identical sequence of amino acids over a short distance of the RNase H region. As described above in Example 1, during the cloning and mutagenesis of the RSV RT genes an RNase H− derivative of the RSV RT β gene was made by site-directed mutagenesis. The oligonucleotide that was used (oligonucleotide #8) changed amino acid Asp450 to an Ala450 and introduced an SstII site (underlined).

Oligonucleotide #8

GGA CCC ACT GTC TTT <u>ACC GCG GCC</u> TCC TCA AGC ACC

The plasmid with the RNase H− mutation in the RSV RT β gene is pAMP18BH- (FIGS. 2, 14). The 129 bp BsrGI-BstEII fragment from pAMP18BH- was cloned into the BsrGI-BstEII sites of pAMVNM, replacing the RNase H+ region in this plasmid and forming pAMVNMH− (FIGS. 23, 29). The effect of this replacement was to change Asp450 to Ala450 in the AMV β gene without changing any other amino acids. To convert the β subunit back to RNase H+, an oligonucleotide primer having the wildtype sequence may be used.

Mutagenesis and subcloning of the gene encoding the AMV RT α subunit. To create a gene which codes for the α subunit of AMV RT, oligonucleotides #9 and #10 were used to mutagenize the amino end of the AMV RT gene from pAMVNM to introduce a translational stop co don where avian retroviral protease p15 normally cleaves the precursor polyprotein to make the α subunit:

Oligonucleotide #9:
5' CAU CAU CAU CAU CCC GGG TTA ATA CGC TTG GAA GGT GGC 3'  (SEQ ID NO:6)

Oligonucleotide #10:
5' CUA CUA CUA CUA TCA TGA CTG TTG CGC TAC ATC TG 3'  (SEQ ID NO:7)

Figure 24:
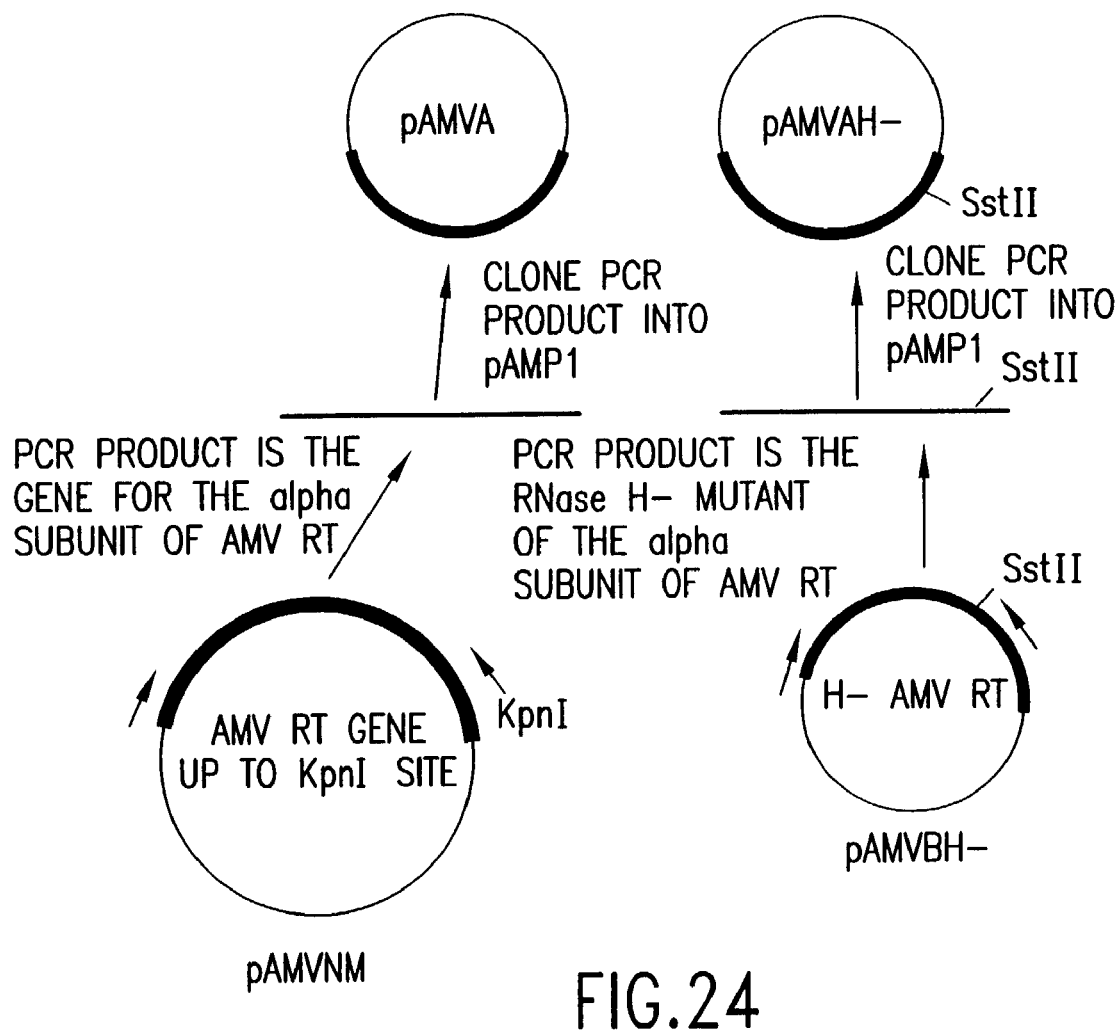
Figure 31:
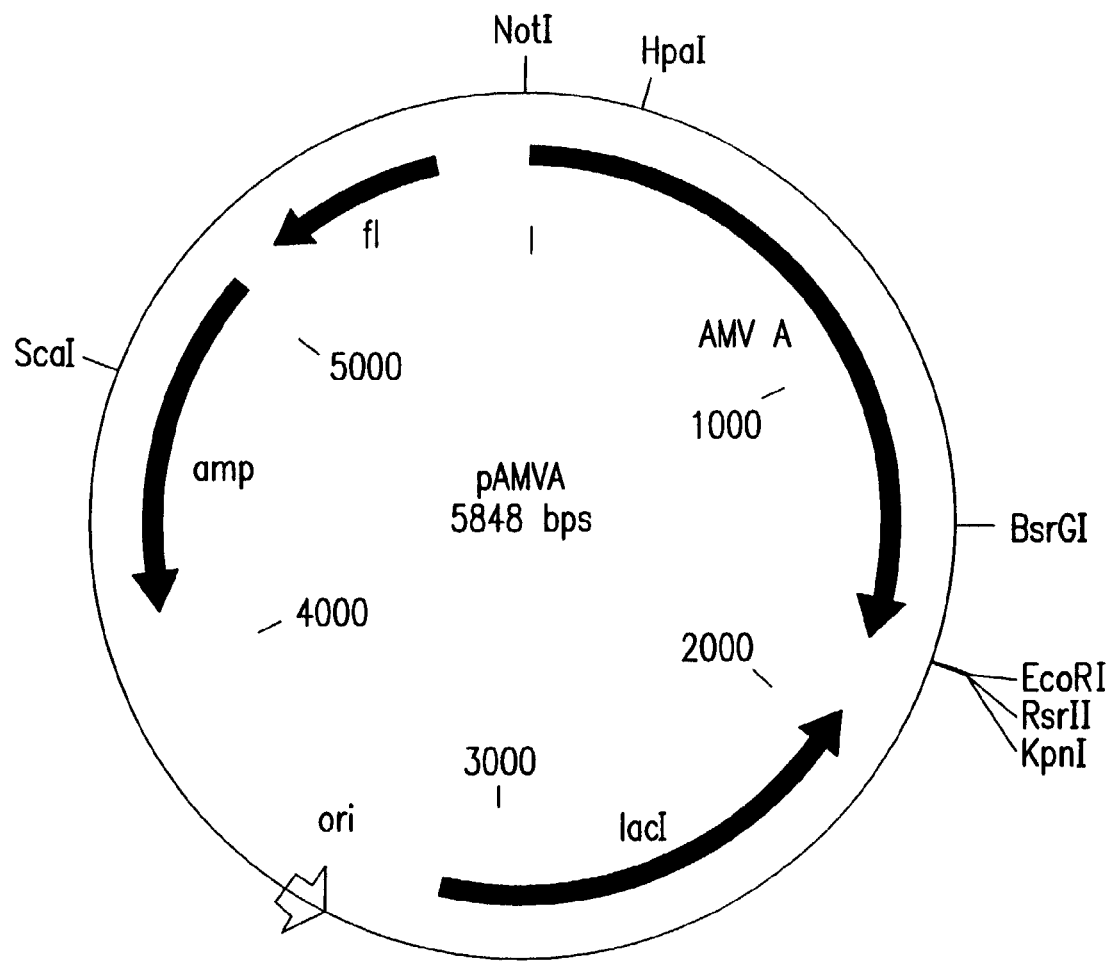
Figure 32:
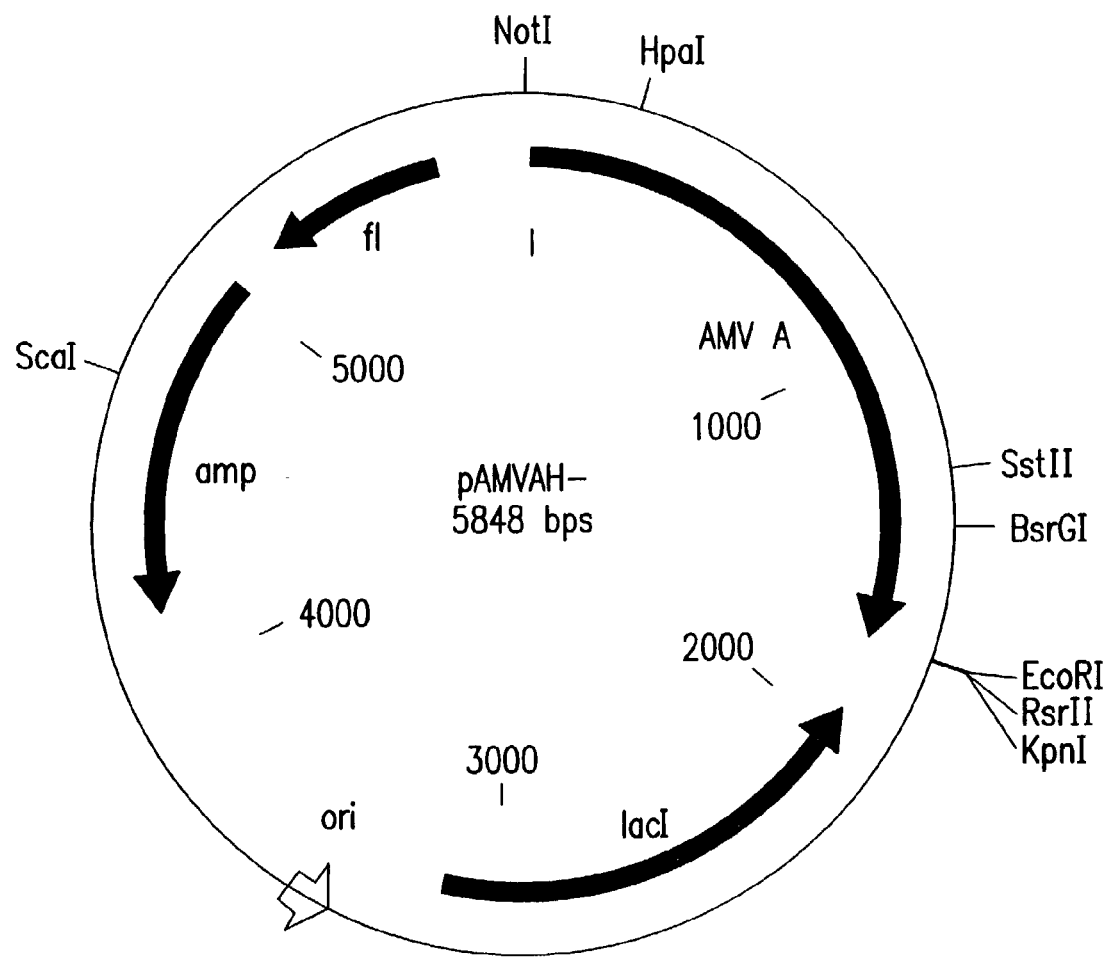

PCR cycling conditions were 5 minutes at 94° C., followed by 8 cycles of 15 seconds at 55° C./2 minutes at 72° C./15 seconds at 94° C., and then 2 minutes at 72° C. The PCR reaction was treated with DpnI to destroy the target and the PCR product was cloned into pAMP 18 by UDG cloning (Buchman, G. W., et al., *Focus* 15:36 (1993)), forming plasmid pAMVA (FIGS. 24, 31). To make the RNaseH− allele of the α subunit of AMV RT, the same procedure was followed using pAMVBH- as a target, forming plasmid pAMVAH- (FIGS. 24, 32).

Figure 25A:
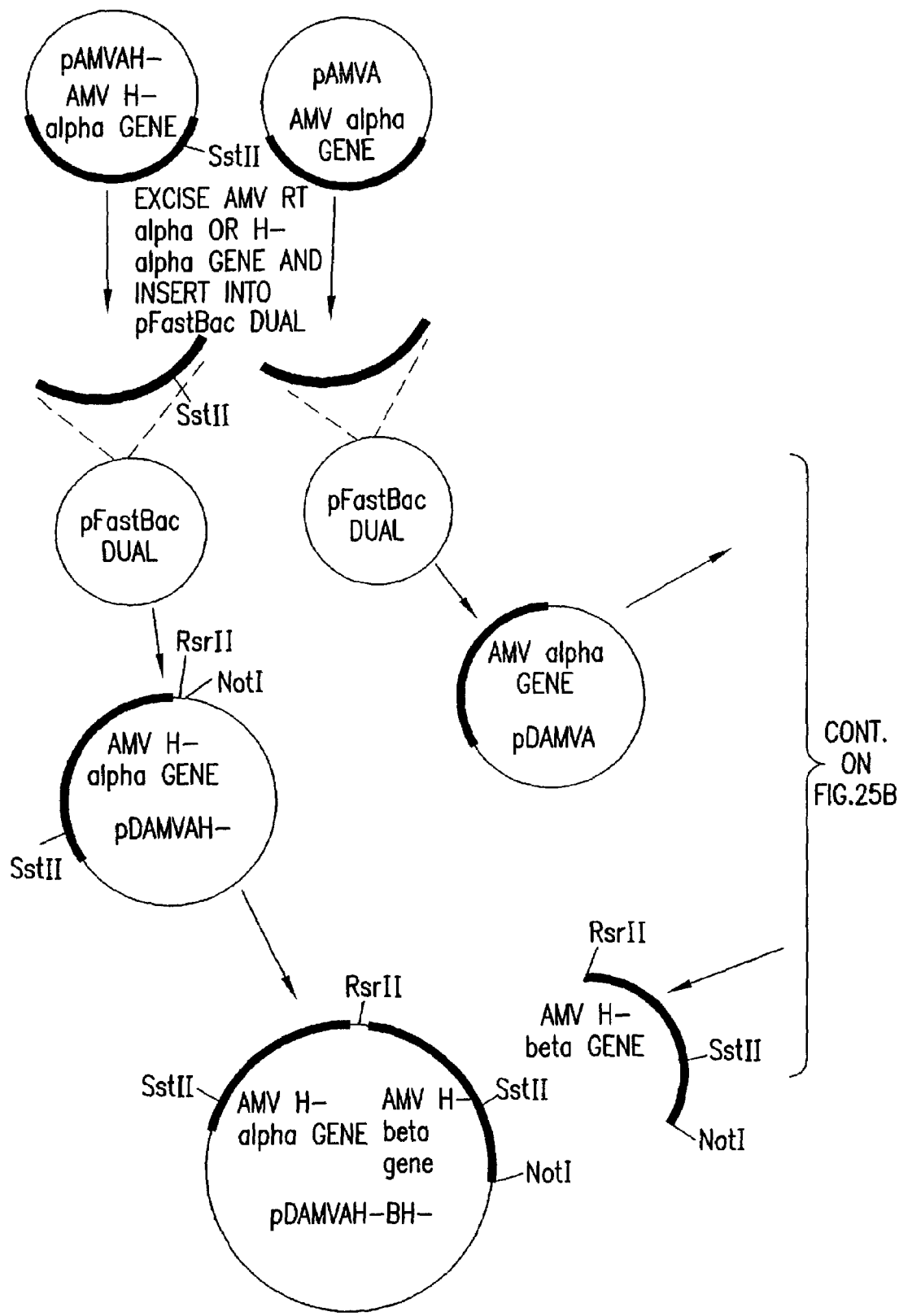
FIGS. 25A and 25B: Construction of vectors comprising the AMV RT α and β genes; pD, pDAMVAH-, pDAM VA, pAMVH-BH-, pDAMVABH- and pJAMVBH-.
Figure 25B:
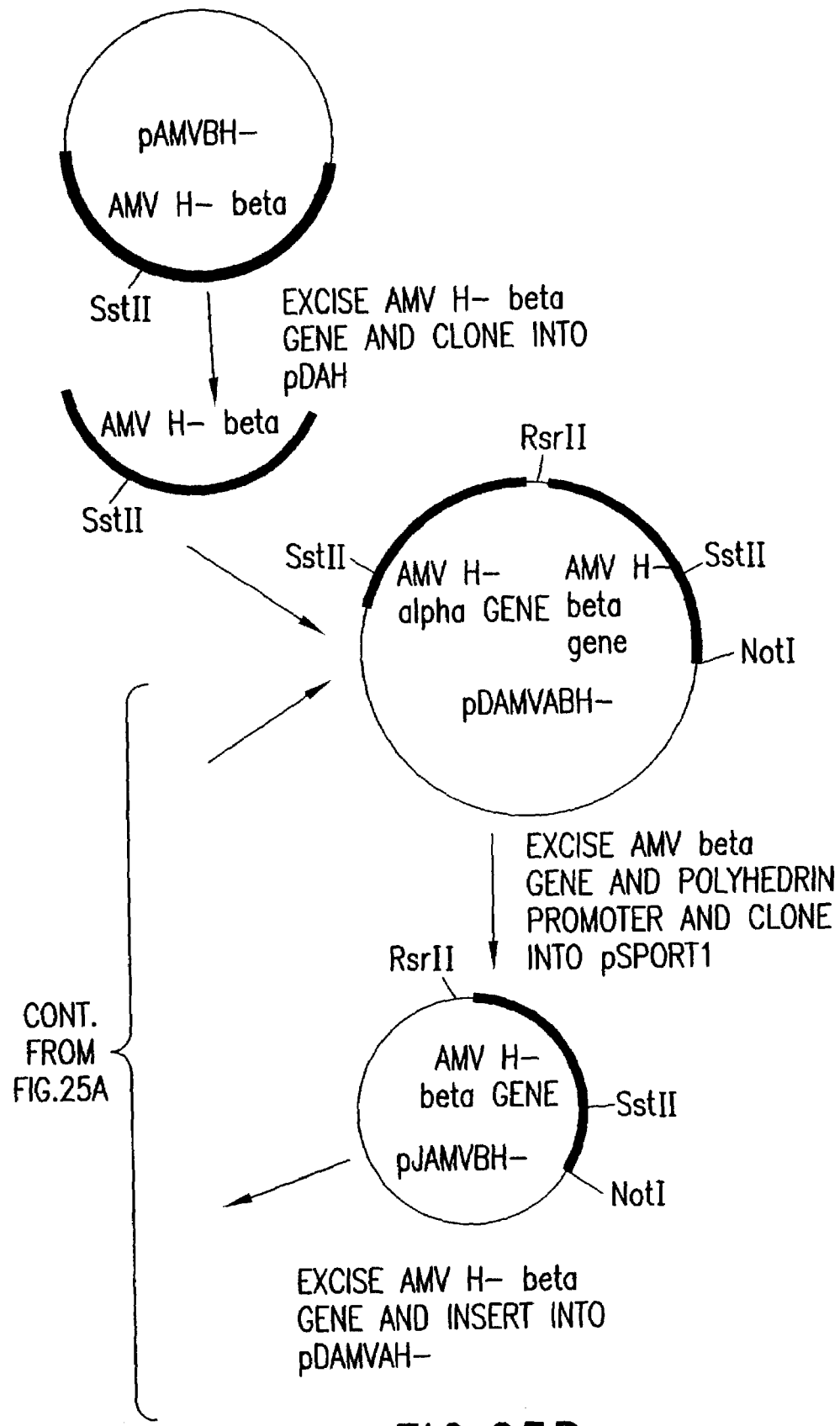
Figure 33:
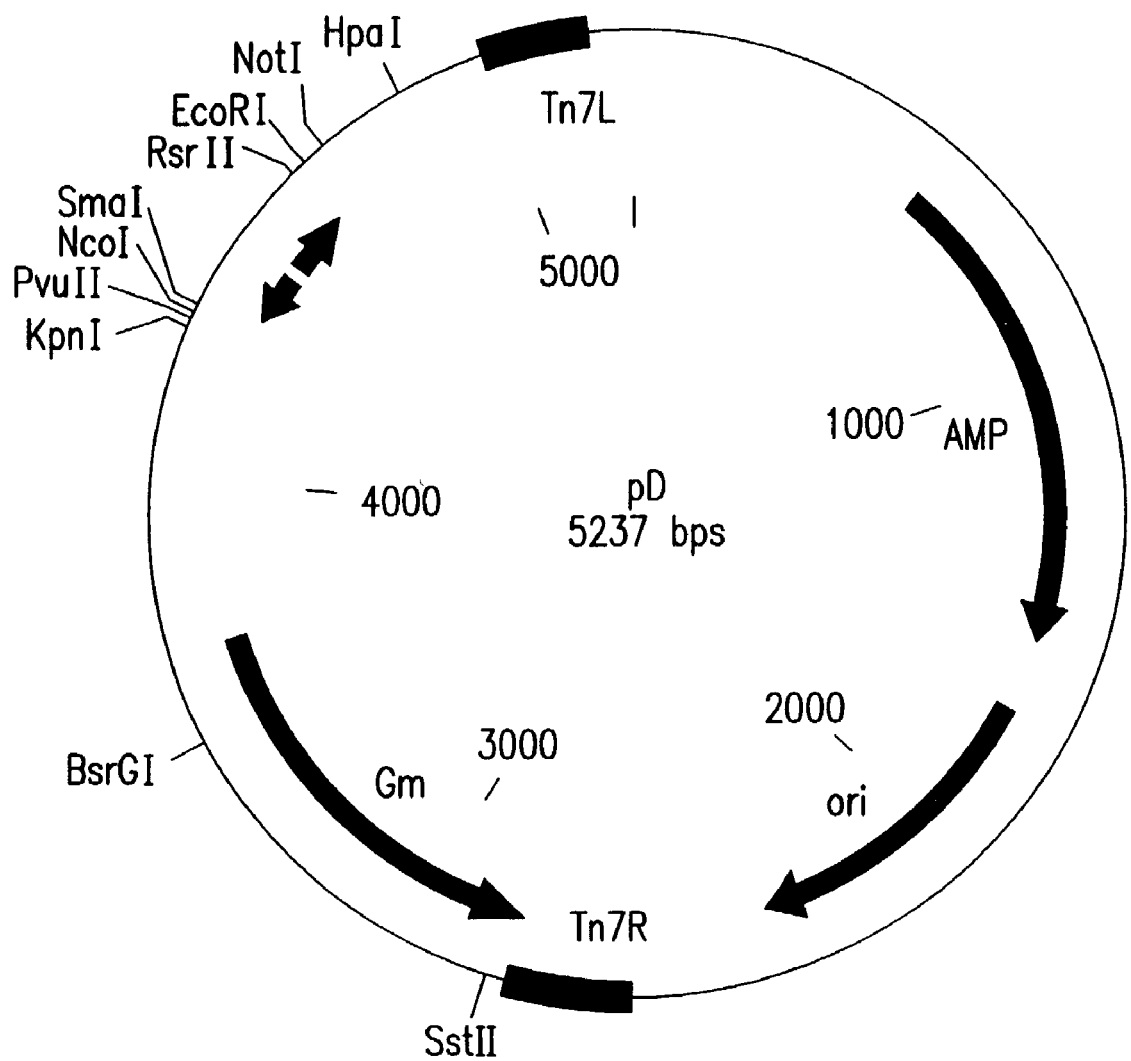
Figure 34:
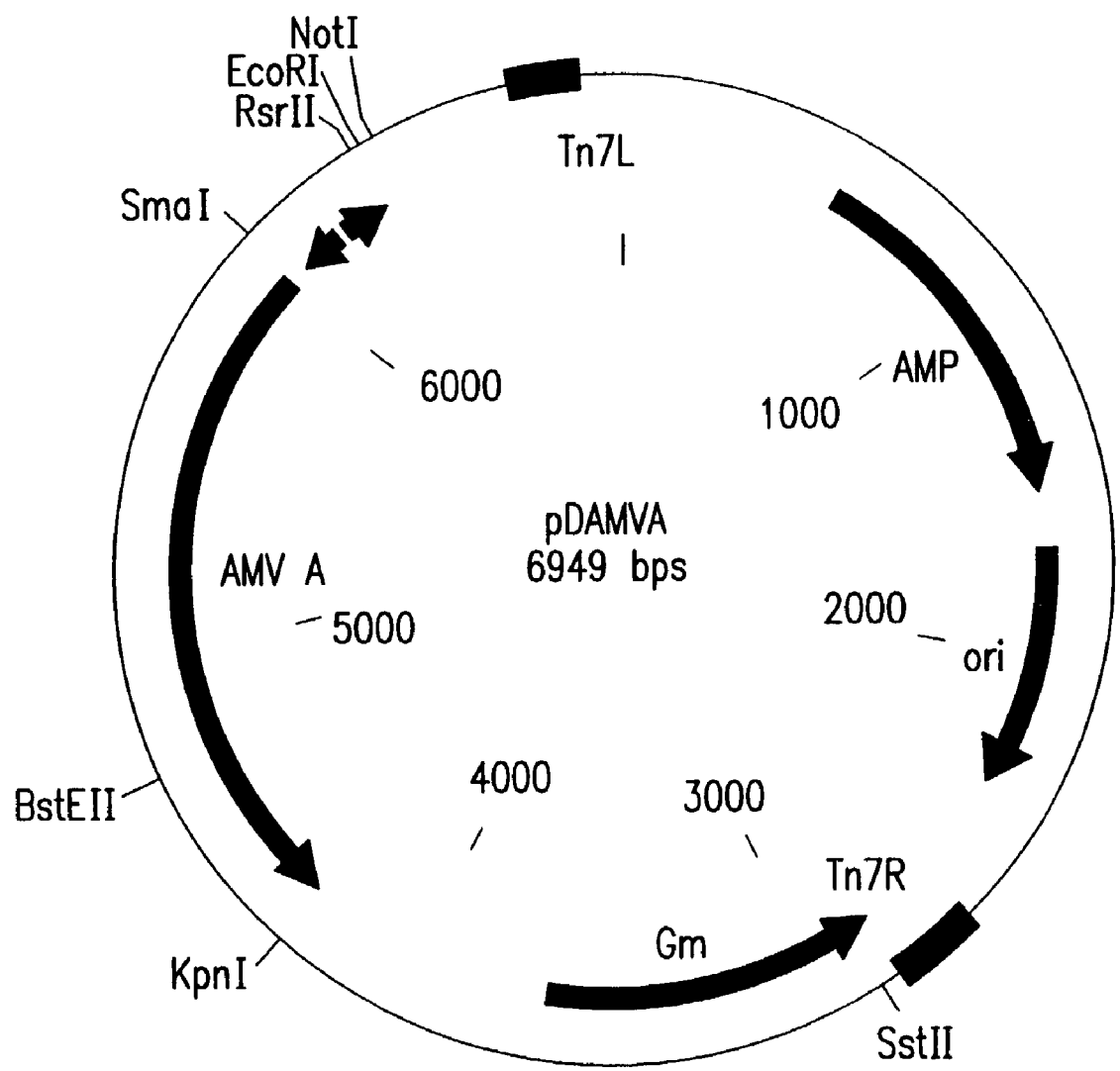
Figure 35:
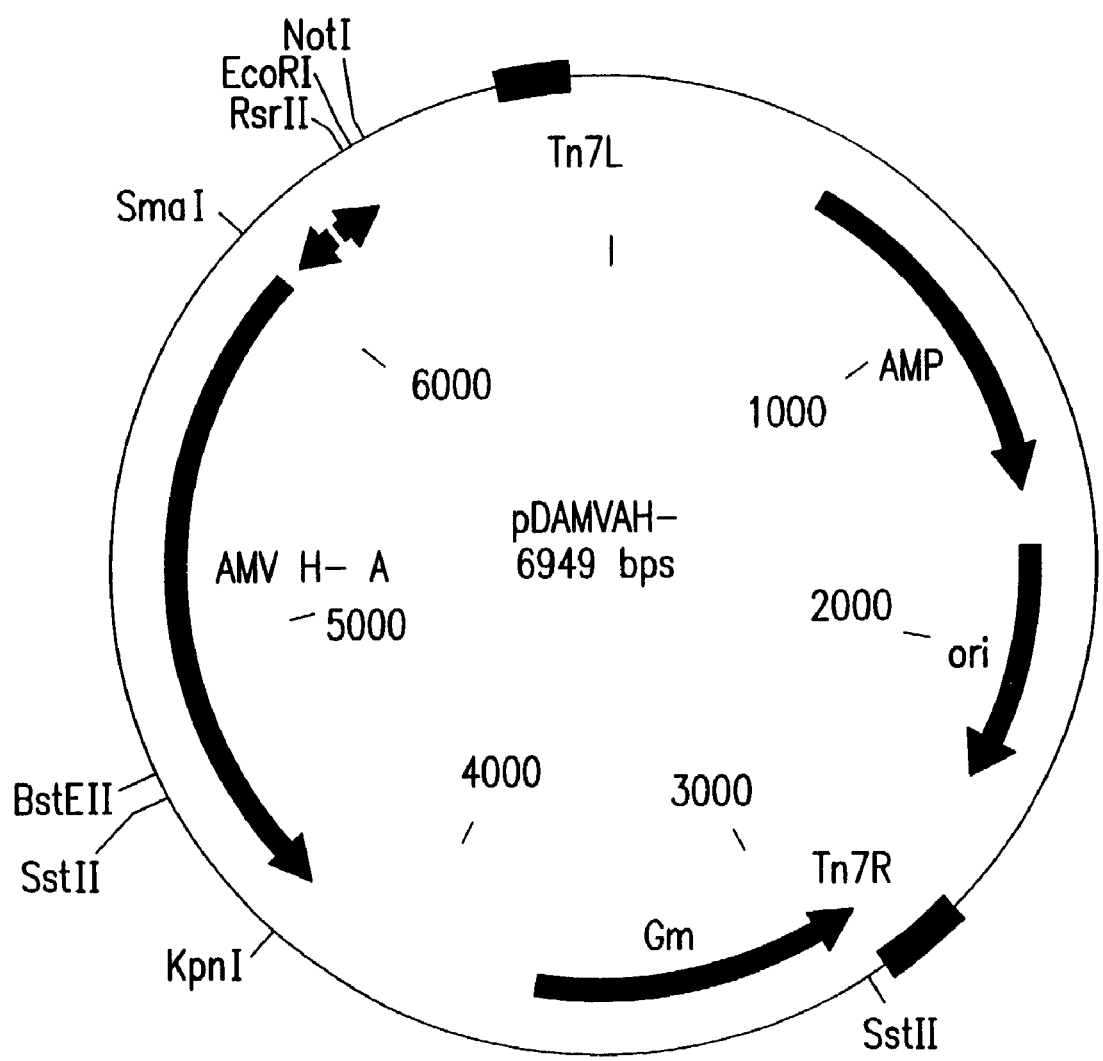
Figure 36:
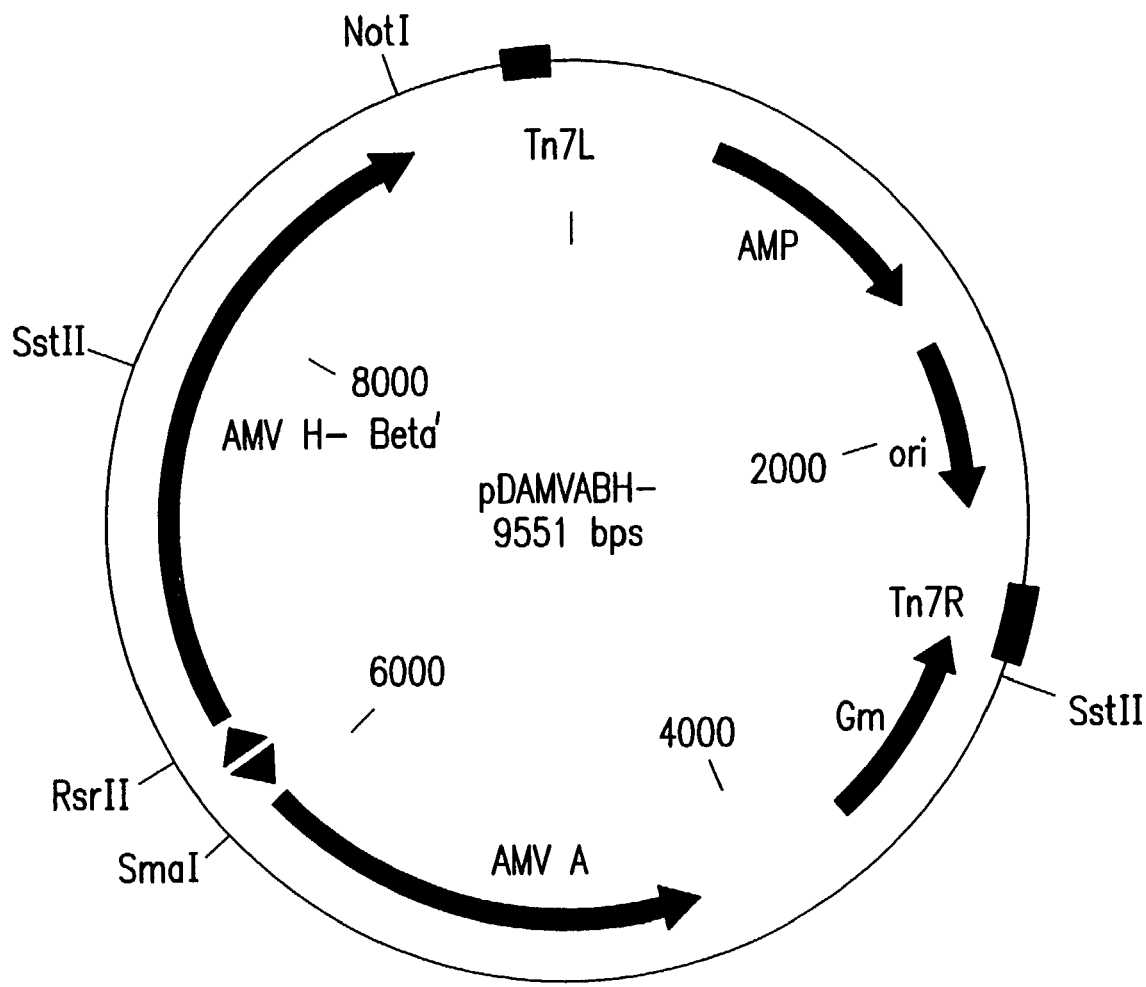
Figure 37:
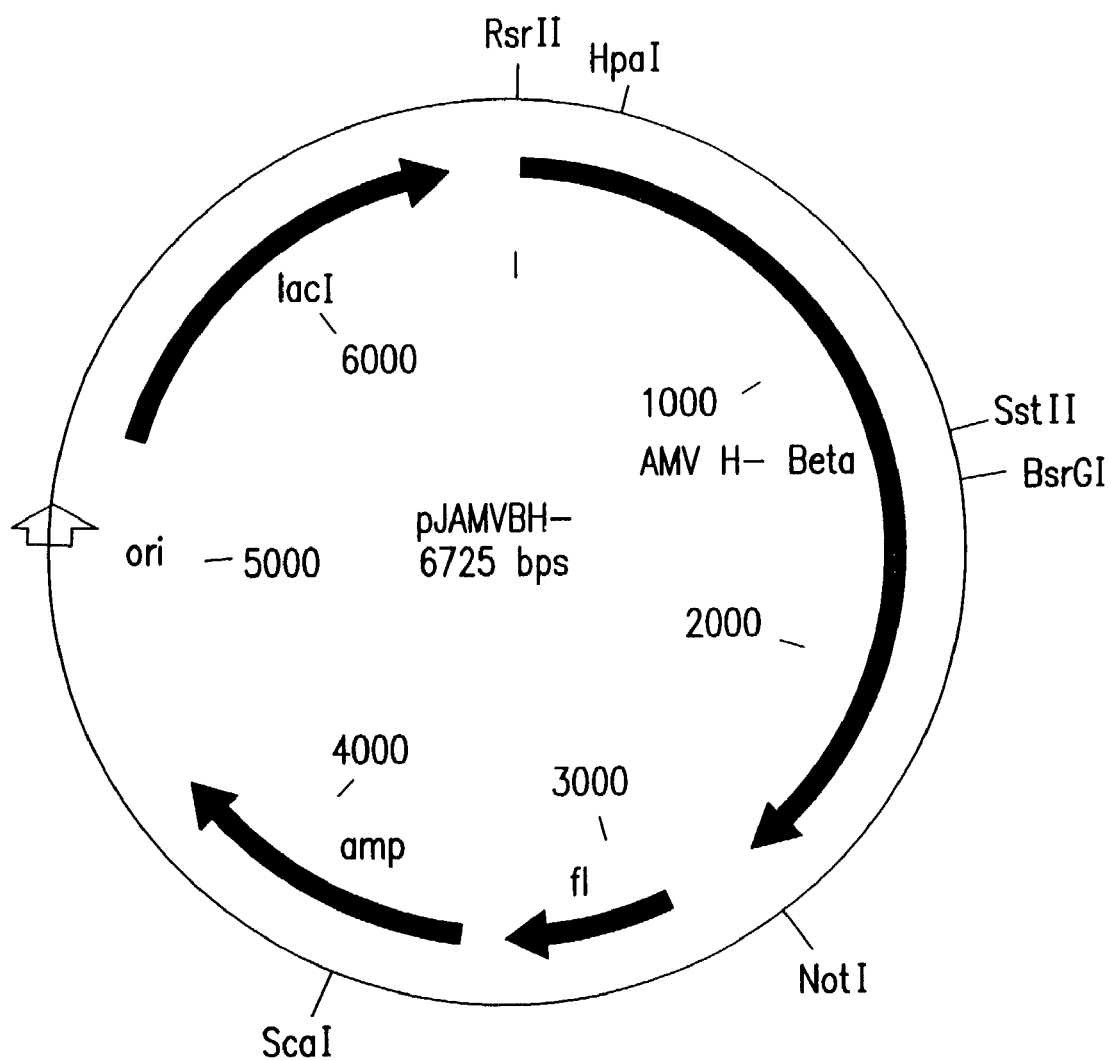
Figure 38:
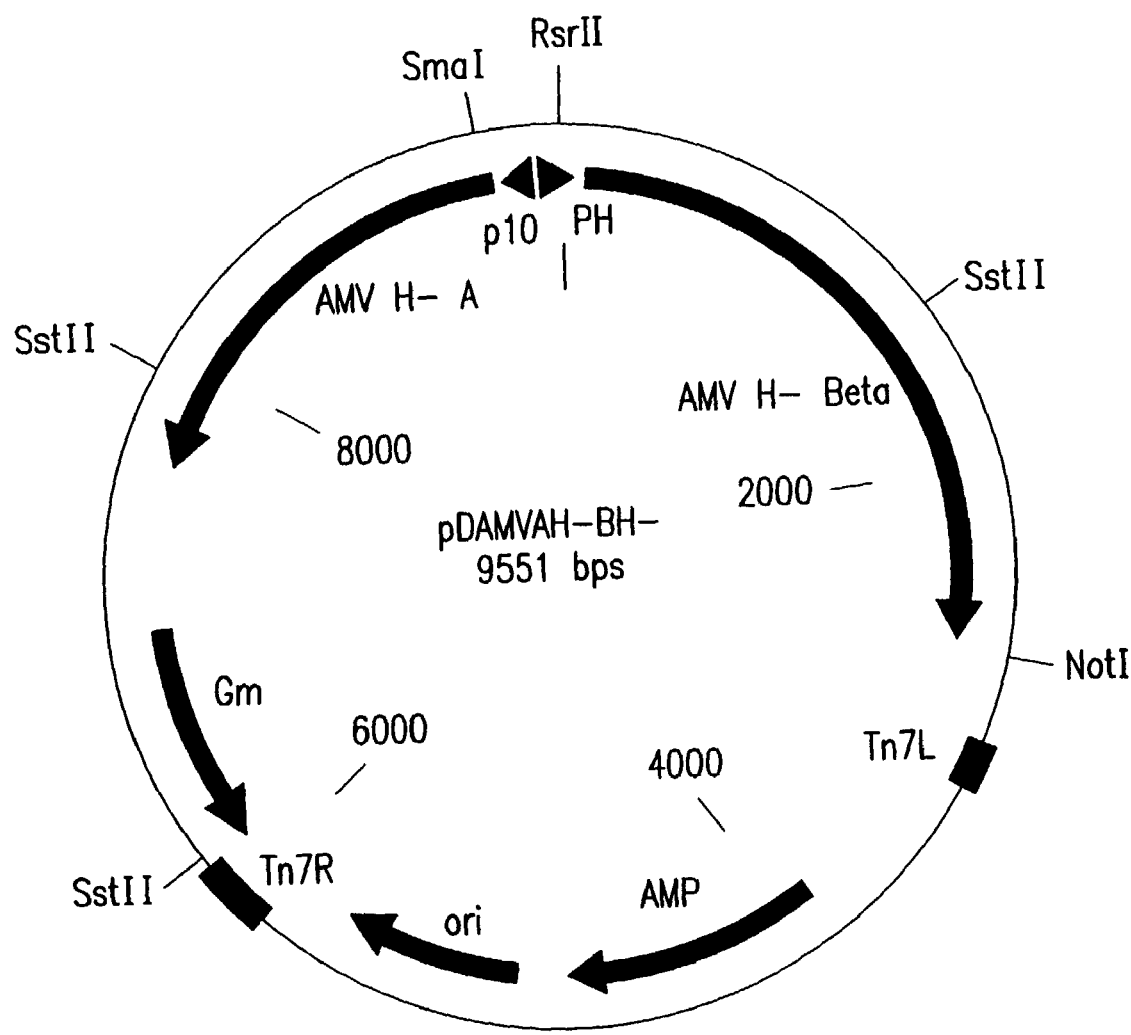
Figure 39A:
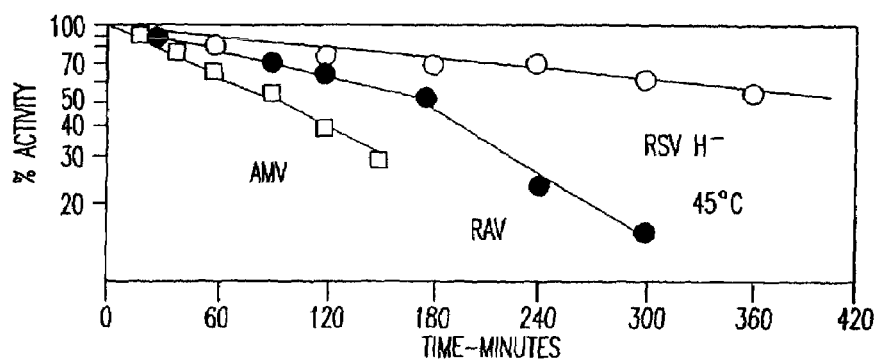
FIGS. 39A–39D show semi-logarithmic graphs demonstrating RT activities of various RTs incubated for the times and at the temperatures indicated.
Figure 39B:
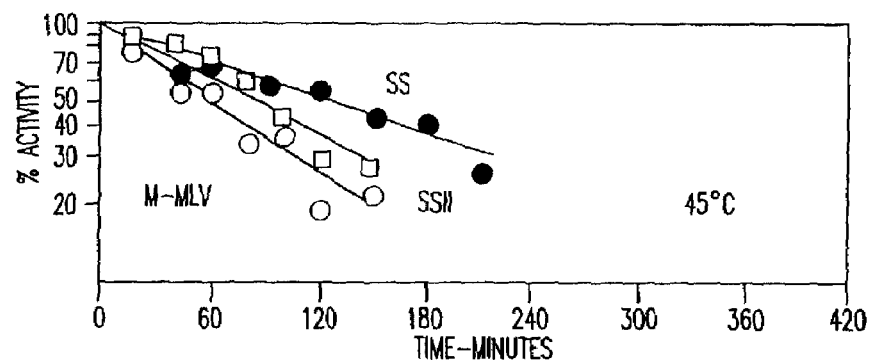
Figure 39C:
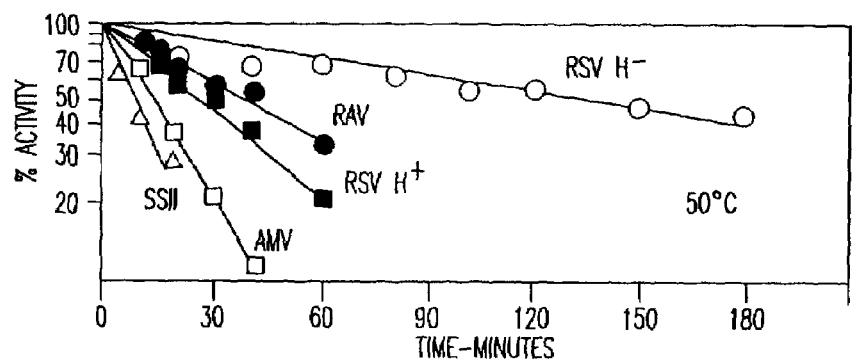
Figure 39D:
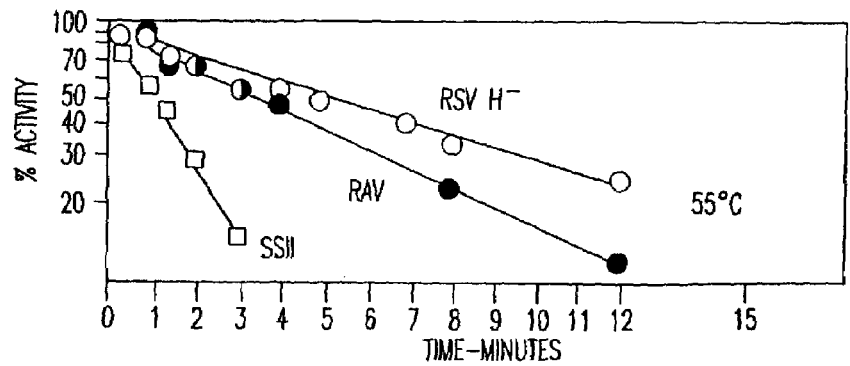

Cloning the AMV RT α and β genes into pFastBac Dual. The α gene was excised from pAMVA with SmaI and BspHI, and subcloned into the NcoI-PvuII sites of pFastBac Dual (pD; FIG. 33), creating plasmid pDAMVA (FIGS. 25, 34). An RNase H− AMV RT α gene was similarly cloned from pAMVAH-, forming plasmid pDAMVAH- (FIGS. 25, 35). In both plasmids, the AMV RT α gene was downstream from the baculovirus P10 promoter. The RNase H- AMV RT β gene was excised from pAMVBH- with EcoRI and cloned into the EcoRI site of pDAMVA. Clones were selected in which the EcoRI insert was oriented such that the AMV RT β gene was downstream from the polyhedrin promoter, forming plasmid pDAMVABH- (FIGS. 25, 36). In this construct, the AMV RT α gene was RNase H$^+$, but the β gene was RNase H$^-$. The AMV RNase H$^-$ RT β gene and polyhedrin promoter were excised from pDAMVABH$^-$ with RsrII and NotI and cloned into the RsrII-NotI sites of pSPORT 1, forming plasmid pJAMVBH- (FIGS. 25, 37). The AMV RNase H$^-$ RT β gene and polyhedrin promoter were excised from pJAMVBH- with RsrII and NotI and cloned into the RsrII-NotI sites of pDAMVAH-, forming plasmid pDAMVAH-BH- (FIGS. 25, 38).

The recombinant host cell comprising plasmid pDAMV-ABH-, *E. coli* DH10B(pDAMVABH-), was deposited on Jun. 17, 1997, with the Collection, Agricultural Research Culture Collection (NRRL), 1815 North University Street, Peoria, Ill. 61604 USA, as Deposit No. NRRL B-21790.

Using the deposited plasmid, one of ordinary skill in the art may easily produce, using standard genetic engineering techniques (such as those for site-directed mutagenesis described above), plasmids encoding various forms of the a and/or β subunits of AMV RT (e.g., α RNase H$^+$/β RNase H$^+$; α RNase H$^-$/β RNase H$^-$; α RNase H$^+$/β RNase H$^-$; and α RNase H$^-$/β RNase H$^+$).

Transfection of insect cells for virus and AMV RT production. To prepare vectors for the transfection of insect cells, it was first necessary to insert the AMV RT gene constructs into a baculovirus genome. This insertion was accomplished using the site-specific transposon Tn7, as described for the insertion of the RSV RT gene constructs into bacmids in Example 1. Plasmid pDAMVABH- was transformed into DH10Bac cells and transposition of sequences encoding the AMV RT β gene (whose synthesis is directed by the baculovirus polyhedrin promoter) and the AMV RT α gene (whose synthesis is directed by the baculovirus P10 promoter) was followed by screening for loss of β-3-galactosidase activity following transposition to the site on the bacmid which codes for the β-galactosidase α peptide (Harris, R., and Polayes, D. A., *FOCUS* 19:6–8 (1997)). Bacmid DNA was then prepared from transformants (10 ml cultures) by a slight modification of a standard miniprep procedure, as described in Example 1. About 1 μg of the bacmid DNA was used to transfect Sf21 insect cells using the cationic lipid Cellfectin (Anderson, D., et al., *FOCUS* 16:53 (1995)).

For expansion of primary virus, the supernatant was removed from the transfected cells about 72 hours after transfection and 1 ml was used to infect 35 ml of Sf21 insect cells (about 1.2×10$^5$ cells/ml). After 72 hours, the culture was centrifuged (2,000 rpm; 10 min) and the supernatant was decanted and used as a secondary viral stock. The secondary virus stock was expanded similarly by infecting 35 ml of Sf21 cells with 0.1 ml of the secondary stock.

Virus stocks were then used to infect Sf21 cells for the expression of AMV RT. In preliminary experiments, expression of RT activity by infected cells was found to be maximal about 72 hours after infection. For test expressions, 70 ml of Sf21 cells were infected with 5 ml of the viral stock, and the cells were harvested 72 hours after infection by centrifugation at 1,000 rpm for 5 minutes, resuspension in PBS (2.5% of the culture volume) and recentrifugation at 1,000 rpm for 5 min. Supernatants were removed and the cells were stored at −70° C. until used. For larger scale production, 600 ml of cells in 2.8 liter Fernbach flasks were infected with 2 ml of viral stock, and the cells were harvested 72 hours after infection. AMV RT was then isolated as described for RSV RT in Example 2.

EXAMPLE 5

Reverse Transcription with Retroviral RTs at Temperatures Above 55° C.

Retroviral reverse transcriptases have historically been used to catalyze reverse transcription of mRNA at temperatures in the range of 37° C. to 42° C. (see technical literature of commercial suppliers of RTs such as LTI, Pharmacia, Perkin Elmer, Boehringer Mannheim and Amersham). There is a prevailing belief that at these temperatures mRNA secondary structure interferes with reverse transcription (Gerard, G. F., et al., *FOCUS* 11:60 (1989); Myers, T. W., and Gelfand, D. H., *Biochem.* 30:7661 (1991)) and the specificity of primer binding is reduced during gene-specific reverse transcription processes, such as RT-PCR, causing high background signal (Myers, T. W., and Gelfand, D. H., Biochem. 30:7661 (1991); Freeman, W. N., et al, *BioTechniques* 20:782 (1996)). It is therefore desirable to carry out RNA reverse transcription at more elevated temperatures, i.e., above 55° C., to help alleviate these problems.

As noted above, retroviral RTs are generally not used at temperatures above 37° C. to 42° C. to copy RNA because of the limited thermal stability of these mesophilic enzymes. In recent years, however, it has been reported that AMV RT can be used to perform RT-PCR of small amplicons (<500 bases) at 50° C., and to a limited extent at 55° C. (Freeman, W. M., et al, *BioTechniques* 20:782 (1996); Mailers, F., et al., *BioTechniques* 18:678 (1995); Wang, R. F., et al., *BioTechniques* 12:702 (1992)) Forms of M-MLV RT lacking RNase H activity, because of removal of the RNase H domain (Gerard, G. F., et al., *FOCUS* 11:66 (1989) or because of point mutations in the RT gene (Gerard, G. F., et al., *FOCUS* 14:91 (1992)), can also be used at 50° C., but not at 55° C., to catalyze cDNA synthesis.

Therefore, the thermal stability of RNase H$^-$ RSV RT and its utility in higher temperature (i. e., above 50° C.) reverse transcription reactions for synthesis of large cDNAs was examined.

Methods

Enzymes and RNAs. SuperScript RT (SS RT), SuperScript II RT (SS II RT), and Moloney murine leukemia virus (M-MLV) RT were from LTI. AMV RT was from Seikagaku America, Inc., or was prepared as described above in Example 4. SS RT is an RNase H$^-$ form of M-MLV RT in which RNase H activity has been eliminated by removing the RNase H domain of the RT polypeptide, resulting in an enzyme with a molecular weight of 57 KDa rather than 78 KDa (Gerard, G. F., et al., *FOCUS* 11:66 (1989); Kotewicz, M. L., et al. *Nuc. Acids Res.* 16:265 (1988)). SS II RT is an RNase H$^-$ form of M-MLV RT in which RNase H activity has been eliminated by the introduction of three point mutations in the RNase H domain of M-MLV RT (Gerard, G. F., et al, *FOCUS* 14:91 (1992)). Rous Associated Virus (RAV) RT was from Amersham. RSV RNase H$^-$ and RSV RNase H$^+$ RT were cloned, expressed and purified as described above in Examples 1 and 2. The RNAs used as templates were synthetic RNAs of 1.4, 2.4, 4.4 and 7.5 Kb, each with a 120 nucleotide poly(A) tail at the 3' end, obtained from LTI. Synthetic CAT mRNA was from LTI.

Model System for Determining Functional Thermal Stability of Reverse Transcriptases. A mixture of 1.4-, 2.4-, 4.4-. and 7.5-Kb mRNAs was used to test the ability of various RTs to synthesize full-length cDNA copies at various temperatures. The cDNA products synthesized were labeled radioactively by the RT-catalyzed incorporation of a $^{32}$P- labeled deoxyribonucleotide triphosphate precursor. The $^{32}$P-labeled cDNA products were fractionated by alkaline agarose gel electrophoresis (Carmichael, G. G., and McMaster, G. K., Meth. Enzymol. 65:380 (1980)). The gel was dried and the size distribution of the cDNA products was established by autoradiography. Using the autoradiographic film as a template, the full length cDNA bands at 1.4, 2.4, 4.4 and 7.5 Kb were cut from the dried gel and counted in scintillant to establish the amount of each full length product synthesized.

cDNA synthesis reaction conditions. All cDNA synthesis reactions were carried out at the indicated temperatures for 30 or 50 minutes. All reaction mixtures were 20 μl and contained the following components unless specified otherwise: 50 mM Tris-HCl (pH 8.4 at 24° C.), 75 mM KCl, 10 mM dithiothreitol, 1 mM each of [$^{32}$P]dCTP (300 cpm/pmole), dGTP, dTTP, and dATP, 25 μg/ml p(dT)$_{25-30}$, 12.5 μg/ml each of 1.4-, 2.4-, 4.4-, and 7.5-Kb mRNA, and 35 units of cloned rat RNase inhibitor. In addition, reaction mixtures contained the following:

| | |
|---|---|
| SS II RT: | 0.5 mM dNTPs (instead of 1 mM), 3 mM MgCl$_2$ and 200 units of SS II RT |
| RSV H$^-$ RT: | 7.5 mM MgCl$_2$ and 21 units of RSV H$^-$ RT; |
| AMV RT: | 50 mM KCl, 10 mM MgCl$_2$, 4 mM sodium pyrophosphate and 29 units of AMV RT |
| RSV H$^+$ RT: | 50 mM KCl, 10 mM MgCl$_2$, 4 mM sodium pyrophosphate and 24 units of RSV H$^+$ RT |
| RAV RT: | 50 mM KCl, 10 mM MgCl$_2$, 4 mM sodium pyrophosphate and 24 units of RAV RT |

Reaction mixtures containing all components except enzyme were preincubated at the desired temperature for three minutes, and then RT was added to initiate cDNA synthesis.

Half Life Determinations. The half lives of RTs were determined by incubating individual tubes of RT at a desired temperature for appropriate lengths of time and stopping the incubation by placing the tube on ice. RSV RTs, RAV RT and AMV RT were incubated in 20 μl aliquots containing 50 mM Tris-HCl (pH 8.4), 75 mM KCl, 7.5 mM MgCl$_2$, 10 mM dithiothreitol, 50 μg/ml CAT mRNA, 25 μg/ml p(dT)$_{12-18}$, and 350–700 units/ml RT. Murine RTs (SS RT, SS II RT, M-MLV RT) were incubated in mixtures containing the same components except MgCl$_2$ was at 3 mM and enzyme was at 2,500 units/ml. An aliquot from each tube (5 μl for avian RTs and 1 μl for murine RTs) was assayed for RT activity in a unit assay reaction mixture to determine residual RT activity.

Unit Assays. Unit assay reaction mixtures (50 μl) contained 50 mM Tris-HCl (pH 8.4), 40 mM KCl, 6 mM MgCl$_2$, 10 mM dithiothreitol, 500 μM [$^3$H]dTTP (30 cpm/pmole), 0.5 mM poly(A), and 0.5 mM (dT)$_{12-18}$. Reaction mixtures were incubated at 37° C. for 10 minutes and labeled products were acid precipitated on GF/C glass filters that were counted in a scintillation counter.

Results and Discussion

With a few exceptions, the half lives in the presence of a template primer at 45° C., 50° C., 55° C. and 60° C. were determined for RSV H$^+$ RT, RAV RT, AMV RT, RSV H$^-$ RT, M-MLV H$^+$RT, SS RT, and SS II RT. The results are shown in FIG. 39 and Table 3.

TABLE 3

HALF LIVES OF REVERSE TRANSCRIPTASES[1]

| | HALF LIFE (MINUTES) AT: | | | |
|---|---|---|---|---|
| ENZYME | 45° C. | 50° C. | 55° C. | 60° C. |
| RSV H$^-$ RT | 440 | 138 | 5 | 0.75 |
| RSV H$^+$ RT | ND[2] | 30 | ND[3] | ND[3] |
| RAV RT | 159 | 37 | 3.8 | ND[3] |
| AMV RT | 96 | 16 | 1.3 | ND[3] |
| SuperScript II RT | 105 | 7 | ND[3] | ND[3] |
| SuperScript RT | 120 | 3 | ND[3] | ND[3] |
| M-MLV RT | 65 | 2.5 | ND[3] | ND[3] |

[1]Half lives were determined from the data shown in FIG. 39.
[2]ND: not determined.
[3]ND: not determined, because half life in this reaction mixture was too short to be determined accurately.

The results shown in FIG. 39 and Table 3 clearly demonstrate that RNase H$^+$RTs (RSV, RAV and AMV) are much more thermo stable than M-MLV RT, and have reasonable half lives at 50° C. Furthermore, mutating these RTs to produce their corresponding RNase H$^-$ forms further increases their half lives. Most dramatically, RNase H$^-$ RSV RT had a much longer half life than any other retroviral RT at 45° C., 50° C. and 55° C. Thus, introduction of a single amino acid change into the RNase H domain of each subunit of RSV RT increases its half life at 50° C. by nearly five-fold.

Figure 40:
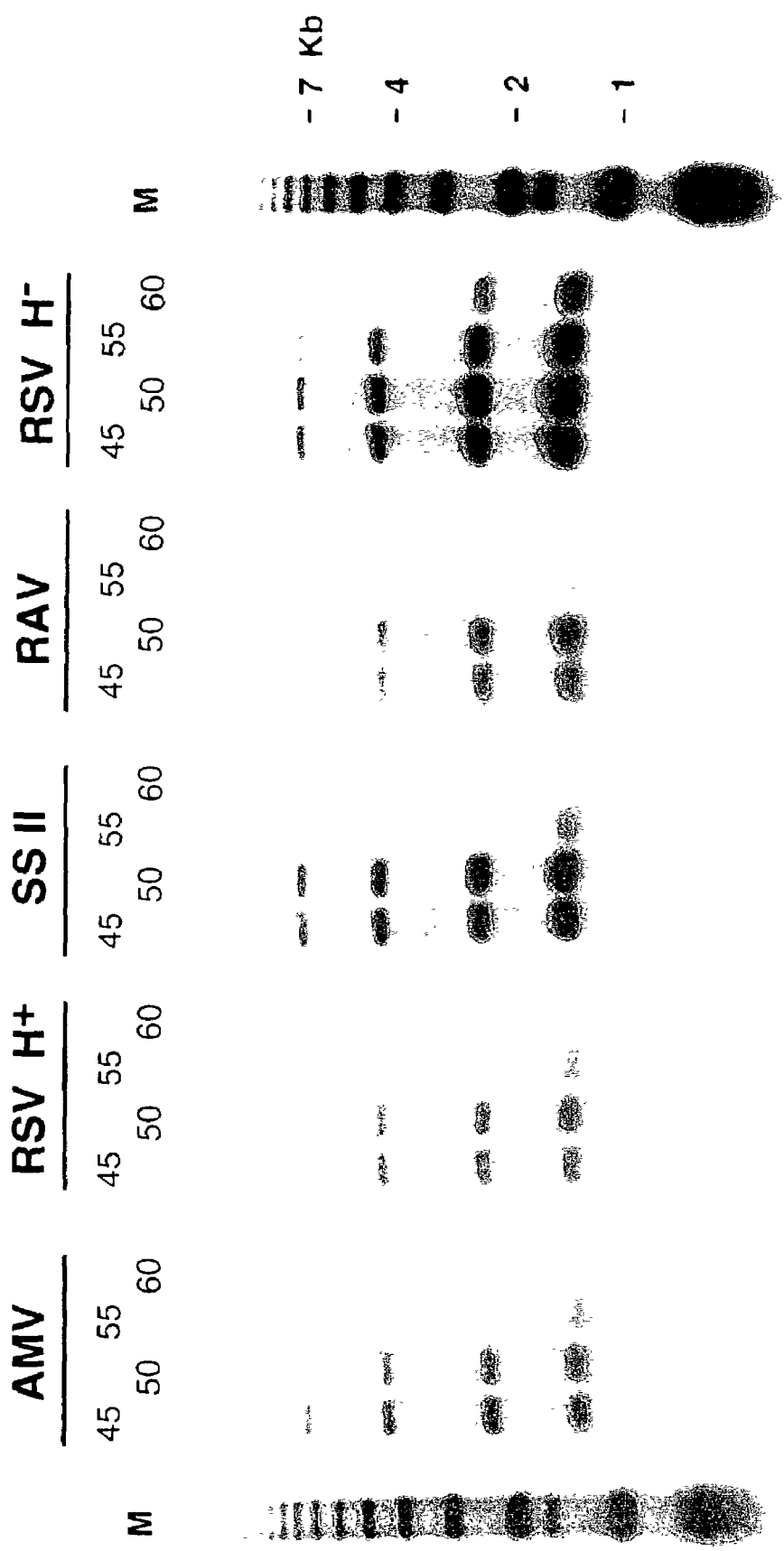
FIG. 40 is an autoradiograph of cDNA products synthesized by various RTs at the temperatures (° C.) indicated from 1.4-, 2.4-, 4.4- and 7.5-Kb mRNAs over 50-minute reactions. M: $^{32}$P-labeled 1 Kb DNA ladder.
Figure 41:
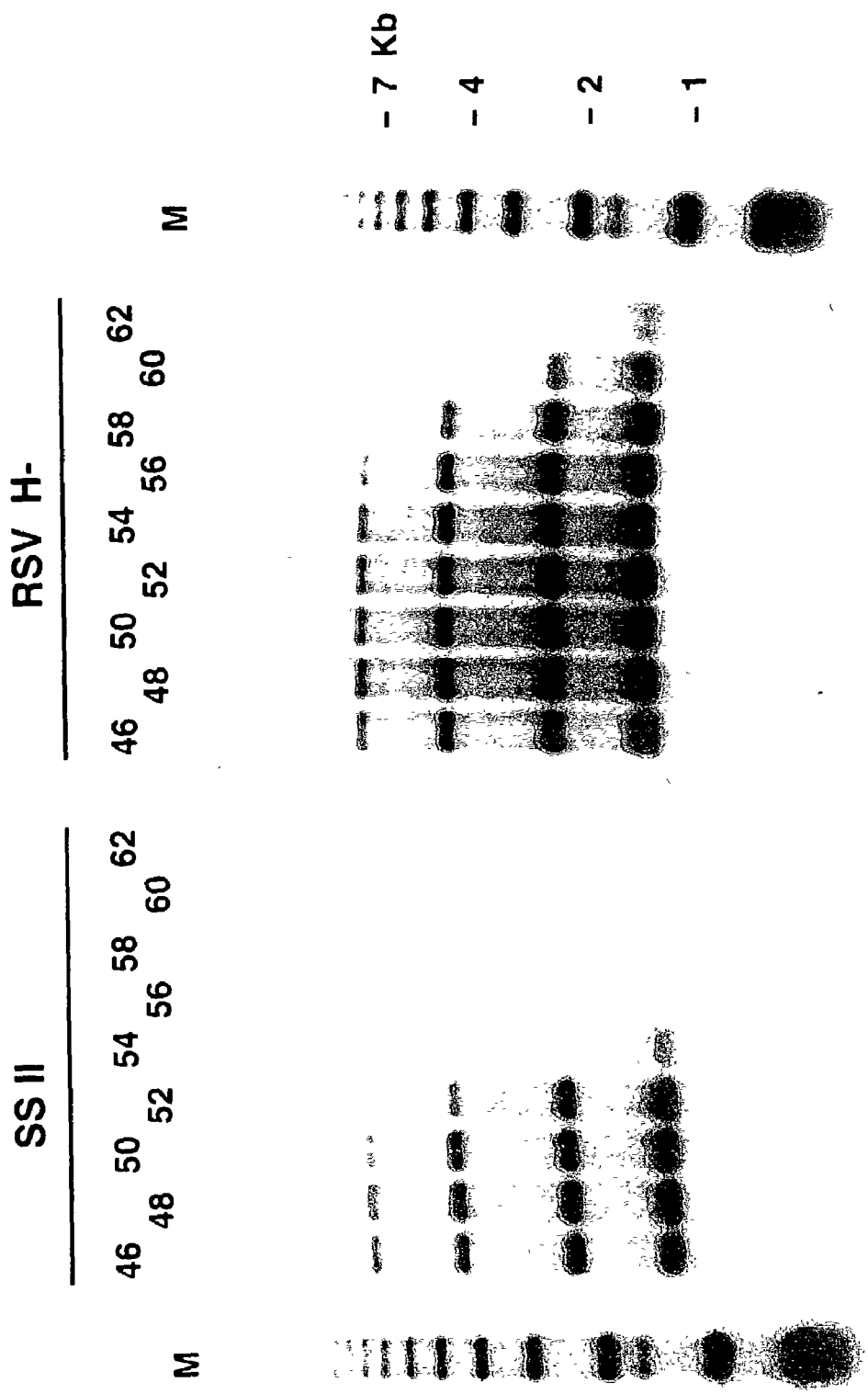
FIG. 41 is an autoradiograph of cDNA products synthesized by RSV H⁻ RT and SS II RT at the temperatures (° C.) indicated from 1.4-, 2.4-, 4.4-, and 7.5-Kb mRNAs over 30-minute reactions. M: $^{32}$P-labeled 1 Kb DNA ladder.
Figure 42A:
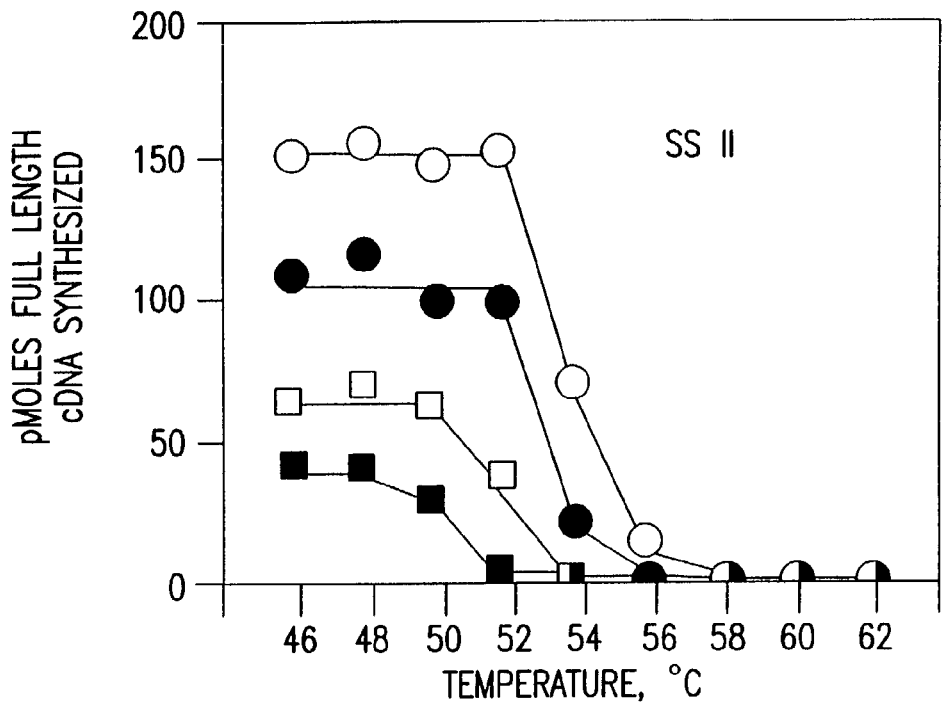
FIGS. 42A and 42B show graphs of the amounts of full length cDNA synthesized by SSII and RSV H⁻ RT in FIG. 41 as a function of incubation temperature.
Figure 42B:
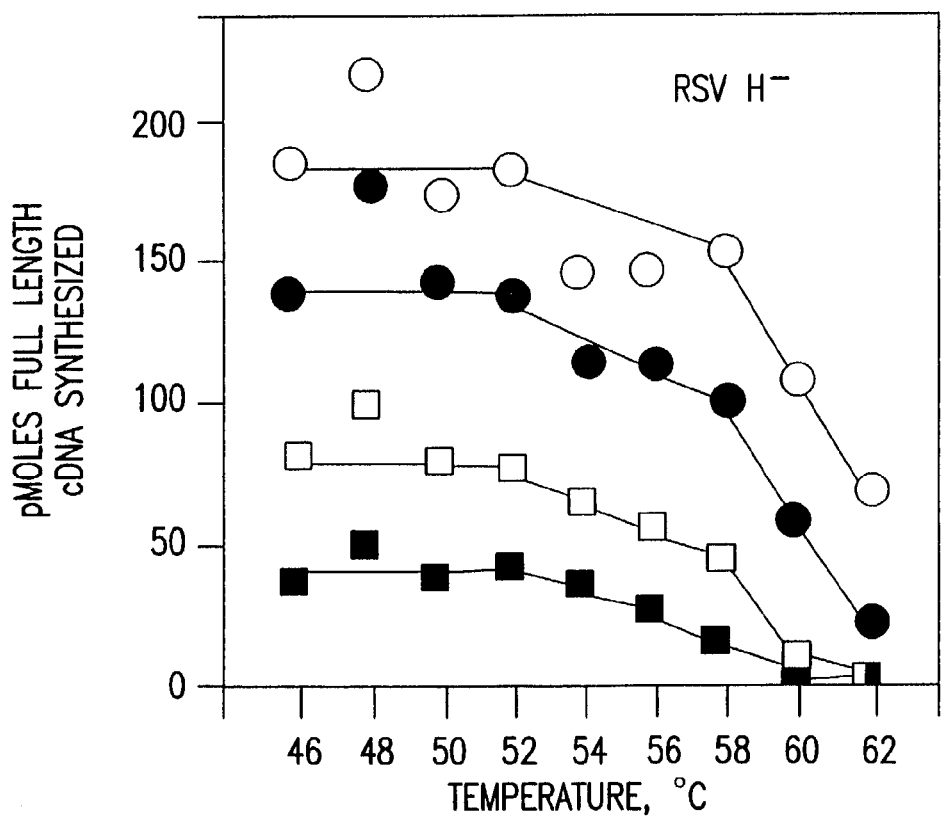

The impact of this increased thermal stability on cDNA synthesis at temperatures above 50° C. was found to be dramatic. FIG. 40 shows the results of a comparison of the performance of these RTs at 45° C., 50° C., 55° C. and 60° C. in copying mRNA of 1.4 to 7.5 Kb in length. With the exception of RSV H$^-$ RT, none of the RTs were found to produce substantial product longer than 2.4 Kb in length at 55° C. or 60° C. RSV H$^-$ RT, in contrast, continued to make full-length 7.5-Kb cDNA at 55° C., and 4.4-Kb cDNA at 60° C. FIGS. 41 and 42 show a more detailed comparison of the two RTs that performed best in FIG. 40 (i.e., SS II RT and RSV H$^-$ RT). At temperatures above 55° C., RSV H$^-$ RT was found to continue to synthesize cDNAs of all lengths, while SS II RT produced only low levels of cDNA greater than 1 Kb in length.

Taken together, these results demonstrate that RNase H$^-$ RSV RT is much more thermoactive than any other retroviral RT available commercially, and can be used to synthesize longer cDNAs (up to 4 Kb long) at 60° C. This enhanced thermoactivity of RNase H$^-$ RSV RT is due to an increased thermal stability, relative to RNase H$^+$ RT, at 50° C. to 60° C., which makes RSV H$^-$ RT an ideal enzyme for use in the reverse transcription of mRNA at 50° C. to 60° C.

EXAMPLE 6

Reverse Transcription with Avian RTs at Elevated Temperatures

In Example 5 (Table 3 and FIG. 39), the half lives of various RTs were presented. In particular, half lives were reported for cloned RSV RT in which the RNase H domain of each subunit was mutated to eliminate RNase H activity (Example 1; Asp450→Ala in both the α subunit and the β subunit).

To further examine the effects of these mutations on RT half life, constructs were produced as described above, in which only one of the two subunits were mutated at one time, such that various combinations of mutants were formed (e.g., α RNase H⁻/β RNase H⁺and α RNase H⁺/β RNase H⁻). The half lives of these RSV RTs, as well as cloned AMV α RNase H⁻/β RNase H⁺ RT, were determined as described above in the Methods section of Example 5.

As shown in Table 4, when the α subunit in RSV or AMV RT was mutated, leaving the β subunit wild type intact, the resulting RT demonstrated greater thermal stability than that observed for other avian RTs. These mutant RTs were also examined for their functional thermal stability using the model system described in the Methods section of Example 5. For each enzyme, the increased thermal stability was found to correlate with improved functional performance—for example, the α RNase H⁻/β RNase H⁺ avian RTs, which demonstrated the highest thermal stability at 50° C. (Table 4), also demonstrated the highest functional activity at various elevated temperatures (Table 5).

TABLE 4

Half Lives of RSV and AMV Reverse Transcriptases

| Enzyme | Half Life (Minutes) at 55° C. |
|---|---|
| RSV αH⁻βH⁻RT | 5 |
| RSV αH⁻βH⁺RT | 7 |
| RSV αH⁺βH⁻RT | 2 |
| RSV αH⁺βH⁺RT | 1.9 |
| AMV αH⁻βH⁺RT | 6 |
| Native AMV RT | 1.3 |
| Native RAV RT | 3.8 |

TABLE 5

Functional Activities of RSV RTs at Elevated Temperatures.

| Enzyme | Temperature, ° C. | Amount of Full-Length Product Produced (pMoles) | | | |
|---|---|---|---|---|---|
| | | 1.4 Kb | 2.4 Kb | 4.4 Kb | 7.4 Kb |
| RSV αH⁻/βH⁻ RT | 45.0 | 132.9 | 80.5 | 56.7 | 28.1 |
| | 55.0 | 115.4 | 70.7 | 40.8 | 12.5 |
| | 57.5 | 81.9 | 43.2 | 17.2 | 3.1 |
| | 60.0 | 7.0 | 1.8 | 0 | 0 |
| | 62.5 | 0 | 0 | 0 | 0 |
| RSV αH⁻/βH⁺ RT | 45.0 | 145.2 | 85.3 | 57.9 | 31.8 |
| | 55.0 | 161.3 | 83.0 | 53.3 | 21.5 |
| | 57.5 | 140.1 | 77.7 | 41.1 | 11.6 |
| | 60.0 | 67.6 | 30.0 | 7.5 | 0.1 |
| | 62.5 | 4.1 | 0.8 | 0 | 0 |

EXAMPLE 7

Alternative Methods of Generating Avian Reverse Transcriptases and Characterization of their Properties As noted above in the Related Art section, three prototypical forms of retroviral RT have been studied thoroughly—M-MLV RT, HIV RT, and ASLV RT (which includes RSV and AMV RT). While each of these retroviral RTs exist as heterodimers of an α and a β subunit, there have been no reports heretofore of the simultaneous expression of cloned ASLV RT α and β genes resulting in the formation of heterodimeric αβ RT.

Examples 1–4 above described the cloning, expression and purification of αβ forms of RSV and AMV RT that copy mRNA efficiently. Formation of αβ RT was achieved in baculovirus-infected insect cells by co-expression of genes for α and β from a dual promoter vector. The studies presented in this Example were designed to generate RSV αβ RT by a variety of other methods that have been used to successfully clone and express HIV p66/p51 RT. In addition, as described below, the individual subunits of RSV RT, including βp4, β and α, have now been cloned, expressed, and purified, and the abilities of these subunits to copy mRNA has now been characterized.

Materials and Methods

General Methods

Mutations and plasmid constructions were conducted using standard molecular biology methods (see e.g., Sambrook, J. et al., *Molecular Coning: A Laboratory Manual*, 2nd Ed., Cold Spring Harbor, N.Y.: Cold Spring Harbor Laboratory Press (1989)), modified as described below. Plasmid preparation, PCR, gel electrophoresis, DNA fragment isolation and cloning, insect cell culture and baculovirus production were all performed as described for RSV RT cloning and expression in Example 1.

Cloning and Expression of RSV RT in *E. coli*

A number of approaches were tried to generate RSV αβ RT from RSV RT βp4 in *E.coli*.

PCR of NdeI-XbaI fragment. The amino end of the RSV RT βp4 gene was mutagenized to introduce an NdeI site by PCR (1 cycle 94° C. for 5 min.; 15 cycles 94° C., 10 sec, 55° C., 15 sec, 72° C., 15 sec.; 1 cycle 72° C., 5 min) of pJD100 (FIG. 7) with the following oligonucleotides:

```
Oligonucleotide #11:              (SEQ ID NO: 17)
5'-ATT ATT CATATG ACT GTT GCG CTA CAT CTG GC-3'

Oligonucleotide #12:              (SEQ ID NO: 18)
5'-TAC GAT CTC TCT CCA GGC CAT TTT C-3'
```

The NdeI site in oligonucleotide #11 above appears in bold and italicized print, while the bases that are underlined in oligonucleotides #11 and #12 were derived from authentic RT gene sequences. The PCR product with these two oligos contained an NdeI site at the beginning of the gene, and retained the XbaI site which is present within the RT gene. The PCR product was cloned into pUC18 between the NdeI and XbaI sites, forming pUC18 #3.

Site-directed mutagenesis to introduce a SmaI site to clone p15. A 3 Kb PstI fragment from pJD100 containing the entire RSV RT gene was cloned into M13mp19. Clone RF-SmaI was then produced by introducing a SmaI site at the carboxy end of the RSV RT βp4 gene by site-directed mutagenesis (see Example 1), using the following mutagenic oligonucleotide:

```
Oligonucleotide #13:              (SEQ ID NO:19)
5'-ACT CGA GCA GCC CGG GAA CCT TTG-3'
```

Reconstruction of the RT gene. The 2.8 kb SmaI-PstI fragment from RF-SmaI was cloned into pUC18 at the SmaI/PstI sites. The clone was designated as pUC18-PstI-SmaI. The NdeI-XbaI fragment from pUC18 #3 was introduced into pUC18-PstI-SmaI to regenerate the entire RSV RT βp4 gene with an NdeI site at the initiation codon. The clone was designated as pUC18-RT.

Cloning entire RTgene in pRE2. The NdeI-XbaI fragment from pUC18 #3 was cloned into expression vector pRE2 to generate pRE2-Nde-Xba. pRE2 contains an inducible lambda pL promoter. The rest of the RSV RT βp4 gene was subcloned as an NdeI-SstI fragment from pUC18-PstI-SmaI into pRE2-Nde-Xba digested with XbaI and SstI, generating pRE2-RT.

Cloning of p15 into pRE2-RT. RSV RT is processed from RSV RT βp4 to the αβ heterodimer by the RSV p15 protease. In order to make authentic αβ, the p15 protease gene was cloned and expressed with the RSV RT βp4 gene as follows. The RSV p15 protease gene was generated by PCR using pJD100 as target and the protocol described above. The oligonucleotides used for PCR were as follows:

```
Oligonucleotide #14:
5'-AT TAC CCG GGA GG A TAT CAT ATG TTA GCG ATG ACA ATG (SEQ ID NO:20)
GAA CAT AAA G-3'

Oligonucleotide #15:
5'-A TAT GTC GAC TCA CAG TGG CCC TCC CTA TAA ATT TG-3' (SEQ ID NO:21)
```

In oligonucleotides #14 and #15 above, the restriction sites (SmaI, NdeI and SalI) are indicated in bold letters while the region of bases underlined is the ribosome binding site. PCR using these oligonucleotides generated a ~450 bp fragment, which was digested with SmaI and SalI and cloned into pUC19. The clone was designated as pUC19-p15. The p15 gene was introduced into pRE2-RT by subcloning the 450 bp SmaI-SalI fragment at the SmaI/SalI sites. The final plasmid was designated pRE2-RT.p15.

Expression of RT from pRE2-RT and pRE2-RTp15. *E. coli* CJ374 containing either pRE2-RT or pRE2-RT.p15 was grown at 30° C. in EG broth in the presence of ampicillin (100 μg/ml) and chloramphenicol (30 μg/ml) to an A590 of 0.5. Half of the culture was induced at 42° C. for 45 min., and then outgrown at 30° C. for 2 hr. The other half was grown at 30° C. as an uninduced control. None of the cultures produced any visible induced protein upon examination by SDS-PAGE. None of the cell extracts displayed any RT activity.

Recloning of RT.p15 in pRE1. The lack of RT expression in the above constructs suggested that it was possible that (i) a mutation had been introduced into the RT gene during PCR to render it inactive, or (ii) during cloning a mutation in the lambda pL promoter arose, since RT is thought to be toxic to *E. coli*. Thus, the entire RT.p15 gene was recloned into pRE1, which was the same as pRE2 except the multiple cloning site was in an opposite orientation, as a NdeI-SalI fragment and the construct was introduced into *E. coli* CJ374. In addition, a 2269 bp HpaI-KpnI fragment of the resulting clone was replaced by the same HpaI-KpnI fragment from pJD100. This replacement left only about a 200 bp amino terminal region derived from PCR. Moreover, this region (NdeI site to HpaI site) was sequenced to confirm that there was no mutation due to PCR. The plasmids were designated as pRE1-RT. 15. This plasmid was also introduced into BL21, a protease-deficient *E. coli* strain. The p15 gene was also deleted from pRE1-RT. 15 by digesting the plasmid with XhoI and SalI and recircularizing the plasmid. The resulting plasmid was designated as pRE1-RT.

Expression of RT in *E. coli* CJ374 and BL21 harboring pRE1-RT and pRE1-RT. 15. The cultures were grown as described above. The soluble cell extract was assayed for RT activity. Although the activity was extremely low, it was clear that the RT activity in the induced cell extract was 10-times higher than that in the uninduced cell extract. The level of activity was similar in both CJ374 and BL21. The levels of expression of RT from pRE1-RT and pRE1-RT. 15 were similar.

Cloning of RT gene under a tac promoter. Since RSV RT βp4 was not expressed well under a lambda pL promoter, expression was attempted under the control of a different promoter. The RSV RT βp4 gene with and without the p15 gene was cloned under a tac promoter. For cloning the RT gene, pRE1-RT was digested with NsiI, blunt-ended with T4 DNA polymerase and finally, digested with XhoI. The RT fragment was purified from an agarose gel. For cloning the RT. 15 gene, pRE1-RT. 15 was digested with NsiI, blunt-ended with T4 DNA polymerase and finally, digested with SalI. The RT. 15 gene combination fragment was purified from an agarose gel. The vector pTrc99A (Pharmacia) was digested with NcoI, blunt-ended with Klenow fragment and finally, digested with SalI. The large vector fragment was purified and ligated with either purified RT or RT. 15 fragment. The resulting constructs were introduced into *E. coli* DH10B. Clones with correct inserts were saved. The clones were designated as pTrcRT and pTrcRT. 15.

Expression of RT under a tac promoter. *E. coli* cells harboring pTrcRT or pTrcRT. 15 were grown at 37° C. in a buffered-rich medium to an A590 to 0.1 or 0.6 before addition of IPTG (1 mM) for induction of RSV RT βp4 expression. The cells were collected 2 hr after induction. The uninduced cultures were grown similarly without addition of any inducer. The RT enzyme activity in soluble cell extract was equivalent to that obtained from constructs with the lambda pL promoter.

SDS polyacrylamide gel electrophoresis of the expressed proteins. RSV RT is composed of two subunits of molecular mass 94 kD (β) and 62 kD (α). The α subunit is a proteolytic fragment derived from the β subunit. The proteolysis is accomplished by RSV p15 protease in vivo. However, when induced *E. coli* extracts bearing the plasmids described were examined, two induced proteins of molecular mass 75 kD and 62 kD were detected. Both proteins were found to be mainly in the insoluble fraction of *E. coli* extracts. The presence of a 75 kD and not the expected 94 kD protein following expression in *E. coli* suggested that (i) there was a mutation near the carboxy end causing premature translation termination, (ii) there was proteolysis in the *E. coli* cytosol, or (iii) there was internal translation initiation of RT. When the carboxy terminal region of the RT gene was sequenced, no mutation was found that might have caused premature translation termination. To test whether there was an internal translation start, the RT gene was cloned as a HpaI-XhoI fragment in pTrc99 digested with SmaI and SalI. No induced protein could be detected suggesting that there was no internal start to generate either a 75 kD or 62 kD protein.

Expression of RT in a variety of *E. coli* hosts. As described above, expression of RSV RT was examined in *E. coli* DH10B, CJ374 and BL21. None of these *E. coli* hosts produced αβ RT, and the level of RT activity in each host was extremely low. Since M-MLV RT expresses well in *E. coli* N4830 and HIV RT expresses well in *E. coli* RR1, the levels of expression of RSV RT in these two hosts were examined. Neither of these hosts was found to express active RT any better than the other hosts tested, nor did they produce any full length 94 kD protein.

Expression of RT as a fusion protein. It is now well established that some proteins that do not express well in *E. coli* are better expressed as a translation fusion, in which the protein from a well expressed gene forms the amino end of the fusion protein. The gene of one such fusion partner, thioredoxin, is present in a vector called pTrxfus (Genetics Institute; Cambridge, Ma.). The level of expression of RSV RT βp4 fused with thioredoxin was therefore examined.

In the course of expressing RSV RT in a baculovirus system, the RSV RT gene fragment was cloned as a SmaI-XhoI fragment in pBacPAK9 to construct pBacPak-RT (see below). To make the thioredoxin fusion, pBacPak-RT was digested with XmaI (same recognition as SmaI) and PstI and the RT fragment was purified on an agarose gel. The vector pTrxfus was digested with XmaI and PstI and the large vector fragment was purified. The purified fragments were ligated and *E. coli* CJ374 and G1724 or G1698 (Genetic Institute, MA) were transformed with the ligated material. Clones with the correct insert were saved. When cultures were induced and the cellular extracts were assayed for enzyme activity, no RT activity was detected. Both induced cultures, however, produced a large amount of insoluble fusion protein of the expected size as judged by SDS-PAGE of the extracts. Other fusions were also tested. The RSV RT β gene was fused to the GST (glutathione S transferase) gene, and the RSV RT α gene was fused to the lambda CRO protein gene. Expression of either fusion from the trc promoter in *E. coli* strain DH10B resulted in a large amount of insoluble protein of the appropriate molecular weight, but little RT activity was detected in extracts of induced cells. An expression vector with both fusions (GST-beta and CRO-alphs) was constructed in which the fusions were co-expressed by induction of the trc promoter. Co-expression of both fusions in *E. coli* strain DH10B resulted in large amounts of insoluble protein of the appropriate molecular weights, but little RT activity.

Cloning and Expression Separately of Genes Encoding RSV RT Subunits α, β, and βp4 in a Baculovirus System Cloning of RSV RT βp4 in a Baculovirus System To clone the RSV RT βp4 gene in the baculovirus transfer vector, pBacPAK9 (Clontech), a fragment of the RSV RT gene was generated by PCR. To facilitate this PCR, the following oligonucleotide was designed with a BamHI site (bold) and the ATG initiation codon at the beginning of the RSV βp4 gene:

```
Oligonucleotide #16:
5'-TAT TAG GAT CCC ATG ACT GTT GCG CTA CAT CTG GC-3' (SEQ ID NO:22)
```

Figure 43:
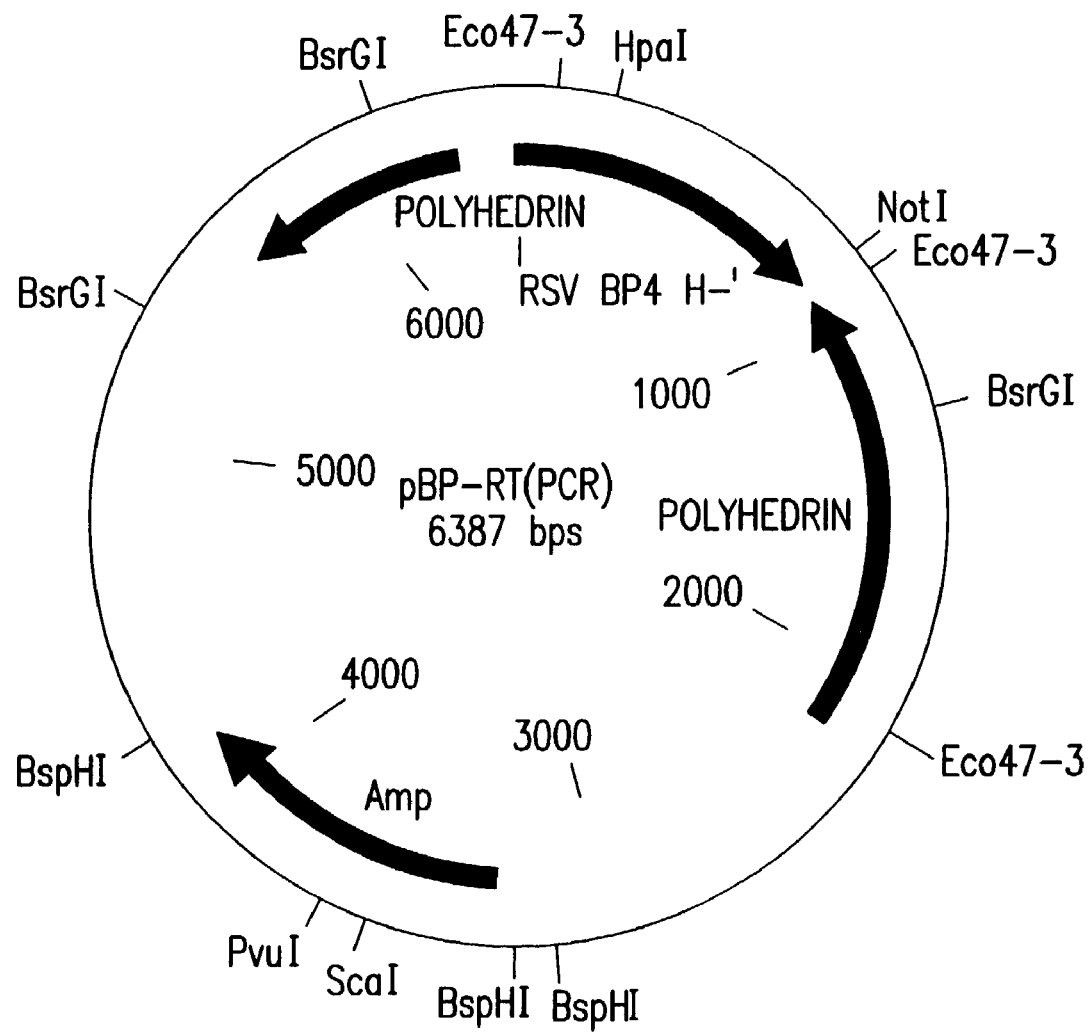
FIG. 43 is a restriction map of plasmid pBP-RT(PCR).
Figure 44:
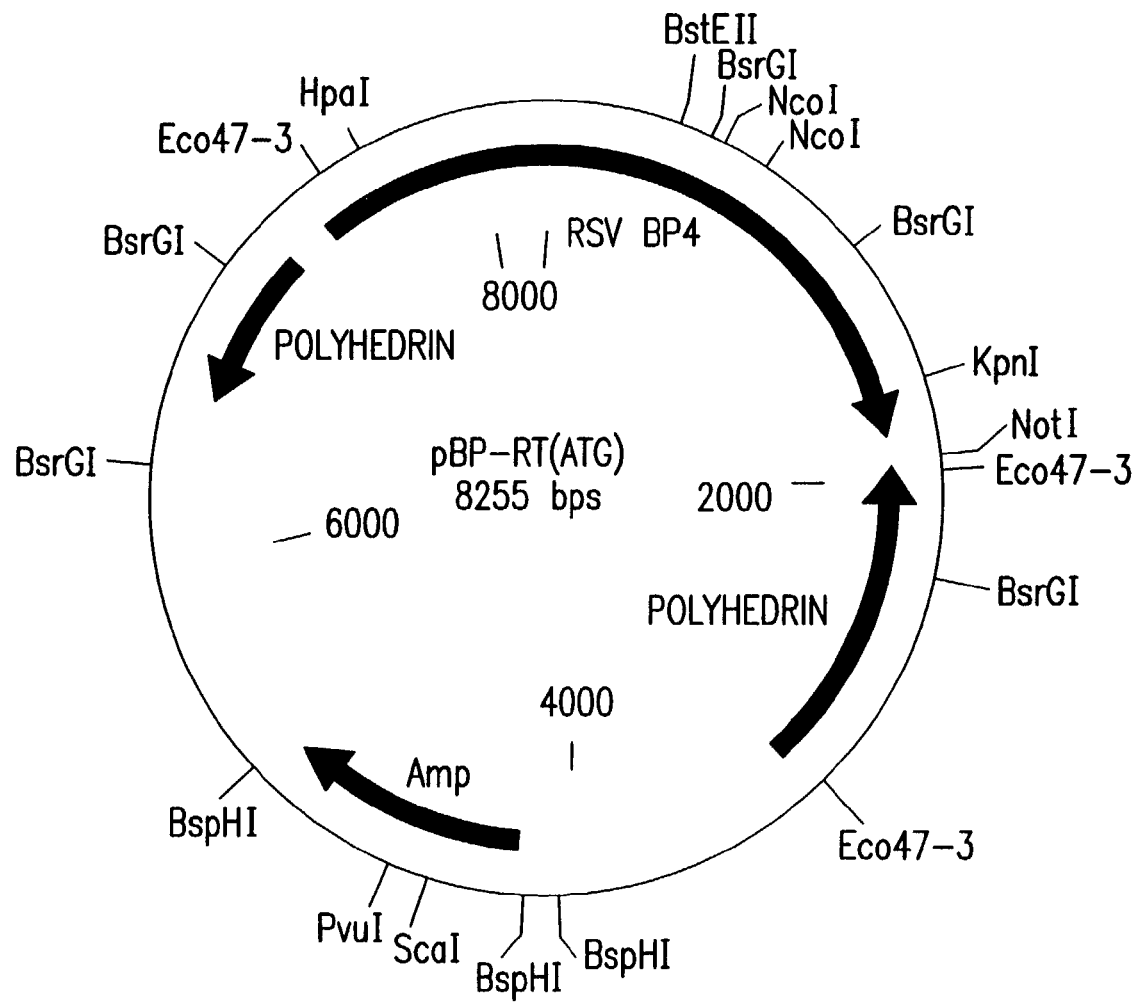
FIG. 44 is a restriction map of plasmid pBP-RT(ATG).

Oligonucleotides #12 and #16 (SEQ ID NOs: 18 and 22, respectively) were used for PCR using pJD100 as template. The PCR product was digested with BamHI and XbaI, and then ligated to pBacPAK9 digested with BamHI and XbaI. One of the clones, pBP-RT(PCR) (FIG. 43), was used for further cloning. To reconstitute the entire RT gene, the small HpaI-XhoI fragment of pBP-RT(PCR) was replaced with the 2500 bp HpaI-AhoI fragment of pRE1-RT. 15. The reconstituted plasmid was designated as pBP-RT(ATG) (FIG. 44).

Figure 45:
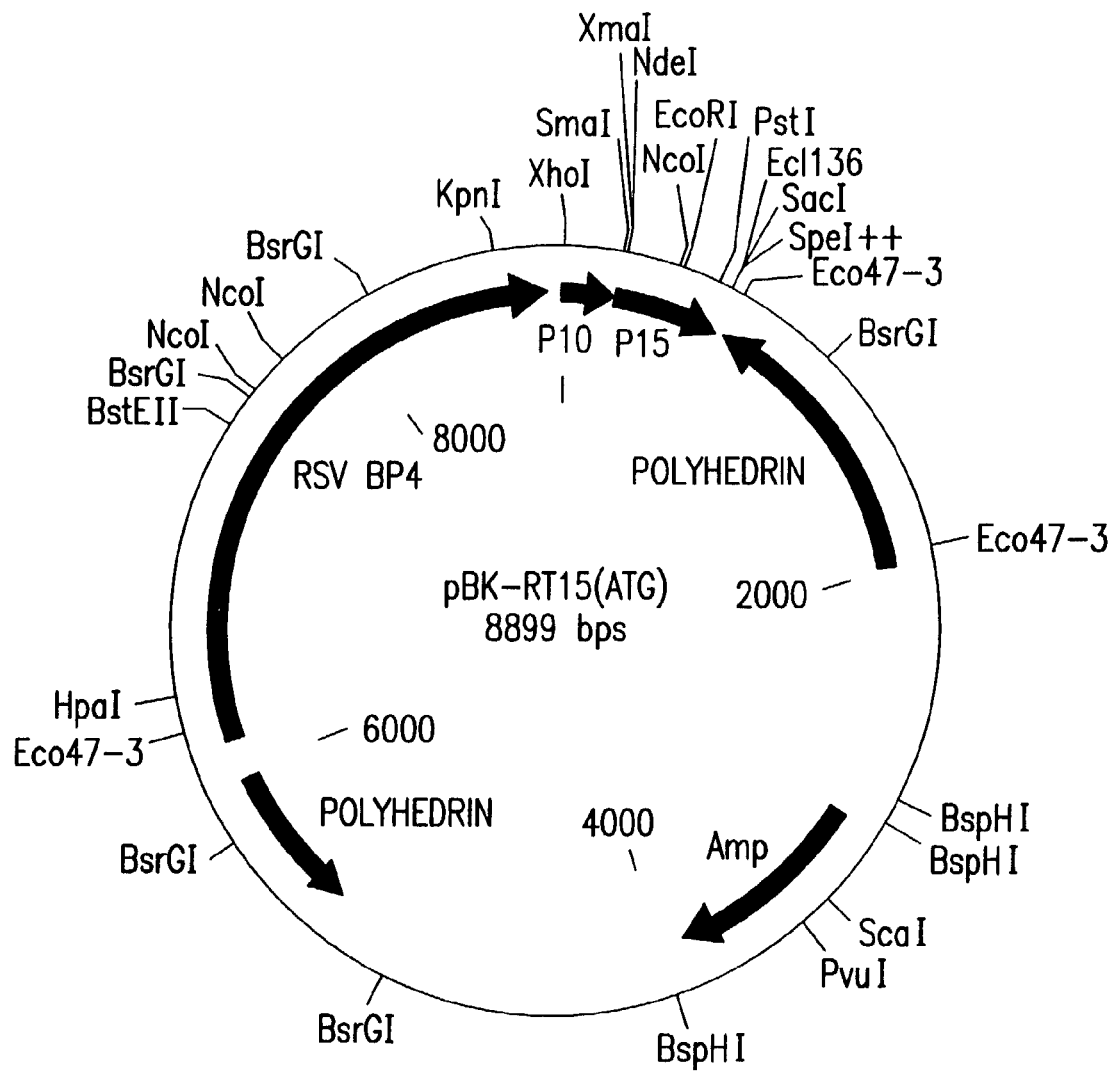
FIG. 45 is a restriction map of plasmid pBK-RT15(ATG).

Cloning of p15 in pBacPAK-RT(ATG). Placing the RSV p15 protease gene in pBP-RT(ATG) was achieved by a three-step cloning. First, a p15 gene fragment was subcloned from pUC19-p15 (see above) into pSport1 (LTI) as a KpnI-SalI fragment to generate pSport-p15. Second, the p15 fragment was subcloned from pSport-p15 as a NotI-SmaI fragment into a baculovirus transfer vector, pAcUW43, to generate pAcUW43-p15. This cloning was done to introduce the p15 gene under a p10 promoter. Finally, the p15 gene including the p10 promoter was subcloned from pAcUW43-p15 as a XhoI-NotI fragment into pBP-RT (ATG) to generate pBP-RT15(ATG) (FIG. 45).

Expressing RSV RT βp4 in insect cells. Insect cells (SF9) were transfected with a mixture of pBP-RT15(ATG) and linearized baculovirus vector DNA (BaculoGold, Pharmingen). In this system, recombination between the pBP-RT15 (ATG) plasmid and the baculoviral DNA results in recombinant viral genomes with the RSV RT βp4 gene downstream of the polyhedrin promoter. Recombinant virus was isolated from the supernatant by standard techniques and viral stocks were made, one of which was chosen for further study. Insect cells were infected with pure viral stock and infected cells were harvested at various times after infection. RT activity was easily detectable in the infected cells.

Generation of an RNase H- RSV RT The generation of a mutation in the RNase H region of the RSV RT βp4 gene is described in detail above in Example 1. To introduce the mutation into pBP-RT(ATG), the HpaI-KpnI fragment of pBP-RT(ATG) was replaced with the HpaI-KpnI fragment of M13RTH- (FIG. 13). The newly constructed plasmid was designated as pBP-RT(H-) ATG. Insect Cells (Sf9) were transfected with a mixture of pBP-RT(H-) and linearized baculovirus vector DNA (BaculoGold, Pharmingen). Recombination between the pBP-RT(H-) plasmid and the baculoviral DNA results in recombinant viral genomes with the RSV RT βH-P4 gene downstream of the polyhedrin promotor. Recombinant virus was isolated from the supernatant by standard techniques. Insect cells were infected with viral stock and infected cells were harvested at various times after infection. RT activity was easily detectable in the infected cells.

Attaching a histidine tag to RSV RT βp4. pBP-RT(H-) was cleaved with BamHI and XbaI and the 0.9 kb fragment with the amino end of the RSV RT βp4 gene was cloned into pFastBacHT at the BamHI-XbaI sites, creating (by translational fusion) a βp4 partial construct with a histidine tag at the amino end (pFBHTβP4). The 2 kb XbaI-XhoI fragment with the carboxy end of RSV RT βH-p4 from pBP-RT(H-) was inserted into the XbaI-XhoI sites of pFBHTβP4, creating pFBH-TβP4. pFHH-TβP4was transformed into *E. coli* DH10Bac cells and the His-tagged RSV RT βH-p4 gene was transposed to bacmid. Bacmid DNA was isolated and transfected into SF9 insect cells. Viral preparations from infected cell cultures were used to infect SF21 cells, and His- tagged RSV RT βH-p4 from infected cells was isolated and characterized.

Transfection of insect cells. The transfection of Sf9 cells was done using Baculogold virus (Pharmingen, CA) and pBP-RT(H-)ATG to generate recombinant virus. Ten wells on two 6-well (60 mm) tissue culture plates were seeded 1×10⁶ Sf9 cells (LTI). The cells were allowed to attach for 30 min at 27° C. While the cells were attaching, ten tubes each containing 200 μl of Sf-900II SFM medium (LTI) were set up. In tube 1, 500 ng of Baculogold and 2 µg of pBP-RT(H-)ATG were added. In tube 2, 250 ng of Baculogold and 1 βg of pBP-RT(H-)ATG; and tube 3, 125 ng of Baculogold and 500 ng of pBP-RT(H-)ATG were added. Tubes 6 through 9 contained 36 µl of lipofectin (LTI). Contents of tube 1, tube 2, tube 3, tube 4 and tube 5 were transferred to tubes 6, 7, 8, 9 and 10, respectively. Into each of these tubes, 2 ml of Sf-900 II SFM were added. The culture medium from each well was removed and 2 ml of the DNA/lipofectin mix was dispensed in two wells, 1 ml each. Thus, the wells containing the mixture of tubes 1 and 6, 2 and 7, and 3 and 8 contained DNA mixtures at different amounts; the wells containing the mixtures of tubes 4 and 9 were controls containing lipofectin but no DNA; and the wells containing the mixtures of tubes 5 and 10 were controls containing neither DNA nor lipofectin. The plates were incubated at 27° C. for 4 hr, the medium was removed and replaced with 4 ml fresh Sf-900 II SFM, and the plates were incubated for an additional 72 hrs at 27° C. The phage supernatants from the DNA containing wells were removed and marked as primary phage stocks. A second infection was done by infecting 1×10⁶ Sf9 cells with 1 ml of the primary phage stock to amplify the recombinant phage. The plates were incubated for 48 hrs at 27° C. and the phage stocks were collected.

Injection of insect larvae. Trichoplusa ni larvae were injected with recombinant virus bearing pBP-RT(H-)ATG and the larvae were harvested as described (Medin, J. A., et al., *Methods in Molecular Biology* 39:26 (1995)).

Expression of RSV RT αH- in a Baculovirus System pDA (FIG. 19) was transformed into *E. coli* DH10Bac cells, the RT αH-gene was transposed to bacmid, and the bacmid DNA was purified and transfected into SF21 insect cells. Viral preparations from infected cell cultures were used to infect SF21 cells, and RSV RT αH⁻ from infected cells was isolated and characterized.

Expression of RSV RT βH-His in a Baculovirus System pDABH-His (FIG. 21) was cleaved with RsrII and PstI, and the 2.6 kb fragment with the βH-His gene was cloned into the RsrII-PstI sites of pFastBac. pFBBH-His was transformed into *E. coli* DH10Bac cells, the RT βH-His gene was transposed to bacmid, and the bacmid DNA was purified and transfected into SF21 insect cells. Viral preparations from infected cell cultures were used to infect SF21 cells, and RSV RT βH-His from infected cells was isolated and characterized.

Cloning and Expression of Genes Encoding RSV αβ RT in which the Polymerase Active Site is Mutated Generation of RSV RTs mutated in the polymerase domain. Alignment of the RSV RT peptide sequence with sequences from HIV RT, M-MLV RT, and sequences of other RT genes revealed the probable location of one of the catalytic residues in the RSV RT polymerase domain, D110 (aspartic acid reside at position number 110). According to the literature, mutation of the corresponding amino acid in the larger chain of HIV RT from D (aspartate) to E (glutamic acid) resulted in nearly total loss of polymerase activity. Single strand DNA was isolated from pJB-His by infection of *E. coli* DH5αFIQ/pJB-His cells with M13KO7, and this DNA was mutated by site-directed mutagenesis (see Example 1 for detailed protocol) with the following oligonucleotide:

```
Oligonucleotide #17:           (SEQ ID NO:23)
5'- GCAATCCTTGAGCTCTAAGACCATCAGGG 3'
```

Figure 46:
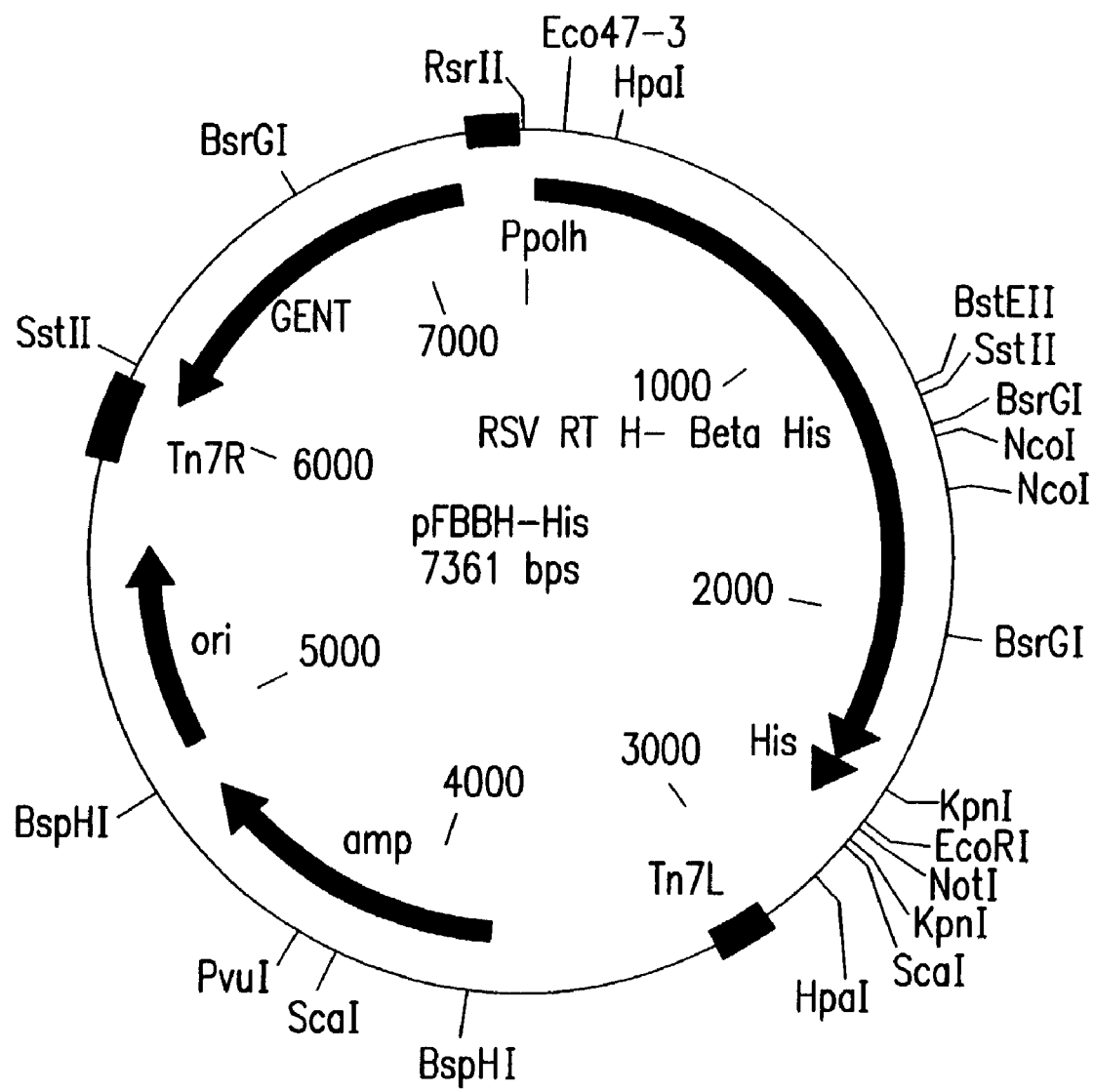
FIG. 46 is a restriction map of plasmid pFBBH-His.
Figure 47:
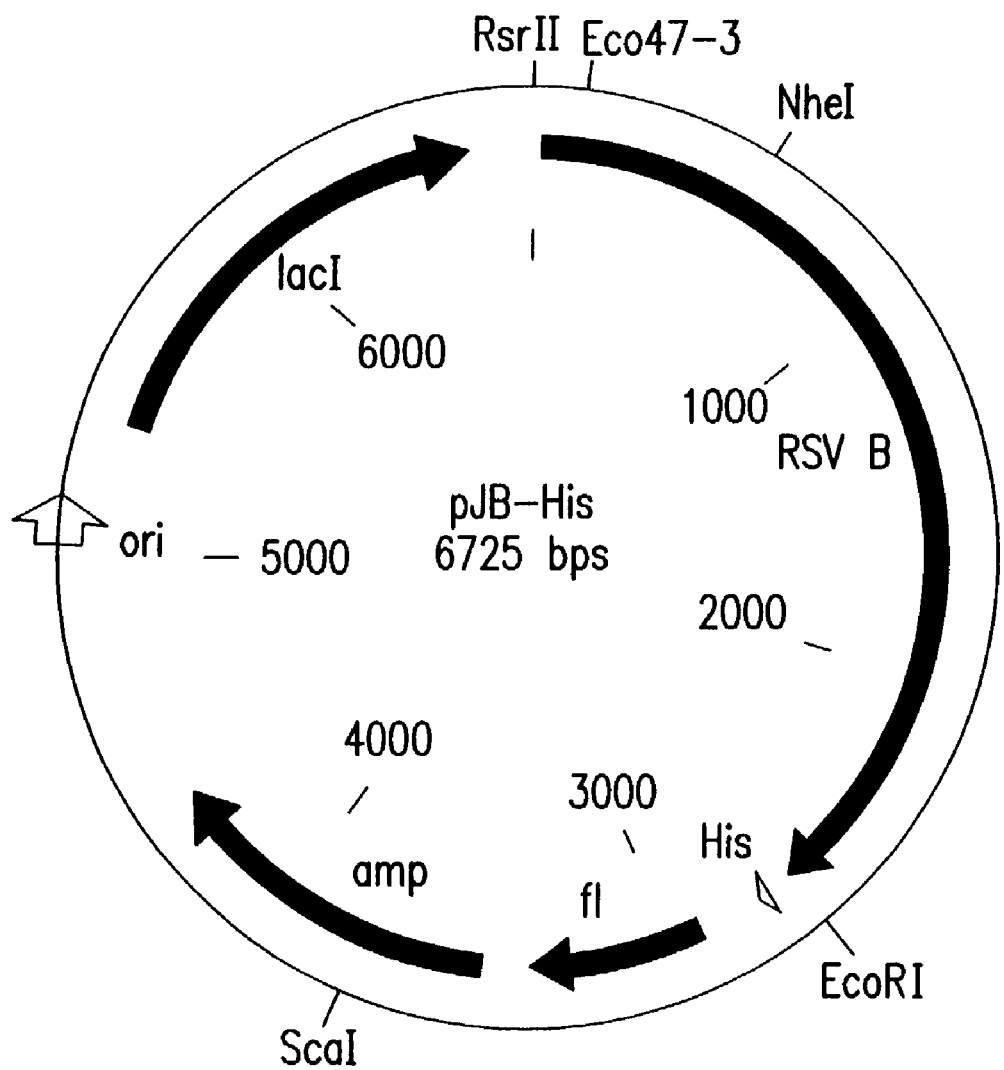
FIG. 47 is a restriction map of plasmid pJB-His.
Figure 48:
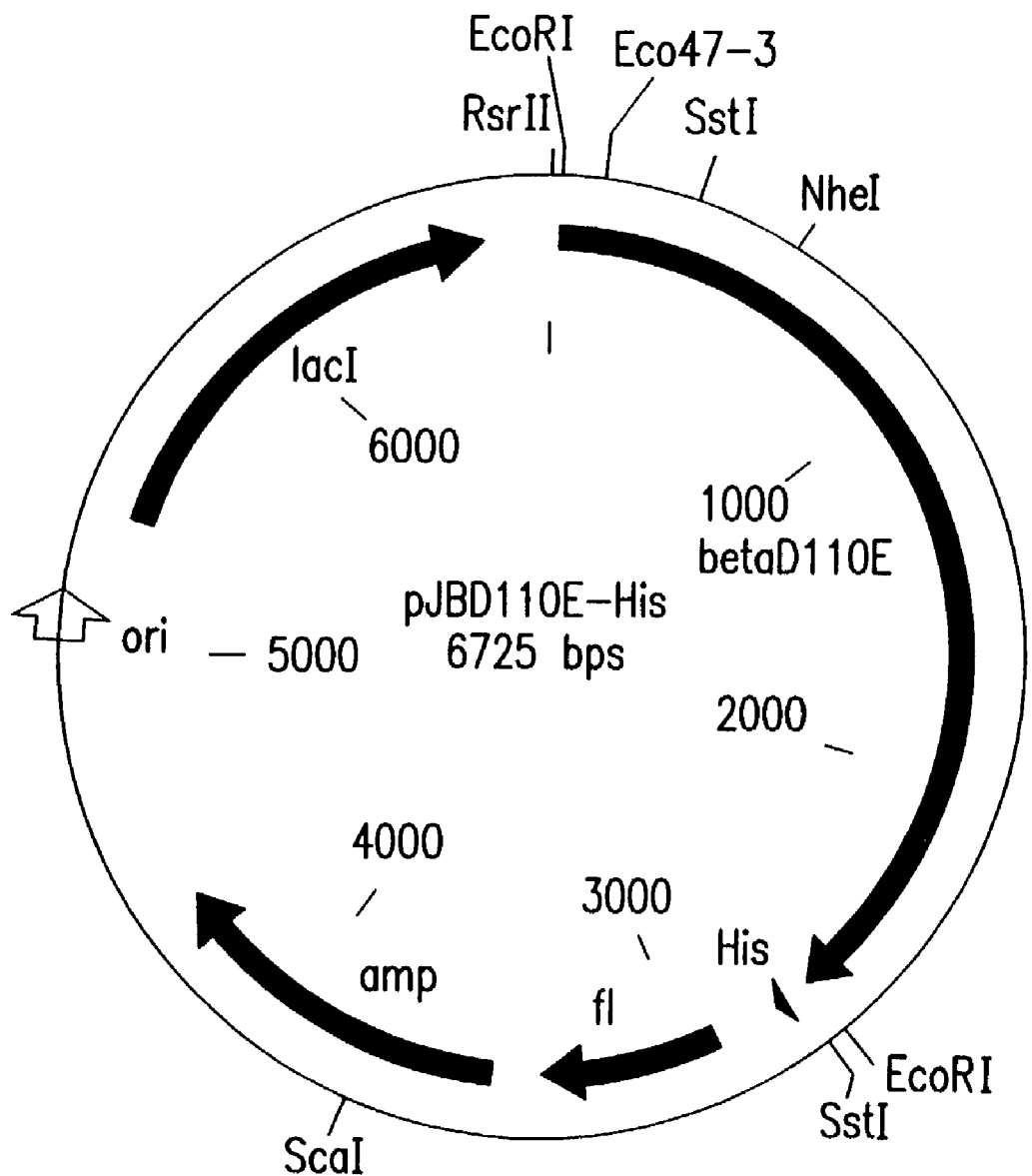
FIG. 48 is a restriction map of plasmid pJBD110E-His.
Figure 49:
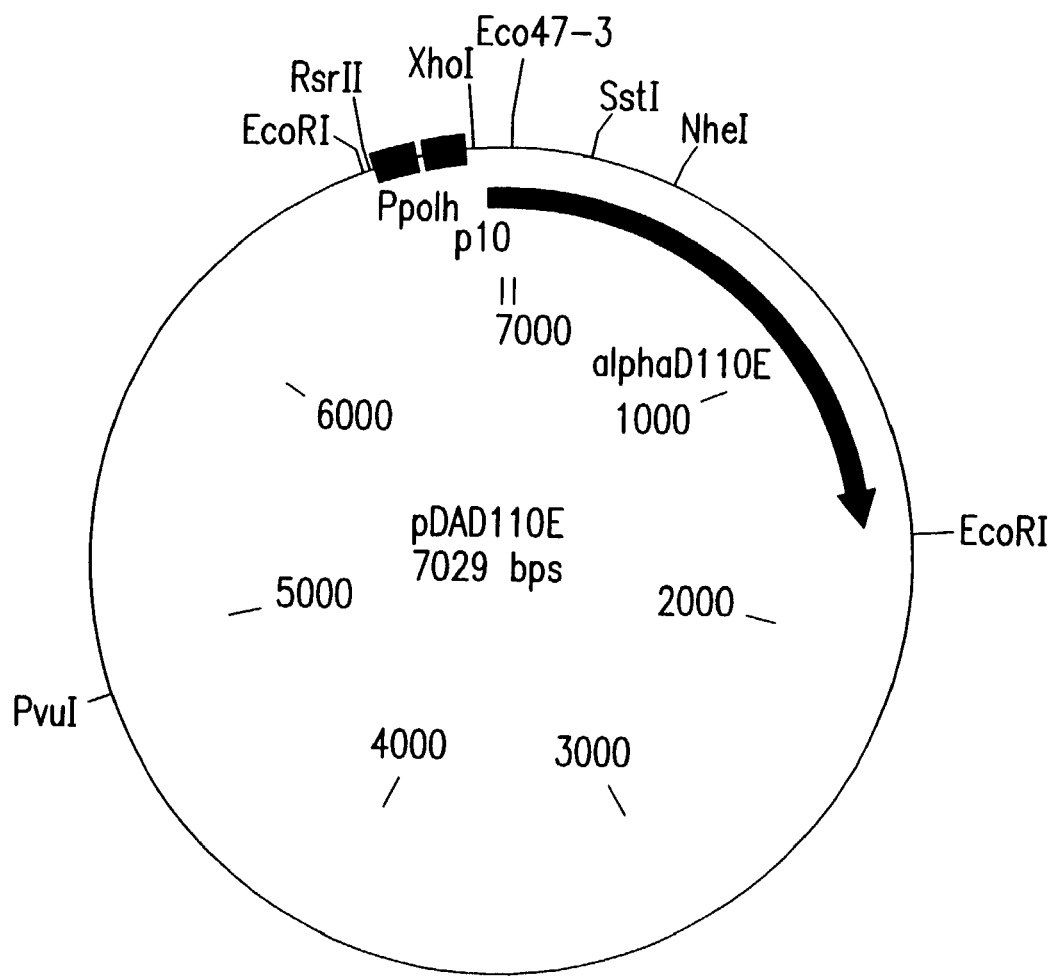
FIG. 49 is a restriction map of plasmid pDAD110E.
Figure 50:
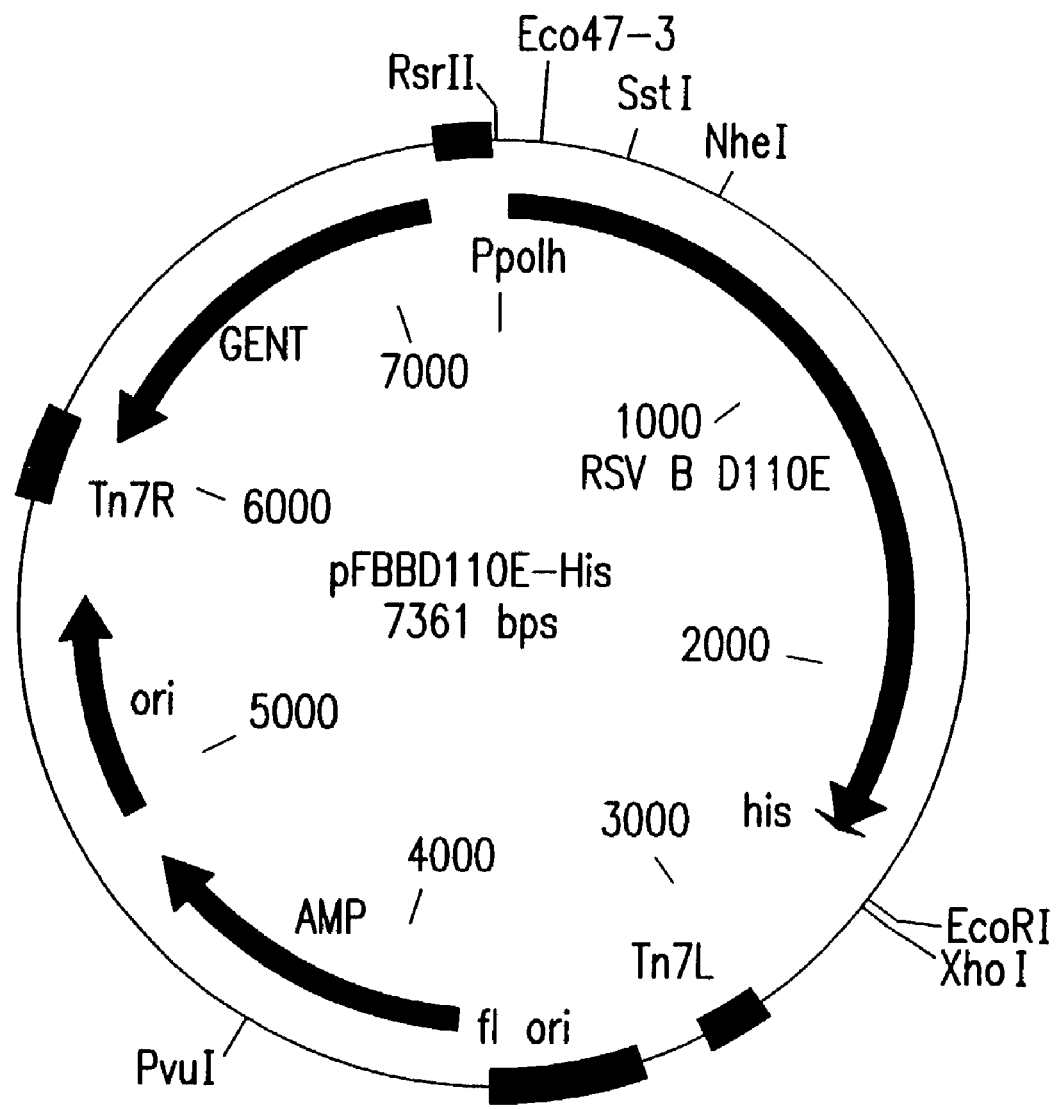
FIG. 50 is a restriction map of plasmid pFBBD110E-His.
Figure 51:
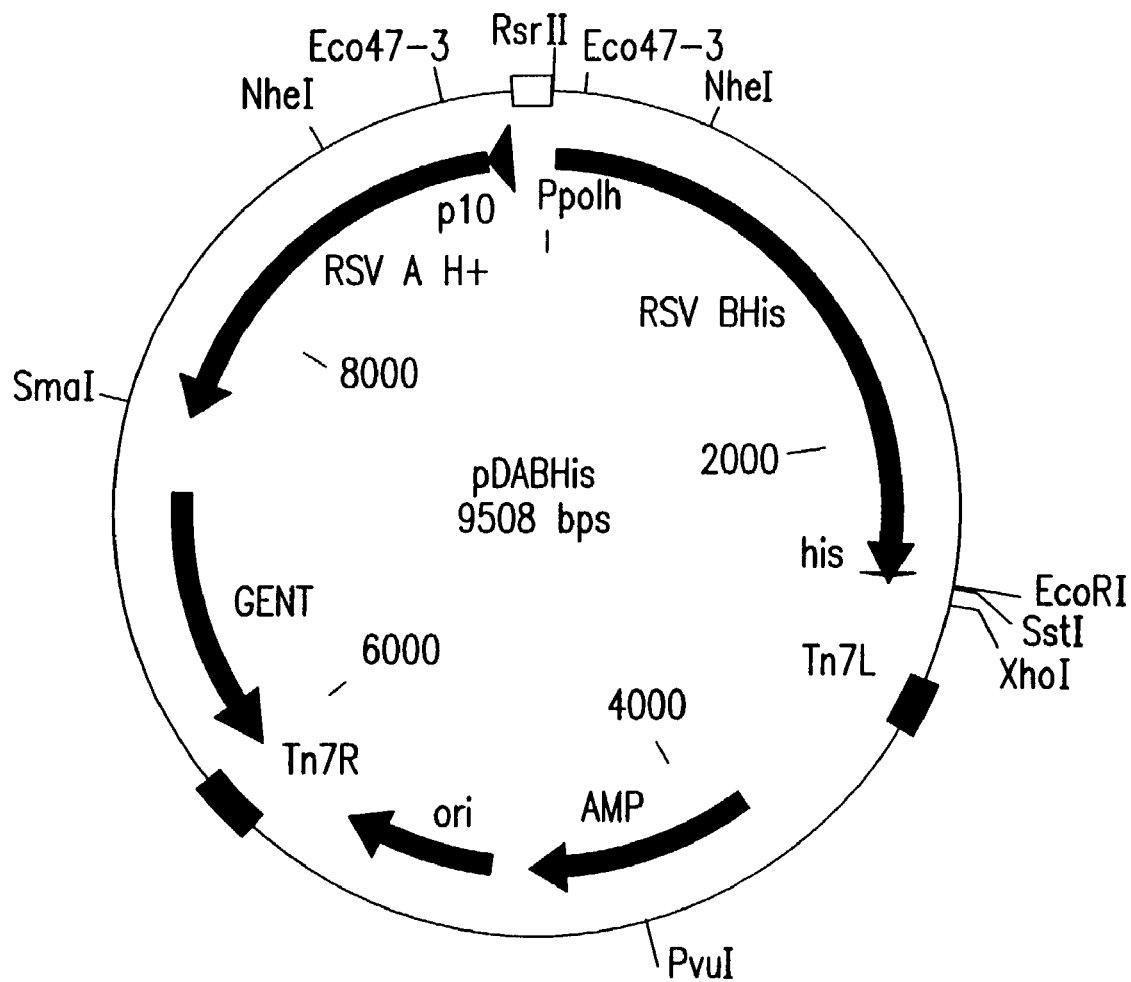
FIG. 51 is a restriction map of plasmid pDABHis.
Figure 52:
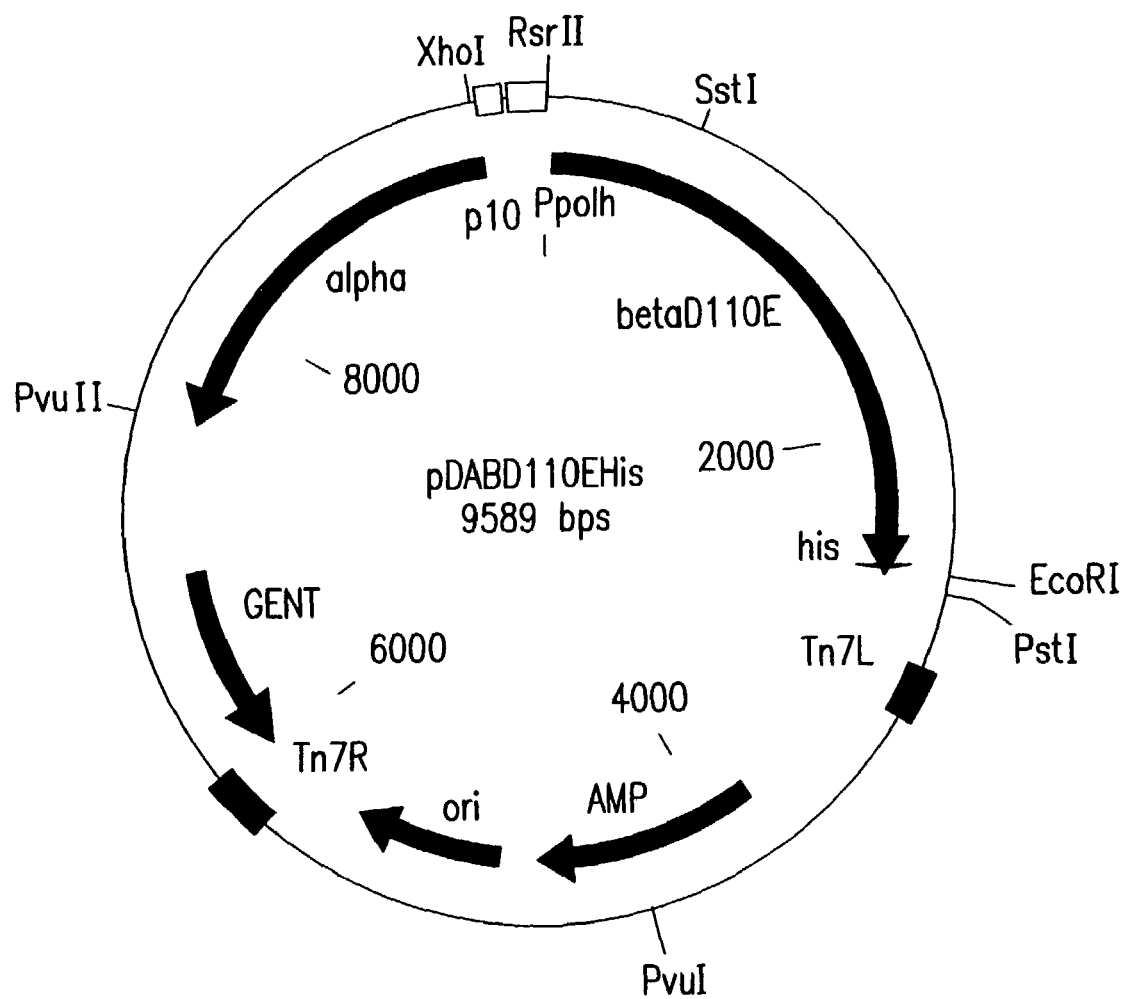
FIG. 52 is a restriction map of plasmid pDABD110EHis.
Figure 53:
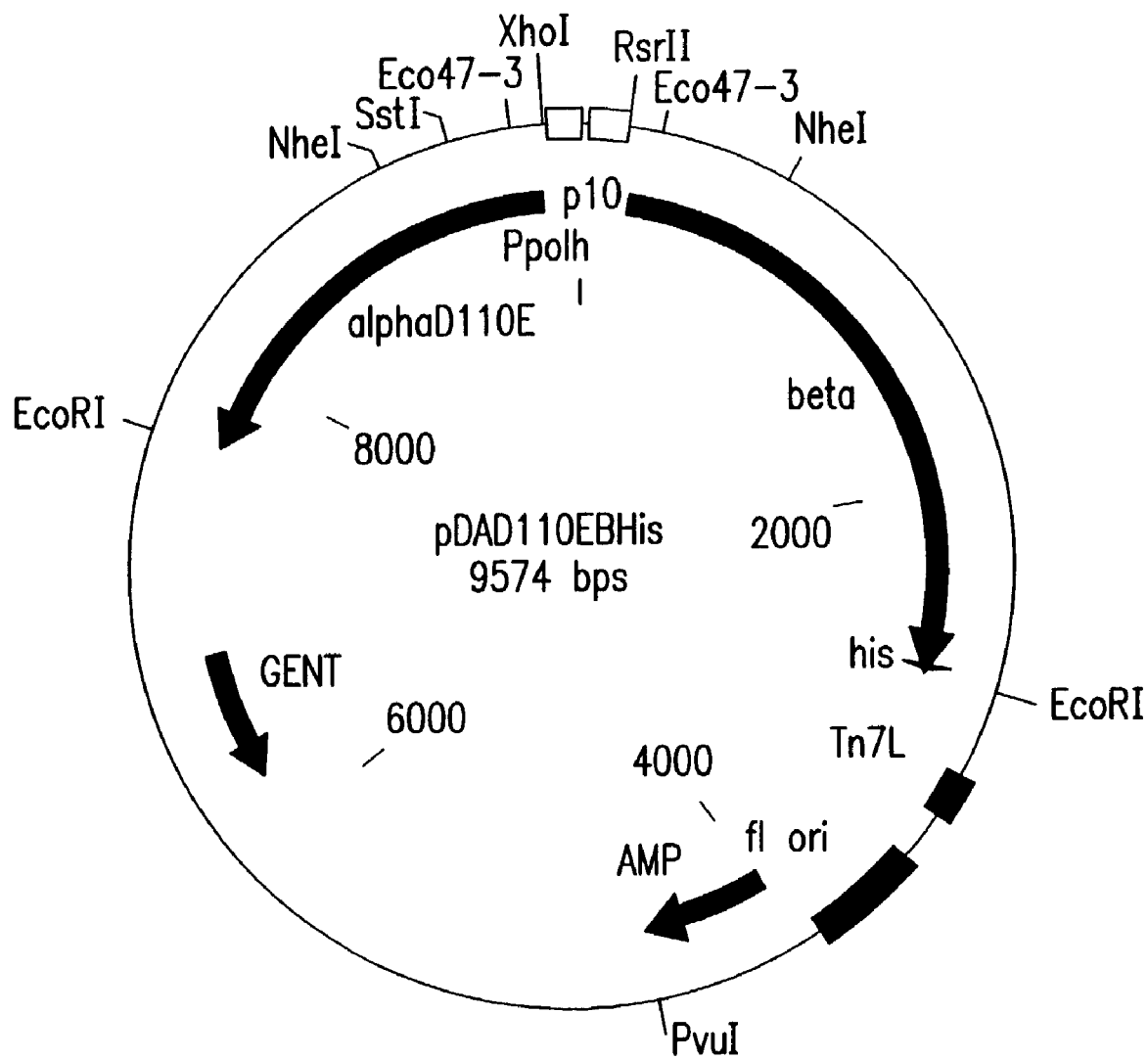
FIG. 53 is a restriction map of plasmid pDAD110EBHis.
Figure 54:
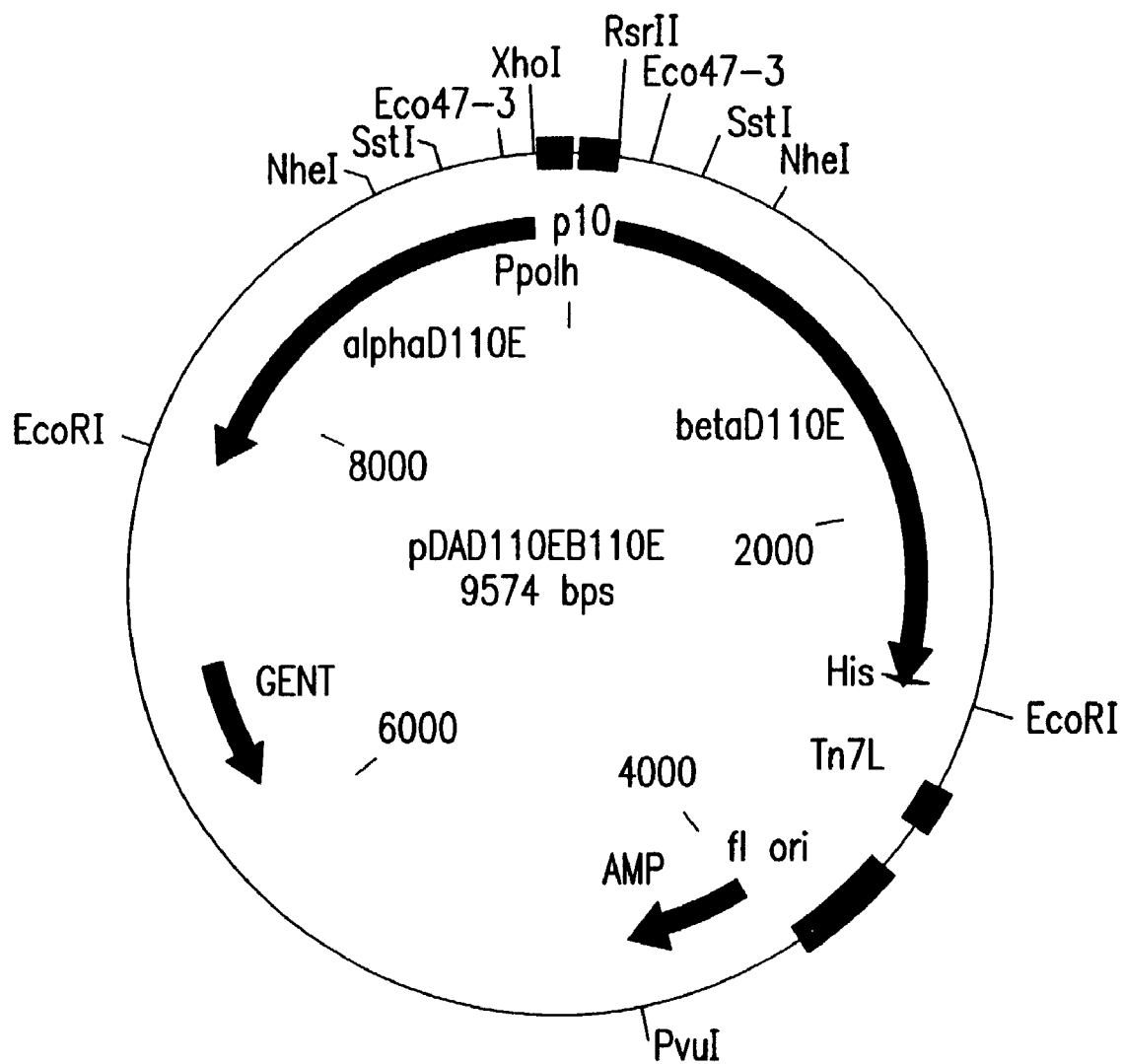
FIG. 54 is a restriction map of plasmid pDAD110EB110E.

This oligonucleotide induces the mutation of the aspartate residue at position #110 or the RSV RT catalytic domain to glutamate (D110E) and adds an SstI site (bold), forming plasmid pJBD110E-His (FIG. 48). This mutated site was introduced into the RSV RT α gene by inserting the 460 bp NheI-Eco47III fragment from pJBD110E-His into the 6.5 kb fragment of NheI-Eco47III cleaved pDA, forming pDAD110E (FIG. 49). The D10E mutation was also introduced into the β gene by inserting the 460 bp NheI-Eco47III fragment into NheI-Eco47III cleaved pFBBH-His (FIG. 46), forming pFBBD110E-His (FIG. 50). The 2.6 kb RSV RT βD110E gene was cloned from pFBBD110E-His into pDABHis (FIG. 51) as a 2.6 kb RsrII-EcoRI fragment, replacing the RSV RT β-His gene, forming pDABD110EHis (FIG. 52). pDABHis was cleaved with AhoI+PvuI, and the 4.6 kb fragment with the β gene was joined to the 4.9 kb pDAD110EXhoI-PvuI fragment, forming pDAD110EBHis (FIG. 53). The 4.6 kb pDABD110EHisXhoI-PvuI fragment with the βD110E gene was joined to the 4.9 kb pDAD110E XhoI-PvuI fragment, forming pDAD110EBD110E (FIG. 54) (which has a his tag despite its truncated name). pDAD110EBHis, pDABD110EHis, and pDAD110EBD110E were transformed into *E. coli* DH10B-Bac, the RT genes were transposed to the bacmid, and the bacmid DNA was purified and transfected into SF21 insect cells. Viral preparations from infected cell cultures were used to infect SF21 cells, and RSV RT from infected cells was isolated and characterized.

The three mutant plasmids are summarized in the following table, where "w.t." refers to the wild type amino acid at the 110 position (D, aspartic acid) and D110E refers to the mutation at the 110 position (D to E, glutamic acid):

| Plasmid | α | β |
| --- | --- | --- |
| pDABHis | w.t | w.t. |
| pDABD110EHis | w.t | D110E |
| pDAD110EBHis | D110E | w.t. |
| pDAD110EB110E | D110E | D110E |

Cloning and Expression of RSV, βp4 RT in Yeast

Cloning of the RSV βp4 RT gene. The pHIL-D2 vector available from In Vitrogen (CA) was digested with EcoRI, blunt ended with Klenow fragment and treated with alkaline phosphatase. pRE1-RT. 15 was digested with NdeI and blunt ended with Klenow fragment. The NdeI digest generated the entire RSV RT gene without the p15 protease gene. The fragments were ligated and *E. coli* DH10B was transformed with ligation mixture. The correct clones were selected for proper insert and orientation. Two of the 8 clones tested had the RT gene fragment in the correct orientation. One of the clones, pHILD2-RT, was used for further experimentation. To introduce the RNase H- domain in this plasmid, pHILD2-RT was digested with BamHI plus XhoI and the wild type fragment was replaced with BamHI-XhoI fragment from pBacPAK-RT(H-)ATG. The final clone was screened with SstII. The clone was designated as pHILD2-RT(H-).

Transformation of *Pichia pastoris*. *Pichia pastoris* GS115 (In Vitrogen) was used for transformation according to the protocol recommended by In Vitrogen. The plasmids, pHILD2-RT and pHELD2RT(H-), were digested with NotI, phenol-chloroform extracted and ethanol precipitated before transformation. The transformation yielded 20 clones for wild type RSV RT and 12 clones for RSV H- RT in the regeneration plates. These clones were screened for their growth in methanol containing plates. Two putative clones were selected from initial 20 clones (wild type RT). One of these two, H1, was completely incapable of growing in methanol, and the other, H2, was capable of growing very slowly in methanol. For the RSV H- RT clones, three clones were selected out of 12 screened. One of the clones, H-3, grew very slowly in methanol. The others, H-4 and H-5, grew moderately in methanol. Clones HI and H-3 were chosen for expression studies.

RSV β4 RT expression in *Pichia pastoris*. Clones H1 and H-3 were grown and induced essentially as described in the user's manual provided by the manufacturer (In Vitrogen). As a control, GS115 containing a β-galactosidase gene (In Vitrogen) was grown and induced side by side. While no RT activity could be detected in the GS115/β-gal cells, an appreciable level of activity was detected in both Hi (wild type RT) and H-3 (H- RT) cells. In addition, the activity increased with increased time of induction.

Isolation of RSV ββ, α and βp4 βp4

RSV ββ RT isolation. RSV ββ RT was purified as described in Example 2 for RSV αβ RT with the following exceptions. RSV ββ RT eluted from the AF-Heparin-650M column from 55–62% Buffer T, and from the Mono S HR 5/5 column from 58–62% Buffer J. RSV ββ RT was 90% homogeneous as judged by SDS-PAGE.

RSV α RT isolation. RSV α RT was purified as described in Example 2 for RSV αβ RT with the following exceptions. The Chelating Sepharose Fast Flow column was equilibrated with 100% Buffer A and washed with 100% Buffer A after the clarified crude extract was passed over the column. RSV α RT was eluted with a 10-column volume linear gradient of 100% Buffer A to 75% Buffer A+25% Buffer B. The peak fractions of RT activity from the Chelating Sepharose Fast Flow column (10–12% Buffer B) were pooled, dithiothreitol and EDTA were added to the pool to achieve final concentrations of 1 mM and 0.1 mM, respectively, and the pool was dialyzed overnight against 95% Buffer S+5% Buffer T. The dialyzed pool was loaded on a 22 ml AF-Heparin-650M column equilibrated in Buffer S. After a wash with 9 column volumes of 95% Buffer S+5% Buffer T, the column was eluted with a 9 column volume linear gradient of 95% Buffer S+5% Buffer T to 60% Buffer S+40% Buffer T. The peak fractions of RT activity (11–20% Buffer J) were pooled and dialyzed for 3 to 4 hours against 97.5% Buffer H and 2.5% Buffer J. The dialyzed pool was loaded unto a 3.5 ml phosphocellulose column (Whatman) equilibrated in 100% Buffer H. After a wash with 12 column volumes of 97.5% Buffer H+2.5 Buffer J, the column was eluted with a 14 column volume linear gradient of 97.5% Buffer H+2.5% Buffer J to 60% Buffer H+40% Buffer J. The peak fractions of RT activity (12–20% Buffer J) were pooled and dialyzed overnight against 99% Buffer S+1% Buffer T. The dialyzed pool was loaded unto a Mono S HR 5/5 column equilibrated in Buffer S. After a wash with 10 column volumes of 100% Buffer S, the column was eluted with a 20 column volume linear gradient of 100% Buffer S to 75% Buffer S+25% Buffer T. The RT peak fractions (15–17% Buffer T) were pooled, dialyzed against Storage Buffer overnight, and stored at −20° C. RSV α RT was found to be 80% homogeneous as judged by SDS-PAGE.

RSV βp4 βp4 RT isolation. RSV βp4βp4 RT was purified as described in Example 2 for RSV αβ with the following exceptions. The pooled RT fractions from the Chelating Sepharose Fast Flow column were dialyzed overnight against 90% Buffer H+10% Buffer J. The RSV βp4βp4 RT precipitated in this buffer. The RT was recovered by centrifugation, dissolved in Storage Buffer containing 0.5 M KCl, and stored at −20° C. RSV βp4βp4 RT was found to be >95% homogeneous as judged by SDS-PAGE.

Estimation of the Amounts of α, αβ and ββ RSV RT in Baculovirus-Infected Insect Cells Chromatography methods described in Example 2 can be used to separate and isolate any α, αβ and ββ RSV RT present in crude extracts from virus-infected insect cells. RSV RT α is separable from the other two enzymes forms by chromatography on a Chelating Sepharose Fast Flow column, where α either does not bind or elutes at <30 mM imidazole, and αβ and ββ elute together at>50 mM imidazole. This is possible by virtue of the $HiS_6$ tag present on β, but not on α. RSV αβ and ββ RT are separable subsequently by chromatography on Heparin-650M (αβ elutes at 0.45M KCl and ββ elutes at 0.58M KCl). Reverse transcriptase is quantitated by assay with poly(C)•oligo(dG) (Gerard, G. F., et al., *Biochemistry* 13: 1632 (1974)). The specific activities of RSV RT α, αβ and ββ with poly(C)•oligo(dG) are 140,000, 90,000 and 6,000 units/mg of protein, respectively.

Cloning, Expression, Purification and Use of RSV Viral Protease p15

RSV viral protease was cloned and expressed as a linked dimer in *E. coli* and purified from inclusion bodies as described (Bizub, D., et al., *J. Biol. Chem.* 266: 4951 (1991)).

Reaction mixtures (25 µl) used to digest RSV βp4 RT with RSV protease contained 100 mM $NaPO_4$ (pH 6.0 to 7.0), 1 mM 2-mercaptoethanol, 0.01% (W/V) Triton X-100, 2.4 M NaCl, 5 µg RSV βp4 RT, and 5 µg RSV protease. Incubations were for 1 to 16 hours at 4° C. Digestion products were analyzed by SDS-PAGE and by assay for recovery of RT activity.

Assay of RNase H Activity of RSV RT

The RNase H activity of RSV RT was determined by monitoring the solubilization of $[^3H]$poly(A) in $[^3H]$poly(A) •poly(dT). Reaction mixtures (50 µl) contained 50 mM Tris-HCl (pH 8.4), 20 mM KCl, 10 mM $MgCl_2$, 10 µM each of $[^3H]$ poly(A) (300 cpm/pmole) and poly(dT) in $[^3H]$poly (A)•poly(dT) and 10 mM dithiothreitol. Reaction mixtures were incubated at 37° C. for 20 minutes. Incubations were terminated by the addition of 80 µl of 20% (W/V) TCA and 10 µl of 1 mg/ml tRNA, and after centrifugation the amount of $[^3H]$poly(A) solubilized was determined by counting the supernatant in aqueous scintillation fluid. One unit of RNase H activity was the amount of enzyme that solubilized one nmole of $[^3H]$poly(A) in 20 minutes at 37° C.

Assay of DNA Polymerase Activity with Poly(C)•Oligo(dG)$_{12-18}$

The RNA-dependent DNA polymerase activity of RSV RT was determined by monitoring the synthesis of acid insoluble $[^3H]$poly(dG) form poly(C)•oligo(dG). Reaction mixtures (50 µl) contained 50 mM Tris-HCl (pH 8.4), 50 mM KCl, 10 mM $MgCl_2$, 0.5 mM poly(C), 0.2 mM oligo $(dG)_{12-18}$, 0.5 mM $[^3H]$dGTP (40 cpm/pmole), and 10 mM dithiothreitol. Reactions were incubated at 37° C. for 10 minutes and labeled products were acid precipitated on GF/C glass filters that were counted in a scintillation counter. One unit of DNA polymerase activity was the amount of enzyme that incorporated one nmole of $[^3H]$dGTP in 10 minutes at 37° C.

Results and Discussion

Alternative Methods of Generating RSV αβ RT

Examples 1 through 6 demonstrated that RNase H⁻ forms of avian RT are more efficient than RNase H⁺ RT in copying mRNA. The studies presented in this Example were designed to determine the efficiency of mRNA copying by RSV RNase H⁻ αβ RT that was generated by co-expression of the RSV α and β genes in several expression systems.

Expression in *E. coli*. Small amounts of soluble and active α, ββ, βp4βp4, and αβ RSV RT have been purified from *E. coli* (Alexander, F., et al., *J. Virol.* 61: 534 (1987); Weis, J. H., and Salstrom, J. S., U.S. Pat. No. 4,663,290 (1987); Soltis, D. A. and Skalka, A. M., *Proc. Nat. Acad. Sci. USA* 85:3372 (1988); and Cherhov, A. P., et al. *Biomed Sci.* 2: 49 (1991)). However, most of the RSV RT expressed in *E. coli* in these previous reports was in an insoluble form.

The present efforts to express amounts of RSV RT proteins easily purified from *E. coli* are documented in the Materials and Methods section of this Example. In general, similar results to those previously published were obtained; that is, most of the RSV RT protein expressed in *E. coli* was insoluble, and only small amounts of RT activity were observed. Because of low RT levels, no attempts were made to purify RSV RT expressed in *E. coli*.

Expression of the RSV RT βp4 or β gene in cultural insect cells. Heterodimeric p66/p51 HIV RT has been produced in *E. coil* and yeast host cells when the cloned gene for HIV p66 was expressed (Lowe, D. M., et al., *Biochemistry* 27:8884 (1988); Muller, B., et al., *J. Biol. Chem.* 264:13975 (1989); and Barr, P. J., et al., *Bio Technology* 5:486 (1987)). Formation of the heterodimer occurs by proteolytic processing of p66/p66 by endogenous host proteases. In contrast, expression of the gene for HIV RT p66 in cultured insect cells yielded only p66/p66 homodimer (Kawa, S., et al., *Prot. Expression and Purification* 4:298 (1993)).

In the present studies, expression of the gene for RSV RT βp4 in cultured insect cells was similarly found to result exclusively in the production of homodimer βp4βp4 (data not shown); little processing to αβ or α was observed. When the RSV RT β gene was expressed in these cells, however, all three forms of RSV RT were produced (Table 6). Most of the RT present in the cells was ββ (50–80%); a small amount of αβ was produced (~10%); and even a was obtained (10–40%). These results suggest that endogenous host proteases in cultured insect cells proteolyze ββ but not βp4βp4, to αβ. The RSV αβ RT generated by proteolysis of ββ had much lower functional activity than αβ generated by co-expression of the RSV RT α and β genes (Table 7).

TABLE 6

Expression Levels of RSV RTs in Insect Cells Infected With RSV RT β Gene

Amount of RT Present per 30 grams of Insect Cells

| | RSV ββ RT | | RSV αβ RT | | RSV α RT | |
|---|---|---|---|---|---|---|
| Infection No. | mg | % | mg | % | mg | % |
| 1 | 0.7 | 54 | 0.1 | 8 | 0.5 | 38 |
| 2 | 0.12 | 79 | 0.017 | 11 | 0.015 | 10 |
| 3 | 0.55 | 83 | 0.05 | 8 | 0.06 | 9 |

Expression of RSV RT βp4 in insect larvae. Baculovirus bearing the RSV RT βp4 gene was also used to infect live larvae by physical injection of virus. The level of proteases present in larvae and in larval extracts is much higher than in cultured insect cells. Processing of βp4 to multiple forms of proteolyzed RT was observed, including processing to α. The major species of RT that could be purified from these extracts had four major bands that migrated on SDS-PAGE at 97 kDa (His-tagged β), 87 kDa (proteolyzed β), 67 kDa (partially processed His-tagged α), and 62 kDa (α with His tag removed by proteolysis). This RSV RT had a specific activity of 55,000 units/mg protein, comparable to RSV αβ RT. In the functional activity assay (Example 3), however, the RT purified from larvae had 85% and 60% of the total product and full length product functional activity, respectively, of RSV αβ RT generated by co-expression of α and β (Table 7).

TABLE 7

Specific and Functional Activities of Various Forms of RSV RTs Expressed in Insect Cells RT Form Isolated

| | RSV αβ RT | | | RSV ββ RT | | | RSV α RT | | | RSV βp4βp4 RT | | |
|---|---|---|---|---|---|---|---|---|---|---|---|---|
| | | Functional Activity[b] | | | Functional | | | Functional Activity | | | Functional Activity | |
| | Specific | | Full- | Specific | Activity | | Specific | | Full- | Spec. | | Full- |
| Gene(s) Expressed | Activity[a] (U/mg) | Total (ng/µg)[c] | length (ng/µg)[d] | Activity (U/mg) | Total (ng/µg) | Full-length (ng/µg) | Activity (U/mg) | Total (ng/µg) | length (ng/µg) | Act. (U/mg) | Total (ng/µg) | length (ng/µg) |
| α and β | 53,191 | 4,092 | 874 | NP[e] | NP | NP | ND[f] | ND | ND | NP | NP | NP |
| β | 25,113 | 1,098 | 116 | 15,819 | 584 | 41 | ND | ND | ND | NP | NP | NP |
| βp4 | NP | NP | NP | NP | NP | NP | NP | NP | NP | 15,984 | 450 | 67 |
| α | NP | NP | NP | NP | NP | NP | 48,759 | 272 | 6 | NP | NP | NP |

[a]Specific activity = units (U) RT activity /mg RT protein in poly(A)•oligo(dT) assay (Houts et al., J. Virol. 29:517 (1979)).
[b]Functional activity established with 7.5 Kb RNA as described in Example 3.
[c]Mass of total reverse transcribed product, ng of product produced per µg of RT used.
[d]Mass of full-length reverse transcribed product, ng of product produced per µg of RT used.
[e]"NP" = RT form not produced by insect cells expressing the indicated gene.
[f]"ND" = RT form produced by insect cells, but not analyzed in present studies.

Co-expression of RSV RT βp4 and RSV protease p15 in cultured insect cells. Heterodimeric p66/p51 HIV RT has been produced efficiently in *E. coli* by co-expression of HIV protease and HIV RT p66 (Mizuahi, V., et al., *Arch. Biochem Biophys*. 273:347(1989) and Le Grice, S. F. J. and Gruninger-Leitch, F., *Eur. J. Biochem*. 187:307 (1990)). Co-expression of the viral protease increased the overall efficiency of converting p66/p66 to heterodimer. As described above in the Materials and Methods section of this Example, co-expression of RSV RT β and RSV protease p15 genes in *E. coli* did not result in enhanced production of RSV αβ RT. Similarly, co-expression of RSV RT βp4 and RSV protease p15 in cultured insect cells did not appreciably enhance the formation of RSV αβ RT.

Processing of RSV RT βp4 with RSV protease p15 in vitro. Heterodimeric p66/p51 HIV RT has been produced from p66 purified from *E. coli* by treatment with HIV protease in vitro (Chattopodhyay, D., et al., *J. Biol. Chem*. 267:14227 (1992)). Purified RSV RT βp4 was treated with RSV protease p15 to generate RSV αβ RT. This approach was successful in generating some αβ from βp4 based upon SDS-PAGE analysis, but several difficulties were encountered. First, contrary to what was observed with viral protease treatment of HIV p66 RT, processing of βp4 to αβ did not always stop at αβ, as α in excess of β was formed as proteolysis proceeded. Second, significant loss of DNA polymerase activity was observed during proteolysis, suggesting RSV RT was partially inactivated by the acid pH reaction conditions required by RSV protease.

Processing of RSV RT βp4 with chymotrypsin in vitro. Heterodimeric p66/p51 HIV RT has also been produced from p66 by limited proteolysis with α-chymotrypsin (Lowe, D. M., et al., *Biochemistry* 27:8884(1988)). This approach was tried unsuccessfully with RSV RT βp4. We found the digestion of βp4 with α-chymotrypsin was difficult to control, and proteolysis was observed to not stop at αβ, but to proceed to conversion of βp4 to α.

Mixing of RSV RT α and β (in vitro) to generate αβHeterodimeric p66/p51 HIV RT has been produced by mixing separate crude cell lysates containing p51 alone and $p^{66}$ alone (Stahlhut, M., et al., *Protein Expression and Purification* 5:614 (1994)). Mixing of the separate subunits results in formation of a 1:1 molar complex of p66/p5 1. In contrast, mixing of purified RSV α RT with purified RSV β RT at approximately a 1:1 molar ratio did not result in the formation of an αβ complex. These results are consistent with the notion that the RSV subunits, once folded separately in an active conformation, prefer to remain separate when mixed.

Relative Ability of Various Forms of RSV RT to Copy RNA

A comparison was made of the ability of four different forms of RSV RT (αβ, ββ, α, and βp4βp4) to copy RNA. The RNase H active site of each subunit in these enzymes was mutated to eliminate RNase H activity. Each RT was expressed in cultured insect cells and purified by methods described above and in Example 1. Two RNAs were used for comparison: synthetic homopolymer poly(A) and 7.5-Kb mRNA. With poly(A)•oligo(dT) as template-primer, a specific activity was calculated by determining an initial rate of poly(dT) synthesis catalyzed at limiting enzyme concentration, and then normalizing the rate to a given mass (mg) of RT in the reaction. This specific activity simply represents the ability of a given RT to incorporate a single deoxynucleotide with an artificial template, and does not necessarily represent the ability of the enzyme to copy heteropolymeric RNA. With 7.5-Kb RNA as template, the ability of the RTs to make a full-length copy of a long heteropolymeric RNA was assessed (see Example 3 for details). The results are shown above in Table 7.

Two different forms of αβ were characterized in Table 7. One form was generated as the result of the expression of the RSV RT β gene and subsequent proteolytic processing in host insect cells, and had reduced specific and functional activity. The other form of αβ was generated by co-expression of the RSV RT α and β genes. This form of αβ had a similar specific activity to α, approximately 50,000 units/mg, and had a higher specific activity than either ββ or βp4βp4 (approximately 16,000 units/mg). Comparison of the functional activity of this αβ to other RT forms showed a much more dramatic contrast. RSV αβ RT produced 7, 9 and 15 times more total cDNA per mass of enzyme than ββ, βp4βp4 and α, respectively, from 7.5-Kb RNA. Even greater differences were observed when yield of full length product was assessed: RSV αβ RT produced 21, 13 and 146 times more full length product per mass of enzyme than ββ, βp4βp4 and α, respectively. RSV αβ RT produced by co-expression of the RSV RT α H⁻ and βH⁻ genes is therefore much more efficient in copying mRNA than is any other form of RSV RT prepared by analogous methods.

Evidence that Only the α Subunit in RSV αβ RT is Active

Selective DNA polymerase active site mutagenesis of the HIV RT heterodimer p66/p51 has shown that only the DNA polymerase active site of p66 is crucial for DNA polymerase activity (LeGrice, S. F. J., et al., *The EMBO Journal* 10: 3905 (1991) and Hostomsky, Z., et al., *J. Virol*. 66: 3179 (1992)). The p51 subunit in the HIV p66/p51 heterodimer apparently assumes a conformation which does not have a substrate binding cleft and therefore does not participate directly in dNTP binding and incorporation (Jacob-Molina, A., et al., *Proc Natl. Acad Sci USA* 90: 6320 (1993)).

In the present studies, the same question was asked for RSV αβ RT. In this case, since each subunit contains both a DNA polymerase and RNase H active site, combinations of DNA polymerase mutants alone and RNase H mutants alone were characterized. The results are shown in Table 8.

TABLE 8

DNA Polymerase and RNase H Activities of Various Forms of RSV RT.

| | Specific Activity (Units/mg) | | Ratio of DNA |
|---|---|---|---|
| RSV RT Form | DNA Polymerase | RNase H | Polymerase/RNase H |
| αH⁺/βH⁺ | 52,095 | 924 | 56.4 |
| αH⁻/βH⁻ | 53,191 | <0.1 | — |
| αH⁺/βH⁻ | 48,250 | 760 | 64.5 |
| αH⁻/βH⁺ | 50,909 | 4.5 | 11,313 |
| βH⁻/βH⁻ | 15,819 | <0.1 | — |
| αH⁻ | 48,759 | <0.1 | — |
| αpol⁺/βpol⁺ | 52,095 | 924 | 56.4 |
| αpol⁻/βpol⁻ | 50 | 600 | 0.08 |
| αpol⁺/βpol⁻ | 57,500 | 900 | 63.9 |
| αpol⁻/βpol⁺ | 1,143 | 629 | 1.82 |

As shown in Table 8, when the RNase H active site in both subunits was mutated to eliminate RNase H activity, RNase H activity in purified enzyme was reduced to below detectable levels, while DNA polymerase activity was unchanged. When the RNase H active site in β was altered with the same mutation and the α RNase H active site was wild type, the enzyme was similar to wild type in polymerase and RNase H activity. In contrast, mutation of the α subunit in RNase H, but not the β subunit, resulted in a 200-fold reduction in RNase H activity. Therefore, in the case of RSV αβ RT, the RNase H domain of the large subunit (β) folds in an inactive conformation. Examination of DNA polymerase active site mutants in RSV αβ RT revealed the same results (Table 8). The α subunit, but not the β subunit, supplies the DNA polymerase catalytic activity. So, in contrast to HIV p66/p51 RT, the smaller RSV αβ RT subunit, not the larger, maintains enzymatic activity. The common element in both enzymes is that the subunit possessing DNA polymerase and RNase H domains folds in an active conformation, while subunits missing the RNase H domain or possessing an additional domain (integrase), fold in an inactive conformation.

In sum, these results demonstrate that only the αβ form of ASLV RT copies mRNA efficiently. In addition, the present results indicate that expression of ASLV RT in E. coli results in little or no production of active RT, while expression and activity increase dramatically by cloning and expression of ASLV RT in insect cells and yeast. Finally, by placing point mutations in either the DNA polymerase or the RNase H active site of the α or β subunit of RSV αβ RT, it has now been discovered that the DNA polymerase and RNase H catalytic activities of the RSV RT αβ heterodimer reside in the α subunit alone.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of producing a Rous Sarcoma Virus (RSV) reverse transcriptase having a RNA-dependent DNA polymerase specific activity of 30,000 units per milligram to 150,000 units per milligram, said method comprising
   (a) obtaining a eukaryotic host cell comprising one or more nucleic acid sequences encoding one or more subunits of RSV reverse transcriptase;
   (b) culturing said host cell under conditions sufficient to produce said RSV reverse transcriptase; and
   (c) isolating or purifying said reverse trascriptase thereby obtaining an RSV reverse transcriptase having a RNA-dependent DNA polymeraso specific activity of 30,000 units per milligram to 150,000 units per milligram.

2. The method of claim 1, wherein said subunits are α subunits.

3. The method of claim 1, wherein said subunits are β subunits.

4. The method of claim 1, wherein said subunits are βp4 subunits.

5. The method of claim 1, wherein said subunits are one α subunit and one β subunit.

6. The method of claim 1, wherein said subunits are co-expressed to form a RSV reverse transcriptase and wherein said RSV reverse transcriptase is isolated from said host cell.

7. The method of claim 1, wherein said subunits of RSV reverse transcriptase are isolated and then mixed to form a RSV reverse transcriptase.

8. The method of claim 3, wherein said β subunits form a RSV reverse transcriptase comprising two β subunits.

9. The method of claim 5, wherein said α and β subunits form a RSV reverse transcriptase comprising an α and a β subunit.

10. The method of claim 1, wherein said nucleic acid sequences are contained in one or more vectors.

11. The method of claim 1, wherein said RSV reverse transcriptase has a RNA-dependent DNA polymerase specific activity of 35,000 units per milligram.

12. The method of claim 1, wherein said RSV reverse transcriptase has a RNA-dependent DNA polymerase specific activity of 30,000 units per milligram to 130,000 units per milligram.

13. The method of claim 1, wherein said RSV reverse transcriptase has a RNA-dependent DNA polyrnerase specific activity of 30,000 units per milligram to 110,000 units per milligram.

14. The method of claim 1, wherein said RSV reverse transcriptase has a RNA-dependent DNA polymerase specific activity of 30,000 units per milligram to 90,000 units per milligram.

15. The method of claim 1, wherein said RSV reverse transcriptase has a RNA-dependent DNA polymerase specific activity of 50,000 units per milligram to 130,000 units per milligram.

16. The method of claim 1, wherein said RSV reverse transcriptase has a RNA-dependent DNA polyrnerase specific activity of 50,000 units per milligram to 110,000 units per milligram.

17. The method of claim 1, wherein said RSV reverse transcriptase has a RNA-dependent DNA polymerase specific activity of 50,000 units per milligram to 90,000 units per milligram.

18. The method of claim 1, wherein said RSV reverse transcriptase has a RNA-dependent DNA polymerase specific activity of 70,000 units per milligram to 130,000 units per milligram.

19. The method of claim 1, wherein said RSV reverse transcriptase has a RNA-dependent DNA polymerase specific activity of 70,000 units per milligram to 110,000 units per milligram.

20. The method of claim 1, wherein said RSV reverse transcriptase has a RNA-dependent DNA polymerase specific activity of 70,000 units per milligram 90,000 per milligram.

21. The method of claim 1, wherein said RSV reverse transcriptase has a RNA-dependent DNA polymerase specific activity from 80,000 units per milligram to 150,000 units per milligram.

22. The method of claim 1, wherein said RSV reverse transcriptase has a RNA-dependent DNA polyrnerase specific activity of 35,000 units per milligram to 150,000 units per milligram.

23. The method of claim 1, wherein said RSV reverse transcriptase has a RNA-dependent DNA polymerase specific activity of 40,000 units per milligram to 150,000 units per milligram.

24. The method of claim 1, wherein said RSV reverse transcriptase has a RNA-dependent DNA polymerase specific activity of 45,000 units per milligram to 150,000 units per milligram.

25. The method of claim 1, wherein said RSV reverse transcriptase has a RNA-dependent DNA polymerase specific activity of 50,000 units per milligram to 150,000 units per milligram.

26. The method of claim 1, wherein said RSV reverse transcriptase has a RNA-dependent DNA polymerase specific activity of 55,000 units per milligram to 150,000 units per milligram.

27. The method of claim 1, wherein said RSV reverse transcriptase has a RNA-dependent DNA polymerase specific activity of 60,000 units per milligram to 150,000 units per milligram.

28. The method of claim 1, wherein said RSV reverse transcriptase has a RNA-dependent DNA polymerase specific activity of 65,000 units per milligram to 150,000 units per milligram.

29. The method of claim 1, wherein said RSV reverse transcriptase has a RNA-dependent DNA polymerase specific activity of 70,000 units per milligram to 150,000 units per milligram.

30. The method of claim 1, wherein said RSV reverse transcriptase has a RNA-dependent DNA polymerase specific activity of 75,000 units per milligram to 150,000 units per milligram.

31. The method of claim 10, wherein said nucleic acid sequences are contained on the same vector.

32. The method of claim 10, wherein said nucleic acid sequences are contained on different vectors.

33. The method of claim 1, wherein said host cell is a cultured insect cell.

34. The method of claim 1, wherein said host cell is an insect larva cell.

35. The method of claim 1, wherein said host cell is a yeast cell.

36. A method of producing a Rous Sarcoma Virus (RSV) reverse transcriptase having a RNA-dependent DNA polymerase specific activity of 30,000 units per milligram to 150,000 units per milligram or a mutant RSV reverse transcriptase having reduced RNase H activity, said method comprising
  (a) obtaining a eukaryotic host cell comprising one or more nucleic acid sequences encoding one or more mutant subunits of RSV reverse transcriptase having reduced RNase H activity relative to the wild-type reverse transcriptase;
  (b) culturing said host cell under conditions sufficient to produce said mutant RSV reverse transcriptase; and
  (c) isolating or purifying said reverse trascriptase thereby obtaining a mutant RSV reverse transcriptase having a RNA-dependent DNA polymerase specific activity of 30,000 units per milligram to 150,000 units per milligram.

37. The method of claim 36, wherein said one or more nucleic acid sequences encoding one or more subunits of RSV reverse transcriptase are contained in one or more vectors subunits of said RSV reverse transcriptase are expressed in said host cell to form said mutant RSV reverse trascriptase.

38. The method of claim 36, wherein said mutant RSV reverse transcriptase subunits are selected from the group consisting of α subunits, β subunits and βp4 subunits.

39. The method of claim 38, wherein said mutant subunits are a subunits.

40. The method of claim 38, wherein said mutant subunits are β subunits.

41. The method of claim 38, wherein said mutant subunits are βp4 subunits.

42. The method of claim 38, wherein said mutant subunits are one α subunit and one β subunit.

43. The method of claim 36, wherein said subunits are co-expressed to form a RSV reverse transcriptase and wherein said RSV reverse transcriptase is isolated from said host cell.

44. The method of claim 36, wherein said subunits of RSV reverse transcriptase are isolated and then mixed to form a RSV reverse transcriptase.

45. The method of claim 40, wherein said mutant β subunits form a RSV reverse transcriptase comprising two β subunits.

46. The method of claim 42, wherein said mutant a and β subunits form a RSV reverse transcriptase comprising an α and a β subunit.

47. The method of claim 36, wherein said subunits are encoded by one or more nucleotides sequences contained on the same or on different vectors nucleic acid sequences are contained in one or more vectors.

48. The method of claim 36, wherein said mutant RSV reverse transcriptase has a RNA-dependent DNA polymerase specific activity of 35,000 units per milligram to 180,000 units per milligram.

49. The method of claim 36, wherein said mutant RSV reverse transcriptase has a RNA-dependent DNA polymerase specific activity of 30,000 units per milligram to 110,000 units per milligram.

50. The meted of claim 36, wherein said mutant RSV reverse transcriptase has a RNA-dependent DNA polymerase specific activity of 30,000 units per milligram to 110,000 units per milligram.

51. The method of claim 36, wherein said mutant RSV reverse transcriptase has a RNA-dependent DNA polymerase specific activity of 30,000 units per milligram to 90,000 units per milligram.

52. The method of claim 36, wherein said mutant RSV reverse transcriptase has a RNA-dependent DNA polymerase specific activity of 50,000 units per milligram to 130,000 units per milligram.

53. The method of claim 36, wherein said mutant RSV reverse transcriptase has a RNA-dependent DNA polymerase specific activity of 50,000 units per milligram to 110,000 units per milligram.

54. The method of claim 36, wherein said mutant RSV reverse transcriptase has a RNA-dependent DNA polymerase specific activity of 50,000 units per milligram to 90,000 units per milligram.

55. The method of claim 36, wherein said mutant RSV reverse transcriptase has a RNA-dependent DNA polymerase specific activity of 70,000 units per milligram to 130,000 units per milligram.

56. The method of claim 36, wherein said mutant RSV reverse transcriptase has a RNA-dependent DNA polymerase specific activity of 70,000 units per milligram to 110,000 unit per milligram.

57. The method of claim 36, wherein said mutant RSV reverse franscriptase has a RNA-dependent DNA polymerase specific activity of 70,000 units per milligram to 90,000 units per milligram.

58. The method of claim 47, wherein said nucleic acid sequences are contained on the same vector.

59. The method of claim 47, wherein said nucleic acid sequences are contained on different vectors.

60. The method of claim 36, wherein said host cell is a cultured insect cell.

61. The method of claim 36, wherein said host cell is an insect larva cell.

62. The method of claim 36, wherein said host cell is a yeast cell.

* * * * *